US012569439B2

(12) United States Patent
Staufer et al.

(10) Patent No.: US 12,569,439 B2
(45) Date of Patent: Mar. 10, 2026

(54) BOTTOM-UP ASSEMBLY OF SYNTHETIC EXTRACELLULAR VESICLES

(71) Applicant: Max-Planck-Gesellschaft zur Förderung der Wissenschaften e.V., Munich (DE)

(72) Inventors: Oskar Staufer, Mannheim (DE); Yilia Plazman, Stuttgart (DE); Joachim P. Spatz, Stuttgart (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 805 days.

(21) Appl. No.: 17/759,768

(22) PCT Filed: Jan. 29, 2021

(86) PCT No.: PCT/EP2021/052145
§ 371 (c)(1),
(2) Date: Jul. 29, 2022

(87) PCT Pub. No.: WO2021/152115
PCT Pub. Date: Aug. 5, 2021

(65) Prior Publication Data
US 2023/0181466 A1      Jun. 15, 2023

(30) Foreign Application Priority Data
Jan. 31, 2020    (EP) .................................... 20155012

(51) Int. Cl.

| | |
|---|---|
| *A61K 9/127* | (2025.01) |
| *A61K 9/1272* | (2025.01) |
| *A61K 9/1277* | (2025.01) |
| *A61K 38/17* | (2006.01) |
| *A61K 38/45* | (2006.01) |
| *A61P 17/02* | (2006.01) |
| *C07K 14/705* | (2006.01) |
| *C12N 15/113* | (2010.01) |
| *C12N 15/88* | (2006.01) |

(52) U.S. Cl.
CPC .......... *A61K 9/1272* (2013.01); *A61K 9/1277* (2013.01); *A61K 38/1709* (2013.01);
(Continued)

(58) Field of Classification Search
CPC .. A61K 9/1272; A61K 47/6909; A61K 38/45; A61K 38/1709; A61K 9/1277;
(Continued)

(56) References Cited

U.S. PATENT DOCUMENTS

| | | | |
|---|---|---|---|
| 2016/0354313 A1 | 12/2016 | De Beer | |
| 2017/0128367 A1 | 5/2017 | Peer | |

(Continued)

FOREIGN PATENT DOCUMENTS

| | | |
|---|---|---|
| WO | WO 2019/027847 | 2/2018 |
| WO | WO 2019/126068 | 6/2019 |

OTHER PUBLICATIONS

Danaei et al., "Impact of Particle Size and Polydispersity Index on the Clinical Applications of Lipidic Nanocarrier Systems" Pharmaceutics (2018) 10(2):57.

(Continued)

*Primary Examiner* — Monica A Huson
(74) *Attorney, Agent, or Firm* — Knobbe, Martens, Olson & Bear, LLP

(57) ABSTRACT

The present invention relates to a method for producing synthetic extracellular vesicles comprising a lipid bilayer including at least two lipids, one or more extracellular vesicle associated proteins, and optionally one or more nucleic acid molecules. The inventive synthetic extracellular vesicles are formed by emulsification using a mechanic emulsifier in the form of polymer shell stabilized synthetic extracellular vesicles. The inventive method allows producing synthetic extracellular vesicles miming the composition and function of natural extracellular vesicles. Therefore, synthetic extracellular vesicles with specific protein and nucleic acids compositions are also disclosed herein, as well as their therapeutic uses.

18 Claims, 15 Drawing Sheets a emulsification

>2h incubation destabilizing surfactant

Surface proteins

Phase separated layers      Droplet stabilized EVs      nucleic acid loaded and released EV      Fully synthetic extracellular vesicles

(52) U.S. Cl.
CPC .......... *A61K 38/1761* (2013.01); *A61K 38/45*
(2013.01); *A61P 17/02* (2018.01); *C07K*
*14/70503* (2013.01); *C07K 14/70575*
(2013.01); *C07K 14/70596* (2013.01); *C12N*
*15/113* (2013.01); *C12N 15/88* (2013.01);
*C12Y 204/02012* (2013.01); *C12N 2310/141*
(2013.01)

(58) Field of Classification Search
CPC ............ A61K 38/1761; A61K 47/6901; A61K
38/00; C12N 15/88; C12N 15/113; C12N
2310/141; C07K 14/70575; C07K
14/70503; C07K 14/70596; C12Y
204/02012; A61P 17/02
See application file for complete search history.

(56) References Cited

U.S. PATENT DOCUMENTS

| | | | |
|---|---|---|---|
| 2019/0202892 A1 | 7/2019 | Lewis et al. | |
| 2019/0343767 A1 | 11/2019 | Haraszti et al. | |

OTHER PUBLICATIONS

Garcia-Manrique et al., "Fully Artificial Exosomes: Towards New Theranostic Biomaterials" Trends in Biotechnology (2017) 36(1):10-14.

Kooijmans et al., "PEGylated and targeted extracellular vesicles display enhanced cell specificity and circulation time" Journal of Controlled Release (2016) 224:77-85.

Tatusova & Madden, "Blast 2 Sequences, a new tool for comparing protein and nucleotide sequences" FEMS Microbiology Letters (1999) 174:247-250.

Thery et al., "Minimal information for studies of extracellular vesicles 2018 (MISEV2018): a position statement of the International Society for Extracellular Vesicles and update of the MISEV2014 guidelines" Journal of Extracellular Vesicles (2018) 7(1):1535750.

Vogel et al., "High-Resolution Single Particle Zeta Potential Characterization of Biological Nanoparticles using Tunable Resistive Pulse Sensing" Scientific Reports (2017) 7(1):17479.

Weiss et al. "Sequential bottom-up assembly of mechanically stabilized synthetic cells by microfluidics" Nature Materials (2018) 17(1):89-96.

International Search Report and Written Opinion mailed Jun. 9, 2021 for PCT/EP2021/052145, filed Jan. 29, 2021.

K562 EVs isolated by ultracentrifugation     Commercially available K562 EVs     fsEV a b fsEV-CD9          fsEV-CD81 fsEV-CD63         fsEV-CD9/63/81

Figure 19 (continue)
c)
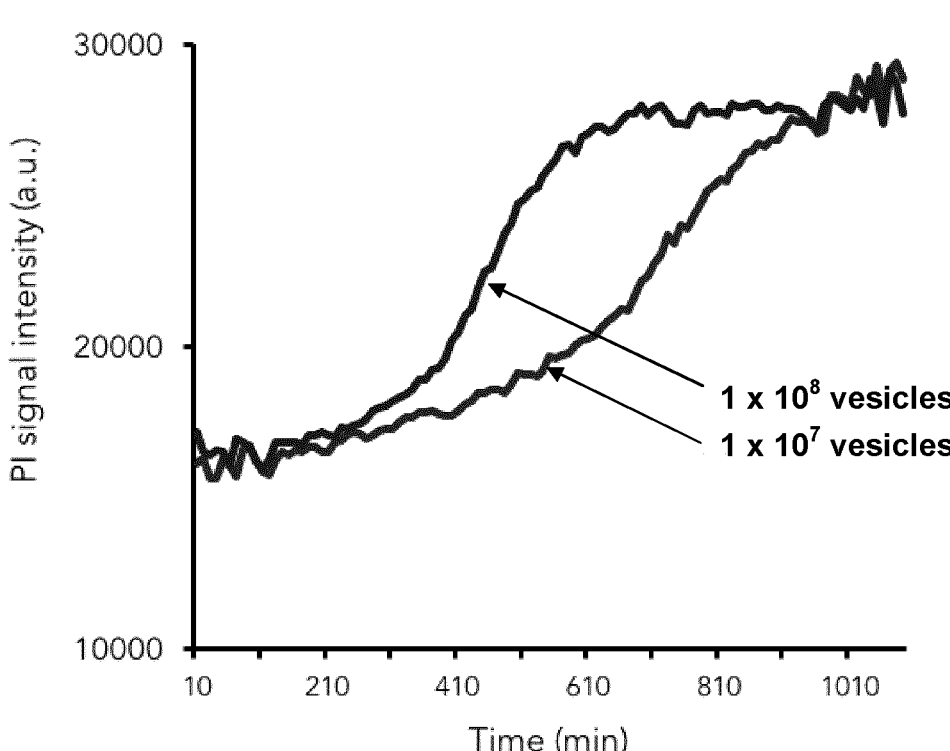

BOTTOM-UP ASSEMBLY OF SYNTHETIC EXTRACELLULAR VESICLES

The present application is the national phase entry of PCT Application No. PCT/EP2021/052145, filed Jan. 29, 2021, which claims priority to EP Application Serial No. 20155012.6, filed Jan. 31, 2020, both of which are hereby incorporated herein by reference in their entireties.

SPECIFICATION

The present invention relates to a method for producing synthetic extracellular vesicles comprising a lipid bilayer including at least two lipids, optionally one or more extracellular vesicle associated proteins, and optionally one or more nucleic acid molecules. The inventive synthetic extracellular vesicles are formed by emulsification using a mechanic emulsifier in the form of polymer shell stabilized synthetic extracellular vesicles. The inventive method allows producing synthetic extracellular vesicles miming the composition and function of natural extracellular vesicles. Therefore, synthetic extracellular vesicles with specific protein and nucleic acids composition are also disclosed herein, as well as their therapeutic uses.

BACKGROUND OF THE INVENTION

Extracellular vesicles are membrane-contained small vesicles, secreted by all types of pro- and eukaryotic cells, and play a crucial role in intercellular signaling under both physiological and pathological conditions.

In physiological conditions, extracellular vesicles are important mediators for cell-to-cell and inter-tissue communication, thus playing a role in regulating homeostasis as well as other conditions. In pathological conditions, the information transferred by extracellular vesicles, mainly cancer cell extracellular vesicles, may have detrimental effects. Indeed, extracellular vesicles have been demonstrated to contribute to various pathologies such as tumorigenesis and metastasis, inflammation, and immune system activation.

As a result of the above-mentioned functions, extracellular vesicles may serve as novel tools for various therapeutic and diagnostic applications, such as anti-tumour therapy, pathogen vaccination, immune-modulatory and regenerative therapies and drug delivery. Indeed, extracellular vesicles can be used for the target-specific delivery of nucleic acid molecules, proteins or small molecules into the intracellular environment, where they also act on a genetic level.

The three main categories of extracellular vesicles are apoptotic bodies, shedding microvesicles and exosomes. Microvesicles and exosomes are smaller compared to apoptotic bodies. Additionally they differ from apoptotic bodies in their content, since they rarely contain DNA.

The main function of microvesicles and exosomes is the intercellular transfer of lipids, RNA, and cytosolic proteins, thereby affecting cell metabolism and functions, including, but not limited to migration, cell proliferation and differentiation.

A detailed and precise characterization of the intercellular signalling mechanisms mediated by extracellular vesicles is essential to develop extracellular vesicle-based therapeutic applications. However, the methods of the current art to isolate and purify extracellular vesicles are very complex, long and error prone providing extracellular vesicle preparations with low yield and purity and high variability between different batches, which hamper a correct understanding of extracellular vesicle biology and of their interactions with the environment. Moreover, the exosome preparations oft contain also microvesicles.

Therefore, synthetic and cleaner vesicle formulations are not only highly sought for therapeutic and clinical applications but also to study fundamental aspects of extracellular vesicle biology, signalling, as well as the role of their individual components.

Currently, synthetic exosomes are prepared by two types of methodologies: top-down or bottom-up (Garcia-Manrique P. et al., 2017. Fully Artificial Exosomes: Towards New Theranostic Biomaterials. *Trends in Biotechnology*). In top-down methodologies, the production of artificial exosomes begins with cultured and eventually engineered cells that are then processed to produce membrane fragments to be used to form the vesicles. Even if these methods enable synthesis of exosomes similarly to their natural counterpart, they still have some drawbacks. Indeed cargo loading is not tightly controlled due to the passive encapsulation of the surrounding medium during membrane fragment self-assembly. Moreover, these exosomes cannot have a defined composition and size, and are usually not homogenous in size. The final purification steps used for exosome isolation are time-consuming and characterized by low purity, yield and reproducibility in term of exosome composition.

The patent applications WO 2019 027847 A1, WO 2019 126068 A1, US 2016 0354313 A1, and US 2016 0354313 A1, and the disclosure of Kooijmans et al. (*J. controlled release*, 2016, 224, 77-85) refer to extracellular vesicles produced by top-down methodologies.

The international patent application WO 2019 027847 A1 describes the synthesis of bispecific nanoparticle vesicles that are able to redirect immune effector cells towards cancer cells for killing. However, the nanoparticle vesicles are prepared by transducing a population of cells comprising vesicles, such as exosomes, with polynucleotides coding the polypeptides of interest, and thus isolating the transduced vesicles or exosomes. The exosomes released into the culture media are purified using traditional approaches as differential centrifugation, density-gradient- or cushion-based ultracentifugation, precipitation with commercial kits, and affinity and size exclusion chromatography. Thus, the extracellular vesicles or exosomes described in WO 2019 027847 A1 do not possess a membrane bilayer with a defined lipid composition. Moreover, the vesicle preparation can still contain impurities due to the isolation procedure.

The international patent application WO 2019 126068 A1 discloses engineered extracellular vesicles (EVs) produced by using a membrane cloaking platform technology, wherein the cloaking imparts to the EVs enhanced delivery to tissues of interest, such as damaged or dysfunctional tissue. The engineered EV compositions can be used to treat diseases. The EVs are obtained from culture media of not-modified cultured cells using standard methods and then tailored with fluorescent molecules or ligand proteins using the membrane cloaking platform technology. This consists in incubating the exosomes with a lipid anchor molecule, such as DMPE-PEG, bound to a member (e.g. streptavidin) of a coupling moiety and then with a biotinylated antibody or protein of interest.

The US Patent Application US 2016 0354313 A1 discloses a hybridosome, i.e. a hybrid biocompatible carrier, which is synthetized from two different vesicles, one is a naturally secreted vesicle (BDM), one is in vitro produced by using standard methods (EDEM) comprising at least one tunable fusogenic moiety. The hybridome are described as able to deliver bioactive agents into leukocytes or glial cells or into cells during ex-vivo expansion.

The scientific article of Kooijmans et al. discloses the engineering of extracellular vesicles derived from Neuro2A cells or platelets by mixing with nanobody-PEG-micelles, where the nanobodies are specific for a cellular target, such as the epidermal growth factor receptor (EGFR). The disclosed EVs are showed to efficiently target EGFR positive tumor cells, and to be stable in plasma for longer than 60 min post-injection.

The US Patent Application US 2019 202892 A1 discloses extracellular vesicles comprising an immune-modulating component, such as a cytokine or a binding partner of a cytokine (for example IL2, IL7, IL10, IL12, IL15 or others), and optionally a second component such as an activator for a positive co-stimulatory molecule or an activator for a binding partner of a positive co-stimulatory molecule (for example a TNF receptor superfamily member). The extracellular vesicles are obtained by isolation from producer cells using standard methods. In particular, the the extracellular vesicles with an immunomodulating component are obtained by modifying a producer cell with the immunomodulating component, and then obtaining the extracellular vesicles from the conditioned culture media of the modified producer cells.

Bottom-up methodologies to prepare synthetic exosomes involves the preparation of a synthetic bilayer that is then functionalized with selected proteins to mimic desired exosome functions. However, most of these methodologies are characterized by low encapsulation efficiency and high costs, as the methods are adapted from conventional liposome production routes. Moreover, methodologies to synthetize exosomes containing a specific composition of both exosome proteins and nucleic acids such as miRNAs are still missing.

The disclosures US 2017 0128367 A1, and US 2019 343767 A1 refer to synthetic extracellular vesicles or exosomes produced by bottom-up methodologies.

The patent application US 2017 0128367 A1 discloses liposomes comprising a cationic lipid and a lipid covalently conjugated to a PEG derivative, which is bound to a glycosaminoglycan coating the liposome. The PEG serves to stabilize the liposome, whereas the glycosaminoglycan, for example hyaluronic acid, is used to target the cells of interest. The produced liposomes are characterized by a narrow dimension range between 20 and 500 nm.

The patent application US 2019 343767 A1 discloses artificial exosomes comprising rab7, desmoplakin, alpha 2-HS glycoprotein (AHSG), and a cardiolipin or a variant thereof. The exosome can also comprise a cargo molecule as a peptide, a polypeptide, a nucleic acid, a virus, a small molecule, a fluorophore, or a combination thereof. The artificial exosomes are produced by mixing the single components DOPC, cholesterol, and a cardiolipin to form a cardiolipin-containing liposome, and incubating the cardiolipin-containing liposome with rab7, desmoplakin, and AHSG to form an artificial exosome. The artificial exosomes can thereafter optionally be loaded with siRNA molecules.

The disclosure of Weiss et al. (*Nature Materials,* 2017, 17, 89-96) teaches a high-throughput microfluidic method to generate liposomes to be used as synthetic model cell systems, called protocells, to study interactions of these synthetic cells with physiologically relevant environments such as extracellular matrices, cells or signalling proteins. These mechanically and chemically stable cell-like compartments, called droplet-stabilized GUVs (dsGUVs), can be loaded with biomolecules such as transmembrane and cytoskeleton proteins by microfluidic pico-injection technology. However, this method allows to regulating the diameter of the dsGUVs in the range from 28 μm to 120 μm.

Thus, none of the prior art documents discloses a method to produce fully synthetic extracellular vesicles at high efficiency, high stability, high controlled composition, high purity and reproducibility between different batches.

Therefore, there is still an urgent need for efficient procedures to produce fully synthetic exosomes, or extracellular vesicles with a high defined composition, low variability between different batches, high purity and efficiency.

It is the objective of the present invention to provide synthetic extracellular vesicles assembled with a highly controlled composition and produced surrounded by a stabilizing polymer shell, which can be used for therapeutic applications.

The objective of the present invention is solved by the teaching of the independent claims. Further advantageous features, aspects and details of the invention are evident from the dependent claims, the description, the figures, and the examples of the present application.

BRIEF DESCRIPTION OF THE INVENTION

The present invention provides a method for high-throughput bottom-up assembly of fully synthetic extracellular vesicles with analogous functionalities to naturally occurring cell-derived extracellular vesicles. The production method is based on charge-mediated assembly of predefined functionalized lipid vesicles and encapsulation of miRNAs within the polymer shell stabilized lipid vesicles. "Charge mediated" assembly refers to the process in which the negative charge of the vesicles and the negative charge on the periphery of the polimer shell stabilized vesicles are complexed by the cations, such as for example $Mg^{2+}$ cations. Following their release into an aqueous environment, the respective protein-functionalized synthetic extracellular vesicles can interact with target cells thus influencing their functions, such as metabolism, proliferation, or growth.

The synthetic extracellular vesicles obtained by the highly controlled droplet-stabilized assembly provide a robust platform for therapeutic applications and moreover allow getting new insights into fundamental functioning-principles of extracellular vesicles.

In comparison with the prior art methods, a first advantage of the invention is to provide extracellular vesicles with high stability (FIG. 22) and high controlled composition (FIG. 2) due to the assembly in stabilizing polymer shell surrounded vesicles. The composition of the extracellular vesicles can be adjusted in term of lipid type and charge, lipid ratio, protein to lipid ratio (FIG. 23), protein to protein ratio (FIG. 20), nucleic acid content. Protein to protein ratios and protein to lipid lipid ratios were shown to influence the activity of the synthetic extracellular vesicles on target cells (FIG. 20 and FIG. 23c, respectively).

The assembly in polymer shell stabilized vesicles allows also encapsulation of nucleic acids at high efficiency (FIG. 5), which is very hard to obtain with the current methods.

Moreover, the inventive method allows adjusting the vesicle dimensions by regulating the emulsification speed (Example 2), which is an important factor influencing the activity of the vesicles (FIG. 17).

To notice, the emulsification process allows reaching throughput rates much higher than the throughput rates allowed by microfluidic techniques.

Importantly, the use of emulsification to produce synthetic extracellular vesicles has never been suggested in the prior art so far.

The method also allows obtaining extracellular vesicles preparations with high purity (FIG. 3) and reproducibility between different batches (replicates in FIG. 4).

Moreover, the inventive method allows design and assembly of fully synthetic extracellular vesicles by a polymer shell-stabilized approach that hold a higher therapeutic potential as their laboriously isolated natural analogues (Examples 5-12, FIGS. 7-23), so that they can be used in a multitude of clinical settings.

Moreover, the inventive method for bottom-up assembly of extracellular vesicles, allows controlling the quantity of each individual extracellular vesicle components, which is an essential aspect for therapeutic applications, and also to decipher their roles on disease related states, representing an essential advantage in comparison with natural exosomes.

Non-limiting examples of the extracellular vesicle types are from the group of vesicles that include an exosome, a microvesicle, an apoptotic vesicle, and a liposome.

In particular, the present invention is directed to a method for producing synthetic extracellular vesicles comprising:

a) providing a water phase comprising at least two lipids, and one or more extracellular vesicle associated proteins, or fragments thereof, wherein the at least two lipids are a negative charged lipid, and a lipid coupled to a functional ligand for conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, and wherein the synthetic extracellular vesicles have a hydrodynamic radius between 70 nm and 5000 nm.

The present invention is also directed to a method for producing synthetic extracellular vesicles comprising:

a) providing a water phase comprising at least two lipids, one or more extracellular vesicle associated proteins, or fragments thereof, and one or more nucleic acid molecules, wherein the at least two lipids are a negative charged lipid, and a lipid coupled to a functional ligand for conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, and wherein the synthetic extracellular vesicles have a hydrodynamic radius between 70 nm and 5000 nm.

According to an aspect of the present invention, the method further comprises after step d) the following steps:

d') removing the polymer shell from the polymer shell-stabilized synthetic extracellular vesicles obtained in step d) by adding a surfactant; and e) purifying the synthetic extracellular vesicles by centrifugation.

According to a more particular aspect of the present invention, the water phase of step a) comprises at least one lipid coupled to a functional ligand selected from biotin, N-hydroxysuccinimide ester, N-hydroxysulfosuccinimide, nitrilotriacetic acid-nickel, amine, carboxylic acid, maleimide, aromatic maleimid, dithiopyridinyl, pyridyl disulfide, pyridyldithiopropionate, N-benzylguanine, cyanuric chloride, carboxyacyl, cyanur, folate, square, galloyl, glycan, thiol, arginylglycylaspartic acid, a fluorescent dye molecule, a magnetic resonance imaging reagent, a chelator; and wherein the method optionally comprises after step e) the following step:

f) coupling the synthetic extracellular vesicles with at least one macromolecule comprising at least one moiety reacting with one of said functional ligands, wherein the macromolecule is selected from the group comprising an extracellular vesicle associated protein, or a fragment thereof, a carbohydrate, a nucleic acid, a polypeptide, a cell receptor, an imaging probe.

According to a still more particular aspect of the present invention, the water phase of step a) comprises one or more nucleic acid molecules selected from the group comprising miRNA molecules miR-17, miR-18a, miR-19a, miR-19b-1, miR-20a, miR-92a; miR-21, miR-30d-5p, miR-33b, miR-124, miR-125, miR-126, miR-130, miR-132, miR-133b, miR-140-5p, miR-191, miR-222, miR-451, miR-494, miR-575, miR-630, miR-638, miR-1202, miR-1207-5p, miR-1225-5p, miR-1268, miR-6087, miR-92a-3p-e, miR-K12-3, let-7a.

Further miRNA molecules suitable for the method and the synthetic extracellular vesicles disclosed herein are listed in Table 3.

According to a still more particular aspect of the present invention, the extracellular vesicle associated protein, or a fragment thereof, is selected from the group comprising:

a transmembrane protein selected from the group comprising tetraspanin proteins CD9, CD37, CD47, CD53, CD63, CD81, CD82, CD151, Tspan8, heterotrimeric G protein subunit alpha, integrin α-chains, integrin β-chains, transferrin receptor 1, transferrin receptor 2, lysosome associated membrane proteins, heparan sulfate proteoglycans, syndecans, extracellular matrix metalloproteinase inducer, A Disintegrin And Metalloproteinase Domain 10, CD3, CD11c, CD14, CD29, CD31, CD41, CD42a, CD44, CD45, CD50 or intercellular adhesion molecule 1, CD55, CD59, CD73, CD80, CD86, CD90, sonic hedgehog, major histocompatibility complex I, major histocompatibility complex II, epidermal growth factor receptor 2, epithelial cell adhesion molecule, glycophorin A, Acetylcholinesterase S and E, amyloid beta precursor protein, multidrug resistance-associated protein 1, stem cells antigen-1, or a fragment thereof;

a cytosolic protein selected from the group comprising the protein complexes endosomal sorting complexes required for transport I, II and III, tumour susceptibility gene 101, charged multivesicular body protein, Apoptosis-Linked Gene 2-Interacting Protein X, vacuolar protein sorting 4 homolog A 4A and 4B, arrestin domain-containing protein, flotillin-1, flotillin-2; caveolins, EH-domain containing 1-4, ras homolog family member A, annexins, heat shock proteins, ADP-ribosylation factor 6, syntenin, microtubule-associated protein Tau, or a fragment thereof;

a functional protein selected from the group comprising cytokines, growth factors, interleukins, milk fat globule-EGF factor 8 protein, adhesion proteins, extracellular matrix proteins, nicotinamide phosphoribosyltransferase, signal transduction proteins, Wnta, Wntb, Fas, Fas Ligand, RANK, RANK Ligand, indolamin-2, 3-dioxygenase, cytotoxic T-lymphocyte-associated protein 4-immunoglobulin fusion protein, tumor necrosis factor-related apoptosis-inducing ligand, or a fragment thereof;

a protein associated to intracellular compartments selected from the group comprising histone proteins, lamin A/C, inner membrane mitochondrial protein, cytochrome C-1, mitochondrial import receptor subunit TOM20, calnexin, heat shock protein 90 kDa beta, member 1, heat shock 70 kDa protein 5, Golgin A2, Autophagy Related 9A, actinin1, actinin4, cytokeratin 18, or a fragment thereof.

Further extracellular vesicle associated proteins suitable for the method and the synthetic extracellular vesicles disclosed herein are listed in Table 4.

According to a still more particular aspect of the present invention, the water phase of step a) comprises at least two lipids selected from the group comprising:

a neutral lipid selected from the group comprising ceramide, sphingomyelin, cephalin, cholesterol, cerebrosides, diacylglycerols, phosphatidylcholines, lysophosphatidylcholines, phosphatidylethanolamines, lysophosphatidylethanolamine, lysoethanolamines, inverted headgroup lipids, sphingosins, sterol-modified phospholipids, ether ester lipids, diether lipids, vinyl ether (plasmalogen);

an anionic lipid selected from the group comprising phosphatidic acids, lysophosphatidic acid derivatives, phosphatidylglycerols, lysophosphatidylglycerols, phosphatidylserines, lysophosphatidylserines, phosphatidylinositols, phosphatidylinositolphosphates, cardiolipins, Bis(Monoacylglycero)Phosphate derivatives;

a cationic lipid selected from the group comprising dioleyl-N,N-dimethylammonium chloride; N-(2,3-dioleyloxy)propyl)-N,N,N-trimethylammonium chloride; N, N-distearyl-N,N-dimethylammonium bromide; N-(2,3-dioleyloxy)propyl)-N,N,N-trimethylammonium chloride; 3β-(N-(N',N'-dimethylaminoethane)-carbamoyl) cholesterol; 1,2-dimyristyloxypropyl dimethyl-hydroxy ethyl ammonium bromide; 2,3-dioleyloxy-N-[2(sperminecarboxamido)ethyl]-N,N-dimethyl-1-propanaminium trifluoroacetate; dioctadecylamidoglycyl carboxyspermine; N-(2,3-dioleyloxy)propyl)-N,N-dimethylammonium chloride and 1,2-Dioleoyl dimethylammonium-propane;

a pH-sensitive lipid selected from the group comprising lipid N-(4-carboxybenzyl)-N,N-dimethyl-2,3-bis (oleoyloxy)propan-1-aminium, 1,2-distearoyl-3-dimethylammonium-propane, 1,2-dipalmitoyl-sn-glycero-3-succinate, 1,2-dioleoyl-sn-glycero-3-succinate, N-palmitoyl homocysteine; a photoswitchable lipid;

acylglycine derivatives, prenol derivatives, prostaglandine derivatives, glycosylated diacyl glycerols, eicosanoid derivatives, (palmitoyloxy)octadecanoic acid derivatives, diacetylene derivatives, diphytanoyl derivatives, fluorinated lipids, brominated lipids, lipopolysaccharides;

one of the aforementioned lipids coupled to a functional ligand selected from the group comprising biotin, N-hydroxysuccinimide ester, nitrilotriacetic acid—nickel, amine, carboxylic acid, maleimides, aromatic maleimid, dithiopyridinyl, pyridyl disulfide, pyridyldithiopropionate, N-benzylguanine, cyanuric chloride, carboxyacyl, cyanur, folate, square, galloyl, glycan, thiol, arginylglycylaspartic acid, a fluorescent dye molecule, a magnetic resonance imaging reagent, a chelator;

one of the aforementioned lipids coupled to polyethyleneglycol with a molecular weight comprised between 350 and 50,000 g/mole.

According to a further aspect of the present invention, step d) comprises producing polymer shell stabilized synthetic extracellular vesicles by emulsifying the combined phases at step c) using a mechanic or electronic emulsifier for at least 5 seconds at speed higher than 1,000 rpm.

A preferred embodiment of the present invention is directed to a synthetic extracellular vesicle having a hydrodynamic radius between 70 nm and 5000 nm, comprising:

a lipid bilayer comprising at least two lipids selected from the group comprising:

a neutral lipid selected from the group comprising ceramide, sphingomyelin, cephalin, cholesterol, cerebrosides, diacylglycerols, phosphatidylcholines, lysophosphatidylcholines, phosphatidylethanolamines, lysophosphatidylethanolamine, lysoethanolamines, inverted headgroup lipids, sphingosins, sterol-modified phospholipids, ether ester lipids, diether lipids, an anionic lipid selected from the group comprising phosphatidic acids, lysophosphatidic acid derivatives, phosphatidylglycerols, lysophosphatidylglycerols, phosphatidylserines, lysophosphatidylserines, phosphatidylinositols, phosphatidylinositolphosphates, cardiolipins, Bis(Monoacylglycero)Phosphate derivatives;

a cationic lipid selected from the group comprising dioleyl-N,N-dimethylammonium chloride; N-(2,3-dioleyloxy)propyl)-N,N,N-trimethylammonium chloride; N,N-distearyl-N,N-dimethylammonium bromide; N-(2,3-dioleyloxy)propyl)-N,N,N-trimethylammonium chloride; 3β-(N-(N',N'-dimethylaminoethane)-carbamoyl)cholesterol; 1,2-dimyristyloxypropyl-3-dimethyl-hydroxy ethyl ammonium bromide; 2,3-dioleyloxy-N-[2(sperminecarboxamido)ethyl]-N,N-dimethyl-1-propanaminium trifluoroacetate; dioctadecylamidoglycyl carboxyspermine; N-(2,3-dioleyloxy)propyl)-N,N-dimethylammonium chloride and 1,2-Dioleoyl-3-dimethylammonium-propane;

a pH-sensitive lipid selected from the group comprising lipid N-(4-carboxybenzyl)-N,N-dimethyl-2,3-bis (oleoyloxy)propan-1-aminium, 1,2-distearoyl-3-dimethylammonium-propane, 1,2-dipalmitoyl-sn-glycero- 3-succinate, 1,2-dioleoyl-sn-glycero-3-succinate, N-palmitoyl homocysteine; a photoswitchable lipid;

acylglycine derivatives, prenol derivatives, prostaglandine derivatives, glycosylated diacyl glycerols, eicosanoid derivatives, (palmitoyloxy)octadecanoic acid derivatives, diacetylene derivatives, diphytanoyl derivatives, fluorinated lipids, brominated lipids, lipopolysaccharides;

one of the aforementioned lipids coupled to a functional ligand selected from the group comprising biotin, N-hydroxysuccinimide ester, nitrilotriacetic acid-nickel, amine, carboxylic acid, maleimides, aromatic maleimid, dithiopyridinyl, pyridyl disulfide, pyridyldithiopropionate, N-benzylguanine, cyanuric chloride, carboxyacyl, cyanur, folate, square, galloyl, glycan, thiol, arginylglycylaspartic acid, a fluorescent dye molecule, a magnetic resonance imaging reagent, a chelator;

one of the aforementioned lipids coupled to polyethyleneglycol with a molecular weight comprised between 350 and 50,000 g/mole.

one or more extracellular vesicle associated selected from the group comprising tetraspanin proteins CD9, CD37, CD47, CD53, CD63, CD81, CD82, CD151, Tspan8, heterotrimeric G protein subunit alpha, integrin α-chains, integrin β-chains, transferrin receptor 1, transferrin receptor 2, lysosome associated membrane proteins, heparan sulfate proteoglycans, syndecans, extracellular matrix metalloproteinase inducer, A Disintegrin And Metalloproteinase Domain 10, CD3, CD11c, CD14, CD29, CD31, CD41, CD42a, CD44, CD45, CD50 or intercellular adhesion molecule 1, CD55, CD59, CD73, CD80, CD86, CD90, sonic hedgehog, major histocompatibility complex I, major histocompatibility complex II, epidermal growth factor receptor 2, epithelial cell adhesion molecule, glycophorin A, acetylcholinesterase S and E, amyloid beta precursor protein, multidrug resistance-associated protein 1, stem cells antigen-1, the protein complexes endosomal sorting complexes required for transport I, II and III, tumour susceptibility gene 101, charged multivesicular body protein, Apoptosis-Linked Gene 2-Interacting Protein X, vacuolar protein sorting 4 homolog A 4A and 4B, arrestin domain-containing protein, flotillin-1, flotillin-2; caveolins, EH-domain containing 1-4, ras homolog family member A, annexins, heat shock proteins, ADP-ribosylation factor 6, syntenin, microtubule-associated protein Tau, cytokines, growth factors, interleukins, milk fat globule-EGF factor 8 protein, adhesion proteins, extracellular matrix proteins, nicotinamide phosphoribosyltransferase, signal transduction proteins, Wnta, Wntb, Fas, Fas Ligand, RANK, RANK Ligand, indolamin-2,3-dioxygenase, cytotoxic T-lymphocyte-associated protein 4-immunoglobulin fusion protein, tumor necrosis factor-related apoptosis-inducing ligand, histone proteins, lamin NC, inner membrane mitochondrial protein, cytochrome C-1, mitochondrial import receptor subunit TOM20, calnexin, heat shock protein 90 kDa beta, member 1, heat shock 70 kDa protein 5, Golgin A2, Autophagy Related 9A, actinin1, actinin4, cytokeratin 18, or a fragment thereof.

A further preferred embodiment of the present invention is directed to a synthetic extracellular vesicle having a hydrodynamic radius between 70 nm and 5000 nm, comprising:

a lipid bilayer comprising at least two lipids selected from the group comprising:

a neutral lipid selected from the group comprising ceramide, sphingomyelin, cephalin, cholesterol, cerebrosides, diacylglycerols, phosphatidylcholines, lysophosphatidylcholines, phosphatidylethanolamines, lysophosphatidylethanolamine, lysoethanolamines, inverted headgroup lipids, sphingosins, sterol-modified phospholipids, ether ester lipids, diether lipids, an anionic lipid selected from the group comprising phosphatidic acids, lysophosphatidic acid derivatives, phosphatidylglycerols, lysophosphatidylglycerols, phosphatidylserines, lysophosphatidylserines, phosphatidylinositols, phosphatidylinositolphosphates, cardiolipins, Bis(Monoacylglycero)Phosphate derivatives;

a cationic lipid selected from the group comprising dioleyl-N,N-dimethylammonium chloride; N-(2,3-dioleyloxy)propyl)-N,N,N-trimethylammonium chloride; N,N-distearyl-N,N-dimethylammonium bromide; N-(2,3-dioleyloxy)propyl)-N,N,N-trimethylammonium chloride; 3β-(N-(N',N'-dimethylaminoethane)-carbamoyl)cholesterol; 1,2-dimyristyloxypropyl-3-dimethyl-hydroxy ethyl ammonium bromide; 2,3-dioleyloxy-N-[2(sperminecarboxamido)ethyl]-N,N-dimethyl-1-propanaminium trifluoroacetate; dioctadecylamidoglycyl carboxyspermine; N-(2,3-dioleyloxy)propyl)-N,N-dimethylammonium chloride and 1,2-Dioleoyl-3-dimethylammonium-propane;

a pH-sensitive lipid selected from the group comprising lipid N-(4-carboxybenzyl)-N,N-dimethyl-2,3-bis (oleoyloxy)propan-1-aminium, 1,2-distearoyl-3-dimethylammonium-propane, 1,2-dipalmitoyl-sn-glycero-3-succinate, 1,2-dioleoyl-sn-glycero-3-succinate, N-palmitoyl homocysteine; a photoswitchable lipid;

acylglycine derivatives, prenol derivatives, prostaglandine derivatives, glycosylated diacyl glycerols, eicosanoid derivatives, (palmitoyloxy)octadecanoic acid derivatives, diacetylene derivatives, diphytanoyl derivatives, fluorinated lipids, brominated lipids, lipopolysaccharides;

one of the aforementioned lipids coupled to a functional ligand selected from the group comprising biotin, N-hydroxysuccinimide ester, nitrilotriacetic acid-nickel, amine, carboxylic acid, maleimides, aromatic maleimid, dithiopyridinyl, pyridyl disulfide, pyridyldithiopropionate, N-benzylguanine, cyanuric chloride, carboxyacyl, cyanur, folate, square, galloyl, glycan, thiol, arginylglycylaspartic acid, a fluorescent dye molecule, a magnetic resonance imaging reagent, a chelator;

one of the aforementioned lipids coupled to polyethyleneglycol with a molecular weight comprised between 350 and 50,000 g/mole;

one or more extracellular vesicle associated selected from the group comprising tetraspanin proteins CD9, CD37, CD47, CD53, CD63, CD81, CD82, CD151, Tspan8, heterotrimeric G protein subunit alpha, integrin α-chains, integrin β-chains, transferrin receptor 1, transferrin receptor 2, lysosome associated membrane proteins, heparan sulfate proteoglycans, syndecans, extracellular matrix metalloproteinase inducer, A Disintegrin And Metalloproteinase Domain 10, CD3, CD11c, CD14, CD29, CD31, CD41, CD42a, CD44, CD45, CD50 or intercellular adhesion molecule 1, CD55, CD59, CD73, CD80, CD86, CD90, sonic hedgehog, major histocompatibility complex I, major histocompatibility complex II, epidermal growth factor receptor 2, epithelial cell adhesion molecule, glyco-phorin A, acetylcholinesterase S and E, amyloid beta precursor protein, multidrug resistance-associated protein 1, stem cells antigen-1, the protein complexes endosomal sorting complexes required for transport I, II and III, tumour susceptibility gene 101, charged multivesicular body protein, Apoptosis-Linked Gene 2-Interacting Protein X, vacuolar protein sorting 4 homolog A 4A and 4B, arrestin domain-containing protein, flotillin-1, flotillin-2; caveolins, EH-domain containing 1-4, ras homolog family member A, annexins, heat shock proteins, ADP-ribosylation factor 6, syntenin, microtubule-associated protein Tau, cytokines, growth factors, interleukins, milk fat globule-EGF factor 8 protein, adhesion proteins, extracellular matrix proteins, nicotinamide phosphoribosyltransferase, signal transduction proteins, Wnta, Wntb, Fas, Fas Ligand, RANK, RANK Ligand, indolamin-2,3-dioxygenase, cytotoxic T-lymphocyte-associated protein 4-immuno-globulin fusion protein, tumor necrosis factor-related apoptosis-inducing ligand, histone proteins, lamin NC, inner membrane mitochondrial protein, cytochrome C-1, mitochondrial import receptor subunit TOM20, calnexin, heat shock protein 90 kDa beta, member 1, heat shock 70 kDa protein 5, Golgin A2, Autophagy Related 9A, actinin1, actinin4, cytokeratin 18, or a fragment thereof; and one or more nucleic acid molecules selected from the group comprising DNA, cDNA, mRNA, siRNA, antisense nucleotides, shRNA, piRNA, snRNA, lncRNA, PNA, left handed DNA, Clustered Regularly Interspaced Short Palindromic Repeats guide RNA, miRNA, wherein the miRNA is optionally selected from the group comprising miR-17, miR-18a, miR-19a, miR-19b-1, miR-20a, miR-92a; miR-21, miR-30d-5p, miR-33b, miR-124, miR-125, miR-126, miR-130, miR-132, miR-133b, miR-140-5p, miR-191, miR-222, miR-451, miR-494, miR-575, miR-630, miR-638, miR-1202, miR-1207-5p, miR-1225-5p, miR-1268, miR-6087, miR-92a-3p-e, miR-K12-3, let-7a.

A particularly preferred embodiment of the present invention is directed to a synthetic extracellular vesicle having a hydrodynamic radius between 70 nm and 5000 nm, with the composition described above and specifically comprising:

a lipid bilayer comprising cholesterol, N-stearoyl-D-erythro-sphingosylphosphorylcholine, 1,2-dioleoyl-sn-glycero-3-phosphocholine, 1,2-dioleoyl-sn-glycero-3-phospho-L-serine, 1,2-dioleoyl-sn-glycero-3-phospho-ethanolamine, 1,2-dioleoyl-sn-glycero-3-phospho-rac-(1-glycerol), 1,2-dioleoyl-sn-glycero-3-phosphate (sodium salt), diacylglycerol, phosphatidylinositol, 1,2-dioleoyl-sn-glycero-3-phosphoethanolamine-N-(lissamine rhodamine B sulfonyl), 1,2-dioleoyl-sn-glycero-3-[(N-(5-amino-1-carboxypentyl)iminodi-acetic acid) succinyl] (nickel salt);

one or more nucleic acid molecules selected from the group comprising miRNA miR-21, miR-124, miR-125, miR-126, miR-130 and miR-132; and one or more transmembrane proteins selected from the group comprising tetraspanin proteins CD9, CD63 and CD81.

Another particularly preferred embodiment of the present invention is directed to a synthetic extracellular vesicle having a hydrodynamic radius between 70 nm and 5000 nm, with the composition described above and specifically comprising:

one or more functional protein nicotinamide phosphori-bosyltransferase, or a fragment thereof;

one or more transmembrane proteins selected from the group comprising tetraspanin proteins CD9, CD63 and CD81, or a fragment thereof; and one or more cytosolic proteins selected from the group comprising Apoptosis-Linked Gene 2-Interacting Protein X (ALIX), tumour susceptibility gene 101 protein (TSG101);

wherein the synthetic extracellular vesicle does not comprise transferrin and albumin, or a fragment thereof.

Another particularly preferred embodiment of the present invention is directed to a synthetic extracellular vesicle having a hydrodynamic radius between 70 nm and 5000 nm, with the composition described above and specifically comprising:

one or more transmembrane proteins selected from the group comprising MHCII, CD80, and CD86, or a fragment thereof;

optionally one or more transmembrane proteins selected from the group comprising CD11c, MHCI, integrin α, integrin β-chains, intercellular adhesion molecule-1, and CD71, or a fragment thereof; and one or more functional proteins selected from the group comprising cytokines, interleukins, interleukin 4, milk fat globule-EGF factor 8 protein, growth factors, Fas, Fas Ligand, indolamin-2,3-dioxygenase, cytotoxic T-lymphocyte-associated protein 4-immunoglobulin fusion protein, tumor necrosis factor-related apoptosis-inducing ligand, or a fragment thereof.

Another particularly preferred embodiment of the present invention is directed to a synthetic extracellular vesicle having a hydrodynamic radius between 70 nm and 5000 nm, with the composition described above and specifically comprising:

a lipid bilayer comprising 1,2-dioleoyl-sn-glycero-3-phosphocholine, 1,2-dioleoyl-sn-glycero-3-phospho-rac-(1-glycerol), 1,2-dioleoyl-sn-glycero-3-phospho-ethanolamine-N-(lissamine rhodamine B sulfonyl), 1,2-dioleoyl-sn-glycero-3-[(N-(5-amino-1-carboxy-pentyl)iminodiacetic acid) succinyl] (nickel salt);

functional protein Fas Ligand, or a fragment thereof; and optionally functional protein intercellular adhesion protein-1, or a fragment thereof.

Another particularly preferred embodiment of the present invention is directed to a synthetic extracellular vesicle having a hydrodynamic radius between 70 nm and 5000 nm, with the composition described above and specifically comprising:

one or more transmembrane proteins selected from the group comprising CD29, CD44, CD90, CD73, CD44, Sca-1, or a fragment thereof;

one or more transmembrane proteins selected from the group comprising tetraspanin proteins CD9, CD63, and CD81, or a fragment thereof;

one or more functional proteins selected from the group comprising Wnta and Wntb, or a fragment thereof;

at least one nucleic acid molecule selected from the group comprising miR-140-5p, miR-92a-3p-e;

one or more nucleic acid molecules selected from the group comprising miR-17, miR-18a, miR-19a, miR-19b-1, miR-20a, miR-92a, let-7a, miR-21, miR124, miR126, miR-133b, miR-191, miR-222, miR-494, miR-6087, miR-30d-5p; and optionally one or more nucleic acid molecules selected from the group comprising miR-33b, miR-451, miR- 575, miR-630, miR-638, miR-1202, miR-1207-5p, miR-1225-5p, miR-1268, miR-K12-3.

A further particularly preferred embodiment of the present invention is directed to a synthetic extracellular vesicle having a hydrodynamic radius between 70 nm and 5000 nm, with the composition described above and specifically comprising:

a lipid bilayer comprising 1,2-dioleoyl-sn-glycero-3-phosphocholine, 1,2-dioleoyl-sn-glycero-3-phosphorac-(1-glycerol), 1,2-dioleoyl-sn-glycero phosphoethanolamine-N-(lissamine rhodamine B sulfonyl), 1,2-dioleoyl-sn-glycero-3-[(N-(5-amino-1-carboxypentyl) iminodiacetic acid) succinyl] (nickel salt); and functional protein RANK, or a fragment thereof.

A more particularly preferred embodiment of the present invention is directed to a synthetic extracellular vesicle as described above for use in the treatment of a disorder selected from the group comprising inflammation, cancer, rheumatic disorder, severe graft versus host disease, osteoarthritis, cardiovascular disorder, epithelial diseases, neurodegenerative disorders, autoimmune disorders, bone and cartilage disorders, osteoporosis, renal osteodystrophy, Paget's disease of bone, osteopetrosis, rickets, neurological disorders, intoxication, neuroendocrinology disorders, endocrinology disorders, genetic disorders, infectious diseases, dental disorders, cosmetic procedures, coagulation disorders, dermatoses, diabetes, age-associated disorders.

DESCRIPTION OF THE INVENTION

Definitions

Unless specifically noted, the embodiments describing "cell-derived vesicles" or "extracellular vesicles" shall include "exosomes", "liposomes", "microvesicles" and "apoptotic vesicles" alone or in combination. When the term "exosome" is used as an example, it is understood that liposomes and microvesicles can be substituted therein.

As used herein, the term "extracellular vesicle" refers to a cell-derived vesicle comprising a membrane that encloses an internal space. Extracellular vesicles comprise all membrane-bound vesicles that have a smaller diameter (here determined as hydrodynamic radius) than the cell from which they are derived. Generally extracellular vesicles range in diameter (hydrodynamic radius) from 20 nm to 1000 nm, and can comprise various macromolecular cargo either within the internal space, displayed on the external surface of the extracellular vesicle, and/or spanning the membrane. The cargo can comprise nucleic acids, proteins, carbohydrates, lipids, small molecules, and/or combinations thereof. Two types of extracellular vesicles are exosomes and microvesicles.

As used herein the term "exosome" refers to a cell-derived small (between 20-300 nm in diameter or hydrodynamic radius, more preferably 20-1000 nm in diameter or hydrodynamic radius) vesicle comprising a membrane that encloses an internal space, and which is generated from the cell by direct plasma membrane budding or by fusion of the late endosome with the plasma membrane. The exosome is a species of extracellular vesicle. The exosome comprises lipid or fatty acid and proteins and optionally comprises a), a polynucleotide (e.g., a nucleic acid, RNA, or DNA), a sugar (e.g., a simple sugar, polysaccharide, or glycan), a functional agent (e.g., a therapeutic agent) or other molecules. The exosome can be derived from a producer cell using a technique known in the prior art, and isolated from the producer cell based on its size, density, biochemical parameters, or a combination thereof.

Microvesicles, on the other hand, are released from a cell upon direct budding from the plasma membrane (PM). Microvesicles are typically larger than exosomes and range from approximately 100 nm to 1 μm.

Although these two vesicle-types, microvesicles, and exosomes, are separate classes of vesicles, due to the fact that they overlap in size, and since the commonly used non-specific protocols for exosome isolation and purification rely solely on the vesicle size differences, it is a fact that in many of the reports published, the exosome samples used are impure, since they probably also include microvesicles and large protein aggregates. Because of this, it has been proposed that the term "extracellular vesicles" (EVs) be used as a general term for all small vesicles/particles, including both vesicle types, and also apoptotic bodies or vesicles.

As used herein the term "synthetic exosome" refers to a synthetic exosome that is not secreted, released, or otherwise produced by a cell in vitro or in vivo. As used herein the term "synthetic exosome" refers to a synthetic exosome generated synthetically from a starting lipid mixture, into which one or more polypeptides and/or nucleic acids may be incorporated. Similarly, the term "synthetic extracellular vesicle" refers to a synthetic extracellular vesicle that is not secreted, released, or otherwise produced by a cell in vitro or in vivo. As used herein the term "synthetic extracellular vesicle" refers to a synthetic extracellular vesicle generated synthetically from a starting lipid mixture, into which one or more polypeptides and/or nucleic acids may be incorporated.

"Liposomes" are microscopic vesicles consisting of concentric lipid bilayers. Structurally, liposomes range in size and shape from long tubes to spheres, with dimensions from a few hundred Angstroms to fractions of a millimeter. Vesicle-forming lipids are selected to achieve a specified degree of fluidity or rigidity of the final complex providing the lipid composition of the outer layer.

"Apoptotic bodies" or "apoptotic vesicles" are released during cell death (apoptosis) and are heterogeneously shaped vesicles with sizes between 50-5000 nm. They are formed from the plasma membrane, and they contain DNA, RNA, histones, and signalling molecules. They usually have high amounts of phosphatidylserine in their membranes, since the outer membrane of apoptotic cells is enriched in PS.

"Membrane" as used herein comprises a lipid bilayer that separates an interior space from an exterior space and comprises one or more biological compounds, typically lipids, and optionally polypeptides and/or carbohydrates such as glycan and/or nucleic acids, and/or other macromolecules. In some embodiments, the membrane comprises lipids and fatty acids. In some embodiments, the membrane comprises phospholipids, glycolipids, fatty acids, sphingolipids, phosphoglycerides, sterols, cholesterols, and phosphatidylserines. The extracellular vesicle comprises a membrane as defined herein.

In some embodiments, the extracellular vesicle or exosome further comprises one or more macromolecule in their lumen.

The term "macromolecule" as used herein is selected from the group comprising an extracellular vesicle associated protein, a carbohydrate, a nucleic acid, a polypeptide, a cell receptor, an imaging probe.

As used herein, the term "homogeneous" in reference to a population of extracellular vesicles refers to population of vesicles that have the same or a similar amount of one or more proteins, or one or more nucleic acid molecules, or one or more macromolecule. A homogenous population is one wherein about 65%, about 70%, about 75%, about 80%, about 85%, about 90%, about 95%, about 98%, or 100% of the vesicles share the one or more proteins, or one or more nucleic acid molecules, or one or more macromolecule.

As used herein, the term "heterogeneous" in reference to a population of engineered vesicles refers to population of vesicles that have differing identity or differing amount of one or more proteins, or one or more nucleic acid molecules, or one or more macromolecule.

Moreover, as used herein, the term "homogeneous" in reference to a population of extracellular vesicles also refers to population of vesicles that have the same or a similar size. A homogenous population in size is one wherein the coefficient of variation calculated as [(standard deviation/average size)*100] is lower than 15%, preferably lower than 13%, preferably lower than 10%, preferably lower than 8%, preferably lower than 7%, most preferably lower than 5%.

The extracellular vesicle or exosome can interact with the target cell via membrane fusion and deliver nucleic acid molecules or intracellular proteins or functional proteins to the surface or cytoplasm of a target cell. In some embodiments, membrane fusion occurs between the extracellular vesicle or exosome and the plasma membrane of a target cell. In other embodiments, membrane fusion occurs between the extracellular vesicle or exosome and an endosomal membrane of a target cell.

As used herein, the term "modulate", "modulating", "modify", and/or "modulator" generally refers to the ability to alter, by increase or decrease, e.g., directly or indirectly promoting, stimulating, up-regulating or interfering with/inhibiting/down-regulating a specific concentration, level, expression, function or behaviour, such as, e.g., to act as an antagonist or agonist. In some instances, a modulator can increase and/or decrease a certain concentration, level, activity or function relative to a control, or relative to the average level of activity that would generally be expected or relative to a control level of activity.

In some embodiments, the extracellular vesicle has a hydrodynamic radius between 20-5000 nm, such as between about 20-150 nm, 20-500 nm, 20-1000 nm, 20-2000, nm, 20-3000 nm, 20-4000 nm, 20-5000 nm, 30-150 nm, 30-500 nm, 30-1000 nm, 30-2000, nm, 30-3000 nm, 30-4000 nm, 30-5000 nm, 40-150 nm, 40-500 nm, 40-1000 nm, 40-2000, nm, 40-3000 nm, 40-4000 nm, 40-5000 nm, 70-2000, nm, 70-3000 nm, 70-4000 nm, 70-5000 nm, 50-150 nm, 50-500 nm, 50-1000 nm, 50-2000, nm, 50-3000 nm, 50-4000 nm, 50-5000 nm, 100-150 nm, 100-500 nm, 100-1000 nm, 100-2000, nm, 100-3000 nm, 100-4000 nm, 100-5000 nm, 500-1000 nm, 500-2000, nm, 500-3000 nm, 500-4000 nm, 500-5000 nm.

In other embodiments, the extracellular vesicle has a hydrodynamic radius between about 20-1000 nm, such as between about 20-100 nm, 20-200 nm, 20-300 nm, 20-400 nm, 20-500 nm, 20-600 nm, 20-700 nm, 20-800 nm, 20-900 nm, 30-100 nm, 30-200 nm, 30-300 nm, 30-400 nm, 30-500 nm, 30-600 nm, 30-700 nm, 30-800 nm, 30-900 nm, 40-100 nm, 40-200 nm, 40-300 nm, 40-400 nm, 40-500 nm, 40-600 nm, 40-700 nm, 40-800 nm, 40-900 nm, 50-150 nm, 50-500 nm, 50-750 nm, 100-200 nm, 100-500 nm, or 500-1000 nm.

In another embodiment, a population of the extracellular vesicles described herein comprise a population wherein 90% of the extracellular vesicles have a hydrodynamic radius 20-5000 nm. In another embodiment, a population of the extracellular vesicles described herein comprise a population wherein 95% of the extracellular vesicles have a hydrodynamic radius 20-5000 nm. In another embodiment, a population of the extracellular vesicles described herein comprise a population wherein 99% of the extracellular vesicles have a hydrodynamic radius 20-5000 nm. In another embodiment, a population of the extracellular vesicles described herein comprise a population wherein 90% of the extracellular vesicles have a hydrodynamic radius 20-1000 nm. In another embodiment, a population of the extracellular vesicles described herein comprise a population wherein 95% of the extracellular vesicles have a hydrodynamic radius 20-1000 nm. In another embodiment, a population of the extracellular vesicles described herein comprise a population wherein 99% of the extracellular vesicles have a hydrodynamic radius 20-1000 nm. In another embodiment, a population of the extracellular vesicles described herein comprise a population wherein 90% of the extracellular vesicles have a hydrodynamic radius 20-500 nm. In another embodiment, a population of the extracellular vesicles described herein comprise a population wherein 95% of the extracellular vesicles have a hydrodynamic radius 20-500 nm. In another embodiment, a population of the extracellular vesicles described herein comprise a population wherein 99% of the extracellular vesicles have a hydrodynamic radius 20-500 nm.

In certain embodiments, the extracellular vesicle is an exosome. In certain embodiments, the extracellular vesicle is a microvesicle.

In some embodiments, the exosome has a hydrodynamic radius between about 20-5000 nm, such as between about 20-150 nm, 20-500 nm, 20-1000 nm, 20-2000, nm, 20-3000 nm, 20-4000 nm, 20-5000 nm, 30-150 nm, 30-500 nm, 30-1000 nm, 30-2000, nm, 30-3000 nm, 30-4000 nm, 30-5000 nm, 40-150 nm, 40-500 nm, 40-1000 nm, 40-2000, nm, 40-3000 nm, 40-4000 nm, 40-5000 nm, 50-150 nm, 50-500 nm, 50-1000 nm, 50-2000, nm, 50-3000 nm, 50-4000 nm, 50-5000 nm, 70-2000, nm, 70-3000 nm, 70-4000 nm, 70-5000 nm, 100-150 nm, 100-500 nm, 100-1000 nm, 100-2000, nm, 100-3000 nm, 100-4000 nm, 100-5000 nm, 500-1000 nm, 500-2000, nm, 500-3000 nm, 500-4000 nm, 500-5000 nm.

In other embodiments, the exosome has a hydrodynamic radius between about 20-1000 nm, such as between about 20-100 nm, 20-200 nm, 20-300 nm, 20-400 nm, 20-500 nm, 20-600 nm, 20-700 nm, 20-800 nm, 20-900 nm, 30-100 nm, 30-200 nm, 30-300 nm, 30-400 nm, 30-500 nm, 30-600 nm, 30-700 nm, 30-800 nm, 30-900 nm, 40-100 nm, 40-200 nm, 40-300 nm, 40-400 nm, 40-500 nm, 40-600 nm, 40-700 nm, 40-800 nm, 40-900 nm, 50-150 nm, 50-500 nm, 50-750 nm, 100-200 nm, 100-500 nm, or 500-1000 nm.

In another embodiment, a population of the exosomes described herein comprise a population wherein 90% of the exosomes have a hydrodynamic radius 20-5000 nm. In another embodiment, a population of the exosomes described herein comprise a population wherein 95% of the exosomes have a hydrodynamic radius 20-5000 nm. In another embodiment, a population of the exosomes described herein comprise a population wherein 99% of the exosomes have a hydrodynamic radius 20-5000 nm. In another embodiment, a population of the exosomes described herein comprise a population wherein 90% of the exosomes have a hydrodynamic radius 20-1000 nm. In another embodiment, a population of the exosomes described herein comprise a population wherein 95% of the exosomes have a hydrodynamic radius 20-1000 nm. In another embodiment, a population of the exosomes described herein comprise a population wherein 99% of the exosomes have a hydrodynamic radius 20-1000 nm. In another embodiment, a population of the exosomes described herein comprise a population wherein 90% of the exosomes have a hydrodynamic radius 20-500 nm. In another embodiment, a population of the exosomes described herein comprise a population wherein 95% of the exosomes have a hydrodynamic radius 20-500 nm. In another embodiment, a population of the exosomes described herein comprise a population wherein 99% of the exosomes have a hydrodynamic radius 20-500 nm.

The present invention is directed to a method for producing synthetic extracellular vesicles comprising:

a) providing a water phase comprising at least two lipids, and one or more extracellular vesicle associated proteins, or fragments thereof, wherein the at least two lipids are a negative charged lipid, and a lipid coupled to a functional ligand for protein conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

wherein the amphiphilic copolymer forms a polymer shell stabilizing the synthetic extracellular vesicle,
wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, and
wherein the synthetic extracellular vesicles have a hydrodynamic radius between 70 nm and 5000 nm.

The present invention is further directed to a method for producing synthetic extracellular vesicles comprising:

a) providing a water phase comprising at least two lipids, one or more extracellular vesicle associated proteins, or fragments thereof, and one or more nucleic acid molecules, wherein the at least two lipids are a negative charged lipid, and a lipid coupled to a functional ligand for protein conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell,
wherein the vesicles are homogenous in size showing a coefficient of variation in size lower than 13%, and
wherein the synthetic extracellular vesicles have a hydrodynamic radius between 70 nm and 5000 nm.

In certain embodiments, the extracellular vesicle is an exosome. In certain embodiments, the extracellular vesicle is a microvesicle.

Therefore, a more particular embodiment of the invention is directed to a method for producing a synthetic exosome comprising:

a) providing a water phase comprising at least two lipids, and one or more extracellular vesicle associated proteins, or fragments thereof, wherein the at least two lipids are a negative charged lipid, and a lipid coupled to a functional ligand for protein conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

wherein the amphiphilic copolymer forms a polymer shell stabilizing the synthetic exosome,
wherein the one or two hydrophobic polymer blocks are arranged at the outer side and the hydrophilic polymer block is arranged at the inner side of the polymer shell,
wherein the synthetic exosomes are homogenous in size showing a coefficient of variation in size lower than 13%, and
wherein the synthetic exosome has a hydrodynamic radius between 70 nm and 5000 nm.

Another still more particular embodiment of the invention is also directed to a method for producing a synthetic exosome comprising:

a) providing a water phase comprising at least two lipids, one or more extracellular vesicle associated proteins, or fragments thereof, and one or more nucleic acid molecules, wherein the at least two lipids are a negative charged lipid, and a lipid coupled to a functional ligand for protein conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

wherein the amphiphilic copolymer forms a polymer shell stabilizing the synthetic exosome,
wherein the one or two hydrophobic polymer blocks are arranged at the outer side and the hydrophilic polymer block is arranged at the inner side of the polymer shell, wherein the synthetic exosomes are homogenous in size showing a coefficient of variation in size lower than 13%, and
wherein the synthetic exosome has a hydrodynamic radius between 70 nm and 700 nm.

Release and Purification Procedure

In accordance with optional step d'), the polymer shell is removed from the polymer shell-stabilized synthetic extracellular vesicles. Since the polymer shell is not necessary any more after assembling the vesicles with all the required components, it is actually preferred to perform the step d') so as to obtain the synthetic extracellular vesicles into an aqueous phase.

The inventors have found that the synthetic extracellular vesicles can be efficiently released from the polymer shell by adding a deemulsifier surfactant to the polymer shell stabilized synthetic extracellular vesicles formed after emulsification. The deemulsifier surfactant destabilizes the structure of the surrounding polymer shell and thus, allows releasing the synthetic extracellular vesicles from the polymer shell into an aqueous buffer, also named "release buffer".

The deemulsifier surfactant is preferably selected from the group comprising 1H, 1H,2H,2H-perfluoro-1-octanol; 1H, 1H-perfluoro-1-pentanol; 1H, 1H-perfluor-1-octanol; 1H, 1H, 8H-perfluoro-1-octanol.

The deemulsifier surfactant is preferentially added at a ratio ranging from 1:1 to 10:1 with the intraluminal buffer (also named production buffer).

Thereafter, the synthetic extracellular vesicles are usually centrifuged after release from the polymer shell to allow purification from vesicles of unwanted dimensions and other impurities.

The centrifugation can be performed for a time comprised between 5-60 min and at acceleration comprised between 800 g-100,000 g depending on the dimension of the synthetic extracellular vesicles of interest.

Moreover, for synthetic extracellular vesicles with hydrodynamic radius comprised between 100-1000 nm, the centrifugation is preferentially performed at acceleration comprised between 30,000-60,000 g and a time comprised between 10-60 min. For synthetic extracellular vesicles with hydrodynamic radius comprised between 1000-3000 nm, the centrifugation is preferentially performed at acceleration comprised between 10,000-30,000 g and a time comprised between 10-60 min. For synthetic extracellular vesicles with hydrodynamic radius comprised between 3000-5000 nm, the centrifugation is preferentially performed at acceleration comprised between 5,000-20,000 g and a time comprised between 10-60 min.

The synthetic extracellular vesicles synthetized following the inventive method, released into an aqueous medium and then purified by centrifugation (FIG. 1), contained considerably less contaminating aggregates and non-vesicular particles compared to exosomes isolated by standard prior art methods (FIG. 3), i.e. exosomes isolated by differential centrifugation from conditioned K562 erythroleukemia cell media or exosomes from the same cell line obtained from a commercial distributer.

Thus, present invention is directed to method for producing synthetic extracellular vesicles comprising:
  a) providing a water phase comprising at least two lipids, and one or more extracellular vesicle associated proteins, or fragments thereof, wherein the at least two lipids are a negative charged lipid, and a lipid coupled to a functional ligand for protein conjugation to an extracellular vesicle associated protein;
  b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;
  c) combining said water phase and said oil phase;

d) producing polymer shell-stabilized synthetic extracellular vesicles by emulsifying the combined phases of step c) using a mechanic or electronic emulsifier;
  d') removing the polymer shell from the polymer shell-stabilized synthetic extracellular vesicles obtained in step d) by adding a surfactant; and
  e) purifying the synthetic extracellular vesicles by centrifugation;
wherein the amphiphilic copolymer forms a polymer shell stabilizing the synthetic extracellular vesicle,
wherein the one or two hydrophobic polymer blocks are arranged at the outer side and the hydrophilic polymer block is arranged at the inner side of the polymer shell,
wherein the vesicles are homogenous in size showing a coefficient of variation in size lower than 13%, and wherein the synthetic extracellular vesicles have a hydrodynamic radius between 70 nm and 5000 nm.

A particular embodiment of the invention is directed to a method for producing synthetic extracellular vesicles comprising:
  a) providing a water phase comprising at least two lipids, one or more extracellular vesicle associated proteins, or fragments thereof, and one or more nucleic acid molecules, wherein the at least two lipids are a negative charged lipid, and a lipid coupled to a functional ligand for protein conjugation to an extracellular vesicle associated protein;
  b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;
  c) combining said water phase and said oil phase;
  d) producing polymer shell-stabilized synthetic extracellular vesicles by emulsifying the combined phases of step c) using a mechanic or electronic emulsifier;
  d') removing the polymer shell from the polymer shell-stabilized synthetic extracellular vesicles obtained in step d) by adding a surfactant; and
  e) purifying the synthetic extracellular vesicles by centrifugation;
wherein the amphiphilic copolymer forms a polymer shell stabilizing the synthetic extracellular vesicle,
wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, and
wherein the synthetic extracellular vesicles have a hydrodynamic radius between 70 nm and 1000 nm.

A more particular embodiment of the invention is directed to a method for producing synthetic extracellular vesicles comprising:
  a) providing a water phase comprising at least two lipids, and one or more extracellular vesicle associated proteins, or fragments thereof, wherein the at least two lipids are a negative charged lipid, and a lipid coupled to a functional ligand for protein conjugation to an extracellular vesicle associated protein;
  b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

d') removing the polymer shell from the polymer shell-stabilized synthetic extracellular vesicles obtained in step d) by adding a surfactant; and e) purifying the synthetic extracellular vesicles by centrifugation, wherein the centrifugation is performed at acceleration comprised between 30,000-60,000 g and a time comprised between 10-60 min;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, and wherein the synthetic extracellular vesicles have a hydrodynamic radius between 70 nm and 5000 nm.

A more particular embodiment of the invention is directed to a method for producing synthetic extracellular vesicles comprising:

a) providing a water phase comprising at least two lipids, one or more extracellular vesicle associated proteins, or fragments thereof, and one or more nucleic acid molecules, wherein the at least two lipids are a negative charged lipid, and a lipid coupled to a functional ligand for protein conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

d') removing the polymer shell from the polymer shell-stabilized synthetic extracellular vesicles obtained in step d) by adding a surfactant; and e) purifying the synthetic extracellular vesicles by centrifugation, wherein the centrifugation is performed at acceleration comprised between 30,000-60,000 g and a time comprised between 10-60 min;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, and wherein the synthetic extracellular vesicles have a hydrodynamic radius between 70 nm and 5000 nm.

A more particular embodiment of the invention is directed to a method for producing synthetic extracellular vesicles comprising:

a) providing a water phase comprising at least two lipids, one or more extracellular vesicle associated proteins, or fragments thereof, wherein the at least two lipids are a negative charged lipid, and a lipid coupled to a functional ligand for protein conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

d') removing the polymer shell from the polymer shell-stabilized synthetic extracellular vesicles obtained in step d) by adding a surfactant; and e) purifying the synthetic extracellular vesicles by centrifugation, wherein the centrifugation is performed at acceleration comprised between 800 g-100,000 g and a time comprised between 5-60 min;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, and wherein the synthetic extracellular vesicles have a hydrodynamic radius between 70 nm and 5000 nm.

A more particular embodiment of the invention is directed to a method for producing synthetic extracellular vesicles comprising:

a) providing a water phase comprising at least two lipids, one or more extracellular vesicle associated proteins, or fragments thereof, and one or more nucleic acid molecules, wherein the at least two lipids are a negative charged lipid, and a lipid coupled to a functional ligand for protein conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

d') removing the polymer shell from the polymer shell-stabilized synthetic extracellular vesicles obtained in step d) by adding a surfactant; and e) purifying the synthetic extracellular vesicles by centrifugation, wherein the centrifugation is performed at acceleration comprised between 800 g-100,000 g and a time comprised between 5-60 min;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, and wherein the synthetic extracellular vesicles have a hydrodynamic radius between 70 nm and 5000 nm.

Protein Associated to the Extracellular Vesicles, Functionalization Procedure

In the inventive methods, the synthetic extracellular vesicles can be decorated with the proteins of interest after release into an aqueous solution, as described above, wherein the proteins are preferably known to be associated with extracellular vesicles.

The proteins can be coupled to the synthetic extracellular vesicles by applying bio-orthogonal surface chemistry such as N-hydroxysuccinimide ester and/or NTA-poly-histidine tag coupling, or they can be added to the water phase of step a) or can be integrated into or on the polymer shell stabilized synthetic extracellular vesicles by microfluidic technology such as pico-injection.

These procedures allow obtaining synthetic extracellular vesicles comprising proteins at a well-defined ratio protein:lipid, and with very low degree of variation in protein composition between different batches.

Preferred protein:lipid ratios as used herein are between 1:20 to 1:100, 1:40 to 1:100, 1:50 to 1:100, 1:20 to 1:200, 1:40 to 1:200, 1:50 to 1:200, 1:75 to 1:200.

When assessing the exosome protein content, the inventor found that K562-derived exosomes isolated from conditioned media and those provided by a commercial distributer, differed greatly in their protein content, underscoring the degree of variation between different vesicle preparation methods (FIG. 4). Furthermore, when comparing between separately prepared batches of prior art exosomes, a substantial degree of variation in the protein composition could be observed. In contrast, the inventive synthetic exosomes equipped with purified recombinant human forms of exosome's surface markers CD9 and TSG101, attached by nitrilotriacetic acid (NTA)-poly histidine tag chemistry, appeared with a clearly defined band pattern and showed almost identical characteristics between separate preparations. Thus, the method disclosed herein allows obtaining synthetic exosomes that outperforms the exosomes obtained by prior art methods in terms of purity and reproducibility.

Important to mention, by applying bio-orthogonal surface chemistry such as N-hydroxysuccinimide ester and/or NTA-poly-histidine tag coupling, or by using microfluidic technologies, the protein to lipid ratio can be precisely adjusted. This ratio is also very homogenous among the vesicle population.

Thus, the inventive synthetic extracellular vesicles show an outstanding improvement in comparison to the non-adjustable extracellular vesicles obtained by prior art methods, such as differential centrifugation of cell culture medium, or membrane fragmentation of engineered cells.

The wording "extracellular vesicle associated protein" refers to proteins that are enriched in exosomes and extracellular vesicles in comparison to cells. Therefore "extracellular vesicle associated proteins" can also be used as marker of exosomes or other extracellular vesicles. Thus the term "extracellular vesicle associated proteins" has the same meaning as "extracellular vesicle protein marker" or "extracellular vesicle marker".

Therefore, in specific embodiments, the extracellular vesicles or exosomes comprise one or more proteins on their surface or in their lumen, wherein said proteins are selected from a group of proteins that was recently identified to be enriched on the surface or inside extracellular vesicles, and were thus defined as "extracellular vesicle associated proteins" (Thery et al., 2018, Minimal information for studies of extracellular vesicles 2018; Exocarta Top100 proteins). A list of extracellular vesicle associated proteins suitable for the method and the extracellular vesicles disclosed herein are listed in Table 4.

As used herein the term "fragment" or "active fragment" of a protein refers to a fragment of that protein that retains the ability to be specifically coupled to the extracellular vesicle or exosome. The term "fragment" or "active fragment" of a protein also refers to a fragment of that protein that retains the ability to exert its function in the target cell.

For example, in the case of membrane proteins, a protein fragment refers to a cytosolic domain, a transmembrane domain or an extracellular domain of said protein.

For example, in the case of enzymes, a protein fragment refers to a catalytic domain of that enzyme.

For example, in the case of antibodies, a protein fragment refers to a fragment of the antibody that retains its capacity to bind specifically to the antigen. The antibody or antigen-binding fragment can be derived from natural sources, or partly or wholly synthetically produced. In some embodiments, the antibody is a monoclonal antibody. In some of these embodiments, the monoclonal antibody is an IgG antibody. In certain embodiments, the monoclonal antibody is an $IgG_1$, $IgG_2$, $IgG_3$, or $IgG_4$. In some other embodiments, the antibody is a polyclonal antibody. In certain embodiments, the antibody fragment, also named antigen-binding fragment, is selected from antigen-binding fragment (Fab), Fab', and F(ab')2, F(ab)2, a viable fragment (Fv), and Fd fragments. In certain embodiments, the antigen-binding fragment is a Single-chain variable fragment (scFv) or (ScFv)2 fragment. In certain other embodiments, the antibody or antigen-binding fragment is a single-domain antibody. In some embodiments, the antibody or antigen binding fragment is a bispecific or multispecific antibody.

For example, in the case of protein antigens, a protein fragment refers to a fragment of the antigen that retains its capacity to induce an immune response in a human or animal, and/or to be specifically recognized by an antibody.

Preferably, a suitable protein fragment of TSG101 (protein ID Q99816) comprises the amino acids 1-145, a suitable protein fragment of CD9 (protein ID P21926) comprises the amino acids 112-195, a suitable protein fragment of CD81 (protein ID P35762), comprises the amino acids 113-201, a suitable protein fragment of CD63 (protein ID P08962) comprises the amino acids 103-203, a suitable protein fragment of RANK (protein ID O35305) comprises the amino acids 31-214, a suitable protein fragment of FasL (protein ID NM_000639.1) comprises the amino acids 134-281, a suitable protein fragment of ICAM-1 (protein ID P05362) comprises the amino acids 1-480.

As used herein the term protein or a fragment thereof also include "variant" of a protein or of a fragment thereof, and refers to a protein or fragment that shares a certain amino acid sequence identity with the reference protein or fragment upon alignment by a method known in the art. A variant of a protein or of a fragment thereof can include a substitution, insertion, deletion, frameshift or rearrangement in another protein. In some embodiments variants share at least 70%, 80%, 85%, 90%, 95% or 99% sequence identity with the reference protein or with the fragment thereof.

Recitation of any protein provided herein encompasses a functional variant of the protein. The term "functional variant" of a protein refers to a variant of the protein that retains the ability to be specifically targeted to exosomes.

The percentage of "sequence identity" is determined by comparing two optimally aligned protein or polypeptide sequences over a "comparison window" on the full length of the reference sequence. A "comparison window" as used herein, refers to the optimal alignment between the reference and variant sequence after that the two sequences are optimally aligned, wherein the variant nucleic acid or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment. Identity percentage is calculated by determining the number of positions at which the identical amino acid residues occurs in both sequences to yield the number of matched positions, dividing the number of matched positions by the total number of positions in the reference sequence (i.e., the full length in amino acid or nucleotide) and multiplying the results by 100 to yield the percentage of sequence identity. Two protein or polypeptide sequences are said to be "identical" if the sequence of nucleotides or amino acids in the two sequences is the same when optimally aligned as described above.

The percentage of "sequence identity" can be determined on the comparison window defined above with the help of blastp with the "BLAST 2 Sequences" tool available at the NCBI website. (Tatusova A. et al., FEMS Microbiol Lett. 1999, 174:247-250).

Alternatively, a variant sequence may also be any amino acid sequence resulting from allowed substitutions at any number of positions of the parent sequence according to the formula below:

Ser substituted by Ser, Thr, Gly, and Asn;

Arg substituted by one of Arg, His, Gin, Lys, and Glu;

Leu substituted by one of Leu, Ile, Phe, Tyr, Met, and Val;

Pro substituted by one of Pro, Gly, Ala, and Thr;

Thr substituted by one of Thr, Pro, Ser, Ala, Gly, His, and Gin;

Ala substituted by one of Ala, Gly, Thr, and Pro;

Val substituted by one of Val, Met, Tyr, Phe, Ile, and Leu;

Gly substituted by one of Gly, Ala, Thr, Pro, and Ser;

Ile substituted by one of Ile, Met, Tyr, Phe, Val, and Leu;

Phe substituted by one of Phe, Trp, Met, Tyr, lie, Val, and Leu;

Tyr substituted by one of Tyr, Trp, Met, Phe, Ile, Val, and Leu;

His substituted by one of His, Glu, Lys, Gin, Thr, and Arg;

Gin substituted by one of Gin, Glu, Lys, Asn, His, Thr, and Arg;

Asn substituted by one of Asn, Glu, Asp, Gin, and Ser;

Lys substituted by one of Lys, Glu, Gin, His, and Arg;

Asp substituted by one of Asp, Glu, and Asn;

Glu substituted by one of Glu, Asp, Lys, Asn, Gin, His, and Arg;

Met substituted by one of Met, Phe, Ile, Val, Leu, and Tyr.

According to the present invention, the extracellular vesicle associated protein is preferentially selected from the group comprising:

a transmembrane proteins selected from the group comprising tetraspanin proteins CD9, CD37, CD47, CD53, CD63, CD81, CD82, CD151, Tspan8, heterotrimeric G protein subunit alpha (GNA), integrin α-chains, integrin β-chains, transferrin receptor 1 (TfR1, CD71), transferrin receptor 2 (TFR2), lysosome associated membrane proteins (LAMP1, LAMP2), heparan sulfate proteoglycans, syndecans, extracellular matrix metalloproteinase inducer (EMMPRIN, BSG), A Disintegrin And Metalloproteinase Domain 10 (ADAM10), CD3, CD11c, CD14, CD29, CD31, CD41, CD42a, CD44, CD45, CD50 (intercellular adhesion molecule 1, ICAM-1), CD55, CD59, CD73, CD80, CD86, CD90, sonic hedgehog (SHH), major histocompatibility complex I (MHCI), major histocompatibility complex II (MHCII), epidermal growth factor receptor 2 (ERBB2), epithelial cell adhesion molecule (EpCAM), Glycophorin A (GYPA); Acetylcholinesterase S and E (AChE-S, AChE-E), amyloid beta precursor protein (APP), multidrug resistance-associated protein 1 (ABCC1), stem cells antigen-1 (Sca-1), or a fragment thereof;

a cytosolic protein selected from the group comprising the protein complexes endosomal sorting complexes required for transport ESCRT-I, ESCRT-II, and ESCRT-III, tumour susceptibility gene 101 (TSG101), charged multivesicular body protein (CHMP), Apoptosis-Linked Gene 2-Interacting Protein X (ALIX), vacuolar protein sorting 4 homolog A 4A and 4B, arrestin domain-containing protein (ARRDC1), flotillin-1, flotillin-2; caveolins, EH-domain containing 1-4 (EHD1-EHD4), Ras homolog family member A (RHOA), annexins, heat shock proteins, ADP-ribosylation factor 6 (ARF6), syntenin, microtubule-associated protein Tau (MAPT), or a fragment thereof;

a functional protein selected from the group comprising cytokines, growth factors, interleukins, milk fat globule-EGF factor 8 protein (MFGE8), adhesion proteins, extracellular matrix proteins, nicotinamide phosphoribosyltransferase, signal transduction proteins, Wnta, Wntb, Fas, Fas Ligand (FasL), RANK, RANK Ligand (RANKL), indolamin-2,3-dioxygenase, cytotoxic T-lymphocyte-associated protein 4-immunoglobulin fusion protein, tumor necrosis factor-related apoptosis-inducing ligand, or a fragment thereof; and a protein associated to intracellular compartments selected from the group comprising histone proteins, lam in NC, inner membrane mitochondrial protein (IMMT), cytochrome C-1 (CYC1), mitochondrial import receptor subunit TOM20, calnexin, heat shock protein 90 kDa beta (Grp94), member 1 (HSP90B1), heat shock 70 kDa protein 5 (HSPA5), Golgin A2 (GM130, GOLGA2), Autophagy Related 9A (ATG9A), actinin1, actinin4 (ACTN1, ACTN4), cytokeratin 18 (KRT18), or a fragment thereof.

Therefore, one embodiment of the present invention is directed to a method for producing synthetic extracellular vesicles comprising:

a) providing a water phase comprising at least two lipids, one or more extracellular vesicle associated proteins, or fragments thereof, and one or more nucleic acid molecules, wherein the at least two lipids are a negative charged lipid, and a lipid coupled to a functional ligand for conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell,

27

28 wherein the vesicles are homogenous in size showing a coefficient of variation in size lower than 13%, and wherein the synthetic extracellular vesicles have a hydrodynamic radius between 70 nm and 5000 nm, and wherein the extracellular vesicle associated protein, or a fragment thereof is selected from the group comprising:

a transmembrane proteins selected from the group comprising tetraspanin proteins CD9, CD37, CD47, CD53, CD63, CD81, CD82, CD151, Tspan8, heterotrimeric G protein subunit alpha (GNA), integrin α-chains, integrin β-chains, transferrin receptor 1 (TfR1, CD71), transferrin receptor 2 (TFR2), lysosome associated membrane proteins (LAMP1, LAMP2), heparan sulfate proteoglycans, syndecans, extracellular matrix metalloproteinase inducer (EMMPRIN, BSG), A Disintegrin And Metalloproteinase Domain 10 (ADAM10), CD3, CD11c, CD14, CD29, CD31, CD41, CD42a, CD44, CD45, CD50 (intercellular adhesion molecule 1, ICAM-1), CD55, CD59, CD73, CD80, CD86, CD90, sonic hedgehog (SHH), major histocompatibility complex I (MHCI), major histocompatibility complex II (MHCII), epidermal growth factor receptor 2 (ERBB2), epithelial cell adhesion molecule (EpCAM), Glycophorin A (GYPA); Acetylcholinesterase S and E (AChE-S, AChE-E), amyloid beta precursor protein (APP), multidrug resistance-associated protein 1 (ABCC1), stem cells antigen-1 (Sca-1), or a fragment thereof;

a cytosolic protein selected from the group comprising the protein complexes endosomal sorting complexes required for transport ESCRT-I, ESCRT-II, and ESCRT-III, tumour susceptibility gene 101 (TSG101), charged multivesicular body protein (CHMP), Apoptosis-Linked Gene 2-Interacting Protein X (ALIX), vacuolar protein sorting 4 homolog A 4A and 4B, arrestin domain-containing protein (ARRDC1), flotillin-1, flotillin-2; caveolins, EH-domain containing 1-4 (EHD1-EHD4), Ras homolog family member A (RHOA), annexins, heat shock proteins, ADP-ribosylation factor 6 (ARF6), syntenin, microtubule-associated protein Tau (MAPT), or a fragment thereof;

a functional protein selected from the group comprising cytokines, growth factors, interleukins, milk fat globule-EGF factor 8 protein (MFGE8), adhesion proteins, extracellular matrix proteins, nicotinamide phosphoribosyltransferase, signal transduction proteins, Wnta, Wntb, Fas, Fas Ligand (FasL), RANK, RANK Ligand (RANKL), indolamin-2,3-dioxygenase, cytotoxic T-lymphocyte-associated protein 4-immunoglobulin fusion protein, tumor necrosis factor-related apoptosis-inducing ligand, or a fragment thereof; and a protein associated to intracellular compartments selected from the group comprising histone proteins, lam in NC, inner membrane mitochondrial protein (IMMT), cytochrome C-1 (CYC1), mitochondrial import receptor subunit TOM20, calnexin, heat shock protein 90 kDa beta (Grp94), member 1 (HSP90B1), heat shock 70 kDa protein 5 (HSPA5), Golgin A2 (GM130, GOLGA2), Autophagy Related 9A (ATG9A), actinint actinin4 (ACTN1, ACTN4), cytokeratin 18 (KRT18), or a fragment thereof.

A further embodiment of the present invention is directed to a method for producing synthetic extracellular vesicles comprising:

a) providing a water phase comprising at least two lipids, and one or more extracellular vesicle associated proteins, or fragments thereof, wherein the at least two lipids are a negative charged lipid, and a lipid coupled to a functional ligand for conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, wherein the synthetic extracellular vesicles have a hydrodynamic radius between 70 nm and 5000 nm, and wherein the extracellular vesicle associated protein, or a fragment thereof is selected from the group comprising:

a transmembrane proteins selected from the group comprising tetraspanin proteins CD9, CD37, CD47, CD53, CD63, CD81, CD82, CD151, Tspan8, heterotrimeric G protein subunit alpha (GNA), integrin α-chains, integrin β-chains, transferrin receptor 1 (TfR1, CD71), transferrin receptor 2 (TFR2), lysosome associated membrane proteins (LAMP1, LAMP2), heparan sulfate proteoglycans, syndecans, extracellular matrix metalloproteinase inducer (EMMPRIN, BSG), A Disintegrin And Metalloproteinase Domain 10 (ADAM10), CD3, CD11c, CD14, CD29, CD31, CD41, CD42a, CD44, CD45, CD50 (intercellular adhesion molecule 1, ICAM-1), CD55, CD59, CD73, CD80, CD86, CD90, sonic hedgehog (SHH), major histocompatibility complex I (MHCI), major histocompatibility complex II (MHCII), epidermal growth factor receptor 2 (ERBB2), epithelial cell adhesion molecule (EpCAM), Glycophorin A (GYPA); Acetylcholinesterase S and E (AChE-S, AChE-E), amyloid beta precursor protein (APP), multidrug resistance-associated protein 1 (ABCC1), stem cells antigen-1 (Sca-1), or a fragment thereof;

a cytosolic protein selected from the group comprising the protein complexes endosomal sorting complexes required for transport ESCRT-I, ESCRT-II, and ESCRT-III, tumour susceptibility gene 101 (TSG101), charged multivesicular body protein (CHMP), Apoptosis-Linked Gene 2-Interacting Protein X (ALIX), vacuolar protein sorting 4 homolog A 4A and 4B, arrestin domain-containing protein (ARRDC1), flotillin-1, flotillin-2; caveolins, EH-domain containing 1-4 (EHD1-EHD4), Ras homolog family member A (RHOA), annexins, heat shock proteins, ADP-ribosylation factor 6 (ARF6), syntenin, microtubule-associated protein Tau (MAPT), or a fragment thereof;

a functional protein selected from the group comprising cytokines, growth factors, interleukins, milk fat globule-EGF factor 8 protein (MFGE8), adhesion proteins, extracellular matrix proteins, nicotinamide phosphoribosyltransferase, signal transduction proteins, Wnta, Wntb, Fas, Fas Ligand (FasL), RANK, RANK Ligand (RANKL), indolamin-2,3-dioxygenase, cytotoxic T-lymphocyte-associated protein 4-immunoglobulin fusion protein, tumor necrosis factor-related apoptosis-inducing ligand, or a fragment thereof; and a protein associated to intracellular compartments selected from the group comprising histone proteins, lam in NC, inner membrane mitochondrial protein (IMMT), cytochrome C-1 (CYC1), mitochondrial import receptor subunit TOM20, calnexin, heat shock protein 90 kDa beta (Grp94), member 1 (HSP90B1), heat shock 70 kDa protein 5 (HSPA5), Golgin A2 (GM130, GOLGA2), Autophagy Related 9A (ATG9A), actinin1, actinin4 (ACTN1, ACTN4), cytokeratin 18 (KRT18), or a fragment thereof.

Therefore, one embodiment of the present invention is directed to a method for producing synthetic extracellular vesicles comprising:

a) providing a water phase comprising at least two lipids, one or more extracellular vesicle associated proteins, or fragments thereof, and one or more nucleic acid molecules, wherein the at least two lipids are a negative charged lipid, and a lipid coupled to a functional ligand for conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

d') removing the polymer shell from the polymer shell-stabilized synthetic extracellular vesicles obtained in step d) by adding a surfactant; and e) purifying the synthetic extracellular vesicles by centrifugation;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, wherein the synthetic extracellular vesicles have a hydrodynamic radius between 70 nm and 5000 nm, and wherein the extracellular vesicle associated protein, or a fragment thereof is selected from the group comprising:

a transmembrane proteins selected from the group comprising tetraspanin proteins CD9, CD37, CD47, CD53, CD63, CD81, CD82, CD151, Tspan8, heterotrimeric G protein subunit alpha (GNA), integrin α-chains, integrin β-chains, transferrin receptor 1 (TfR1, CD71), transferrin receptor 2 (TFR2), lysosome associated membrane proteins (LAMP1, LAMP2), heparan sulfate proteoglycans, syndecans, extracellular matrix metalloproteinase inducer (EMMPRIN, BSG), A Disintegrin And Metalloproteinase Domain 10 (ADAM10), CD3, CD11c, CD14, CD29, CD31, CD41, CD42a, CD44, CD45, CD50 (intercellular adhesion molecule 1, ICAM-1), CD55, CD59, CD73, CD80, CD86, CD90, sonic hedgehog (SHH), major histocompatibility complex I (MHCI), major histocompatibility complex II (MHCII), epidermal growth factor receptor 2 (ERBB2), epithelial cell adhesion molecule (EpCAM), Glycophorin A (GYPA); Acetylcholinesterase S and E (AChE-S, AChE-E), amyloid beta precursor protein (APP), multidrug resistance-associated protein 1 (ABCC1), stem cells antigen-1 (Sca-1), or a fragment thereof;

a cytosolic protein selected from the group comprising the protein complexes endosomal sorting complexes required for transport ESCRT-I, ESCRT-II, and ESCRT-III, tumour susceptibility gene 101 (TSG101), charged multivesicular body protein (CHMP), Apoptosis-Linked Gene 2-Interacting Protein X (ALIX), vacuolar protein sorting 4 homolog A 4A and 4B, arrestin domain-containing protein (ARRDC1), flotillin-1, flotillin-2; caveolins, EH-domain containing 1-4 (EHD1-EHD4), Ras homolog family member A (RHOA), annexins, heat shock proteins, ADP-ribosylation factor 6 (ARF6), syntenin, microtubule-associated protein Tau (MAPT), or a fragment thereof;

a functional protein selected from the group comprising cytokines, growth factors, interleukins, milk fat globule-EGF factor 8 protein (MFGE8), adhesion proteins, extracellular matrix proteins, nicotinamide phosphoribosyltransferase, signal transduction proteins, Wnta, Wntb, Fas, Fas Ligand (FasL), RANK, RANK Ligand (RANKL), indolamin-2,3-dioxygenase, cytotoxic T-lymphocyte-associated protein 4-immunoglobulin fusion protein, tumor necrosis factor-related apoptosis-inducing ligand, or a fragment thereof; and a protein associated to intracellular compartments selected from the group comprising histone proteins, lam in NC, inner membrane mitochondrial protein (IMMT), cytochrome C-1 (CYC1), mitochondrial import receptor subunit TOM20, calnexin, heat shock protein 90 kDa beta (Grp94), member 1 (HSP90B1), heat shock 70 kDa protein 5 (HSPA5), Golgin A2 (GM130, GOLGA2), Autophagy Related 9A (ATG9A), actinin1, actinin4 (ACTN1, ACTN4), cytokeratin 18 (KRT18), or a fragment thereof.

A further embodiment of the present invention is directed to a method for producing synthetic extracellular vesicles comprising:

a) providing a water phase comprising at least two lipids, and one or more extracellular vesicle associated proteins, or fragments thereof, wherein the at least two lipids are a negative charged lipid, and a lipid coupled to a functional ligand for conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

d') removing the polymer shell from the polymer shell-stabilized synthetic extracellular vesicles obtained in step d) by adding a surfactant; and e) purifying the synthetic extracellular vesicles by centrifugation;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, wherein the synthetic extracellular vesicles have a hydrodynamic radius between 70 nm and 5000 nm, and wherein the extracellular vesicle associated protein, or a fragment thereof is selected from the group comprising:

a transmembrane proteins selected from the group comprising tetraspanin proteins CD9, CD37, CD47, CD53, CD63, CD81, CD82, CD151, Tspan8, heterotrimeric G protein subunit alpha (GNA), integrin α-chains, integrin β-chains, transferrin receptor 1 (TfR1, CD71), transferrin receptor 2 (TFR2), lysosome associated membrane proteins (LAMP1, LAMP2), heparan sulfate proteoglycans, syndecans, extracellular matrix metalloproteinase inducer (EMMPRIN, BSG), A Disintegrin And Metalloproteinase Domain 10 (ADAM10), CD3, CD11c, CD14, CD29, CD31, CD41, CD42a, CD44, CD45, CD50 (intercellular adhesion molecule 1, ICAM-1), CD55, CD59, CD73, CD80, CD86, CD90, sonic hedgehog (SHH), major histocompatibility complex I (MHCI), major histocompatibility complex II (MHCII), epidermal growth factor receptor 2 (ERBB2), epithelial cell adhesion molecule (EpCAM), Glycophorin A (GYPA); Acetylcholinesterase S and E (AChE-S, AChE-E), amyloid beta precursor protein (APP), multidrug resistance-associated protein 1 (ABCC1), stem cells antigen-1 (Sca-1), or a fragment thereof;

a cytosolic protein selected from the group comprising the protein complexes endosomal sorting complexes required for transport ESCRT-I, ESCRT-II, and ESCRT-III, tumour susceptibility gene 101 (TSG101), charged multivesicular body protein (CHMP), Apoptosis-Linked Gene 2-Interacting Protein X (ALIX), vacuolar protein sorting 4 homolog A 4A and 4B, arrestin domain-containing protein (ARRDC1), flotillin-1, flotillin-2; caveolins, EH-domain containing 1-4 (EHD1-EHD4), Ras homolog family member A (RHOA), annexins, heat shock proteins, ADP-ribosylation factor 6 (ARF6), syntenin, microtubule-associated protein Tau (MAPT), or a fragment thereof;

a functional protein selected from the group comprising cytokines, growth factors, interleukins, milk fat globule-EGF factor 8 protein (MFGE8), adhesion proteins, extracellular matrix proteins, nicotinamide phosphoribosyltransferase, signal transduction proteins, Wnta, Wntb, Fas, Fas Ligand (FasL), RANK, RANK Ligand (RANKL), indolamin-2,3-dioxygenase, cytotoxic T-lymphocyte-associated protein 4-immunoglobulin fusion protein, tumor necrosis factor-related apoptosis-inducing ligand, or a fragment thereof; and a protein associated to intracellular compartments selected from the group comprising histone proteins, lamin NC, inner membrane mitochondrial protein (IMMT), cytochrome C-1 (CYC1), mitochondrial import receptor subunit TOM20, calnexin, heat shock protein 90 kDa beta (Grp94), member 1 (HSP90B1), heat shock 70 kDa protein 5 (HSPA5), Golgin A2 (GM130, GOLGA2), Autophagy Related 9A (ATG9A), actinin1, actinin4 (ACTN1, ACTN4), cytokeratin 18 (KRT18), or a fragment thereof.

Further extracellular vesicle associated proteins suitable for the method and the synthetic extracellular vesicles disclosed herein are listed in Table 4.

For bio-orthogonal surface chemistry, suitable functional ligands are selected from the group comprising biotin, N-hydroxysuccinimide ester, N-hydroxysulfosuccinimide, nitrilotriacetic acid-nickel, amine, carboxylic acid, maleimide, aromatic maleimid, dithiopyridinyl, pyridyl disulfide, pyridyldithiopropionate, N-benzylguanine, cyanuric chloride, carboxyacyl, cyanur, folate, square, galloyl, glycan, thiol, arginylglycylaspartic acid, a fluorescent dye molecule, a magnetic resonance imaging reagent, a chelator.

Table 2 lists the possible functional ligands that can be attached to the lipids, their function and the interacting moieties.

These functional ligands react with particular moieties at high affinity, as for example the ligand biotin reacts with the moiety streptavidin or avidin. Thus, proteins and other macromolecules of interest can be coupled to the surface of the released extracellular vesicles by using the interaction at high affinity between a functional ligand and the respective reacting moiety.

Thus, a particular embodiment of the invention is directed to a method for producing synthetic extracellular vesicles comprising:

a) providing a water phase comprising at least two lipids, and one or more extracellular vesicle associated proteins, or fragments thereof, wherein the at least two lipids are a negative charged lipid, and a lipid coupled to a functional ligand for conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

d') removing the polymer shell from the polymer shell-stabilized synthetic extracellular vesicles obtained in step d) by adding a surfactant; and e) purifying the synthetic extracellular vesicles by centrifugation;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, wherein the synthetic extracellular vesicles have a hydrodynamic radius between 70 nm and 5000 nm, and wherein the water phase of step a) comprises at least one lipid coupled to a functional ligand selected from biotin, N-hydroxysuccinimide ester, N-hydroxysulfosuccinimide, nitrilotriacetic acid-nickel, amine, carboxylic acid, maleimide, aromatic maleimid, dithiopyridinyl, pyridyl disulfide, pyridyldithiopropionate, N-benzylguanine, cyanuric chloride, carboxyacyl, cyanur, folate, square, galloyl, glycan, thiol, arginylglycylaspartic acid, a fluorescent dye molecule, a magnetic resonance imaging reagent, a chelator; and wherein the method optionally comprises after step e) the following step:

f) coupling the synthetic extracellular vesicles with at least one macromolecule comprising at least one moiety reacting with one of said functional ligands, wherein the macromolecule is selected from the group comprising an extracellular vesicle associated protein, or a fragment thereof, a carbohydrate, a nucleic acid, a polypeptide, a cell receptor, an imaging probe.

A more particular embodiment of the invention is directed to a method for producing synthetic extracellular vesicles comprising:

a) providing a water phase comprising at least two lipids, one or more extracellular vesicle associated proteins, or fragments thereof, and one or more nucleic acid molecules, wherein the at least two lipids are a negative charged lipid, and a lipid coupled to a functional ligand for conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

d') removing the polymer shell from the polymer shell-stabilized synthetic extracellular vesicles obtained in step d) by adding a surfactant; and e) purifying the synthetic extracellular vesicles by centrifugation;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, wherein the synthetic extracellular vesicles have a hydrodynamic radius between 70 nm and 5000 nm, wherein the water phase of step a) comprises at least one lipid coupled to a functional ligand selected from biotin, N-hydroxysuccinimide ester, N-hydroxysulfosuccinimide, nitrilotriacetic acid-nickel, amine, carboxylic acid, maleimide, aromatic maleimid, dithiopyridinyl, pyridyl disulfide, pyridyldithiopropionate, N-benzylguanine, cyanuric chloride, carboxyacyl, cyanur, folate, square, galloyl, glycan, thiol, arginylglycylaspartic acid, a fluorescent dye molecule, a magnetic resonance imaging reagent, a chelator; and wherein the method optionally comprises after step e) the following step:

f) coupling the synthetic extracellular vesicles with at least one macromolecule comprising at least one moiety reacting with one of said functional ligands, wherein the macromolecule is selected from the group comprising an extracellular vesicle associated protein, or a fragment thereof, a carbohydrate, a nucleic acid, a polypeptide, a cell receptor, an imaging probe.

Thus, a particular embodiment of the invention is directed to a method for producing synthetic extracellular vesicles comprising:

a) providing a water phase comprising at least two lipids, and one or more extracellular vesicle associated proteins, or fragments thereof, wherein the at least two lipids are a negative charged lipid, and a lipid coupled to a functional ligand for conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

d') removing the polymer shell from the polymer shell-stabilized synthetic extracellular vesicles obtained in step d) by adding a surfactant; and e) purifying the synthetic extracellular vesicles by centrifugation;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, wherein the synthetic extracellular vesicles have a hydrodynamic radius between 70 nm and 5000 nm, wherein the water phase of step a) comprises at least one lipid coupled to a functional ligand selected from biotin, N-hydroxysuccinimide ester, N-hydroxysulfosuccinimide, nitrilotriacetic acid-nickel, amine, carboxylic acid, maleimide, aromatic maleimid, dithiopyridinyl, pyridyl disulfide, pyridyldithiopropionate, N-benzylguanine, cyanuric chloride, carboxyacyl, cyanur, folate, square, galloyl, glycan, thiol, arginylglycylaspartic acid, a fluorescent dye molecule, a magnetic resonance imaging reagent, a chelator;

wherein the method optionally comprises after step e) the following step:

f) coupling the synthetic extracellular vesicles with at least one macromolecule comprising at least one moiety reacting with one of said functional ligands, wherein the macromolecule is selected from the group comprising an extracellular vesicle associated protein, or a fragment thereof, a carbohydrate, a nucleic acid, a polypeptide, a cell receptor, an imaging probe; and wherein the extracellular vesicle associated protein, or a fragment thereof is selected from the group comprising:

a transmembrane proteins selected from the group comprising tetraspanin proteins CD9, CD37, CD47, CD53, CD63, CD81, CD82, CD151, Tspan8, heterotrimeric G protein subunit alpha (GNA), integrin α-chains, integrin β-chains, transferrin receptor 1 (TfR1, CD71), transferrin receptor 2 (TFR2), lysosome associated membrane proteins (LAMP1, LAMP2), heparan sulfate proteoglycans, syndecans, extracellular matrix metalloproteinase inducer (EMMPRIN, BSG), A Disintegrin And Metalloproteinase Domain 10 (ADAM10), CD3, CD11c, CD14, CD29, CD31, CD41, CD42a, CD44, CD45, CD50 (intercellular adhesion molecule 1, ICAM-1), CD55, CD59, CD73, CD80, CD86, CD90, sonic hedgehog (SHH), major histocompatibility complex I (MHCI), major histocompatibility complex II (MHCII), epidermal growth factor receptor 2 (ERBB2), epithelial cell adhesion molecule (EpCAM), Glycophorin A (GYPA); Acetylcholinesterase S and E (AChE-S, AChE-E), amyloid beta precursor protein (APP), multidrug resistance-associated protein 1 (ABCC1), stem cells antigen-1 (Sca-1), or a fragment thereof;

a cytosolic protein selected from the group comprising the protein complexes endosomal sorting complexes required for transport ESCRT-I, ESCRT-II, and ESCRT-III, tumour susceptibility gene 101 (TSG101), charged multivesicular body protein (CHMP), Apoptosis-Linked Gene 2-Interacting Protein X (ALIX), vacuolar protein sorting 4 homolog A 4A and 4B, arrestin domain-containing protein (ARRDC1), flotillin-1, flotillin-2; caveolins, EH-domain containing 1-4 (EHD1-EHD4), Ras homolog family member A (RHOA), annexins, heat shock proteins, ADP-ribosylation factor 6 (ARF6), syntenin, microtubule-associated protein Tau (MAPT), or a fragment thereof;

a functional protein selected from the group comprising cytokines, growth factors, interleukins, milk fat globule-EGF factor 8 protein (MFGE8), adhesion proteins, extracellular matrix proteins, nicotinamide phosphoribosyltransferase, signal transduction proteins, Wnta, Wntb, Fas, Fas Ligand (FasL), RANK, RANK Ligand (RANKL), indolamin-2,3-dioxygenase, cytotoxic T-lymphocyte-associated protein 4-immunoglobulin fusion protein, tumor necrosis factor-related apoptosis-inducing ligand, or a fragment thereof; and a protein associated to intracellular compartments selected from the group comprising histone proteins, lamin NC, inner membrane mitochondrial protein (IMMT), cytochrome C-1 (CYC1), mitochondrial import receptor subunit TOM20, calnexin, heat shock protein 90 kDa beta (Grp94), member 1 (HSP90B1), heat shock 70 kDa protein 5 (HSPA5), Golgin A2 (GM130, GOLGA2), Autophagy Related 9A (ATG9A), actinin1, actinin4 (ACTN1, ACTN4), cytokeratin 18 (KRT18), or a fragment thereof.

A more particular embodiment of the invention is directed to a method for producing synthetic extracellular vesicles comprising:

a) providing a water phase comprising at least two lipids, one or more extracellular vesicle associated proteins, or fragments thereof, and one or more nucleic acid molecules, wherein the at least two lipids are a negative charged lipid, and a lipid coupled to a functional ligand for conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

d') removing the polymer shell from the polymer shell-stabilized synthetic extracellular vesicles obtained in step d) by adding a surfactant; and e) purifying the synthetic extracellular vesicles by centrifugation;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, wherein the synthetic extracellular vesicles have a hydrodynamic radius between 70 nm and 5000 nm, wherein the water phase of step a) comprises at least one lipid coupled to a functional ligand selected from biotin, N-hydroxysuccinimide ester, N-hydroxysulfosuccinimide, nitrilotriacetic acid-nickel, amine, carboxylic acid, maleimide, aromatic maleimid, dithiopyridinyl, pyridyl disulfide, pyridyldithiopropionate, N-benzylguanine, cyanuric chloride, carboxyacyl, cyanur, folate, square, galloyl, glycan, thiol, arginylglycylaspartic acid, a fluorescent dye molecule, a magnetic resonance imaging reagent, a chelator;

wherein the method optionally comprises after step e) the following step:

f) coupling the synthetic extracellular vesicles with at least one macromolecule comprising at least one moiety reacting with one of said functional ligands, wherein the macromolecule is selected from the group comprising an extracellular vesicle associated protein, or a fragment thereof, a carbohydrate, a nucleic acid, a polypeptide, a cell receptor, an imaging probe; and wherein the extracellular vesicle associated protein, or a fragment thereof is selected from the group comprising:

a transmembrane proteins selected from the group comprising tetraspanin proteins CD9, CD37, CD47, CD53, CD63, CD81, CD82, CD151, Tspan8, heterotrimeric G protein subunit alpha (GNA), integrin α-chains, integrin β-chains, transferrin receptor 1 (TfR1, CD71), transferrin receptor 2 (TFR2), lysosome associated membrane proteins (LAMP1, LAMP2), heparan sulfate proteoglycans, syndecans, extracellular matrix metalloproteinase inducer (EMMPRIN, BSG), A Disintegrin And Metalloproteinase Domain 10 (ADAM10), CD3, CD11c, CD14, CD29, CD31, CD41, CD42a, CD44, CD45, CD50 (intercellular adhesion molecule 1, ICAM-1), CD55, CD59, CD73, CD80, CD86, CD90, sonic hedgehog (SHH), major histocompatibility complex I (MHCI), major histocompatibility complex II (MHCII), epidermal growth factor receptor 2 (ERBB2), epithelial cell adhesion molecule (EpCAM), Glycophorin A (GYPA); Acetylcholinesterase S and E (AChE-S, AChE-E), amyloid beta precursor protein (APP), multidrug resistance-associated protein 1 (ABCC1), stem cells antigen-1 (Sca-1), or a fragment thereof;

a cytosolic protein selected from the group comprising the protein complexes endosomal sorting complexes required for transport ESCRT-I, ESCRT-II, and ESCRT-III, tumour susceptibility gene 101 (TSG101), charged multivesicular body protein (CHMP), Apoptosis-Linked Gene 2-Interacting Protein X (ALIX), vacuolar protein sorting 4 homolog A 4A and 4B, arrestin domain-containing protein (ARRDC1), flotillin-1, flotillin-2; caveolins, EH-domain containing 1-4 (EHD1-EHD4), Ras homolog family member A (RHOA), annexins, heat shock proteins, ADP-ribosylation factor 6 (ARF6), syntenin, microtubule-associated protein Tau (MAPT), or a fragment thereof;

a functional protein selected from the group comprising cytokines, growth factors, interleukins, milk fat globule-EGF factor 8 protein (MFGE8), adhesion proteins, extracellular matrix proteins, nicotinamide phosphoribosyltransferase, signal transduction proteins, Wnta, Wntb, Fas, Fas Ligand (FasL), RANK, RANK Ligand (RANKL), indolamin-2,3-dioxygenase, cytotoxic T-lymphocyte-associated protein 4-immunoglobulin fusion protein, tumor necrosis factor-related apoptosis-inducing ligand, or a fragment thereof; and a protein associated to intracellular compartments selected from the group comprising histone proteins, lamin A/C, inner membrane mitochondrial protein (IMMT), cytochrome C-1 (CYC1), mitochondrial import receptor subunit TOM20, calnexin, heat shock protein 90 kDa beta (Grp94), member 1 (HSP90B1), heat shock 70 kDa protein 5 (HSPA5), Golgin A2 (GM130, GOLGA2), Autophagy Related 9A (ATG9A), actinin1, actinin4 (ACTN1, ACTN4), cytokeratin 18 (KRT18), or a fragment thereof.

Nucleic Acid Molecules and miRNA

The phrase "nucleic acid molecule" refers to a single or double-stranded polymer of deoxyribonucleotide or ribonucleotide bases. It includes chromosomal DNA and self-replicating plasmids, vectors, DNA, cDNA, mRNA, siRNA, antisense nucleotide sequence, shRNA, piRNA, snRNA, lncRNA, PNA, left handed DNA, Clustered Regularly Interspaced Short Palindromic Repeats (CRISPR) guide RNA.

Abbreviations used in this application include the following: "mRNA" refers to messenger RNA, "miRNA" refers to microRNA, "siRNA" refers to small interfering RNA, "antisense nucleotide sequence" refers to a single stranded sequence that is complementary to a nucleotide sequence of interest, "shRNA" refers to small or short hairpin RNA, "lncRNA" refers to long non-coding RNA, and "dsDNA" refers to double stranded DNA.

As used herein, the term "microRNAs" or "miRNAs" refers to post-transcriptional regulators that typically bind to complementary sequences in the three prime untranslated regions (3' UTRs) of target messenger RNA transcripts (mRNAs), usually resulting in gene silencing. Typically, miRNAs are short, non-coding ribonucleic acid (RNA) molecules, for example, 21 or 22 nucleotides long. The terms "microRNA" and "miRNA" are used interchangeably.

The content of miRNA molecules is preferably comprised between 75 pg/$10^{12}$ vesicles-1000 pg/$10^{12}$ vesicles, between 75 pg/$10^{12}$ vesicles-5000 pg/$10^{12}$ vesicles, 75 pg/$10^{12}$ vesicles-10,000 pg/$10^{12}$ vesicles, between 75 pg/$10^{12}$ vesicles-20,000 pg/$10^{12}$ vesicle, between 75 pg/$10^{12}$ vesicles-50,000 pg/$10^{12}$ vesicles, between 75 pg/$10^{12}$ vesicles-100,000 pg/$10^{12}$ vesicles, between 75 pg/$10^{12}$ vesicles-150,000 pg/$10^{12}$ vesicles, between 75 pg/$10^{12}$ vesicles-200,000 pg/$10^{12}$ vesicles, between 75 pg/$10^{12}$ vesicles-300,000 pg/$10^{12}$ vesicles, between 500 pg/$10^{12}$ vesicles-1000 pg/$10^{12}$ vesicles, between 500 pg/$10^{12}$ vesicles-5000 pg/$10^{12}$ vesicles, 500 pg/$10^{12}$ vesicles-10,000 pg/$10^{12}$ vesicles, between 500 pg/$10^{12}$ vesicles-20,000 pg/$10^{12}$ vesicle, 500 pg/$10^{12}$ vesicles-50,000 pg/$10^{12}$ vesicles, between 500 pg/$10^{12}$ vesicles-100,000 pg/$10^{12}$ vesicles, between 500 pg/$10^{12}$ vesicles-150,000 pg/$10^{12}$ vesicles, between 500 pg/$10^{12}$ vesicles-200,000 pg/$10^{12}$ vesicles, between 500 pg/$10^{12}$ vesicles-300,000 pg/$10^{12}$ vesicles, between 5000 pg/$10^{12}$ vesicles-10,000 pg/$10^{12}$ vesicles, between 5000 pg/$10^{12}$ vesicles-20,000 pg/$10^{12}$ vesicle, 5000 pg/$10^{12}$ vesicles-50,000 pg/$10^{12}$ vesicles, between 5000 pg/$10^{12}$ vesicles-100,000 pg/$10^{12}$ vesicles, between 5000 pg/$10^{12}$ vesicles-150,000 pg/$10^{12}$ vesicles, between 5000 pg/$10^{12}$ vesicles-200,000 pg/$10^{12}$ vesicles, between 5000 pg/$10^{12}$ vesicles-300,000 pg/$10^{12}$ vesicles.

In one aspect, the therapeutic agent is a short interfering RNA, also known as siRNA. Methods to prepare and screen interfering RNA and select for the ability to block polynucleotide expression are known in the art and non-limiting examples of which are shown below. These interfering RNA are provided by this invention alone or in combination with a suitable vector or within a host cell. Compositions containing the RNAi are further provided. RNAi is useful to knock-out or knock-down select functions in a cell or tissue as known in the art.

siRNA sequences can be designed by obtaining the target mRNA sequence and determining an appropriate siRNA complementary sequence. siRNAs of the invention are designed to interact with a target sequence, meaning they complement a target sequence sufficiently to hybridize to that sequence. An siRNA can be 100% identical to the target sequence. However, homology of the siRNA sequence to the target sequence can be less than 100% as long as the siRNA can hybridize to the target sequence. Thus, for example, the siRNA molecule can be at least 70%, 75%, 80%, 85%, 90%, 95%, 96%, 97%, 98%, 99% or 100% identical to the target sequence or the complement of the target sequence. Therefore, siRNA molecules with insertions, deletions or single point mutations relative to a target may also be used. The generation of several different siRNA sequences per target mRNA is recommended to allow screening for the optimal target sequence. A homology search, such as a BLAST search, should be performed to ensure that the siRNA sequence does not contain homology to any known mammalian gene.

As a general guide, siRNAs that include one or more of the following conditions are particularly useful in gene silencing in mammalian cells:GC ratio of between 45-55%, no runs of more than 9 G/C residues, G/C at the 5' end of the sense strand; NU at the 5' end of the antisense strand; and at least 5 NU residues in the first 7 bases of the 5' terminal of the antisense strand.

siRNA are, in general, from about 10 to about 30 nucleotides in length. For example, the siRNA can be 10-30 nucleotides long, 12-28 nucleotides long, 15-25 nucleotides long, 19-23 nucleotides long, or 21-23 nucleotides long. When an siRNA contains two strands of different lengths, the longer of the strands designates the length of the siRNA. In this situation, the unpaired nucleotides of the longer strand would form an overhang.

The term siRNA includes short hairpin RNAs (shRNAs). shRNAs comprise a single strand of RNA that forms a stem-loop structure, where the stem consists of the complementary sense and antisense strands that comprise a double-stranded siRNA, and the loop is a linker of varying size. The stem structure of shRNAs generally is from about 10 to about 30 nucleotides long. For example, the stem can be 10-30 nucleotides long, 12-28 nucleotides long, 15-25 nucleotides long, 19-23 nucleotides long, or 21-23 nucleotides long.

Tools to assist siRNA design are readily available to the public. For example, a computer-based siRNA design tool is available on the internet at www.dharmacon.com.

In some embodiments, the extracellular vesicle or exosome delivers their nucleic acid or intracellular protein or functional protein to a cell target. The delivery can occur in vitro or in a subject.

Preferentially, the extracellular vesicles disclosed herein include miRNA molecules selected from the group comprising miR-17, miR-18a, miR-19a, miR-19b-1, miR-20a, miR-92a; miR-21, miR-30d-5p, miR-33b, miR-124, miR-125, miR-126, miR-130, miR-132, miR-133b, miR-140-5p, miR-191, miR-222, miR-451, miR-494, miR-575, miR-630, miR-638, miR-1202, miR-1207-5p, miR-1225-5p, miR-1268, miR-6087, miR-92a-3p-e, miR-K12-3, let-7a.

Furthermore, the extracellular vesicles disclosed herein can include one or more miRNA molecules as listed in Table 3.

Thus, one embodiment of the present invention is directed to a method for producing synthetic extracellular vesicles comprising:

a) providing a water phase comprising at least two lipids, one or more extracellular vesicle associated proteins, or fragments thereof, and one or more nucleic acid molecules, wherein the at least two lipids are a negative charged lipid, and a lipid coupled to a functional ligand for conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, wherein the synthetic extracellular vesicles have a hydrodynamic radius between 70 nm and 5000 nm, and wherein the water phase of step a) comprises one or more nucleic acid molecules selected from the group comprising miRNA molecules miR-17, miR-18a, miR-19a, miR-19b-1, miR-20a, miR-92a; miR-21, miR-30d-5p, miR-33b, miR-124, miR-125, miR-126, miR-130, miR-132, miR-133b, miR-140-5p, miR-191, miR-222, miR-451, miR-494, miR-575, miR-630, miR-638, miR-1202, miR-1207-5p, miR-1225-5p, miR-1268, miR-6087, miR-92a-3p-e, miR-K12-3, let-7a.

Another embodiment of the present invention is directed to a method for producing synthetic extracellular vesicles comprising:

a) providing a water phase comprising at least two lipids, one or more extracellular vesicle associated proteins, or fragments thereof, and one or more nucleic acid molecules, wherein the at least two lipids are a negative charged lipid, and a lipid coupled to a functional ligand for conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, wherein the synthetic extracellular vesicles have a hydrodynamic radius between 70 nm and 5000 nm, and wherein the water phase of step a) comprises one or more nucleic acid molecules selected from the group comprising chromosomal DNA and self-replicating plasmids, vectors, DNA, cDNA, mRNA, siRNA, antisense nucleotide sequence, shRNA, piRNA, snRNA, lncRNA, PNA, left handed DNA, Clustered Regularly Interspaced Short Palindromic Repeats (CRISPR) guide RNA.

A further embodiment of the present invention is directed to a method for producing synthetic extracellular vesicles comprising:

a) providing a water phase comprising at least two lipids, one or more extracellular vesicle associated proteins, or fragments thereof, and one or more nucleic acid molecules, wherein the at least two lipids are a negative charged lipid, and a lipid coupled to a functional ligand for conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, wherein the synthetic extracellular vesicles have a hydrodynamic radius between 70 nm and 5000 nm, wherein the water phase of step a) comprises one or more nucleic acid molecules selected from the group comprising miRNA molecules miR-17, miR-18a, miR-19a, miR-19b-1, miR-20a, miR-92a, miR-21, miR-30d-5p, miR-33b, miR-124, miR-125, miR-126, miR-130, miR-132, miR-133b, miR-140-5p, miR-191, miR-222, miR-451, miR-494, miR-575, miR-630, miR-638, miR-1202, miR-1207-5p, miR-1225-5p, miR-1268, miR-6087, miR-92a-3p-e, miR-K12-3, let-7a; and wherein the extracellular vesicle associated protein, or a fragment thereof is selected from the group comprising:

a transmembrane proteins selected from the group comprising tetraspanin proteins CD9, CD37, CD47, CD53, CD63, CD81, CD82, CD151, Tspan8, heterotrimeric G protein subunit alpha (GNA), integrin α-chains, integrin β-chains, transferrin receptor 1 (TfR1, CD71), transferrin receptor 2 (TFR2), lysosome associated membrane proteins (LAMP1, LAMP2), heparan sulfate proteoglycans, syndecans, extracellular matrix metalloproteinase inducer (EMMPRIN, BSG), A Disintegrin And Metalloproteinase Domain 10 (ADAM10), CD3, CD11c, CD14, CD29, CD31, CD41, CD42a, CD44, CD45, CD50 (intercellular adhesion molecule 1, ICAM-1), CD55, CD59, CD73, CD80, CD86, CD90, sonic hedgehog (SHH), major histocompatibility complex I (MHCI), major histocompatibility complex II (MHCII), epidermal growth factor receptor 2 (ERBB2), epithelial cell adhesion molecule (EpCAM), Glycophorin A (GYPA); Acetylcholinesterase S and E (AChE-S, AChE-E), amyloid beta precursor protein (APP), multidrug resistance-associated protein 1 (ABCC1), stem cells antigen-1 (Sca-1), or a fragment thereof;

a cytosolic protein selected from the group comprising the protein complexes endosomal sorting complexes required for transport ESCRT-I, ESCRT-II, and ESCRT-III, tumour susceptibility gene 101 (TSG101), charged multivesicular body protein (CHMP), Apoptosis-Linked Gene 2-Interacting Protein X (ALIX), vacuolar protein sorting 4 homolog A 4A and 4B, arrestin domain-containing protein (ARRDC1), flotillin-1, flotillin-2; caveolins, EH-domain containing 1-4 (EHD1-EHD4), Ras homolog family member A (RHOA), annexins, heat shock proteins, ADP-ribosylation factor 6 (ARF6), syntenin, microtubule-associated protein Tau (MAPT), or a fragment thereof;

a functional protein selected from the group comprising cytokines, growth factors, interleukins, milk fat globule-EGF factor 8 protein (MFGE8), adhesion proteins, extracellular matrix proteins, nicotinamide phosphoribosyltransferase, signal transduction proteins, Wnta, Wntb, Fas, Fas Ligand (FasL), RANK, RANK Ligand (RANKL), indolamin-2,3-dioxygenase, cytotoxic T-lymphocyte-associated protein 4-immunoglobulin fusion protein, tumor necrosis factor-related apoptosis-inducing ligand, or a fragment thereof; and a protein associated to intracellular compartments selected from the group comprising histone proteins, lamin A/C, inner membrane mitochondrial protein (IMMT), cytochrome C-1 (CYC1), mitochondrial import receptor subunit TOM20, calnexin, heat shock protein 90 kDa beta (Grp94), member 1 (HSP90B1), heat shock 70 kDa protein 5 (HSPA5), Golgin A2 (GM130, GOLGA2), Autophagy Related 9A (ATG9A), actinin1, actinin4 (ACTN1, ACTN4), cytokeratin 18 (KRT18), or a fragment thereof.

A more particular embodiment of the invention is directed to a method for producing synthetic extracellular vesicles comprising:

a) providing a water phase comprising at least two lipids, one or more extracellular vesicle associated proteins, or fragments thereof, and one or more nucleic acid molecules, wherein the at least two lipids are a negative charged lipid, and a lipid coupled to a functional ligand for conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

d') removing the polymer shell from the polymer shell-stabilized synthetic extracellular vesicles obtained in step d) by adding a surfactant; and e) purifying the synthetic extracellular vesicles by centrifugation;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, wherein the synthetic extracellular vesicles have a hydrodynamic radius between 70 nm and 5000 nm, wherein the water phase of step a) comprises at least one lipid coupled to a functional ligand selected from biotin, N-hydroxysuccinimide ester, N-hydroxysulfosuccinimide, nitrilotriacetic acid-nickel, amine, carboxylic acid, maleimide, aromatic maleimid, dithiopyridinyl, pyridyl disulfide, pyridyldithiopropionate, N-benzylguanine, cyanuric chloride, carboxyacyl, cyanur, folate, square, galloyl, glycan, thiol, arginylglycylaspartic acid, a fluorescent dye molecule, a magnetic resonance imaging reagent, a chelator;

wherein the method optionally comprises after step e) the following step:

f) coupling the synthetic extracellular vesicles with at least one macromolecule comprising at least one moiety reacting with one of said functional ligands, wherein the macromolecule is selected from the group comprising an extracellular vesicle associated protein, or a fragment thereof, a carbohydrate, a nucleic acid, a polypeptide, a cell receptor, an imaging probe;

wherein the water phase of step a) comprises one or more nucleic acid molecules selected from the group comprising miRNA molecules miR-17, miR-18a, miR-19a, miR-19b-1, miR-20a, miR-92a; miR-21, miR-30d-5p, miR-33b, miR-124, miR-125, miR-126, miR-130, miR-132, miR-133b, miR-140-5p, miR-191, miR-222, miR-451, miR-494, miR-575, miR-630, miR-638, miR-1202, miR-1207-5p, miR-1225-5p, miR-1268, miR-6087, miR-92a-3p-e, miR-K12-3, let-7a; and wherein the extracellular vesicle associated protein, or a fragment thereof is selected from the group comprising:

a transmembrane proteins selected from the group comprising tetraspanin proteins CD9, CD37, CD47, CD53, CD63, CD81, CD82, CD151, Tspan8, heterotrimeric G protein subunit alpha (GNA), integrin α-chains, integrin β-chains, transferrin receptor 1 (TfR1, CD71), transferrin receptor 2 (TFR2), lysosome associated membrane proteins (LAMP1, LAMP2), heparan sulfate proteoglycans, syndecans, extracellular matrix metalloproteinase inducer (EMMPRIN, BSG), A Disintegrin And Metalloproteinase Domain 10 (ADAM10), CD3, CD11c, CD14, CD29, CD31, CD41, CD42a, CD44, CD45, CD50 (intercellular adhesion molecule 1, ICAM-1), CD55, CD59, CD73, CD80, CD86, CD90, sonic hedgehog (SHH), major histocompatibility complex I (MHCI), major histocompatibility complex II (MHCII), epidermal growth factor receptor 2 (ERBB2), epithelial cell adhesion molecule (EpCAM), Glycophorin A (GYPA); Acetylcholinesterase S and E (AChE-S, AChE-E), amyloid beta precursor protein (APP), multidrug resistance-associated protein 1 (ABCC1), stem cells antigen-1 (Sca-1), or a fragment thereof;

a cytosolic protein selected from the group comprising the protein complexes endosomal sorting complexes required for transport ESCRT-I, ESCRT-II, and ESCRT-III, tumour susceptibility gene 101 (TSG101), charged multivesicular body protein (CHMP), Apoptosis-Linked Gene 2-Interacting Protein X (ALIX), vacuolar protein sorting 4 homolog A 4A and 4B, arrestin domain-containing protein (ARRDC1), flotillin-1, flotillin-2; caveolins, EH-domain containing 1-4

(EHD1-EHD4), Ras homolog family member A (RHOA), annexins, heat shock proteins, ADP-ribosylation factor 6 (ARF6), syntenin, microtubule-associated protein Tau (MAPT), or a fragment thereof;

a functional protein selected from the group comprising cytokines, growth factors, interleukins, milk fat globule-EGF factor 8 protein (MFGE8), adhesion proteins, extracellular matrix proteins, nicotinamide phosphoribosyltransferase, signal transduction proteins, Wnta, Wntb, Fas, Fas Ligand (FasL), RANK, RANK Ligand (RANKL), indolamin-2,3-dioxygenase, cytotoxic T-lymphocyte-associated protein 4-immunoglobulin fusion protein, tumor necrosis factor-related apoptosis-inducing ligand, or a fragment thereof; and a protein associated to intracellular compartments selected from the group comprising histone proteins, lamin A/C, inner membrane mitochondrial protein (IMMT), cytochrome C-1 (CYC1), mitochondrial import receptor subunit TOM20, calnexin, heat shock protein 90 kDa beta (Grp94), member 1 (HSP90B1), heat shock 70 kDa protein 5 (HSPA5), Golgin A2 (GM130, GOLGA2), Autophagy Related 9A (ATG9A), actinin1, actinin4 (ACTN1, ACTN4), cytokeratin 18 (KRT18), or a fragment thereof.

Lipid Composition

Lipids are the major scaffolding components of extracellular vesicles such as exosomes, and pivotal for their signaling capabilities. Therefore, synthetic extracellular vesicles were assembled with lipid compositions resembling those found in natural synthetic extracellular vesicles (FIG. 2), although the technology allows for the integration of an almost unrestricted number of possible lipid types into synthetic extracellular vesicles membrane.

The lipid composition of the final synthetic extracellular vesicles can be easily fine-tuned on the basis of the composition of the initial lipid solution, as no lipid ratio change was observed during the emulsification and release procedures.

This technology also allows to finely regulating the charge of the synthetic extracellular vesicles by adjusting the ratio of cationic, neutral and anionic lipids.

The molar percentage (mol %) of a lipid is measured as the moles of a lipid of interest on the total lipid moles of the vesicle.

In some embodiments, the molar percentage (mol %) of a cationic lipid typically comprises from 0% to 10%, from 10% to 20%, from 10% to 30%, from 10% to 40%, %, from 10% to 50%, from 10% to 60%, from 20% to 30%, from 20% to 40%, from 20% to 50%, from 20% to 60% of the total lipid present in vesicle.

In some embodiments, the molar percentage (mol %) of an anionic lipid typically comprises from 0% to 10%, from 10% to 20%, from 10% to 30%, from 10% to 40%, %, from 10% to 50%, from 10% to 60%, from 20% to 30%, from 20% to 40%, from 20% to 50%, from 20% to 60% of the total lipid present in vesicle.

In some embodiments, the molar percentage (mol %) of neutral lipid typically comprises from 49% to 99%, from 49% to 89%, from 49% to 79%, from 49% to 69%, %, from 59% to 99%, from 59% to 89%, from 59% to 79%, from 59% to 69% of the total lipid present in vesicle.

The present invention is not particularly limited concerning the chemical nature of the at least one lipid contained in the water phase of step a) and thus in the inner space of the polymer shell stabilized synthetic extracellular vesicle, as long as it is able to form a lipid bilayer. Good results are in particular achieved with phospholipids and in particular with a lipid being selected from the group comprising phosphocholine, phosphocholine derivatives, phosphoethanolamine, phosphoethanolamine derivatives, phosphatidylcholine, phosphatidylcholine derivatives, phosphatidylglycerol, phosphatidylglycerol derivatives and arbitrary combinations of two or more of the aforementioned lipids.

At least one of the lipids is an amphiphilic lipid, defined as having a hydrophilic and a hydrophobic portion, typically a hydrophilic head and a hydrophobic tail. The hydrophobic portion typically orients into a hydrophobic phase, e.g., within the bilayer, while the hydrophilic portion typically orients toward the aqueous phase, e.g., outside the bilayer, and possibly between adjacent apposed bilayer surfaces. The hydrophilic portion may comprise polar or charged groups such as carbohydrates, phosphate, carboxylic, sulfato, amino, sulfhydryl, nitro, hydroxy and other like groups. The hydrophobic portion may comprise apolar groups that include without limitation long chain saturated and unsaturated aliphatic hydrocarbon groups and groups substituted by one or more aromatic, cyclo-aliphatic or heterocyclic groups. Examples of amphipathic lipids include, but are not limited to, phospholipids, aminolipids and sphingolipids.

Typically, the lipids are phospholipids. Phospholipids include without limitation phosphatidylcholine, phosphatidylethanolamine, phosphatidylglycerol, phosphatidylinositol, phosphatidylserine, and their derivatives. It is to be understood that other lipid membrane components, such as cholesterol, sphingomyelin, cardiolipin, etc. may be used.

Lipids can be "uncharged lipids" or "charged lipids." "Uncharged lipids" refer to lipids that do not carry any charged or ionizable groups such as phosphate groups or choline groups. Examples of uncharged lipids include, but are not limited to, diacyl glycerols and prostaglandins.

"Charged lipids" include neutrally charged, i.e. zwitterionic lipids, cationic lipids and anionic lipids. Generally, lipids bearing a net positive or negative charge exhibit poor solubility in oil phases.

Neutral lipids exist in an uncharged or neutral zwitterionic form at a selected pH.

"Zwitterionic lipids" carry both positively-charged groups and ionizable groups such as amino groups and choline groups that bear a net positive charge, and negatively-charged groups and ionizable groups, such as phosphates, sulfates and carboxylates. Examples of zwitterionic lipids include, but are not limited to, phosphorylcholine and phosphorylethanolamine "Anionic lipids" are lipids negatively charged at physiological pH. "Cationic lipids" are lipids positively charged at physiological pH.

Further suitable lipids are pH sensitive lipids. A "pH-sensitive" lipid refers to a lipid whose ability to form and/or maintain formation of a lipid bilayer depends at least in part on the pH of the surrounding environment. Synthetic extracellular vesicles containing such lipids are destabilized under acidic conditions of the endocytotic pathway. Therefore, the encapsulated content is delivered into the intracellular bio-environment through destabilization or its fusion with the endosomal membrane.

Specific examples of the lipids suitable to synthetize the synthetic extracellular vesicles according to the method disclosed herein are listed in Table 1.

Preferably, the lipids are biodegradable in order to allow release of the internal proteins or nucleic acid molecules in vivo and/or in vitro. Biodegradable lipids include but are not limited to 1,2-dioleoyl-sn-glycero-3-phosphocholine (dioleoyl-phosphocholine, DOPC), anionic 1,2-di-(9Z-octadecenoyl)-sn-glycero-3-phospho-(1'-rac-glycerol) (dioleoylphosphoglycerol, DOPG), and 1,2-distearoyl-sn-glycero-3-phosphoethanolamine (distearoyl-phosphoethanolamine, DSPE).

Functionalized Lipids

According to an embodiment of the present invention, the at least one lipid comprised in the water phase of step a) is a lipid coupled with a functional ligand and/or with polyethylenglycol. Specific examples of the suitable functional ligands, the reacting moieties, and of the functionalized lipids containing are listed in Table 2.

Functionalized and non-functionalized lipids are available from a number of commercial sources including Avanti Polar Lipids (Alabaster, Alabama).

TABLE 1

Suitable lipids

| | Class | Specific example | Abbreviation |
|---|---|---|---|
| Neutral lipids | ceramide | | Cer |
| | sphingomyelin | Egg sphingomyelin, brain sphingomyelin, Milk sphingomyelin, Lyso sphingomyelin, | SM |
| | cholesterol | | Chol |
| | cerebrosides | Galactocerebroside, Glucocerebroside | Gal-Cer, Glc-Cer |
| | diacylglycerols | 1-oleoyl-2-acetyl-sn-glycerol | DAG, DG |
| | phosphatidylcholines | egg L-α-phosphatidylcholine | EggPC |
| | | distearoylphosphatidylcholine | DSPC |
| | | 1-palmitoyl-2-oleoyl-sn-glycero-3-phosphocholine | POPC |
| | | 1,2-dimyristoyl-sn-glycero-3-phosphocholine | DMPC |
| | | 1,2-dipalmitoyl-sn-glycero-3-phosphocholine | DPPC |
| | | 1,2-dioleoyl-sn-glycero-3-phosphocholine | 18:1 DOPC |
| | | dioleoylphosphatidylglycerol | DOPG |
| | | dipalmitoylphosphatidylglycerol | DPPG |
| | | palmitoyloleoylphosphatidylglycerol | POPG |
| | lysophosphatidylcholines | 1-palmitoyl-sn-glycero-3-phosphocholine | PC(16:0/0:0) |
| | phosphatidylethanolamines (also named "cephalin") | 1-stearoyl-2-oleoyl-sn-glycero-3-phosphoethanolamine | SOPE, 18:0-18:1 PE |
| | | 1,2-dimyristoyl-sn-glycero-3-phosphoethanolamine | DMPE, 14:0 PE |
| | | 1,2-dipalmitoyl-sn-glycero-3-phosphoethanolamine | DPPE |
| | | 1,2-dioleoyl-sn-glycero-3-phosphoethanolamine | 18:1 DOPE |
| | lysophosphatidylethanolamine | 1,2-Distearoyl-sn-glycero-3-phosphoethanolamine | DSPE |
| | | palmitoyloleoyl-phosphatidylethanolamine | POPE |
| | lysoethanolamines | 1-stearoyl-sn-glycero-3-phosphoethanolamine | 18:0 Lyso PE, egg Lyso PE |
| | Inverted Headgroups | 2-((2,3-bis(oleoyloxy)propyl)dimethylammonio)ethyl hydrogen phosphate | DOCP |
| | | 2-((2,3-bis(oleoyloxy)propyl)dimethylammonio)ethyl ethyl phosphate | DOCPe |
| | Sphingosin | (R,E)-2-aminooctadec-4-en-1-ol | 3-deoxy sphingosine |
| | | (2S,3S,4E)-2-aminooctadec-4-ene-1,3-diol | L-threo-sphingosine (d18:1) |
| | | D-erythro-sphingosine | Sphingosine (d18:1) |
| | | D-erythro-sphingosine (C17 base) | Sphingosine (d17:1) |
| | | D-erythro-sphingosine (C20 base) | Sphingosine (d20:1) |
| | | D-erythro-Sphingosine (C22 base) | Sphingosine (d22:1) |
| | | (2S,3R,4E,14Z)-2-aminooctadec-4,14-diene-1,3-diol | 4E,14Z-Sphingadiene |
| | | (2S,3R,4E,8Z)-2-aminooctadec-4,8-diene-1,3-diol | 4E,8Z-Sphingadiene |
| | | (2S,3R,4E,11Z)-2-aminooctadec-4,11-diene-1,3-diol | 4E,11Z-Sphingadiene |
| | | D-erythro-Sphingosine (C16 base) | Sphingosine (d16:1) |
| | | D-erythro-Sphingosine (C14 Base) | Sphingosine (d14:1) |
| | | Mito-Caged Sphingosine | Mito-So |
| | Sterol-modified phospholipids | 1-palmitoyl-2-cholesterylhemisuccinoyl-sn-glycero-3-phosphocholine | PChemsPC |
| | | 1-oleoyl-2-cholesterylhemisuccinoyl-sn-glycero-3-phosphocholine | OChems PC |
| | | 1-palmitoyl-2-cholesterylcarbonoyl-sn-glycero-3-phosphocholine, | PChcPC |
| | | 1,2-dicholesterylhemisuccinoyl-sn-glycero-3-phosphocholine, | DChemsPC |
| | Ether ester lipids | 1-O-heptadecyl-2-acetyl-sn-glycero-3-phosphocholine, | C17 PAF, C17-02:0 PC (Phosphocholine), |
| | | 1-O-hexadecyl-2-acetyl-sn-glycero-3-phosphocholine, | C16-02:0 PC, |
| | | 1-O-hexadecyl-2-oleoyl-sn-glycero-3-phosphocholine, | C16-18:1 PC, |
| | | 1-O-hexadecyl-2-arachidonoyl-sn-glycero-3-phosphocholine, | C16-20:4 PC, |
| | | 1-O-octadecyl-2-acetyl-sn-glycero-3-phosphocholine, | C18-02:0 PC, |
| | | 1-O-hexadecyl-2-butyryl-sn-glycero-3-phosphocholine, | C16-04:0 PC, |
| | | 1-O-octadecyl-2-butyryl-sn-glycero-3-phosphocholine, | C18-04:0 PC, |
| | | 1-O-hexadecyl-2-(8Z,11Z,14Z-eicosatrienoyl)-sn-glycero-3-phosphocholine, | C16-20:3 PC, |
| | | 1-O-hexadecyl-2-(5Z,8Z,11Z,14Z,17Z-eicosapentaenoyl)-sn-glycero-3-phosphocholine, | C16-20:5 PC, C16-22:6 PC, |
| | | 1-O-hexadecyl-2-docosahexaenoyl-sn-glycero-3-phosphocholine | C16-18:1 PE |
| | | 1-hexadecyl-2-(9Z-octadecenoyl)-sn-glycero-3-phosphoethanolamine | |

TABLE 1-continued

| Suitable lipids | | |
| --- | --- | --- |
| Class | Specific example | Abbreviation |
| Diether Lipids | 1-O-hexadecanyl-2-O-(9Z-octadecenyl)-sn-glycero-3-phospho-(1'-rac-glycerol) (ammonium salt) | 16:0-18:1 Diether PG, |
| | 1-O-hexadecanyl-2-O-(9Z-octadecenyl)-sn-glycero-3-phosphoethanolamine | 16:0-18:1 Diether PE |
| | 1-O-hexadecanyl-2-O-(9Z-octadecenyl)-sn-glycero-3-phosphocholine | 16:0-18:1 Diether PC |
| | 1,2-di-O-(9Z-octadecenyl)-sn-glycero-3-phosphocholine | 18:1 Diether PC |
| | 1,2-di-O-octadecyl-sn-glycero-3-phosphocholine | 18:0 Diether PC |
| | 1,2-di-O-hexadecyl-sn-glycero-3-phosphocholine | 16:0 Diether PC |
| | 1-O-octadecyl-2-O-methyl-sn-glycero-3-phosphocholine | Edelfosine |
| Vinyl Ether | 1-(1Z-hexadecenyl)-sn-glycero-3-phosphocholine | C16(Plasm) LPC |
| (Plasmalogen) | 1-O-1'-(Z)-octadecenyl-2-hydroxy-sn-glycero-3-phosphocholine, | C18(Plasm) LPC |
| | 1-(1Z-octadecenyl)-2-oleoyl-sn-glycero-3-phosphocholine | C18(Plasm)-18:1 PC |
| | 1-(1Z-octadecenyl)-2-arachidonoyl-sn-glycero-3-phosphocholine | C18(Plasm)-20:4 PC |
| | 1-O-1'-(Z)-octadecenyl-2-hydroxy-sn-glycero-3-phosphoethanolamine | C18(Plasm) LPE |
| | 1-(1Z-octadecenyl)-2-docosahexaenoyl-sn-glycero-3-phosphocholine | C18(Plasm)-22:6 PC |
| | 1-(1Z-octadecenyl)-2-oleoyl-sn-glycero-3-phosphoethanolamine | C18(Plasm)-18:1 PE |
| | 1-(1Z-octadecenyl)-2-arachidonoyl-sn-glycero-3-phosphoethanolamine | C18(Plasm)-20:4 PE |
| | 1-(1Z-octadecenyl)-2-docosahexaenoyl-sn-glycero-3-phosphoethanolamine | C18(Plasm)-22:6 PE |
| N-Acylglycine | N-palmitoylglycine | |
| | N-arachidonoylglycine | |
| | N-oleoylglycine | |
| Very Long Chain Fatty Acids (VLCFA) | 14Z,17Z,20Z,23Z,26Z,29Z-dotriacontahexaenoic acid | C32:6 fatty acid |
| Prenols | Coenzyme Q6 (S. cerevisiae) | CoQ6 |
| | Coenzyme Q8 (E. coli) | CoQ8 |
| | Dolichol Mixture (13~21) | |
| | Polyprenol mixture (13~21) | |
| | Polyprenal mixture (13~21) | |
| Prostaglandins | Prostaglandin E1 | PGE1 |
| | Prostaglandin F1α | PGF1α |
| | Prostaglandin F2α (15 beta epimer) | 15-beta PGF2α |
| | Prostaglandin F1β | PGF1β |
| | Prostaglandin F1α(15 beta epimer) | 15beta-PGF1α |
| | Prostaglandin F1α-d9 | PGF1α-d9 |
| | Prostaglandin E1-d9 | PGE1-d9 |
| | Prostaglandin E2 Ethanolamide | PGE2-EA |
| | Prostaglandin A1 | PGA1 |
| | Prostaglandin E2 | PGE2 |
| | Prostaglandin F2β | PGF2β |
| | Prostaglandin B1 | PGB1 |
| | Prostaglandin F2α | PGF2α |
| | 15-keto Prostaglandin F2α | 15-keto PGF2α |
| Glycosylated Diacyl Glycerols | 1,2-diacyl-3-O-(α-D-glucopyranosyl)-sn-glycerol (E. coli) | MGlc-DAG |
| | 1-oleoyl-2-palmitoyl-3-(α-D-galactosyl)-sn-glycerol | BbGL-2 |
| | 1-palmitoyl-2-oleoyl-3-(β-D-glucosyl)-sn-glycerol | 16:0-18:1 DG glucose |
| Eicosanoids | 5-Oxo-6E,8Z,11Z,14Z-eicosatetraenoic acid | 5-OxoETE |
| | 17(S)-hydroxy Docosahexaenoic acid | 17(S)-HDHA |
| | (±)14(15)-epoxy-5Z,8Z,11Z-eicosatrienoic acid | 14(15) EET |
| | 15S-hydroxy-5Z,8Z,11Z,13E-eicosatetraenoic acid | 15(S)-HETE |
| | 15(S)-hydroxy-N-(2-hydroxyethyl)-5Z,8Z,11Z,13E-eicosatetraenamide | 15(S)-HAEA |
| | 13S-Hydroxy-9Z,11E-octadecadienoic acid | 13(S)HODE |
| | 13S-Hydroxy-N-(2-hydroxyethyl)-9Z,11E-octadecadienamide | 13(S)HODE Ethanolamide |
| Palmitic Acid-Hydroxy Stearic Acid, PAHSA | 9-(palmitoyloxy)octadecanoic acid | 9-PAHSA |
| | 5-(palmitoyloxy)octadecanoic acid | 5-PAHSA |
| | 9'-(palmitoyloxy)octadecanoic acid | 12-PAHSA |
| | 1-palmitoyl-2-[9'-(palmitoyloxy)octadecanoyl]-sn-glycero-3-phosphoholine | 16:0-(12-PAHSA) PC |

TABLE 1-continued

| | | Suitable lipids | |
|---|---|---|---|
| | Class | Specific example | Abbreviation |
| Anionic lipids | phosphatidic acids lysophosphatidic acids | 1-palmitoyl-2-oleoyl-sn-glycero-3-phosphate | 16:0-18:1 PA, POPA |
| | | 1-oleoyl-2-hydroxy-sn-glycero-3-phosphate | 18:1 Lyso PA |
| | | 1-stearoyl-2-hydroxy-sn-glycero-3-phosphate | 18:0 Lyso PA |
| | | 1-heptadecanoyl-2-hydroxy-sn-glycero-3-phosphate (sodium salt) | 17:0 Lyso PA |
| | | 1-arachidonoyl-2-hydroxy-sn-glycero-3-phosphate | 20:4 Lyso PA |
| | | 1-palmitoyl-2-hydroxy-sn-glycero-3-phosphate (sodium salt) | 16:0 Lyso PA |
| | | 1-myristoyl-2-hydroxy-sn-glycero-3-phosphate (sodium salt) | 14:0 Lyso PA |
| | phosphatidylglycerols | Egg L-α-phosphatidylglycerol | EggPG |
| | | 1,2-di-(9Z-octadecenoyl)-sn-glycero-3-phospho-(1'-rac-glycerol), or L-α-Phosphatidyl-DL-glycerol | 18:1 DOPG |
| | | 1-palmitoyl-2-oleoyl-sn-glycero-3-phospho-(1'-rac-glycerol) | POPG |
| | lysophosphatidylglycerols | 1-palmitoyl-2-hydroxy-sn-glycero-3-phospho-(1'-rac-glycerol) | 16:0 Lyso PG |
| | phosphatidylserines | 1,2-dioleoyl-sn-glycero-3-phospho-L-serine | DOPS |
| | | 1-stearoyl-2-oleoyl-sn-glycero-3-phospho-L-serine | SOPS |
| | lysophosphatidylserines | 1-stearoyl-sn-glycero-3-phospho-L-serine | PS (18:1/18:0) |
| | phosphatidylinositols | 1-stearoyl-2-arachidonoyl-sn-glycero-3-phospho-(1'-myo-inositol) | 18:0/20:4-PI |
| | phosphatidylinositolphosphates | 1-stearoyl-2-arachidonoyl-sn-glycero-3-phospho-(1'-myo-inositol-4'phosphate) | 18:0-20:4 PI(4)P |
| | | 1-stearoyl-2-arachidonoyl-sn-glycero-3-phospho-(1'-myo-inositol-4',5'-bisphosphate) | 18:0-20:4 PI(4,5)P2 |
| | | phosphatidylinositol 4,5-bisphosphate | PIP2 |
| | cardiolipins | 1',3'-bis[1,2-dilinoleoyl-sn-glycero-3-phospho]-sn-glycerol. | 18:1 Cardiolipin |
| | | 1',3'-bis[1,2-dimyristoleoyl-sn-glycero-3-phospho]-glycerol | 14:1 Cardiolipin |
| | | 1',3'-bis[1,2-dipalmitoyl-sn-glycero-3-phospho]-glycerol | 16:0 Cardiolipin |
| | | 1',3'-bis[1-Palmitoyl-2-oleoyl-sn-glycero-3-phospho]-glycerol | 16:0-18:1 Cardiolipin |
| | | 1',3'-bis[1,2-dipalmitoleoyl-sn-glycero-3-phospho]-glycerol | 16:1 Cardiolipin |
| | | 1',3'-bis[1,2-Distearoyl-sn-glycero-3-phospho]-glycerol | 18:0 Cardiolipin |
| | Bis(Monoacylglycero)Phosphate (BMP) | bis(monomyristoylglycero)phosphate (S, R Isomer) (ammonium salt), | 14:0 BMP (S, R) |
| | | sn-(3-myristoyl-2-hydroxy)-glycerol-1-phospho-sn-3'-(1',2'-dimyristoyl)-glycerol (ammonium salt) | 14:0 Hemi BMP (S, R) |
| | | bis(monooleoylglycero)phosphate (S, R Isomer) (ammonium salt) | 18:1 BMP (S, R) |
| | | sn-(3-oleoyl-2-hydroxy)-glycerol-1-phospho-sn-3'-(1',2'-dioleoyl)-glycerol (ammonium salt) | 18:1 Hemi BMP (S, R) |
| | | sn-(3-oleoyl-2-hydroxy)-glycerol-1-phospho-sn-1'-(3'-oleoyl-2'-hydroxy)-glycerol (ammonium salt) | 18:1 BMP (S, S) |
| | | sn-(1-oleoyl-2-hydroxy)-glycerol-3-phospho-sn-3'-(1'-oleoyl-2'-hydroxy)-glycerol (ammonium salt) | 18:1 BMP (R, R) |
| | | sn-[2,3-dioleoyl]-glycerol-1-phospho-sn-1'-[2',3'-dioleoyl]-glycerol (ammonium salt) | 18:1 BDP (S, S) |
| Cationic lipids | | 2,3-dioleyloxy-N-[2(sperminecarboxamido) ethyl]-N,N-dimethyl-1-propanaminium trifluoroacetate | DOSPA |
| | | 1,2-dimyristyloxypropyl-3-dimethyl-hydroxy ethyl ammonium bromide | DMRIE |
| | | N-(2,3-dioleyloxy)propyl)-N,N-dimethylammonium chloride | DODMA |
| | | dioctadecylamidoglycyl carboxyspermine | DOGS |
| | | 1,2-Dioleoyl-3-dimethylammonium-propane | DODAP |
| | | dioleyl-N,N-dimethylammonium chloride | DODAC |
| | | N-(2,3-dioleyloxy)propyl)-N,N,N-trimethylammonium chloride | DOTMA |
| | | N,N-distearyl-N,N-dimethylammonium bromide | DDAB |
| | | 1,2-dioleoyl-3-trimethylammonium-propane | 18:1 DOTAP |
| | | 3β-(N-(N',N'-dimethylaminoethane)-carbamoyl)cholesterol | DC-Chol |

TABLE 1-continued

| | Suitable lipids | |
|---|---|---|
| Class | Specific example | Abbreviation |
| pH sensitive lipids | N-(4-carboxybenzyl)-N,N-dimethyl-2,3-bis(oleoyloxy)propan-1-aminium | DOBAQ (cationic) |
| | 1,2-distearoyl-3-dimethylammonium-propane | DAP (cationic) |
| | 1,2-dipalmitoyl-sn glycero-3-succinate | 16:0 DGS |
| | 1,2-dioleoyl-sn-glycero-3-succinate | 18:1 DGS |
| | N-palmitoyl homocysteine | PHC |
| Biodegradable lipids | 1,2-dioleoyl-sn-glycero-3-phosphocholine | DOPC |
| | 1,2-di-(9Z-octadecenoyl)-sn-glycero-3-phospho-(1'-rac-glycerol) | DOPG |
| | 1,2-distearoyl-sn-glycero-3-phosphoethanolamine | DSPE |
| Photoswitchable lipid | N-[(E)-4-(4-((4-butylphenyl)diazenyl)phenyl)butanoyl]-D-erythro-sphingosine | ACe-1 |
| | 1-stearoyl-2-[(E)-4-(4-((4-butylphenyl)diazenyl)phenyl)butanoyl]-sn-glycerol | 18:0-PhoDAG |
| | 1-stearoyl-2-[(E)-4-(4-((4-butylphenyl)diazenyl)phenyl)butanoyl]-sn-glycero-3-phosphocholine | 18:0-azo PC |
| | N-[(E)-4-(4-((4-butylphenyl)diazenyl)phenyl)butanoyl]-D-erythro-sphingosylphosphorylcholine | Azo SM |
| | (E)-4-(4-((4-butylphenyl)diazenyl)phenyl)-N-(3-hydroxy-4-methoxybenzyl)butanamide | Trans-AzCA4 |
| | 4-Butyl-Azo-4:0-Acid-1 | Trans-F AAzo-4 |
| | 1-(E)-4-(4-((4-butylphenyl)diazenyl)phenyl)butanoyl]-2-hydroxy-sn-glycero-3-phosphate | Azo Lyso PA |

TABLE 2

| | Functional moieties and examples of functionalized lipid | |
|---|---|---|
| Functional Ligand | Example | Reacting moiety/Function |
| biotin | 1-oleoyl-2-(12-biotinyl-(aminododecanoyl))-sn-glycero-3-phosphoethanolamine (18:1-12:0 Biotin PE); 1,2-dipalmitoyl-sn-glycero-3-phosphoethanolamine-N-(biotinyl), 16:0 Biotinyl PE 1,2-dioleoyl-sn-glycero-3-phosphoethanolamine-N-(biotinyl), 18:1 Biotinyl PE 1,2-dioleoyl-sn-glycero-3-phosphoethanolamine-N-(cap biotinyl), 18:1 Biotinyl Cap PE; 1,2-dipalmitoyl-sn-glycero-3-phosphoethanolamine-N-(cap biotinyl), 16:0 Biotinyl Cap PE | Avidin, Streptavidin |
| N-hydroxysuccinimide ester (NHS), N-Hydroxysulfosuccinimide (sulfo-NHS) | NHS Palmitic acid N-hydroxysuccinimide ester | Amine |
| nitrilotriacetic acid (NTA)-nickel | 1,2-dioleoyl-sn-glycero-3-[(N-(5-amino-1-carboxypentyl)iminodiacetic acid) succinyl], 18:1 DGS-NTA (Ni) | Histidine (His) tags, e.g. 6 × His-Tag |
| amines | 1,2-dioleoyl-sn-glycero-3-phosphoethanolamine-N-(hexanoylamine)18:1 Caproylamine PE 1,2-Dipalmitoyl-sn-Glycero-3-Phosphoethanolamine-N-(hexanoylamine), 16:0 Caproylamine PE 1,2-dipalmitoyl-sn-glycero-3-phosphoethanolamine-N-(dodecanylamine), 16:0 Dodecanylamine PE 1,2-dioleoyl-sn-glycero-3-phosphoethanolamine-N-(dodecanylamine), 18:1 Dodecanylamine PE | NHS, N-Hydroxysulfosuccinimide |
| arginylglycylaspartic acid (RGD) | 1,2-distearoyl-sn-glycero-3-phosphoethanolamine-N-[4-(p-(cysarginylglycylaspartate-maleimidomethyl)-cyclohexane-carboxamide], DSPE-RGD | Integrin receptors on target cells |
| maleimides, aromatic maleimides N-[4-(p-maleimidophenyl)-butyryl], MPB; 4-(N-maleimidomethyl) cyclohexane-1-carboxylate, MCC | 1,2-dipalmitoyl-sn-glycero-3-phosphoethanolamine-N-[4-(p-maleimidomethyl) cyclohexane-carboxamide] (sodium salt), 16:0 PE MCC; 1,2-dioleoyl-sn-glycero-3-phosphoethanolamine-N-[4-(p-maleimidomethyl) cyclohexane-carboxamide] (sodium salt), 18:1 PE MCC; 1,2-dioleoyl-sn-glycero-3-phosphocholine (N-aminoethyl), 18:1 aminoethyl PC; 1,2-dioleoyl-sn-glycero-3-phosphoethanolamine-N-[4-(p-maleimidophenyl) butyramide] (sodium salt), 18:1 MPB PE 1,2-dipalmitoyl-sn-glycero-3-phosphoethanolamine-N-[4-(p-maleimidophenyl) butyramide] (sodium salt), 16:0 MPB PE | Thiol (e.g. thiolated antibodies) |

TABLE 2-continued

| Functional Ligand | Example | Reacting moiety/Function |
|---|---|---|
| | Functional moieties and examples of functionalized lipid | |
| pyridyldithiopropionate (PDP) | 1,2-dioleoyl-sn-glycero-3-phosphoethanolamine-N-[3-(2-pyridyldithio)propionate] (sodium salt), 18:1 PDP PE 1,2-dipalmitoyl-sn-glycero-3-phosphoethanolamine-N-[3-(2-pyridyldithio)propionate] (sodium salt), 16:0 PDP PE | maleimide-functionalized antibodies bind to sulfhydril group obtained after reduction of a PDP-phopholipid |
| pyridyl disulfide (DPS) dithiopyridinyl 4,4'-dithiodipyridine (4-PDS or 4-DTDP), | | maleimide maleimide |
| N-benzylguanine | 1,2-dioleoyl-sn-glycero-3-phosphoethanolamine-N-benzylguanine, 18:1 PE-benzylguanine 1,2-dioleoyl-sn-glycero-3-phosphoethanolamine-N-[benzylguanine(polyethylene glycol)-2000], 18:1 PE-PEG2000-benzylguanine | SNAP-tag |
| fluorescent dye molecule, such as lissamine rhodamine B sulfonyl, Atto488, Alexa Fluor 488, Alexa Fluor 647, Fluorescein, N-(7-Nitrobenz-2-Oxa-1,3-Diazol-4-yl (NBD), Cy5, Cy5.5, Cy7, Topfluor ® Alexa Fluor488, Topfluor ® Alexa Fluor594 | 1,2-dioleoyl-sn-glycero-3-phosphoethanolamine-N-(lissamine rhodamine B sulfonyl) (RhB DOPE or LissRhod PE), 1,1'-dioctadecyl-3,3,3',3'-tetramethylindotricarbocyanine iodide (DiR); 1,1'-dioctadecyl-3,3,3',3'-tetramethylindodicarbocyanine (DiD) | |
| sulfhydryl/thiol group | 1,2-Dipalmitoyl-sn-Glycero-3-Phosphothioethanol (DPPTE)/16:0 Ptd Thioethanol | Maleimides, Iodoacetamides, benzylic halide, and bromomethylketones, |
| Carboxyacyl such as Succinyl, Glutaryl, dodecanoyl | 1,2-dioleoyl-sn-glycero-3-phosphoethanolamine-N-(succinyl) (sodium salt), 18:1 Succinyl PE; 1,2-dipalmitoyl-sn-glycero-3-phosphoethanolamine-N-(succinyl) (sodium salt), 16:0 Succinyl PE; 1,2-dioleoyl-sn-glycero-3-phosphoethanolamine-N-(glutaryl) (sodium salt), 18:1 Glutaryl PE; 1,2-dipalmitoyl-sn-glycero-3-phosphoethanolamine-N-(glutaryl) (sodium salt), 16:0 Glutaryl PE; 1,2-dioleoyl-sn-glycero-3-phosphoethanolamine-N-(dodecanoyl) (sodium salt), 18:1 Dodecanyl PE; 1,2-dipalmitoyl-sn-glycero-3-phosphoethanolamine-N-(dodecanoyl) (sodium salt), 16:0 Dodecanoyl PE | |
| cyanuric chloride | cyanur-DSPE cyanur-PEG2000-PE (ammonium salt) 1,2-distearoyl-sn-glycero-3-phosphoethanolamine-N-[cyanur(polyethylene glycol)-2000] (ammonium salt), DSPE-PEG(2000) Cyanur 1,2-dipalmitoyl-sn-glycero-3-phosphoethanolamine-N-(cyanur), 16:0 Cyanur PE | coupling to amine-containing biomolecules such as peptides, antibodies, nanoparticles |
| Folate | 1,2-dipalmitoyl-sn-glycero-3-phosphoethanolamine-N-(6-((folate)amino)hexanoyl), 16:0 Folate Cap PE, | Folate receptor on cancer cells (endocitosis) |
| Carbohydrate/Glycan: for example β-galactose, α-mannose-, β-mannose-, and α-fucose | 1,2-dipalmitoyl-sn-glycero-3-phospho((ethyl-1',2',3'-triazole)triethyleneglycolmannose), 16:0 PA-PEG3-mannose β-galactose, α-mannose-, β-mannose-, and α-fucose; 1,2-dioleoyl-sn-glycero-3-phosphoethanolamine-N-lactosyl (ammonium salt), (18:1 Lactosyl PE) 1,2-diacyl-3-O-(α-D-glucopyranosyl)-sn-glycerol (E. coli), MGlc-DAG 1-oleoyl-2-palmitoyl-3-(α-D-galactosyl)-sn-glycerol, BbGL-2 1-palmitoyl-2-oleoyl-3-(β-D-glucosyl)-sn-glycerol, 16:0-18:1 DG glucose | Carbohydrate binding cell receptor |
| Square | 1,2-dioleoyl-sn-glycero-3-phosphoethanolamine-N-square, 18:1 PE-Square 1,2-distearoyl-sn-glycero-3-phosphoethanolamine-N-square, 18:0 PE-square | Square is a dye for Resonance Energy Transfer (RET), Flow Cytometry |
| Galloyl | 1,2-dipalmitoyl-sn-glycero-3-galloyl (16:0 DG Galloyl) | Self-adhering lipid so that bilayers strongly adhere to each other |
| Azide | 1,2-dioleoyl-sn-glycero-3-phosphoethanolamine-N-[azido(polyethylene glycol)-2000] (ammonium salt), DOPE-PEG(2000) Azide | Photochemically induced cross-linking with transmembrane peptides |
| Carboxylic acid | 1,2-dioleoyl-sn-glycero-3-phosphoethanolamine-N-[carboxy(polyethylene glycol)-2000] (sodium salt), DOPE-PEG(2000) Carboxylic acid | Amine moieties |
| Chelator: NTA, diethylenetriamine pentaacetic acid, DTPA | 1,2-dipalmitoyl-sn-glycero-3-phosphoethanolamine-N-diethylenetriaminepentaacetic acid (16:0 PE-DTPA), 1,2-dioleoyl-sn-glycero-3-[(N-(5-amino-1-carboxypentyl)iminodiacetic acid) succinyl] (18:1 DGS-NTA), | gadolinium chelated with diethylenentriaminepentaacetyl (DTPA) provides contrast in magnetic resonance imaging |

TABLE 2-continued

| Functional moieties and examples of functionalized lipid | | |
| --- | --- | --- |
| Functional Ligand | Example | Reacting moiety/Function |
| | 1,2-dioleoyl-sn-glycero-3-[(N-(5-amino-1-carboxypentyl)iminodiacetic acid) succinyl] (Cobalt salt) (18:1 DGS-NTA)(Co), 1,2-dioleoyl-sn-glycero-3-[(N-(5-amino-1-carboxypentyl)iminodiacetic acid) succinyl] (nickel salt) (18:1 DGS-NTA)(Ni), 1,2-dimyristoyl-sn-glycero-3-phosphoethanolamine-N-diethylenetriaminepentaacetic acid (copper salt), (14:0 PE-DTPA(Cu)), DTPA-bis(stearylamide) (gadolinium salt), (DTPA-BSA (Gd)), 1,2-distearoyl-sn-glycero-3-phosphoethanolamine-N-diethylenetriaminepentaacetic acid (gadolinium salt), (18:0 PE-DTPA (Gd)), bis(1,2-dimyristoyl-sn-glycero-3-phosphoethanolamine)-N-N'-diethylenetriaminepentaacetic acid (gadolinium salt) (bis(14:0 PE)-DTPA(Gd)), bis(1,2-dipalmitoyl-sn-glycero-3-phosphoethanolamine)-N-N'-diethylenetriaminepentaacetic acid (gadolinium salt) (bis(16:0 PE)-DTPA(Gd)), bis(1,2-distearoyl-sn-glycero-3-phosphoethanolamine)-N-N'-diethylenetriaminepentaacetic acid (gadolinium salt) (bis(18:0 PE)-DTPA(Gd)), 1,2-distearoyl-sn-glycero-3-phosphoethanolamine-N-diethylenetriaminepentaacetic acid (18:0 PE-DTPA). | |
| Magnetic resonance imaging, MRI imaging | 1,2-dipalmitoyl-sn-glycero-3-phosphoethanolamine-N-diethylenetriaminepentaacetic acid (gadolinium salt), (16:0 PE-DTPA (Gd)), 1,2-distearoyl-sn-glycero-3-phosphoethanolamine-N-diethylenetriaminepentaacetic acid (gadolinium salt), (18:0 PE-DTPA (Gd)), bis(1,2-dimyristoyl-sn-glycero-3-phosphoethanolamine)-N-N'-diethylenetriaminepentaacetic acid (gadolinium salt) (bis(14:0 PE)-DTPA(Gd)), bis(1,2-dipalmitoyl-sn-glycero-3-phosphoethanolamine)-N-N'-diethylenetriaminepentaacetic acid (gadolinium salt) (bis(16:0 PE)-DTPA(Gd)), bis(1,2-distearoyl-sn-glycero-3-phosphoethanolamine)-N-N'-diethylenetriaminepentaacetic acid (gadolinium salt) (bis(18:0 PE)-DTPA(Gd)), 1,2-distearoyl-sn-glycero-3-phosphoethanolamine-N-diethylenetriaminepentaacetic acid (18:0 PE-DTPA). | |
| polyethylene glycol PEG200, PEG350, PEG550, PEG750, PEG1000, PEG2000, PEG3000, PEG5000, PEG20000, PEG50000, | 1,2-dipalmitoyl-sn-glycero-3-phosphoethanolamine-N-[methoxy(polyethylene glycol)-350], 18:1 PEG350 PE 1,2-dioleoyl-sn-glycero-3-phosphoethanolamine-N-[methoxy(polyethylene glycol)-750], 18:1 PEG750 PE 1,2-dioleoyl-sn-glycero-3-phosphoethanolamine-N-[methoxy(polyethylene glycol)-1000], 18:1 PEG1000 PE | Surface passivation |
| Diacetylene | 1,2-bis(10,12-tricosadiynoyl)-sn-glycero-3-phosphoethanolamine, 23:2 Diyne PE [DC(8,9)PE] 1-palmitoyl-2-(10,12-tricosadiynoyl)-sn-glycero-3-phosphocholine, 16:0-23:2 Diyne PC 1-palmitoyl-2-(10,12-tricosadiynoyl)-sn-glycero-3-phosphoethanolamine, 16:0-23:2 Diyne PE 1,2-bis(10,12-tricosadiynoyl)-sn-glycero-3-phosphocholine, 23:2 Diyne PC [DC(8,9)PC] | Photopolymerization |
| Diphytanoyl Lipids | 1,2-diphytanoyl-sn-glycero-3-phosphoethanolamine-N-(7-nitro-2-1,3-benzoxadiazol-4-yl), 4ME 16:0 NBD PE (NBD-DPhPE) 1,2-diphytanoyl-sn-glycero-3-phosphocholine, 4ME 16:0 PC 1,2-diphytanoyl-sn-glycero-3-phosphoethanolamine, 4ME 16:0 PE 1,2-diphytanoyl-sn-glycero-3-phospho-(1'-rac-glycerol), 4ME 16:0 PG 1,2-diphytanoyl-sn-glycero-3-phosphate, 4ME 16:0 PA 1,2-diphytanoyl-sn-glycero-3-phospho-L-serine, 4ME 16:0 PS phytanoyl Coenzyme A, 4ME 16:0 Coenzyme A 1,2-di-O-phytanyl-sn-glycero-3-phosphocholine, 4ME 16:0 Diether PC 1,2-di-O-phytanyl-sn-glycero-3-phosphoethanolamine, 4ME 16:0 Diether PE 1,2-di-O-phytanyl-sn-glycerol, 4ME 16:0 Diether DG | Lipids containing diphytanoyl fatty acid chains allow to produce stable planar lipid membranes |
| Fluorinated lipids | 1-palmitoyl-2-(16-fluoropalmitoyl)-sn-glycero-3-phosphocholine, 16:0-16:0 (16-F) PC | |
| Brominated Lipid | 1,2-di-(9,10-dibromo)stearoyl-sn-glycero-3-phosphocholine, 18:0 (9,10dibromo) PC 1-palmitoyl-2-stearoyl(4,5)dibromo-sn-glycero-3-phosphocholine, 16:0-18:0(4,5-dibromo) PC | Fluorescence quenching |

TABLE 2-continued

Functional moieties and examples of functionalized lipid

| Functional Ligand | Example | Reacting moiety/Function |
|---|---|---|
| | 1-palmitoyl-2-(6,7-dibromo)stearoyl-sn-glycero-3-phosphocholine, 16:0-18:0 (6-7BR) PC 1-palmitoyl-2-(9,10-dibromo)stearoyl-sn-glycero-3-phosphocholine, 16:0-18:0 (9-10BR) PC 1-palmitoyl-2-(11,12-dibromo)stearoyl-sn-glycero-3-phosphocholine, 16:0-18:0 (11-12BR) PC | |

Sulfhydryls, also called thiols, exist in proteins in the side-chain of cysteine (Cys, C) amino acids. Sulfhydryl-reactive chemical groups include haloacetyls, maleimides, aziridines, acryloyls, arylating agents, vinylsulfones, pyridyl disulfides, TNB-thiols and disulfide reducing agents.

Different lipids which are offered for thioether conjugation contain maleimide, aromatic maleimides such as N-[4-(p-maleimidophenyl)-butyryl] (MPB) or 4-(N-maleimidomethyl)cyclohexane-1-carboxylate (MCC) group. The maleimide function group of MCC which contains an aliphatic cyclohexane ring is more stable toward hydrolysis in aqueous reaction environments rather than the aromatic phenyl group of MPB Carbohydrates are selected from the group comprising β-galactose, α-mannose-, β-mannose-, and α-fucose. It has been shown that said carbohydrates can be conjugated to cholesterols to be incorporated into liposomes, and in vitro results showed that the sugar-conjugated liposomes are efficiently recognized by cells that overexpress carbohydrate-binding receptors on their surface (Rajabi and Mousa, 2016, *Current Pharmaceutical Biotechnology*, 17, 8).

SNAP-tag is a self-labeling protein tag commercially available in various expression vectors. SNAP-tag is a 182 residues polypeptide (19.4 kDa) that can be fused to any protein of interest and further specifically and covalently tagged with a suitable ligand, such as a fluorescent dye.

A functional ligand for coupling to lipids for carry out the present invention is preferably selected from the group comprising biotin, N-hydroxysuccinimide ester, nitrilotriacetic acid-nickel, amine, carboxylic acid, maleimides, dithiopyridinyl, pyridyl disulfide, pyridyldithiopropionate, N-benzylguanine, carboxyacyl, cyanur, folate, square, galloyl, glycan, thiol, arginylglycylaspartic acid, a fluorescent dye molecule, a magnetic resonance imaging reagent, a chelator.

Therefore, one embodiment of the present invention is directed to a method for producing synthetic extracellular vesicles comprising:

a) providing a water phase comprising at least two lipids, and one or more extracellular vesicle associated proteins, or fragments thereof, wherein the at least two lipids are a negative charged lipid, and a lipid coupled to a functional ligand for protein conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, the synthetic extracellular vesicles have a hydrodynamic radius between 70 nm and 5000 nm, and wherein the water phase of step a) comprises at least two lipids selected from the group comprising:

a neutral lipid selected from the group comprising ceramide, sphingomyelin, cephalin, cholesterol, cerebrosides, diacylglycerols, phosphatidylcholines, lysophosphatidylcholines, phosphatidylethanolamines, lysophosphatidylethanolamine, lysoethanolamines, inverted headgroup lipids, sphingosins, sterol-modified phospholipids, ether ester lipids, diether lipids, vinyl ether (plasmalogen);

an anionic lipid selected from the group comprising phosphatidic acids, lysophosphatidic acid derivatives, phosphatidylglycerols, lysophosphatidylglycerols, phosphatidylserines, lysophosphatidylserines, phosphatidylinositols, phosphatidylinositolphosphates, cardiolipins, Bis(Monoacylglycero)Phosphate derivatives;

a cationic lipid selected from the group comprising dioleyl-N,N-dimethylammonium chloride; N-(2,3-dioleyloxy)propyl)-N,N,N-trimethylammonium chloride; N,N-distearyl-N,N-dimethylammonium bromide; N-(2,3-dioleyloxy)propyl)-N,N,N-trimethylammonium chloride; 3β-(N-(N',N'-dimethylaminoethane)-carbamoyl)cholesterol; 1,2-dimyristyloxypropyl dimethyl-hydroxy ethyl ammonium bromide; 2,3-dioleyloxy-N-[2(sperminecarboxamido)ethyl]-N,N-dimethyl-1-propanaminium trifluoroacetate; dioctadecylamidoglycyl carboxyspermine; N-(2,3-dioleyloxy)propyl)-N,N-dimethylammonium chloride and 1,2-Dioleoyl dimethylammonium-propane;

a pH-sensitive lipid selected from the group comprising lipid N-(4-carboxybenzyl)-N,N-dimethyl-2,3-bis(oleoyloxy)propan-1-aminium, 1,2-distearoyl-3-dimethylammonium-propane, 1,2-dipalmitoyl-sn-glycero-3-succinate, 1,2-dioleoyl-sn-glycero-3-succinate, N-palmitoyl homocysteine; a photoswitchable lipid;

acylglycine derivatives, prenol derivatives, prostaglandine derivatives, glycosylated diacyl glycerols, eicosanoid derivatives, (palmitoyloxy)octadecanoic acid derivatives, diacetylene derivatives, diphytanoyl derivatives, fluorinated lipids, brominated lipids, lipopolysaccharides;

one of the aforementioned lipids coupled to a functional ligand selected from the group comprising biotin, N-hydroxysuccinimide ester, nitrilotriacetic acid-nickel, amine, carboxylic acid, maleimides, aromatic maleimid, dithiopyridinyl, pyridyl disulfide, pyridyldithiopropionate, N-benzylguanine, cyanuric chloride, carboxyacyl, cyanur, folate, square, galloyl, glycan, thiol, arginylglycylaspartic acid, a fluorescent dye molecule, a magnetic resonance imaging reagent, a chelator; and one of the aforementioned lipids coupled to polyethyleneglycol with a molecular weight comprised between 350 and 50,000 g/mole.

A further embodiment of the present invention is directed to a method for producing synthetic extracellular vesicles comprising:

a) providing a water phase comprising at least two lipids, one or more extracellular vesicle associated proteins, or fragments thereof, and one or more nucleic acid molecules, wherein the at least two lipids are a negative charged lipid, and a lipid coupled to a functional ligand for protein conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, the synthetic extracellular vesicles have a hydrodynamic radius between 70 nm and 5000 nm, and wherein the water phase of step a) comprises at least two lipids selected from the group comprising:

a neutral lipid selected from the group comprising ceramide, sphingomyelin, cephalin, cholesterol, cerebrosides, diacylglycerols, phosphatidylcholines, lysophosphatidylcholines, phosphatidylethanolamines, lysophosphatidylethanolamine, lysoethanolamines, inverted headgroup lipids, sphingosins, sterol-modified phospholipids, ether ester lipids, diether lipids, vinyl ether (plasmalogen);

an anionic lipid selected from the group comprising phosphatidic acids, lysophosphatidic acid derivatives, phosphatidylglycerols, lysophosphatidylglycerols, phosphatidylserines, lysophosphatidylserines, phosphatidylinositols, phosphatidylinositolphosphates, cardiolipins, Bis(Monoacylglycero)Phosphate derivatives;

a cationic lipid selected from the group comprising dioleyl-N,N-dimethylammonium chloride; N-(2,3-dioleyloxy)propyl)-N,N,N-trimethylammonium chloride; N,N-distearyl-N,N-dimethylammonium bromide; N-(2,3-dioleyloxy)propyl)-N,N,N-trimethylammonium chloride; 3β-(N-(N',N'-dimethylaminoethane)-carbamoyl)cholesterol; 1,2-dimyristyloxypropyl-3-dimethyl-hydroxy ethyl ammonium bromide; 2,3-dioleyloxy-N-[2(sperminecarboxamido)ethyl]-N,N-dimethyl-1-propanaminium trifluoroacetate; dioctadecylamidoglycyl carboxyspermine; N-(2,3-dioleyloxy)propyl)-N,N-dimethylammonium chloride and 1,2-Dioleoyl dimethylammonium-propane;

a pH-sensitive lipid selected from the group comprising lipid N-(4-carboxybenzyl)-N,N-dimethyl-2,3-bis (oleoyloxy)propan-1-aminium, 1,2-distearoyl-3-dimethylammonium-propane, 1,2-dipalmitoyl-sn-glycero succinate, 1,2-dioleoyl-sn-glycero-3-succinate, N-palmitoyl homocysteine;

a photoswitchable lipid;

acylglycine derivatives, prenol derivatives, prostaglandine derivatives, glycosylated diacyl glycerols, eicosanoid derivatives, (palmitoyloxy)octadecanoic acid derivatives, diacetylene derivatives, diphytanoyl derivatives, fluorinated lipids, brominated lipids, lipopolysaccharides;

one of the aforementioned lipids coupled to a functional ligand selected from the group comprising biotin, N-hydroxysuccinimide ester, nitrilotriacetic acid-nickel, amine, carboxylic acid, maleimides, aromatic maleimid, dithiopyridinyl, pyridyl disulfide, pyridyldithiopropionate, N-benzylguanine, cyanuric chloride, carboxyacyl, cyanur, folate, square, galloyl, glycan, thiol, arginylglycylaspartic acid, a fluorescent dye molecule, a magnetic resonance imaging reagent, a chelator; and one of the aforementioned lipids coupled to polyethyleneglycol with a molecular weight comprised between 350 and 50,000 g/mole.

A particular embodiment of the present invention is directed to a method for producing synthetic extracellular vesicles comprising:

a) providing a water phase comprising at least two lipids, and one or more extracellular vesicle associated proteins, or fragments thereof, wherein the at least two lipids are a negative charged lipid, and a lipid coupled to a functional ligand for protein conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

d') removing the polymer shell from the polymer shell-stabilized synthetic extracellular vesicles obtained in step d) by adding a surfactant; and e) purifying the synthetic extracellular vesicles by centrifugation;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, the synthetic extracellular vesicles have a hydrodynamic radius between 70 nm and 5000 nm, and wherein the water phase of step a) comprises at least two lipids selected from the group comprising:

a neutral lipid selected from the group comprising ceramide, sphingomyelin, cephalin, cholesterol, cerebrosides, diacylglycerols, phosphatidylcholines, lysophosphatidylcholines, phosphatidylethanolamines, lysophosphatidylethanolamine, lysoethanolamines, inverted headgroup lipids, sphingosins, sterol-modified phospholipids, ether ester lipids, diether lipids, vinyl ether (plasmalogen);

an anionic lipid selected from the group comprising phosphatidic acids, lysophosphatidic acid derivatives, phosphatidylglycerols, lysophosphatidylglycerols, phosphatidylserines, lysophosphatidylserines, phosphatidylinositols, phosphatidylinositolphosphates, cardiolipins, Bis(Monoacylglycero)Phosphate derivatives;

a cationic lipid selected from the group comprising dioleyl-N,N-dimethylammonium chloride; N-(2,3-dioleyloxy)propyl)-N,N,N-trimethylammonium chloride; N,N-distearyl-N,N-dimethylammonium bromide; N-(2,3-dioleyloxy)propyl)-N,N,N-trimethylammonium chloride; 3β-(N-(N',N'-dimethylaminoethane)-carbamoyl)cholesterol; 1,2-dimyristyloxypropyl-3-dimethyl-hydroxy ethyl ammonium bromide; 2,3-dioleyloxy-N-[2(sperminecarboxamido)ethyl]-N,N-dimethyl-1-propanaminium trifluoroacetate; dioctadecylamidoglycyl carboxyspermine; N-(2,3-dioleyloxy)propyl)-N,N-dimethylammonium chloride and 1,2-Dioleoyl-3-dimethylammonium-propane;

a pH-sensitive lipid selected from the group comprising lipid N-(4-carboxybenzyl)-N,N-dimethyl-2,3-bis (oleoyloxy)propan-1-aminium, 1,2-distearoyl-3-dimethylammonium-propane, 1,2-dipalmitoyl-sn-glycero succinate, 1,2-dioleoyl-sn-glycero-3-succinate, N-palmitoyl homocysteine; a photoswitchable lipid;

acylglycine derivatives, prenol derivatives, prostaglandine derivatives, glycosylated diacyl glycerols, eicosanoid derivatives, (palmitoyloxy)octadecanoic acid derivatives, diacetylene derivatives, diphytanoyl derivatives, fluorinated lipids, brominated lipids, lipopolysaccharides;

one of the aforementioned lipids coupled to a functional ligand selected from the group comprising biotin, N-hydroxysuccinimide ester, nitrilotriacetic acid-nickel, amine, carboxylic acid, maleimides, aromatic maleimid, dithiopyridinyl, pyridyl disulfide, pyridyldithiopropionate, N-benzylguanine, cyanuric chloride, carboxyacyl, cyanur, folate, square, galloyl, glycan, thiol, arginylglycylaspartic acid, a fluorescent dye molecule, a magnetic resonance imaging reagent, a chelator; and one of the aforementioned lipids coupled to polyethyleneglycol with a molecular weight comprised between 350 and 50,000 g/mole.

A further particular embodiment of the present invention is directed to a method for producing synthetic extracellular vesicles comprising:

a) providing a water phase comprising at least two lipids, one or more extracellular vesicle associated proteins, or fragments thereof, and one or more nucleic acid molecules, wherein the at least two lipids are a negative charged lipid, and a lipid coupled to a functional ligand for protein conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

d') removing the polymer shell from the polymer shell-stabilized synthetic extracellular vesicles obtained in step d) by adding a surfactant; and e) purifying the synthetic extracellular vesicles by centrifugation;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, the synthetic extracellular vesicles have a hydrodynamic radius between 70 nm and 5000 nm, and wherein the water phase of step a) comprises at least two lipids selected from the group comprising:

a neutral lipid selected from the group comprising ceramide, sphingomyelin, cephalin, cholesterol, cerebrosides, diacylglycerols, phosphatidylcholines, lysophosphatidylcholines, phosphatidylethanolamines, lysophosphatidylethanolamine, lysoethanolamines, inverted headgroup lipids, sphingosins, sterol-modified phospholipids, ether ester lipids, diether lipids, vinyl ether (plasmalogen);

an anionic lipid selected from the group comprising phosphatidic acids, lysophosphatidic acid derivatives, phosphatidylglycerols, lysophosphatidylglycerols, phosphatidylserines, lysophosphatidylserines, phosphatidylinositols, phosphatidylinositolphosphates, cardiolipins, Bis(Monoacylglycero)Phosphate derivatives;

a cationic lipid selected from the group comprising dioleyl-N,N-dimethylammonium chloride; N-(2,3-dioleyloxy)propyl)-N,N,N-trimethylammonium chloride; N,N-distearyl-N,N-dimethylammonium bromide; N-(2,3-dioleyloxy)propyl)-N,N,N-trimethylammonium chloride; 3β-(N-(N',N'-dimethylaminoethane)-carbamoyl)cholesterol; 1,2-dimyristyloxypropyl-3-dimethyl-hydroxy ethyl ammonium bromide; 2,3-dioleyloxy-N-[2(sperminecarboxamido)ethyl]-N,N-dimethyl-1-propanaminium trifluoroacetate; dioctadecylamidoglycyl carboxyspermine; N-(2,3-dioleyloxy)propyl)-N,N-dimethylammonium chloride and 1,2-Dioleoyl-3-dimethylammonium-propane;

a pH-sensitive lipid selected from the group comprising lipid N-(4-carboxybenzyl)-N,N-dimethyl-2,3-bis (oleoyloxy)propan-1-aminium, 1,2-distearoyl-3-dimethylammonium-propane, 1,2-dipalmitoyl-sn-glycero-3-succinate, 1,2-dioleoyl-sn-glycero-3-succinate, N-palmitoyl homocysteine; a photoswitchable lipid;

acylglycine derivatives, prenol derivatives, prostaglandine derivatives, glycosylated diacyl glycerols, eicosanoid derivatives, (palmitoyloxy)octadecanoic acid derivatives, diacetylene derivatives, diphytanoyl derivatives, fluorinated lipids, brominated lipids, lipopolysaccharides;

one of the aforementioned lipids coupled to a functional ligand selected from the group comprising biotin, N-hydroxysuccinimide ester, nitrilotriacetic acid-nickel, amine, carboxylic acid, maleimides, aromatic maleimid, dithiopyridinyl, pyridyl disulfide, pyridyldithiopropionate, N-benzylguanine, cyanuric chloride, carboxyacyl, cyanur, folate, square, galloyl, glycan, thiol, arginylglycylaspartic acid, a fluorescent dye molecule, a magnetic resonance imaging reagent, a chelator; and one of the aforementioned lipids coupled to polyethyleneglycol with a molecular weight comprised between 350 and 50,000 g/mole.

Suitable Copolymer to Stabilize the Extracellular Vesicles

In order to allow a good dispersion of the polymer shell stabilized vesicles in the oil phase and in order to allow a good dispersion of the lipid containing aqueous phase within the polymer shell of the vesicle, it is preferred that the polymer shell is made of an amphiphilic copolymer with a hydrophobic end arranged at the outer side and a hydrophilic end arranged at the inner side of the polymer shell.

This may be achieved by forming the polymer shell of the extracellular vesicle, from a diblock copolymer, or a triblock copolymer, to form a water-in-oil droplet.

Good results are particularly obtained, if the polymer shell of the droplet is made of a diblock copolymer consisting of an hydrophobic block arranged at the outer side and a hydrophilic block arranged at the inner side of the polymer shell, or a triblock copolymer consisting of two hydrophobic polymer blocks and a hydrophilic polymer block, and wherein the oil phase comprises a fluorosurfactant triblock, so that the one or two hydrophobic polymer blocks are arranged at the outer side and the hydrophilic polymer block is arranged at the inner side of the polymer shell.

The hydrophobic block may be, but is not restricted to members, e.g. selected from the group consisting of perfluorinated polymers, such as perfluorinated polyethers, polystyrene or poly(olefin oxides), such as poly(propylene oxide), whereas the hydrophilic block may be selected e.g. from polyether glycols, polyetheramine, polyacrylate acid, polymethylacrylate acid or poly[poly(ethylene glycol) methyl ether methacrylate].

Likewise, good results are obtained, if the polymer shell of the droplet is made of a triblock copolymer consisting of two hydrophobic perfluorinated polymer end blocks and therebetween a hydrophilic polyether glycol block, wherein the triblock copolymer is folded so that the hydrophobic perfluorinated polymer blocks are arranged at the outer side and that the hydrophilic polyether glycol block is arranged at the inner side of the polymer shell. Examples for the hydrophobic blocks and the hydrophilic blocks are the same as those mentioned above.

Preferably, the perfluorinated polymer block is a perfluorinated polyether block (PFPE) and more preferably a perfluorinated polyether block having a weight average molecular weight of 1,000 to 10,000 g/mol. Likewise preferably, the polyether glycol (PEG) and polyetheramine (JEFFAMINE) blocks have preferably a weight average molecular weight of 100 to 50,000 g/mol. More specifically, suitable examples for the respective copolymers are PFPE-carboxylic acid (Krytox, MW 2500 or 7000 g/mol) and suitable examples for the respective diblock copolymers are PFPE (7000 g/mol)-PEG (1400 g/mol), PFPE (7000 g/mol)-PEG (600 g/mol), PFPE (2500 g/mol)-PEG (600 g/mol), PFPE (4000 g/mol)-PEG (600 g/mol), PFPE (4000 g/mol)-PEG (1400 g/mol), PFPE (2000 g/mol)-PEG (600 g/mol), PFPE (7000 g/mol)-JEFFAMINE (600 g/mol), PFPE (7000 g/mol)-JEFFAMINE (900 g/mol), PFPE (2500 g/mol)-JEFFAMINE (600 g/mol), PFPE (2500 g/mol)-JEFFAMINE (900 g/mol), PFPE (4000 g/mol)-JEFFAMINE (900 g/mol), PFPE (2500 g/mol)-JEFFAMINE (600 g/mol), PFPE (2000 g/mol)-JEFFAMINE (600 g/mol), PFPE (2000 g/mol)-JEFFAMINE (900 g/mol) and suitable examples for the respective triblock copolymers are PFPE (7000 g/mol)-PEG (1400 g/mol)-

PFPE (7000 g/mol), PFPE (7000 g/mol)-PEG (600 g/mol)-PFPE (7000 g/mol), PFPE (4000 g/mol)-PEG (1400 g/mol)-PFPE (4000 g/mol) PFPE (2500 g/mol)-PEG (600 g/mol)-PFPE (2500 g/mol), PFPE (2000 g/mol)-PEG (600 g/mol)-PFPE (2000 g/mol), PFPE (7000 g/mol)-JEFFAMINE (900 g/mol)-PFPE (7000 g/mol) PFPE (7000 g/mol)-JEFFAMINE (600 g/mol)-PFPE (7000 g/mol), PFPE (4000 g/mol)-JEFFAMINE (900 g/mol)-PFPE (4000 g/mol), PFPE (4000 g/mol)-JEFFAMINE (600 g/mol)-PFPE (4000 g/mol), PFPE (2500 g/mol)-JEFFAMINE (900 g/mol)-PFPE (2500 g/mol), PFPE (2500 g/mol)-JEFFAMINE (600 g/mol)-PFPE (2500 g/mol), PFPE (2000 g/mol)-JEFFAMINE (900 g/mol)-PFPE (2000 g/mol) and PFPE (2000 g/mol)-JEFFAMINE (600 g/mol)-PFPE (2000 g/mol). The molecular weight is determined by gel permeation chromatography using a polystyrene standard.

Therefore, the present invention is directed to a method for producing synthetic extracellular vesicles comprising:
a) providing a water phase comprising at least two lipids, and one or more extracellular vesicle associated proteins, or fragments thereof, wherein the at least two lipids are a negative charged lipid, and a lipid coupled to a functional ligand for conjugation to an extracellular vesicle associated protein;
b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;
c) combining said water phase and said oil phase;
d) producing polymer shell-stabilized synthetic extracellular vesicles by emulsifying the combined phases of step c) using a mechanic or electronic emulsifier;
wherein the amphiphilic copolymer forms a polymer shell stabilizing the synthetic extracellular vesicle,
wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, and
wherein the synthetic extracellular vesicles have a hydrodynamic radius between 70 nm and 5000 nm.

Moreover, the present invention is directed to a method for producing synthetic extracellular vesicles comprising:
a) providing a water phase comprising at least two lipids, one or more extracellular vesicle associated proteins, or fragments thereof, and one or more nucleic acid molecules, wherein the at least two lipids are a negative charged lipid, and a lipid coupled to a functional ligand for conjugation to an extracellular vesicle associated protein;
b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;
c) combining said water phase and said oil phase;
d) producing polymer shell-stabilized synthetic extracellular vesicles by emulsifying the combined phases of step c) using a mechanic or electronic emulsifier;
wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, and wherein the synthetic extracellular vesicles have a hydrodynamic radius between 70 nm and 5000 nm.

In one embodiment, the present invention is directed to a method for producing synthetic extracellular vesicles comprising:

a) providing a water phase comprising at least two lipids, and one or more extracellular vesicle associated proteins, or fragments thereof, wherein the at least two lipids are a negative charged lipid, and a lipid coupled to a functional ligand for conjugation to an extracellular vesicle associated protein;

b) providing an amphiphilic copolymer dissolved in an oil phase wherein the amphiphilic copolymer is a triblock copolymer consisting of two polyether glycol end blocks and one perfluorinated polymer end block, or of a triblock copolymer consisting of two perfluorinated polymer end blocks and one polyether glycol block, or of a diblock copolymer consisting of one perfluorinated polymer end block and a polyether glycol block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

wherein the amphiphilic copolymer forms a polymer shell stabilizing the synthetic extracellular vesicle, wherein the triblock or diblock copolymer is folded so that the perfluorinated polymer end blocks are arranged at the outer side and that the polyether glycol block is arranged at the inner side of the polymer shell, wherein the vesicles are homogenous in size showing a coefficient of variation in size lower than 13%, and wherein the synthetic extracellular vesicles have a hydrodynamic radius between 70 nm and 5000 nm.

In one embodiment, the present invention is directed to a method for producing synthetic extracellular vesicles comprising:

a) providing a water phase comprising at least two lipids, one or more extracellular vesicle associated proteins, or fragments thereof, and one or more nucleic acid molecules, wherein the at least two lipids are a negative charged lipid, and a lipid coupled to a functional ligand for conjugation to an extracellular vesicle associated protein;

b) providing an amphiphilic copolymer dissolved in an oil phase wherein the amphiphilic copolymer is a triblock copolymer consisting of two polyether glycol end blocks and one perfluorinated polymer end block, or of a triblock copolymer consisting of two perfluorinated polymer end blocks and one polyether glycol block, or of a diblock copolymer consisting of one perfluorinated polymer end block and a polyether glycol block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier;

wherein the amphiphilic copolymer forms a polymer shell stabilizing the synthetic extracellular vesicle, wherein the triblock or diblock copolymer is folded so that the perfluorinated polymer end blocks are arranged at the outer side and that the polyether glycol block is arranged at the inner side of the polymer shell, wherein the vesicles are homogenous in size showing a coefficient of variation in size lower than 13%, and wherein the synthetic extracellular vesicles have a hydrodynamic radius between 70 nm and 5000 nm.

Emulsification Conditions Influencing Extracellular Vesicle Dimension

One embodiment of the present invention is directed to a method for producing synthetic extracellular vesicles comprising:

a) providing a water phase comprising at least two lipids, and one or more extracellular vesicle associated proteins, or fragments thereof, wherein the at least two lipids are a negative charged lipid, and a lipid coupled to a functional ligand for conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier for at least 5 seconds at speed higher than 1,000 rpm;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, and wherein the synthetic extracellular vesicles have a hydrodynamic radius between 70 nm and 5000 nm.

Moreover, the present invention is directed to a method for producing synthetic extracellular vesicles comprising:

a) providing a water phase comprising at least two lipids, one or more extracellular vesicle associated proteins, or fragments thereof, and one or more nucleic acid molecules, wherein the at least two lipids are a negative charged lipid, and a lipid coupled to a functional ligand for conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier for at least 5 seconds at speed higher than 1,000 rpm;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, and wherein the synthetic extracellular vesicles have a hydrodynamic radius between 70 nm and 5000 nm.

The emulsification procedure is usually performed with a mechanically or electronic emulsifier, for at least 5 seconds at speed higher than 1,000 rpm. This procedure holds the considerable advantage to regulate the vesicle dimension by changing the time and shear stress of emulsification. As shown in Example 2, synthetic extracellular vesicles radii between 292 nm±12 nm, (coefficient of variation (CV) =4.1%; n=3) were obtained by emulsification for 30 sec at 30,000 rpm and radii of 627 nm±15 nm, (CV=2.4%; n=3) were obtained by emulsification for 30 sec at 14,000 rpm.

Notably, this procedure allowed obtaining extracellular vesicles very homogenous in size, as the coefficient of variation of the synthetized extracellular vesicles varied between 2.4%, for vesicles of size 292 nm±12 nm, and 4.1% for vesicles of size 627 nm±15 nm, which are variation levels much lower than observed in the natural exosome samples. Indeed the variation value of commercial K562 exosomes was CV=42.5% for dimensions 468 nm±199 nm, (n=3), and that of exosomes isolated from conditioned K562 cell culture medium was CV=13.3%, for dimensions 240 nm±32 nm (n=3).

Another embodiment of the present invention is directed to a method for producing synthetic extracellular vesicles comprising:

a) providing a water phase comprising at least two lipids, and one or more extracellular vesicle associated proteins, or fragments thereof, wherein the at least two lipids are a negative charged lipid, and a lipid coupled to a functional ligand for conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier for at least 20 seconds at speed higher than 10,000 rpm;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, and wherein the synthetic extracellular vesicles have a hydrodynamic radius between 70 nm and 5000 nm.

Another particular embodiment of the present invention is directed to a method for producing synthetic extracellular vesicles comprising:

a) providing a water phase comprising at least two lipids, one or more extracellular vesicle associated proteins, or fragments thereof, and one or more nucleic acid molecules, wherein the at least two lipids are a negative charged lipid, and a lipid coupled to a functional ligand for conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier for at least 20 seconds at speed higher than 10,000 rpm;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, and wherein the synthetic extracellular vesicles have a hydrodynamic radius between 70 nm and 5000 nm.

A further embodiment of the present invention is directed to a method for producing synthetic extracellular vesicles comprising:

a) providing a water phase comprising at least two lipids, and one or more extracellular vesicle associated proteins, or fragments thereof, wherein the at least two lipids are a negative charged lipid, and a lipid coupled to a functional ligand for conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier for at least 20 seconds at speed higher than 14,000 rpm;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, and wherein the synthetic extracellular vesicles have a hydrodynamic radius between 70 nm and 5000 nm.

A further particular embodiment of the present invention is directed to a method for producing synthetic extracellular vesicles comprising:

a) providing a water phase comprising at least two lipids, one or more extracellular vesicle associated proteins, or fragments thereof, and one or more nucleic acid molecules, wherein the at least two lipids are a negative charged lipid, and a lipid coupled to a functional ligand for conjugation to an extracellular vesicle associated protein;

b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;

c) combining said water phase and said oil phase;

d) producing polymer shell-stabilized synthetic extracellular vesicles by emulsifying the combined phases of step c) using a mechanic or electronic emulsifier for at least 20 seconds at speed higher than 14,000 rpm;

wherein the amphiphilic copolymer forms a polymer shell stabilizing the synthetic extracellular vesicle, wherein the one or two hydrophobic polymer blocks are arranged at the outer side and the hydrophilic polymer block is arranged at the inner side of the polymer shell, wherein the vesicles are homogenous in size showing a coefficient of variation in size lower than 13%, and wherein the synthetic extracellular vesicles have a hydrodynamic radius between 70 nm and 5000 nm.

Composition of Synthetic Extracellular Vesicles

A particular embodiment of the present invention is directed to a synthetic extracellular vesicle having a diameter between 70 nm and 5000 nm, comprising:

a lipid bilayer comprising at least two lipids selected from the group comprising:

a neutral lipid selected from the group comprising ceramide, sphingomyelin, cephalin, cholesterol, cerebrosides, diacylglycerols, phosphatidylcholines, lysophosphatidylcholines, phosphatidylethanolamines, lysophosphatidylethanolamine, lysoethanolamines, inverted headgroup lipids, sphingosins, sterol-modified phospholipids, ether ester lipids, diether lipids, vinyl ether (plasmalogen);

an anionic lipid selected from the group comprising phosphatidic acids, lysophosphatidic acid derivatives, phosphatidylglycerols, lysophosphatidylglycerols, phosphatidylserines, lysophosphatidylserines, phosphatidylinositols, phosphatidylinositolphosphates, cardiolipins, Bis(Monoacylglycero)Phosphate derivatives;

a cationic lipid selected from the group comprising dioleyl-N,N-dimethylammonium chloride; N-(2,3-dioleyloxy)propyl)-N,N,N-trimethylammonium chloride; N,N-distearyl-N,N-dimethylammonium bromide; N-(2,3-dioleyloxy)propyl)-N,N,N-trimethylammonium chloride; 3β-(N-(N',N'-dimethylaminoethane)-carbamoyl)cholesterol; 1,2-dimyristyloxypropyl-3-dimethyl-hydroxy ethyl ammonium bromide; 2,3-dioleyloxy-N-[2(sperminecarboxamido)ethyl]-N,N-dimethyl-1-propanaminium trifluoroacetate; dioctadecylamidoglycyl carboxyspermine; N-(2,3-dioleyloxy)propyl)-N,N-dimethylammonium chloride and 1,2-Dioleoyl-3-dimethylammonium-propane;

a pH-sensitive lipid selected from the group comprising lipid N-(4-carboxybenzyl)-N,N-dimethyl-2,3-bis (oleoyloxy)propan-1-aminium, 1,2-distearoyl-3-dimethylammonium-propane, 1,2-dipalmitoyl-sn-glycero-3-succinate, 1,2-dioleoyl-sn-glycero-3-succinate, N-palmitoyl homocysteine; a photoswitchable lipid;

acylglycine derivatives, prenol derivatives, prostaglandine derivatives, glycosylated diacyl glycerols, eicosanoid derivatives, (palmitoyloxy)octadecanoic acid derivatives, diacetylene derivatives, diphytanoyl derivatives, fluorinated lipids, brominated lipids, lipopolysaccharides;

one of the aforementioned lipids coupled to a functional ligand selected from the group comprising biotin, N-hydroxysuccinimide ester, nitrilotriacetic acid-nickel, amine, carboxylic acid, maleimides, aromatic maleimid, dithiopyridinyl, pyridyl disulfide, pyridyldithiopropionate, N-benzylguanine, cyanuric chloride, carboxyacyl, cyanur, folate, square, galloyl, glycan, thiol, arginylglycylaspartic acid, a fluorescent dye molecule, a magnetic resonance imaging reagent, a chelator;

one of the aforementioned lipids coupled to polyethyleneglycol with a molecular weight comprised between 350 and 50,000 g/mole; and one or more transmembrane proteins selected from the group comprising tetraspanin proteins CD9, CD37, CD47, CD53, CD63, CD81, CD82, CD151, Tspan8, heterotrimeric G protein subunit alpha (GNA), integrin α-chains, integrin β-chains, transferrin receptor 1 (TfR1, CD71), transferrin receptor 2 (TFR2), lysosome associated membrane proteins (LAMP1, LAMP2), heparan sulfate proteoglycans, syndecans, extracellular matrix metalloproteinase inducer (EMMPRIN, BSG), A Disintegrin And Metalloproteinase Domain 10 (ADAM10), CD3, CD11c, CD14, CD29, CD31, CD41, CD42a, CD44, CD45, CD55, CD59, CD73, CD80, CD86, CD90, sonic hedgehog (SHH), major histocompatibility complex I (MHCI), major histocompatibility complex II (MHCII), epidermal growth factor receptor 2 (ERBB2), epithelial cell adhesion molecule (EpCAM), glycophorin A (GYPA); acetylcholinesterase S and E (AChE-S, AChE-E), amyloid beta precursor protein (APP), multidrug resistance-associated protein 1 (ABCC1), intercellular adhesion molecule 1 (CD50, ICAM-1), stem cells antigen-1 (Sca-1), protein complexes endosomal sorting complexes required for transport ESCRT-I, ESCRT-II, and ESCRT-III, tumour susceptibility gene 101 (TSG101), charged multivesicular body protein (CHMP), Apoptosis-Linked Gene 2-Interacting Protein X (ALIX), vacuolar protein sorting 4 homolog A 4A and 4B, arrestin domain-containing protein (ARRDC1), flotillin-1, flotillin-2; caveolins, EH-domain containing 1-4 (EHD1-EHD4), Ras homolog family member A (RHOA), annexins, heat shock proteins, ADP-ribosylation factor 6 (ARF6), syntenin, microtubule-associated protein Tau (MAPT), cytokines, growth factors, interleukins, milk fat globule-EGF factor 8 protein (MFGE8), adhesion proteins, extracellular matrix proteins, nicotinamide phosphoribosyltransferase, signal transduction proteins, Wnta, Wntb, Fas, Fas Ligand (FasL), RANK, RANK Ligand (RANKL), indolamin-2,3-dioxygenase, cytotoxic T-lymphocyte-associated protein 4-immunoglobulin fusion protein, tumor necrosis factor-related apoptosis-inducing ligand, histone proteins, lamin A/C, inner membrane mitochondrial protein (IMMT), cytochrome C-1 (CYC1), mitochondrial import receptor subunit TOM20, calnexin, heat shock protein 90 kDa beta (Grp94), member 1 (HSP90B1), heat shock 70 kDa protein 5 (HSPA5), Golgin A2 (GM130, GOLGA2), Autophagy Related 9A (ATG9A), actinin1, actinin4 (ACTN1, ACTN4), cytokeratin 18 (KRT18), or a fragment thereof.

A more particular embodiment of the present invention is directed to a synthetic extracellular vesicle having a hydrodynamic radius between 70 nm and 5000 nm, comprising:

a lipid bilayer comprising at least two lipids selected from the group comprising:

a neutral lipid selected from the group comprising ceramide, sphingomyelin, cephalin, cholesterol, cerebrosides, diacylglycerols, phosphatidylcholines, lysophosphatidylcholines, phosphatidylethanolamines, lysophosphatidylethanolamine, lysoethanolamines, inverted headgroup lipids, sphingosins, sterol-modified phospholipids, ether ester lipids, diether lipids, vinyl ether (plasmalogen);

an anionic lipid selected from the group comprising phosphatidic acids, lysophosphatidic acid derivatives, phosphatidylglycerols, lysophosphatidylglycerols, phosphatidylserines, lysophosphatidylserines, phosphatidylinositols, phosphatidylinositolphosphates, cardiolipins, Bis(Monoacylglycero)Phosphate derivatives;

a cationic lipid selected from the group comprising diol-eyl-N,N-dimethylammonium chloride; N-(2,3-dioleyloxy)propyl)-N,N,N-trimethylammonium chloride; N,N-distearyl-N,N-dimethylammonium bromide; N-(2,3-dioleyloxy)propyl)-N,N,N-trimethylammonium chloride; 3β-(N-(N',N'-dimethylaminoethane)-carbamoyl)cholesterol; 1,2-dimyristyloxypropyl-3-dimethyl-hydroxy ethyl ammonium bromide; 2,3-dioleyloxy-N-[2(sperminecarboxamido)ethyl]-N,N-dimethyl-1-propanaminium trifluoroacetate; dioctadecylamidoglycyl carboxyspermine; N-(2,3-dioleyloxy)propyl)-N,N-dimethylammonium chloride and 1,2-Dioleoyl-3-dimethylammonium-propane;

a pH-sensitive lipid selected from the group comprising lipid N-(4-carboxybenzyl)-N,N-dimethyl-2,3-bis (oleoyloxy)propan-1-aminium, 1,2-distearoyl-3-dimethylammonium-propane, 1,2-dipalmitoyl-sn-glycero-3-succinate, 1,2-dioleoyl-sn-glycero-3-succinate, N-palmitoyl homocysteine; a photoswitchable lipid;

acylglycine derivatives, prenol derivatives, prostaglandine derivatives, glycosylated diacyl glycerols, eicosanoid derivatives, (palmitoyloxy)octadecanoic acid derivatives, diacetylene derivatives, diphytanoyl derivatives, fluorinated lipids, brominated lipids, lipopolysaccharides;

one of the aforementioned lipids coupled to a functional ligand selected from the group comprising biotin, N-hydroxysuccinimide ester, nitrilotriacetic acid-nickel, amine, carboxylic acid, maleimides, aromatic maleimid, dithiopyridinyl, pyridyl disulfide, pyridyldithiopropionate, N-benzylguanine, cyanuric chloride, carboxyacyl, cyanur, folate, square, galloyl, glycan, thiol, arginylglycylaspartic acid, a fluorescent dye molecule, a magnetic resonance imaging reagent, a chelator;

one of the aforementioned lipids coupled to polyethyleneglycol with a molecular weight comprised between 350 and 50,000 g/mole;

one or more transmembrane proteins selected from the group comprising tetraspanin proteins CD9, CD37, CD47, CD53, CD63, CD81, CD82, CD151, Tspan8, heterotrimeric G protein subunit alpha (GNA), integrin α-chains, integrin β-chains, transferrin receptor 1 (TfR1, CD71), transferrin receptor 2 (TFR2), lysosome associated membrane proteins (LAMP1, LAMP2), heparan sulfate proteoglycans, syndecans, extracellular matrix metalloproteinase inducer (EMMPRIN, BSG), A Disintegrin And Metalloproteinase Domain 10 (ADAM10), CD3, CD11c, CD14, CD29, CD31, CD41, CD42a, CD44, CD45, CD55, CD59, CD73, CD80, CD86, CD90, sonic hedgehog (SHH), major histocompatibility complex I (MHCI), major histocompatibility complex II (MHCII), epidermal growth factor receptor 2 (ERBB2), epithelial cell adhesion molecule (Ep-CAM), glycophorin A (GYPA); acetylcholinesterase S and E (AChE-S, AChE-E), amyloid beta precursor protein (APP), multidrug resistance-associated protein 1 (ABCC1), intercellular adhesion molecule 1 (CD50, ICAM-1), stem cells antigen-1 (Sca-1), protein complexes endosomal sorting complexes required for transport ESCRT-I, ESCRT-II, and ESCRT-III, tumour susceptibility gene 101 (TSG101), charged multivesicular body protein (CHMP), Apoptosis-Linked Gene 2-Interacting Protein X (ALIX), vacuolar protein sorting 4 homolog A 4A and 4B, arrestin domain-containing protein (ARRDC1), flotillin-1, flotillin-2; caveolins, EH-domain containing 1-4 (EHD1-EHD4), Ras homolog family member A (RHOA), annexins, heat shock proteins, ADP-ribosylation factor 6 (ARF6), syntenin, microtubule-associated protein Tau (MAPT), cytokines, growth factors, interleukins, milk fat globule-EGF factor 8 protein (MFGE8), adhesion proteins, extracellular matrix proteins, nicotinamide phosphoribosyltransferase, signal transduction proteins, Wnta, Wntb, Fas, Fas Ligand (FasL), RANK, RANK Ligand (RANKL), indolamin-2,3-dioxygenase, cytotoxic T-lymphocyte-associated protein 4-immunoglobulin fusion protein, tumor necrosis factor-related apoptosis-inducing ligand, histone proteins, lamin A/C, inner membrane mitochondrial protein (IMMT), cytochrome C-1 (CYC1), mitochondrial import receptor subunit TOM20, calnexin, heat shock protein 90 kDa beta (Grp94), member 1 (HSP90B1), heat shock 70 kDa protein 5 (HSPA5), Golgin A2 (GM130, GOLGA2), Autophagy Related 9A (ATG9A), actinin1, actinin4 (ACTN1, ACTN4), cytokeratin 18 (KRT18), or a fragment thereof; and one or more nucleic acid molecules selected from the group comprising DNA, cDNA, mRNA, siRNA, antisense nucleotides, shRNA, piRNA, snRNA, lncRNA, PNA, left handed DNA, Clustered Regularly Interspaced Short Palindromic Repeats guide RNA, and miRNA.

A still more particular embodiment of the present invention is directed to a synthetic extracellular vesicle having a hydrodynamic radius between 70 nm and 5000 nm, comprising:

a lipid bilayer comprising at least two lipids selected from the group comprising:

a neutral lipid selected from the group comprising ceramide, sphingomyelin, cephalin, cholesterol, cerebrosides, diacylglycerols, phosphatidylcholines, lysophosphatidylcholines, phosphatidylethanolamines, lysophosphatidylethanolamine, lysoethanolamines, inverted headgroup lipids, sphingosins, sterol-modified phospholipids, ether ester lipids, diether lipids, vinyl ether (plasmalogen);

an anionic lipid selected from the group comprising phosphatidic acids, lysophosphatidic acid derivatives, phosphatidylglycerols, lysophosphatidylglycerols, phosphatidylserines, lysophosphatidylserines, phosphatidylinositols, phosphatidylinositolphosphates, cardiolipins, Bis(Monoacylglycero)Phosphate derivatives;

a cationic lipid selected from the group comprising diol-eyl-N,N-dimethylammonium chloride; N-(2,3-dioleyloxy)propyl)-N,N,N-trimethylammonium chloride; N,N-distearyl-N,N-dimethylammonium bromide; N-(2,3-dioleyloxy)propyl)-N,N,N-trimethylammonium chloride; 3β-(N-(N',N'-dimethylaminoethane)-carbamoyl)cholesterol; 1,2-dimyristyloxypropyl-3-dimethyl-hydroxy ethyl ammonium bromide; 2,3-dioleyloxy-N-[2(sperminecarboxamido)ethyl]-N,N-dimethyl-1-propanaminium trifluoroacetate; dioctadecylamidoglycyl carboxyspermine; N-(2,3-dioleyloxy)propyl)-N,N-dimethylammonium chloride and 1,2-Dioleoyl-3-dimethylammonium-propane;

a pH-sensitive lipid selected from the group comprising lipid N-(4-carboxybenzyl)-N,N-dimethyl-2,3-bis (oleoyloxy)propan-1-aminium, 1,2-distearoyl-3-dimethylammonium-propane, 1,2-dipalmitoyl-sn-glycero-3-succinate, 1,2-dioleoyl-sn-glycero-3-succinate, N-palmitoyl homocysteine; a photoswitchable lipid;

acylglycine derivatives, prenol derivatives, prostaglandine derivatives, glycosylated diacyl glycerols, eicosanoid derivatives, (palmitoyloxy)octadecanoic acid derivatives, diacetylene derivatives, diphytanoyl derivatives, fluorinated lipids, brominated lipids, lipopolysaccharides;

one of the aforementioned lipids coupled to a functional ligand selected from the group comprising biotin, N-hydroxysuccinimide ester, nitrilotriacetic acid-nickel, amine, carboxylic acid, maleimides, aromatic maleimid, dithiopyridinyl, pyridyl disulfide, pyridyldithiopropionate, N-benzylguanine, cyanuric chloride, carboxyacyl, cyanur, folate, square, galloyl, glycan, thiol, arginylglycylaspartic acid, a fluorescent dye molecule, a magnetic resonance imaging reagent, a chelator;

one of the aforementioned lipids coupled to polyethyleneglycol with a molecular weight comprised between 350 and 50,000 g/mole;

one or more transmembrane proteins selected from the group comprising tetraspanin proteins CD9, CD37, CD47, CD53, CD63, CD81, CD82, CD151, Tspan8, heterotrimeric G protein subunit alpha (GNA), integrin α-chains, integrin β-chains, transferrin receptor 1 (TfR1, CD71), transferrin receptor 2 (TFR2), lysosome associated membrane proteins (LAMP1, LAMP2), heparan sulfate proteoglycans, syndecans, extracellular matrix metalloproteinase inducer (EMMPRIN, BSG), A Disintegrin And Metalloproteinase Domain 10 (ADAM10), CD3, CD11c, CD14, CD29, CD31, CD41, CD42a, CD44, CD45, CD55, CD59, CD73, CD80, CD86, CD90, sonic hedgehog (SHH), major histocompatibility complex I (MHCI), major histocompatibility complex II (MHCII), epidermal growth factor receptor 2 (ERBB2), epithelial cell adhesion molecule (Ep-CAM), glycophorin A (GYPA); acetylcholinesterase S and E (AChE-S, AChE-E), amyloid beta precursor protein (APP), multidrug resistance-associated protein 1 (ABCC1), intercellular adhesion molecule 1 (CD50, ICAM-1), stem cells antigen-1 (Sca-1), protein complexes endosomal sorting complexes required for transport ESCRT-I, ESCRT-II, and ESCRT-III, tumour susceptibility gene 101 (TSG101), charged multivesicular body protein (CHMP), Apoptosis-Linked Gene 2-Interacting Protein X (ALIX), vacuolar protein sorting 4 homolog A 4A and 4B, arrestin domain-containing protein (ARRDC1), flotillin-1, flotillin-2; caveolins, EH-domain containing 1-4 (EHD1-EHD4), Ras homolog family member A (RHOA), annexins, heat shock proteins, ADP-ribosylation factor 6 (ARF6), syntenin, microtubule-associated protein Tau (MAPT), cytokines, growth factors, interleukins, milk fat globule-EGF factor 8 protein (MFGE8), adhesion proteins, extracellular matrix proteins, nicotinamide phosphoribosyltransferase, signal transduction proteins, Wnta, Wntb, Fas, Fas Ligand (FasL), RANK, RANK Ligand (RANKL), indolamin-2,3-dioxygenase, cytotoxic T-lymphocyte-associated protein 4-immunoglobulin fusion protein, tumor necrosis factor-related apoptosis-inducing ligand, histone proteins, lamin NC, inner membrane mitochondrial protein (IMMT), cytochrome C-1 (CYC1), mitochondrial import receptor subunit TOM20, calnexin, heat shock protein 90 kDa beta (Grp94), member 1 (HSP90B1), heat shock 70 kDa protein 5 (HSPA5), Golgin A2 (GM130, GOLGA2), Autophagy Related 9A (ATG9A), actinin1, actinin4 (ACTN1, ACTN4), cytokeratin 18 (KRT18), or a fragment thereof; and one or more nucleic acid molecules selected from the group comprising DNA, cDNA, mRNA, siRNA, antisense nucleotides, shRNA, piRNA, snRNA, lncRNA, PNA, left handed DNA, Clustered Regularly Interspaced Short Palindromic Repeats guide RNA, miRNA, wherein the miRNA is selected from the group comprising miR-17, miR-18a, miR-19a, miR-19b-1, miR-20a, miR-92a; miR-21, miR-30d-5p, miR-33b, miR-124, miR-125, miR-126, miR-130, miR-132, miR-133b, miR-140-5p, miR-191, miR-222, miR-451, miR-494, miR-575, miR-630, miR-638, miR-1202, miR-1207-5p, miR-1225-5p, miR-1268, miR-6087, miR-92a-3p-e, miR-K12-3, let-7a.

As mentioned above, in certain embodiments, the synthetic extracellular vesicle is an exosome. In certain embodiments, the synthetic extracellular vesicle is a microvesicle.

A particularly preferred embodiment of the present invention is directed to a synthetic extracellular vesicle between 70 nm and 5000 nm with the composition described above and specifically comprising:

a lipid bilayer comprising cholesterol, N-stearoyl-D-erythro-sphingosylphosphorylcholine (SM), 1,2-dioleoyl-sn-glycero-3-phosphocholine (DOPC), 1,2-dioleoyl-sn-glycero-3-phospho-L-serine (DOPS), 1,2-dioleoyl-sn-glycero-3-phospho-ethanolamine (DOPE), 1,2-dioleoyl-sn-glycero-3-phospho-rac-(1-glycerol) (DOPG), 1,2-dioleoyl-sn-glycero-3-phosphate (sodium salt) (PA), diacylglycerol, phosphatidylinositol, 1,2-dioleoyl-sn-glycero-3-phosphoethanolamine-N-(lissamine rhodamine B sulfonyl) (LissRhod PE), 1,2-dioleoyl-sn-glycero-3-[(N-(5-amino-1-carboxypentyl) iminodiacetic acid) succinyl] (nickel salt) (DGS-NTA ($Ni^{2+}$));

one or more nucleic acid molecules selected from the group comprising miRNA miR-21, miR-124, miR-125, miR-126, miR-130 and miR-132; and one or more transmembrane proteins selected from the group comprising tetraspanin proteins CD9, CD63 and CD81, or a fragment thereof.

Another particularly preferred embodiment of the present invention is directed to a synthetic extracellular vesicle between 70 nm and 5000 nm with the composition described above and specifically comprising:

one or more functional protein nicotinamide phosphoribosyltransferase, or a fragment thereof;

one or more transmembrane proteins selected from the group comprising tetraspanin proteins CD9, CD63 and CD81, or a fragment thereof;

one or more cytosolic proteins selected from the group comprising Apoptosis-Linked Gene 2-Interacting Protein X (ALIX), tumour susceptibility gene 101 protein (TSG101), or a fragment thereof; and wherein the synthetic extracellular vesicle does not comprise transferrin and albumin, or a fragment thereof.

Another particularly preferred embodiment of the present invention is directed to a synthetic extracellular vesicle between 70 nm and 5000 nm with the composition described above and specifically comprising:

one or more transmembrane proteins selected from the group comprising MHCII, CD80, and CD86, or a fragment thereof;

optionally one or more transmembrane proteins selected from the group comprising CD11c, MHCI, integrin α, integrin β-chains, ICAM-1, and CD71, or a fragment thereof; and one or more functional proteins selected from the group comprising cytokines, interleukins, interleukin 4, milk fat globule-EGF factor 8 protein (MFGE8), growth factors, Fas, Fas Ligand (FasL), indolamin-2,3-dioxygenase, cytotoxic T-lymphocyte-associated protein 4-immunoglobulin fusion protein (CTLA4-Ig), tumor necrosis factor-related apoptosis-inducing ligand (Apo2L, TRAIL), or a fragment thereof.

Another particularly preferred embodiment of the present invention is directed to a synthetic extracellular vesicle between 70 nm and 5000 nm with the composition described above and specifically comprising:

a lipid bilayer comprising 1,2-dioleoyl-sn-glycero-3-phosphocholine (DOPC), 1,2-dioleoyl-sn-glycero-3-phospho-rac-(1-glycerol) (DOPG), 1,2-dioleoyl-sn-glycero-3-phosphoethanolamine-N-(lissamine rhodamine B sulfonyl) (LissRhod PE), 1,2-dioleoyl-sn-glycero-3-[(N-(5-amino-1-carboxypentyl)iminodi-acetic acid) succinyl] (nickel salt) (DGS-NTA(Ni$^{2+}$));

functional protein Fas Ligand, or a fragment thereof; and optionally functional protein intercellular adhesion protein-1, or a fragment thereof.

Another particularly preferred embodiment of the present invention is directed to a synthetic extracellular vesicle between 70 nm and 5000 nm with the composition described above and specifically comprising:

a lipid bilayer comprising 1,2-dioleoyl-sn-glycero-3-phosphocholine (DOPC), 1,2-dioleoyl-sn-glycero-3-phospho-rac-(1-glycerol) (DOPG), 1,2-dioleoyl-sn-glycero-3-phosphoethanolamine-N-(lissamine rhodamine B sulfonyl) (LissRhod PE), 1,2-dioleoyl-sn-glycero-3-[(N-(5-amino carboxypentyl)iminodiacetic acid) succinyl] (nickel salt) (DGS-NTA(Ni$^{2+}$)); a fragment of functional protein Fas Ligand;

optionally functional protein intercellular adhesion protein-1, or a fragment thereof;

wherein the Fas Ligand fragment comprises amino acids Pro134-Leu281 (FasL protein ID NM_000639.1); and wherein the intercellular adhesion protein-1 fragment comprises amino acids 1-480 of ICAM-1 (protein ID P05362).

Another particularly preferred embodiment of the present invention is directed to a synthetic extracellular vesicle between 70 nm and 5000 nm specifically comprising:

one or more transmembrane proteins selected from the group comprising CD29, CD44, CD90, CD73, CD44, Sca-1, ora fragment thereof;

one or more transmembrane proteins selected from the group comprising tetraspanin proteins CD9, CD63, and CD81, or a fragment thereof;

one or more functional proteins selected from the group comprising Wnta and Wntb, or a fragment thereof;

at least one nucleic acid molecule selected from the group comprising miR-140-5p, miR-92a-3p-e;

one or more nucleic acid molecules selected from the group comprising miR-17, miR-18a, miR-19a, miR-19b-1, miR-20a, miR-92a, let-7a, miR-21, miR124, miR126, miR-133b, miR-191, miR-222, miR-494, miR-6087, miR-30d-5p; and optionally one or more nucleic acid molecules selected from the group comprising miR-33b, miR-451, miR- 575, miR-630, miR-638, miR-1202, miR-1207-5p, miR-1225-5p, miR-1268, miR-K12-3.

A further particularly preferred embodiment of the present invention is directed to a synthetic extracellular vesicle between 70 nm and 5000 nm specifically comprising:

a lipid bilayer comprising 1,2-dioleoyl-sn-glycero-3-phosphocholine (DOPC), 1,2-dioleoyl-sn-glycero-3-phospho-rac-(1-glycerol) (DOPG), 1,2-dioleoyl-sn-glycero-3-phosphoethanolamine-N-(lissamine rhodamine B sulfonyl) (LissRhod PE), 1,2-dioleoyl-sn-glycero-3-[(N-(5-amino carboxypentyl)iminodiacetic acid) succinyl] (nickel salt) (DGS-NTA(Ni$^{2+}$)); and functional protein RANK, or a fragment thereof.

A further more particularly preferred embodiment of the present invention is directed to a synthetic extracellular vesicle between 70 nm and 5000 nm specifically comprising:

a lipid bilayer comprising 1,2-dioleoyl-sn-glycero-3-phosphocholine (DOPC), 1,2-dioleoyl-sn-glycero-3-phospho-rac-(1-glycerol) (DOPG), 1,2-dioleoyl-sn-glycero-3-phosphoethanolamine-N-(lissamine rhodamine B sulfonyl) (LissRhod PE), 1,2-dioleoyl-sn-glycero-3-[(N-(5-amino-1-carboxypentyl)iminodi-acetic acid) succinyl] (nickel salt) (DGS-NTA(Ni$^{2+}$));

and a fragment of functional protein RANK, wherein said fragment of functional protein RANK comprises amino acids 31-214 (RANK protein ID O35305).

Uses of the Disclosed Extracellular Vesicles

The examples of the present invention show that the synthetic extracellular vesicles are able to deliver their protein and nucleic acid contents into target cells, thus affecting their gene expression, protein expression, signalling pathways and metabolism.

Thus, the inventive synthetic extracellular pathways can be used for therapy of a wide range of disorders by acting at cellular levels.

For example, it has been here shown that the synthetic extracellular vesicles resembling those of fibrocyte origin can stimulate epithelial cell proliferation, migration, and collagen deposition, ultimately leading to wound healing.

Therefore, one embodiment of the present invention is directed to a synthetic extracellular vesicle having a hydrodynamic radius between 70 nm and 5000 nm, comprising:

a lipid bilayer comprising at least two lipids selected from the group comprising:

a neutral lipid selected from the group comprising ceramide, sphingomyelin, cephalin, cholesterol, cerebrosides, diacylglycerols, phosphatidylcholines, lysophosphatidylcholines, phosphatidylethanolamines, lysophosphatidylethanolamine, lysoethanolamines, inverted headgroup lipids, sphingosins, sterol-modified phospholipids, ether ester lipids, diether lipids, vinyl ether (plasmalogen);

an anionic lipid selected from the group comprising phosphatidic acids, lysophosphatidic acid derivatives, phosphatidylglycerols, lysophosphatidylglycerols, phosphatidylserines, lysophosphatidylserines, phosphatidylinositols, phosphatidylinositolphosphates, cardiolipins, Bis(Monoacylglycero)Phosphate derivatives;

a cationic lipid selected from the group comprising dioleyl-N,N-dimethylammonium chloride; N-(2,3-dioleyloxy)propyl)-N,N,N-trimethylammonium chloride; N,N-distearyl-N,N-dimethylammonium bromide; N-(2,3-dioleyloxy)propyl)-N,N,N-trimethylammonium chloride; 3β-(N-(N',N'-dimethylaminoethane)-carbamoyl)cholesterol; 1,2-dimyristyloxypropyl-3-dimethyl-hydroxy ethyl ammonium bromide; 2,3- dioleyloxy-N-[2(sperminecarboxamido)ethyl]-N,N-dimethyl-1-propanaminium trifluoroacetate; dioctadecylamidoglycyl carboxyspermine; N-(2,3-dioleyloxy)propyl)-N,N-dimethylammonium chloride and 1,2-Dioleoyl-3-dimethylammonium-propane;

a pH-sensitive lipid selected from the group comprising lipid N-(4-carboxybenzyl)-N,N-dimethyl-2,3-bis(oleoyloxy)propan-1-aminium, 1,2-distearoyl-3-dimethylammonium-propane, 1,2-dipalmitoyl-sn-glycero-3-succinate, 1,2-dioleoyl-sn-glycero-3-succinate, N-palmitoyl homocysteine; a photoswitchable lipid;

acylglycine derivatives, prenol derivatives, prostaglandine derivatives, glycosylated diacyl glycerols, eicosanoid derivatives, (palmitoyloxy)octadecanoic acid derivatives, diacetylene derivatives, diphytanoyl derivatives, fluorinated lipids, brominated lipids, lipopolysaccharides;

one of the aforementioned lipids coupled to a functional ligand selected from the group comprising biotin, N-hydroxysuccinimide ester, nitrilotriacetic acid-nickel, amine, carboxylic acid, maleimides, aromatic maleimid, dithiopyridinyl, pyridyl disulfide, pyridyldithiopropionate, N-benzylguanine, cyanuric chloride, carboxyacyl, cyanur, folate, square, galloyl, glycan, thiol, arginylglycylaspartic acid, a fluorescent dye molecule, a magnetic resonance imaging reagent, a chelator;

one of the aforementioned lipids coupled to polyethyleneglycol with a molecular weight comprised between 350 and 50,000 g/mole; and one or more transmembrane proteins selected from the group comprising tetraspanin proteins CD9, CD37, CD47, CD53, CD63, CD81, CD82, CD151, Tspan8, heterotrimeric G protein subunit alpha (GNA), integrin α-chains, integrin β-chains, transferrin receptor 1 (TfR1, CD71), transferrin receptor 2 (TFR2), lysosome associated membrane proteins (LAMP1, LAMP2), heparan sulfate proteoglycans, syndecans, extracellular matrix metalloproteinase inducer (EMMPRIN, BSG), A Disintegrin And Metalloproteinase Domain 10 (ADAM10), CD3, CD11c, CD14, CD29, CD31, CD41, CD42a, CD44, CD45, CD50 (intercellular adhesion molecule 1, ICAM-1), CD55, CD59, CD73, CD80, CD86, CD90, sonic hedgehog (SHH), major histocompatibility complex I (MHCI), major histocompatibility complex II (MHCII), epidermal growth factor receptor 2 (ERBB2), epithelial cell adhesion molecule (Ep-CAM), glycophorin A (GYPA); acetylcholinesterase S and E (AChE-S, AChE-E), amyloid beta precursor protein (APP), multidrug resistance-associated protein 1 (ABCC1), stem cells antigen-1 (Sca-1), protein complexes endosomal sorting complexes required for transport ESCRT-I, ESCRT-II, and ESCRT-III, tumour susceptibility gene 101 (TSG101), charged multivesicular body protein (CHMP), Apoptosis-Linked Gene 2-Interacting Protein X (ALIX), vacuolar protein sorting 4 homolog A 4A and 4B, arrestin domain-containing protein (ARRDC1), flotillin-1, flotillin-2; caveolins, EH-domain containing 1-4 (EHD1-EHD4), Ras homolog family member A (RHOA), annexins, heat shock proteins, ADP-ribosylation factor 6 (ARF6), syntenin, microtubule-associated protein Tau (MAPT), cytokines, growth factors, interleukins, milk fat globule-EGF factor 8 protein (MFGE8), adhesion proteins, extracellular matrix proteins, nicotinamide phosphoribosyltransferase, signal transduction proteins, Wnta, Wntb, Fas, Fas Ligand (FasL), RANK, RANK Ligand (RANKL), indolamin-2,3-dioxygenase, cytotoxic T-lymphocyte-associated protein 4-immunoglobulin fusion protein, tumor necrosis factor-related apoptosis-inducing ligand, histone proteins, lamin NC, inner membrane mitochondrial protein (IMMT), cytochrome C-1 (CYC1), mitochondrial import receptor subunit TOM20, calnexin, heat shock protein 90 kDa beta (Grp94), member 1 (HSP90B1), heat shock 70 kDa protein 5 (HSPA5), Golgin A2 (GM130, GOLGA2), Autophagy Related 9A (ATG9A), actinin1, actinin4 (ACTN1, ACTN4), cytokeratin 18 (KRT18), or a fragment thereof;

for use in the treatment of a disorder selected from the group comprising inflammation, cancer, rheumatic disorder, severe graft versus host disease, osteoarthritis, cardiovascular disorder, epithelial diseases, neurodegenerative disorders, autoimmune disorders, bone and cartilage disorders, osteoporosis, renal osteodystrophy, Paget's disease of bone, osteopetrosis, rickets, neurological disorders, intoxication, neuroendocrinology disorders, endocrinology disorders, genetic disorders, infectious diseases, dental disorders, cosmetic procedures, coagulation disorders, dermatoses, diabetes, age-associated disorders.

A particular embodiment of the present invention is directed to a synthetic extracellular vesicle having a hydrodynamic radius between 70 nm and 5000 nm, comprising:

a lipid bilayer comprising at least two lipids selected from the group a neutral lipid selected from the group comprising ceramide, sphingomyelin, cephalin, cholesterol, cerebrosides, diacylglycerols, phosphatidylcholines, lysophosphatidylcholines, phosphatidylethanolamines, lysophosphatidylethanolamine, lysoethanolamines, inverted headgroup lipids, sphingosins, sterol-modified phospholipids, ether ester lipids, diether lipids, vinyl ether (plasmalogen);

an anionic lipid selected from the group comprising phosphatidic acids, lysophosphatidic acid derivatives, phosphatidylglycerols, lysophosphatidylglycerols, phosphatidylserines, lysophosphatidylserines, phosphatidylinositols, phosphatidylinositolphosphates, cardiolipins, Bis(Monoacylglycero)Phosphate derivatives;

a cationic lipid selected from the group comprising dioleyl-N,N-dimethylammonium chloride; N-(2,3-dioleyloxy)propyl)-N,N,N-trimethylammonium chloride; N,N-distearyl-N,N-dimethylammonium bromide; N-(2,3-dioleyloxy)propyl)-N,N,N-trimethylammonium chloride; 3β-(N-(N',N'-dimethylaminoethane)-carbamoyl)cholesterol; 1,2-dimyristyloxypropyl-3-dimethyl-hydroxy ethyl ammonium bromide; 2,3-dioleyloxy-N-[2(sperminecarboxamido)ethyl]-N,N-dimethyl-1-propanaminium trifluoroacetate; dioctadecylamidoglycyl carboxyspermine; N-(2,3-dioleyloxy)propyl)-N,N-dimethylammonium chloride and 1,2-Dioleoyl-3-dimethylammonium-propane;

a pH-sensitive lipid selected from the group comprising lipid N-(4-carboxybenzyl)-N,N-dimethyl-2,3-bis(oleoyloxy)propan-1-aminium, 1,2-distearoyl-3-dimethylammonium-propane, 1,2-dipalmitoyl-sn-glycero-3-succinate, 1,2-dioleoyl-sn-glycero-3-succinate, N-palmitoyl homocysteine; a photoswitchable lipid;

acylglycine derivatives, prenol derivatives, prostaglandine derivatives, glycosylated diacyl glycerols, eicosanoid derivatives, (palmitoyloxy)octadecanoic acid derivatives, diacetylene derivatives, diphytanoyl derivatives, fluorinated lipids, brominated lipids, lipopolysaccharides;

one of the aforementioned lipids coupled to a functional ligand selected from the group comprising biotin, N-hydroxysuccinimide ester, nitrilotriacetic acid-nickel, amine, carboxylic acid, maleimides, aromatic maleimid, dithiopyridinyl, pyridyl disulfide, pyridyldithiopropionate, N-benzylguanine, cyanuric chloride, carboxyacyl, cyanur, folate, square, galloyl, glycan, thiol, arginylglycylaspartic acid, a fluorescent dye molecule, a magnetic resonance imaging reagent, a chelator;

one of the aforementioned lipids coupled to polyethyleneglycol with a molecular weight comprised between 350 and 50,000 g/mole;

one or more transmembrane proteins selected from the group comprising tetraspanin proteins CD9, CD37, CD47, CD53, CD63, CD81, CD82, CD151, Tspan8, heterotrimeric G protein subunit alpha (GNA), integrin α-chains, integrin β-chains, transferrin receptor 1 (TfR1, CD71), transferrin receptor 2 (TFR2), lysosome associated membrane proteins (LAMP1, LAMP2), heparan sulfate proteoglycans, syndecans, extracellular matrix metalloproteinase inducer (EMMPRIN, BSG), A Disintegrin And Metalloproteinase Domain 10 (ADAM10), CD3, CD11c, CD14, CD29, CD31, CD41, CD42a, CD44, CD45, CD50 (intercellular adhesion molecule 1, ICAM-1), CD55, CD59, CD73, CD80, CD86, CD90, sonic hedgehog (SHH), major histocompatibility complex I (MHCI), major histocompatibility complex II (MHCII), epidermal growth factor receptor 2 (ERBB2), epithelial cell adhesion molecule (EpCAM), glycophorin A (GYPA); acetylcholinesterase S and E (AChE-S, AChE-E), amyloid beta precursor protein (APP), multidrug resistance-associated protein 1 (ABCC1), stem cells antigen-1 (Sca-1), protein complexes endosomal sorting complexes required for transport ESCRT-I, ESCRT-II, and ESCRT-III, tumour susceptibility gene 101 (TSG101), charged multivesicular body protein (CHMP), Apoptosis-Linked Gene 2-Interacting Protein X (ALIX), vacuolar protein sorting 4 homolog A 4A and 4B, arrestin domain-containing protein (ARRDC1), flotillin-1, flotillin-2; caveolins, EH-domain containing 1-4 (EHD1-EHD4), Ras homolog family member A (RHOA), annexins, heat shock proteins, ADP-ribosylation factor 6 (ARF6), syntenin, microtubule-associated protein Tau (MAPT), cytokines, growth factors, interleukins, milk fat globule-EGF factor 8 protein (MFGE8), adhesion proteins, extracellular matrix proteins, nicotinamide phosphoribosyltransferase, signal transduction proteins, Wnta, Wntb, Fas, Fas Ligand (FasL), RANK, RANK Ligand (RANKL), indolamin-2,3-dioxygenase, cytotoxic T-lymphocyte-associated protein 4-immunoglobulin fusion protein, tumor necrosis factor-related apoptosis-inducing ligand, histone proteins, lamin A/C, inner membrane mitochondrial protein (IMMT), cytochrome C-1 (CYC1), mitochondrial import receptor subunit TOM20, calnexin, heat shock protein 90 kDa beta (Grp94), member 1 (HSP90B1), heat shock 70 kDa protein 5 (HSPA5), Golgin A2 (GM130, GOLGA2), Autophagy Related 9A (ATG9A), actinin1, actinin4 (ACTN1, ACTN4), cytokeratin 18 (KRT18), or a fragment thereof; and one or more nucleic acid molecules selected from the group comprising DNA, cDNA, mRNA, siRNA, antisense nucleotides, shRNA, piRNA, snRNA, lncRNA, PNA, left handed DNA, Clustered Regularly Interspaced Short Palindromic Repeats guide RNA, and miRNA;

for use in the treatment of a disorder selected from the group comprising inflammation, cancer, rheumatic disorder, severe graft versus host disease, osteoarthritis, cardiovascular disorder, epithelial diseases, neurodegenerative disorders, autoimmune disorders, bone and cartilage disorders, osteoporosis, renal osteodystrophy, Paget's disease of bone, osteopetrosis, rickets, neurological disorders, intoxication, neuroendocrinology disorders, endocrinology disorders, genetic disorders, infectious diseases, dental disorders, cosmetic procedures, coagulation disorders, dermatoses, diabetes, age-associated disorders.

A more particular embodiment of the present invention is directed to a synthetic extracellular vesicle having a hydrodynamic radius between 70 nm and 5000 nm, comprising:

a lipid bilayer comprising at least two lipids selected from the group comprising:

a neutral lipid selected from the group comprising ceramide, sphingomyelin, cephalin, cholesterol, cerebrosides, diacylglycerols, phosphatidylcholines, lysophosphatidylcholines, phosphatidylethanolamines, lysophosphatidylethanolamine, lysoethanolamines, inverted headgroup lipids, sphingosins, sterol-modified phospholipids, ether ester lipids, diether lipids, vinyl ether (plasmalogen);

an anionic lipid selected from the group comprising phosphatidic acids, lysophosphatidic acid derivatives, phosphatidylglycerols, lysophosphatidylglycerols, phosphatidylserines, lysophosphatidylserines, phosphatidylinositols, phosphatidylinositolphosphates, cardiolipins, Bis(Monoacylglycero)Phosphate derivatives;

a cationic lipid selected from the group comprising dioleyl-N,N-dimethylammonium chloride; N-(2,3-dioleyloxy)propyl)-N,N,N-trimethylammonium chloride; N,N-distearyl-N,N-dimethylammonium bromide; N-(2,3-dioleyloxy)propyl)-N,N,N-trimethylammonium chloride; 3β-(N-(N',N''-dimethylaminoethane)carbamoyl)cholesterol; 1,2-dimyristyloxypropyl dimethyl-hydroxy ethyl ammonium bromide; 2,3-dioleyloxy-N-[2(sperminecarboxamido)ethyl]-N,N-dimethyl-1-propanaminium trifluoroacetate; dioctadecylamidoglycyl carboxyspermine; N-(2,3-dioleyloxy)propyl)-N,N-dimethylammonium chloride and 1,2-Dioleoyl dimethylammonium-propane;

a pH-sensitive lipid selected from the group comprising lipid N-(4-carboxybenzyl)-N,N-dimethyl-2,3-bis(oleoyloxy)propan-1-aminium, 1,2-distearoyl-3-dimethylammonium-propane, 1,2-dipalmitoyl-sn-glycero succinate, 1,2-dioleoyl-sn-glycero-3-succinate, N-palmitoyl homocysteine; a photoswitchable lipid;

acylglycine derivatives, prenol derivatives, prostaglandine derivatives, glycosylated diacyl glycerols, eicosanoid derivatives, (palmitoyloxy)octadecanoic acid derivatives, diacetylene derivatives, diphytanoyl derivatives, fluorinated lipids, brominated lipids, lipopolysaccharides;

one of the aforementioned lipids coupled to a functional ligand selected from the group comprising biotin, N-hydroxysuccinimide ester, nitrilotriacetic acid-nickel, amine, carboxylic acid, maleimides, aromatic maleimid, dithiopyridinyl, pyridyl disulfide, pyridyldithiopropionate, N-benzylguanine, cyanuric chloride, carboxyacyl, cyanur, folate, square, galloyl, glycan, thiol, arginylglycylaspartic acid, a fluorescent dye molecule, a magnetic resonance imaging reagent, a chelator;

one of the aforementioned lipids coupled to polyethyleneglycol with a molecular weight comprised between 350 and 50,000 g/mole;

one or more transmembrane proteins selected from the group comprising tetraspanin proteins CD9, CD37, CD47, CD53, CD63, CD81, CD82, CD151, Tspan8, heterotrimeric G protein subunit alpha (GNA), integrin α-chains, integrin β-chains, transferrin receptor 1 (TfR1, CD71), transferrin receptor 2 (TFR2), lysosome associated membrane proteins (LAMP1, LAMP2), heparan sulfate proteoglycans, syndecans, extracellular matrix metalloproteinase inducer (EMMPRIN, BSG), A Disintegrin And Metalloproteinase Domain 10 (ADAM10), CD3, CD11c, CD14, CD29, CD31, CD41, CD42a, CD44, CD45, CD50 (intercellular adhesion molecule 1, ICAM-1), CD55, CD59, CD73, CD80, CD86, CD90, sonic hedgehog (SHH), major histocompatibility complex I (MHCI), major histocompatibility complex II (MHCII), epidermal growth factor receptor 2 (ERBB2), epithelial cell adhesion molecule (Ep-CAM), glycophorin A (GYPA); acetylcholinesterase S and E (AChE-S, AChE-E), amyloid beta precursor protein (APP), multidrug resistance-associated protein 1 (ABCC1), stem cells antigen-1 (Sca-1), protein complexes endosomal sorting complexes required for transport ESCRT-I, ESCRT-II, and ESCRT-III, tumour susceptibility gene 101 (TSG101), charged multivesicular body protein (CHMP), Apoptosis-Linked Gene 2-Interacting Protein X (ALIX), vacuolar protein sorting 4 homolog A 4A and 4B, arrestin domain-containing protein (ARRDC1), flotillin-1, flotillin-2; caveolins, EH-domain containing 1-4 (EHD1-EHD4), Ras homolog family member A (RHOA), annexins, heat shock proteins, ADP-ribosylation factor 6 (ARF6), syntenin, microtubule-associated protein Tau (MAPT), cytokines, growth factors, interleukins, milk fat globule-EGF factor 8 protein (MFGE8), adhesion proteins, extracellular matrix proteins, nicotinamide phosphoribosyltransferase, signal transduction proteins, Wnta, Wntb, Fas, Fas Ligand (FasL), RANK, RANK Ligand (RANKL), indolamin-2,3-dioxygenase, cytotoxic T-lymphocyte-associated protein 4-immunoglobulin fusion protein, tumor necrosis factor-related apoptosis-inducing ligand, histone proteins, lamin NC, inner membrane mitochondrial protein (IMMT), cytochrome C-1 (CYC1), mitochondrial import receptor subunit TOM20, calnexin, heat shock protein 90 kDa beta (Grp94), member 1 (HSP90B1), heat shock 70 kDa protein 5 (HSPA5), Golgin A2 (GM130, GOLGA2), Autophagy Related 9A (ATG9A), actinin1, actinin4 (ACTN1, ACTN4), cytokeratin 18 (KRT18), or a fragment thereof; and one or more nucleic acid molecules selected from the group comprising DNA, cDNA, mRNA, siRNA, antisense nucleotides, shRNA, piRNA, snRNA, lncRNA, PNA, left handed DNA, Clustered Regularly Interspaced Short Palindromic Repeats guide RNA, miRNA, wherein the miRNA is selected from the group comprising miR-17, miR-18a, miR-19a, miR-19b-1, miR-20a; miR-21, miR-92a; miR-30d-5p, miR-33b, miR-124, miR-125, miR-126, miR-130, miR-132, miR-133b, miR-140-5p, miR-191, miR-222, miR-451, miR-494, miR-575, miR-630, miR-638, miR-1202, miR-1207-5p, miR-1225-5p, miR-1268, miR-6087, miR-92a-3p-e, miR-K12-3, let-7a;

for use in the treatment of a disorder selected from the group comprising inflammation, cancer, rheumatic disorder, severe graft versus host disease, osteoarthritis, cardiovascular disorder, epithelial diseases, neurodegenerative disorders, autoimmune disorders, bone and cartilage disorders, osteoporosis, renal osteodystrophy, paget's disease of bone, osteopetrosis, rickets, neurological disorders, intoxication, neuroendocrinology disorders, endocrinology disorders, genetic disorders, infectious diseases, dental disorders, cosmetic procedures, coagulation disorders, dermatoses, diabetes, age-associated disorders.

In certain embodiments, the extracellular vesicle is an exosome. In certain embodiments, the extracellular vesicle is a microvesicle.

One preferred embodiment of the present invention is directed to a synthetic extracellular vesicle between 70 nm and 5000 nm specifically comprising:

a lipid bilayer comprising cholesterol, N-stearoyl-D-erythro-sphingosylphosphorylcholine (SM), 1,2-dioleoyl-sn-glycero-3-phosphocholine (DOPC), 1,2-dioleoyl-sn-glycero-3-phospho-L-serine (DOPS), 1,2-dioleoyl-sn-glycero-3-phospho-ethanolamine (DOPE), 1,2-dioleoyl-sn-glycero-3-phospho-rac-(1-glycerol) (DOPG), 1,2-dioleoyl-sn-glycero-3-phosphate (sodium salt) (PA), diacylglycerol, phosphatidylinositol, 1,2-dioleoyl-sn-glycero-3-phosphoethanolamine-N-(lissamine rhodamine B sulfonyl) (LissRhod PE), 1,2-dioleoyl-sn-glycero-3-[(N-(5-amino-1-carboxypentyl) iminodiacetic acid) succinyl] (nickel salt) (DGS-NTA ($Ni^{2+}$));

one or more nucleic acid molecules selected from the group comprising miRNA miR-21, miR-124, miR-125, miR-126, miR-130 and miR-132; and one or more transmembrane proteins selected from the group comprising tetraspanin proteins CD9, CD63 and CD81, or a fragment thereof;

for use in the treatment of a disorder selected from the group comprising inflammation, cancer, rheumatic disorder, severe graft versus host disease, osteoarthritis, cardiovascular disorder, epithelial diseases, neurodegenerative disorders, autoimmune disorders, bone and cartilage disorders, osteoporosis, renal osteodystrophy, paget's disease of bone, osteopetrosis, rickets, neurological disorders, intoxication, neuroendocrinology disorders, endocrinology disorders, genetic disorders, infectious diseases, dental disorders, cosmetic procedures, coagulation disorders, dermatoses, diabetes, age-associated disorders.

A preferred embodiment of the present invention is directed to a synthetic extracellular vesicle between 70 nm and 5000 nm specifically comprising:

a lipid bilayer comprising cholesterol, N-stearoyl-D-erythro-sphingosylphosphorylcholine (SM), 1,2-dioleoyl-sn-glycero-3-phosphocholine (DOPC), 1,2-dioleoyl-sn-glycero-3-phospho-L-serine (DOPS), 1,2-dioleoyl-sn-glycero-3-phospho-ethanolamine (DOPE), 1,2-dioleoyl-sn-glycero-3-phospho-rac-(1-glycerol) (DOPG), 1,2-dioleoyl-sn-glycero-3-phosphate (sodium salt) (PA), diacylglycerol, phosphatidylinositol, 1,2-dioleoyl-sn-glycero-3-phosphoethanolamine-N-(lissamine rhodamine B sulfonyl) (LissRhod PE), 1,2-dioleoyl-sn-glycero-3-[(N-(5-amino-1-carboxypentyl) iminodiacetic acid) succinyl] (nickel salt) (DGS-NTA ($Ni^{2+}$));

one or more nucleic acid molecules selected from the group comprising miRNA miR-21, miR-124, miR-125, miR-126, miR-130 and miR-132; and one or more transmembrane proteins selected from the group comprising tetraspanin proteins CD9, CD63 and CD81, or a fragment thereof;

for use in the treatment of a disorder selected from the group comprising epithelial diseases, cosmetic procedures, coagulation disorders.

A particularly preferred embodiment of the present invention is directed to a synthetic extracellular vesicle between 70 nm and 5000 nm specifically comprising:

one or more functional protein nicotinamide phosphoribosyltransferase, or a fragment thereof;

one or more transmembrane proteins selected from the group comprising tetraspanin proteins CD9, CD63 and CD81, or a fragment thereof; and one or more cytosolic proteins selected from the group comprising Apoptosis-Linked Gene 2-Interacting Protein X (ALIX), tumour susceptibility gene 101 protein (TSG101), or a fragment thereof;

wherein the synthetic extracellular vesicle does not comprise transferrin and albumin, or a fragment thereof;

for use in the treatment of a disorder selected from the group comprising inflammation, cancer, rheumatic disorder, severe graft versus host disease, osteoarthritis, cardiovascular disorder, epithelial diseases, neurodegenerative disorders, autoimmune disorders, bone and cartilage disorders, osteoporosis, renal osteodystrophy, Paget's disease of bone, osteopetrosis, rickets, neurological disorders, intoxication, neuroendocrinology disorders, endocrinology disorders, genetic disorders, infectious diseases, dental disorders, cosmetic procedures, coagulation disorders, dermatoses, diabetes, age-associated disorders.

A particularly preferred embodiment of the present invention is directed to a synthetic extracellular vesicle between 70 nm and 5000 nm specifically comprising:

one or more functional protein nicotinamide phosphoribosyltransferase, or a fragment thereof;

one or more transmembrane proteins selected from the group comprising tetraspanin proteins CD9, CD63 and CD81, or a fragment thereof; and one or more cytosolic proteins selected from the group comprising Apoptosis-Linked Gene 2-Interacting Protein X (ALIX), tumour susceptibility gene 101 protein (TSG101), or a fragment thereof;

wherein the synthetic extracellular vesicle does not comprise transferrin and albumin, or a fragment thereof, for use in the treatment of age-associated disorders.

Another particularly preferred embodiment of the present invention is directed to a synthetic extracellular vesicle between 70 nm and 5000 nm specifically comprising:

one or more transmembrane proteins selected from the group comprising MHCII, CD80, and CD86, or a fragment thereof;

optionally one or more transmembrane proteins selected from the group comprising CD11c, MHCI, integrin α, integrin β-chains, ICAM-1, and CD71, or a fragment thereof; and one or more functional proteins selected from the group comprising cytokines, interleukins, interleukin 4, milk fat globule-EGF factor 8 protein (MFGE8), growth factors, Fas, Fas ligand (FasL), indolamin-2,3-dioxygenase, cytotoxic T-lymphocyte-associated protein 4-immunoglobulin fusion protein (CTLA4-Ig), tumor necrosis factor-related apoptosis-inducing ligand (Apo2L, TRAIL), or a fragment thereof;

for use in the treatment of a disorder selected from the group comprising inflammation, cancer, rheumatic disorder, severe graft versus host disease, osteoarthritis, cardiovascular disorder, epithelial diseases, neurodegenerative disorders, autoimmune disorders, bone and cartilage disorders, osteoporosis, renal osteodystrophy, Paget's disease of bone, osteopetrosis, rickets, neurological disorders, intoxication, neuroendocrinology disorders, endocrinology disorders, genetic disorders, infectious diseases, dental disorders, cosmetic procedures, coagulation disorders, dermatoses, diabetes, age-associated disorders.

Another particularly preferred embodiment of the present invention is directed to a synthetic extracellular vesicle between 70 nm and 5000 nm specifically comprising:

one or more transmembrane proteins selected from the group comprising MHCII, CD80, and CD86, or a fragment thereof;

optionally one or more transmembrane proteins selected from the group comprising CD11c, MHCI, integrin α, integrin β-chains, ICAM-1, and CD71, or a fragment thereof; and one or more functional proteins selected from the group comprising cytokines, interleukins, interleukin 4, milk fat globule-EGF factor 8 protein (MFGE8), growth factors, Fas, Fas ligand (FasL), indolamin-2,3-dioxygenase, cytotoxic T-lymphocyte-associated protein 4-immunoglobulin fusion protein (CTLA4-Ig), tumor necrosis factor-related apoptosis-inducing ligand (Apo2L, TRAIL), or a fragment thereof;

for use in the treatment of a disorder selected from the group comprising inflammation, cancer, rheumatic disorder, severe graft versus host disease, osteoarthritis, epithelial diseases, autoimmune disorders, infectious diseases, diabetes, age-associated disorders.

Another particularly preferred embodiment of the present invention is directed to a synthetic extracellular vesicle between 70 nm and 5000 nm specifically comprising:

a lipid bilayer comprising 1,2-dioleoyl-sn-glycero-3-phosphocholine (DOPC), 1,2-dioleoyl-sn-glycero-3-phospho-rac-(1-glycerol) (DOPG), 1,2-dioleoyl-sn-glycero-3-phosphoethanolamine-N-(lissamine rhodamine B sulfonyl) (LissRhod PE), 1,2-dioleoyl-sn-glycero-3-[(N-(5-amino-1-carboxypentyl)iminodiacetic acid) succinyl] (nickel salt) (DGS-NTA(Ni$^{2+}$));

functional protein Fas Ligand, or a fragment thereof; and optionally functional protein intercellular adhesion protein-1, or a fragment thereof;

for use in the treatment of a disorder selected from the group comprising inflammation, cancer, rheumatic disorder, severe graft versus host disease, osteoarthritis, cardiovascular disorder, epithelial diseases, neurodegenerative disorders, autoimmune disorders, bone and cartilage disorders, osteoporosis, renal osteodystrophy, Paget's disease of bone, osteopetrosis, rickets, neurological disorders, intoxication, neuroendocrinology disorders, endocrinology disorders, genetic disorders, infectious diseases, dental disorders, cosmetic procedures, coagulation disorders, dermatoses, diabetes, age-associated disorders.

Another particularly preferred embodiment of the present invention is directed to a synthetic extracellular vesicle between 70 nm and 5000 nm specifically comprising:

a lipid bilayer comprising 1,2-dioleoyl-sn-glycero-3-phosphocholine (DOPC), 1,2-dioleoyl-sn-glycero-3-phospho-rac-(1-glycerol) (DOPG), 1,2-dioleoyl-sn-glycero-3-phosphoethanolamine-N-(lissamine rhodamine B sulfonyl) (LissRhod PE), 1,2-dioleoyl-snglycero-3-[(N-(5-amino-1-carboxypentyl)iminodi-
acetic acid) succinyl] (nickel salt) (DGS-NTA(Ni$^{2+}$));
functional protein Fas Ligand, or a fragment thereof; and
optionally functional protein intercellular adhesion pro-
tein-1, or a fragment thereof;

for use in the treatment of a disorder selected from the group
comprising inflammation, cancer, rheumatic disorder, severe
graft versus host disease, autoimmune disorders, infectious
diseases.

Another particularly preferred embodiment of the present
invention is directed to a synthetic extracellular vesicle
between 70 nm and 5000 nm specifically comprising:

one or more transmembrane proteins selected from the
group comprising CD29, CD44, CD90, CD73, CD44,
Sca-1, or a fragment thereof;

one or more transmembrane proteins selected from the
group comprising tetraspanin proteins CD9, CD63, and
CD81, or a fragment thereof;

one or more functional proteins selected from the group
comprising Wnta and Wntb, or a fragment thereof;

at least one nucleic acid molecule selected from the group
comprising miR-140-5p, miR-92a-3p-e;

one or more nucleic acid molecules selected from the
group comprising miR-17, miR-18a, miR-19a, miR-
19b-1, miR-20a, miR-92a, let-7a, miR-21, miR124,
miR126, miR-133b, miR-191, miR-222, miR-494,
miR-6087, miR-30d-5p; and optionally one or more nucleic acid molecules selected
from the group comprising miR-33b, miR-451, miR-
575, miR-630, miR-638, miR-1202, miR-1207-5p,
miR-1225-5p, miR-1268, miR-K12-3;

for use in the treatment of a disorder selected from the group
comprising inflammation, cancer, rheumatic disorder, severe
graft versus host disease, osteoarthritis, cardiovascular dis-
order, epithelial diseases, neurodegenerative disorders, auto-
immune disorders, bone and cartilage disorders, osteoporo-
sis, renal osteodystrophy, Paget's disease of bone,
osteopetrosis, rickets, neurological disorders, intoxication,
neuroendocrinology disorders, endocrinology disorders,
genetic disorders, infectious diseases, dental disorders, cos-
metic procedures, coagulation disorders, dermatoses, diabe-
tes, age-associated disorders.

Another more particularly preferred embodiment of the
present invention is directed to a synthetic extracellular
vesicle between 70 nm and 5000 nm specifically compris-
ing:

a lipid bilayer comprising 1,2-dioleoyl-sn-glycero-3-
phosphocholine (DOPC), 1,2-dioleoyl-sn-glycero-3-
phospho-rac-(1-glycerol) (DOPG), 1,2-dioleoyl-sn-
glycero-3-phosphoethanolamine-N-(lissamine
rhodamine B sulfonyl) (LissRhod PE), 1,2-dioleoyl-sn-
glycero-3-[(N-(5-amino-1-carboxypentyl)iminodi-
acetic acid) succinyl] (nickel salt) (DGS-NTA(Ni$^{2+}$));
and functional protein RANK, or a fragment thereof;

for use in the treatment of a disorder selected from the group
comprising inflammation, cancer, rheumatic disorder, severe
graft versus host disease, osteoarthritis, cardiovascular dis-
order, epithelial diseases, neurodegenerative disorders, auto-
immune disorders, bone and cartilage disorders, osteoporo-
sis, renal osteodystrophy, Paget's disease of bone,
osteopetrosis, rickets, neurological disorders, intoxication,
neuroendocrinology disorders, endocrinology disorders,
genetic disorders, infectious diseases, dental disorders, cos-
metic procedures, coagulation disorders, dermatoses, diabe-
tes, age-associated disorders.

Another more particularly preferred embodiment of the
present invention is directed to a synthetic extracellular
vesicle between 70 nm and 5000 nm specifically compris-
ing:

a lipid bilayer comprising 1,2-dioleoyl-sn-glycero-3-
phosphocholine (DOPC), 1,2-dioleoyl-sn-glycero-3-
phospho-rac-(1-glycerol) (DOPG), 1,2-dioleoyl-sn-
glycero-3-phosphoethanolamine-N-(lissamine
rhodamine B sulfonyl) (LissRhod PE), 1,2-dioleoyl-sn-
glycero-3-[(N-(5-amino-1-carboxypentyl)iminodi-
acetic acid) succinyl] (nickel salt) (DGS-NTA(Ni$^{2+}$));
and functional protein RANK, or a fragment thereof;

for use in the treatment of a disorder selected from the group
comprising osteoarthritis, bone and cartilage disorders,
osteoporosis, renal osteodystrophy, Paget's disease of bone,
osteopetrosis, rickets.

Also described herein is a method for treating or amelio-
rating a disorder comprising administering to a patient
suffering from said disorder a therapeutically effective
amount of a synthetic extracellular vesicle as disclosed
herein, wherein the disorder is selected from the group
comprising inflammation, cancer, rheumatic disorder, severe
graft versus host disease, osteoarthritis, cardiovascular dis-
order, epithelial diseases, neurodegenerative disorders, auto-
immune disorders, bone and cartilage disorders, osteoporo-
sis, renal osteodystrophy, Paget's disease of bone,
osteopetrosis, rickets, neurological disorders, intoxication,
neuroendocrinology disorders, endocrinology disorders,
genetic disorders, infectious diseases, dental disorders, cos-
metic procedures, coagulation disorders, dermatoses, diabe-
tes, age-associated disorders.

Also described herein is a method for treating or amelio-
rating a disorder comprising administering to a patient
suffering from said disorder a therapeutically effective
amount of a synthetic extracellular vesicle having a hydro-
dynamic radius between 70 nm and 5000 nm, comprising:

a lipid bilayer comprising at least two lipids selected from
the group comprising:

a neutral lipid selected from the group comprising cer-
amide, sphingomyelin, cephalin, cholesterol, cerebro-
sides, diacylglycerols, phosphatidylcholines, lysophos-
phatidylcholines, phosphatidylethanolamines,
lysophosphatidylethanolamine, lysoethanolamines,
inverted headgroup lipids, sphingosins, sterol-modified
phospholipids, ether ester lipids, diether lipids, vinyl
ether (plasmalogen);

an anionic lipid selected from the group comprising
phosphatidic acids, lysophosphatidic acid derivatives,
phosphatidylglycerols, lysophosphatidylglycerols,
phosphatidylserines, lysophosphatidylserines, phos-
phatidylinositols, phosphatidylinositolphosphates, car-
diolipins, Bis(Monoacylglycero)Phosphate derivatives;

a cationic lipid selected from the group comprising diol-
eyl-N,N-dimethylammonium chloride; N-(2,3-dioley-
loxy)propyl)-N,N,N-trimethylammonium chloride;
N,N-distearyl-N,N-dimethylammonium bromide;
N-(2,3-dioleyloxy)propyl)-N,N,N-trimethylammo-
nium chloride; 3β-(N-(N',N'-dimethylaminoethane)-
carbamoyl)cholesterol; 1,2-dimyristyloxypropyl-3-di-
methyl-hydroxy ethyl ammonium bromide; 2,3-
dioleyloxy-N-[2(sperminecarboxamido)ethyl]-N,N-
dimethyl-1-propanaminium trifluoroacetate;
dioctadecylamidoglycyl carboxyspermine; N-(2,3-di-
oleyloxy)propyl)-N,N-dimethylammonium chloride
and 1,2-Dioleoyl-3-dimethylammonium-propane;

a pH-sensitive lipid selected from the group comprising
lipid N-(4-carboxybenzyl)-N,N-dimethyl-2,3-bis (oleoyloxy)propan-1-aminium, 1,2-distearoyl-3-dimethylammonium-propane, 1,2-dipalmitoyl-sn-glycero-3-succinate, 1,2-dioleoyl-sn-glycero-3-succinate, N-palmitoyl homocysteine;

a photoswitchable lipid;

acylglycine derivatives, prenol derivatives, prostaglandine derivatives, glycosylated diacyl glycerols, eicosanoid derivatives, (palmitoyloxy)octadecanoic acid derivatives, diacetylene derivatives, diphytanoyl derivatives, fluorinated lipids, brominated lipids, lipopolysaccharides;

one of the aforementioned lipids coupled to a functional ligand selected from the group comprising biotin, N-hydroxysuccinimide ester, nitrilotriacetic acid-nickel, amine, carboxylic acid, maleimides, dithiopyridinyl, pyridyl disulfide, pyridyldithiopropionate, N-benzylguanine, carboxyacyl, cyanur, folate, square, galloyl, glycan, thiol, arginylglycylaspartic acid, a fluorescent dye molecule, a magnetic resonance imaging reagent, a chelator;

one of the aforementioned lipids coupled to polyethyleneglycol with a molecular weight comprised between 350 and 50,000 g/mole;

one or more nucleic acid molecules selected from the group comprising DNA, cDNA, mRNA, siRNA, antisense nucleotides, shRNA, piRNA, snRNA, lncRNA, PNA, left handed DNA, Clustered Regularly Interspaced Short Palindromic Repeats (CRISPR) guide RNA, miRNA molecules selected from the group comprising miR-17, miR-18a, miR-19a, miR-19b-1, miR-20a, miR-92a; miR-21, miR-30d-5p, miR-33b, miR-124, miR-125, miR-126, miR-130, miR-132, miR-133b, miR-140-5p, miR-191, miR-222, miR-451, miR-494, miR-575, miR-630, miR-638, miR-1202, miR-1207-5p, miR-1225-5p, miR-1268, miR-6087, miR-92a-3p-e, miR-K12-3, let-7a; and one or more extracellular vesicle associated proteins selected from the group comprising tetraspanin proteins CD9, CD37, CD47, CD53, CD63, CD81, CD82, CD151, Tspan8, heterotrimeric G protein subunit alpha (GNA), integrin α-chains, integrin β-chains, transferrin receptor 1 (TfR1, CD71), transferrin receptor 2 (TFR2), lysosome associated membrane proteins (LAMP1, LAMP2), heparan sulfate proteoglycans, syndecans, extracellular matrix metalloproteinase inducer (EMMPRIN, BSG), A Disintegrin And Metalloproteinase Domain 10 (ADAM10), CD3, CD11c, CD14, CD29, CD31, CD41, CD42a, CD44, CD45, CD50 (intercellular adhesion molecule 1, ICAM-1), CD55, CD59, CD73, CD80, CD86, CD90, sonic hedgehog (SHH), major histocompatibility complex I (MHCI), major histocompatibility complex II (MHCII), epidermal growth factor receptor 2 (ERBB2), epithelial cell adhesion molecule (EpCAM), Glycophorin A (GYPA); Acetylcholinesterase S and E (AChE-S, AChE-E), amyloid beta precursor protein (APP), multidrug resistance-associated protein 1 (ABCC1), stem cells antigen-1 (Sca-1), protein complexes endosomal sorting complexes required for transport ESCRT-I, ESCRT-II, and ESCRT-III, tumour susceptibility gene 101 (TSG101), charged multivesicular body protein (CHMP), Apoptosis-Linked Gene 2-Interacting Protein X (ALIX), vacuolar protein sorting 4 homolog A 4A and 4B, arrestin domain-containing protein (ARRDC1), flotillin-1, flotillin-2; caveolins, EH-domain containing 1-4 (EHD1-EHD4), Ras homolog family member A (RHOA), annexins, heat shock proteins, ADP-ribosylation factor 6 (ARF6), syntenin, microtubule-associated protein Tau (MAPT), cytokines, growth factors, interleukins, milk fat globule-EGF factor 8 protein (MFGE8), adhesion proteins, extracellular matrix proteins, nicotinamide phosphoribosyltransferase, signal transduction proteins, Wnta, Wntb, Fas, Fas Ligand (FasL), RANK, RANK Ligand (RANKL), indolamin-2,3-dioxygenase, cytotoxic T-lymphocyte-associated protein 4-immunoglobulin fusion protein, tumor necrosis factor-related apoptosis-inducing ligand, histone proteins, lamin NC, inner membrane mitochondrial protein (IMMT), cytochrome C-1 (CYC1), mitochondrial import receptor subunit TOM20, calnexin, heat shock protein 90 kDa beta (Grp94), member 1 (HSP90B1), heat shock 70 kDa protein 5 (HSPA5), Golgin A2 (GM130, GOLGA2), Autophagy Related 9A (ATG9A), actinin1, actinin4 (ACTN1, ACTN4), cytokeratin 18 (KRT18), or a fragment thereof;

wherein the disorder is selected from the group comprising inflammation, cancer, rheumatic disorder, severe graft versus host disease, osteoarthritis, cardiovascular disorder, epithelial diseases, neurodegenerative disorders, autoimmune disorders, bone and cartilage disorders, osteoporosis, renal osteodystrophy, Paget's disease of bone, osteopetrosis, rickets, neurological disorders, intoxication, neuroendocrinology disorders, endocrinology disorders, genetic disorders, infectious diseases, dental disorders, cosmetic procedures, coagulation disorders, dermatoses, diabetes, age-associated disorders.

Also described herein is a method for treating or ameliorating a disorder comprising administering to a patient suffering from said disorder a therapeutically effective amount of a synthetic extracellular vesicle as disclosed herein, wherein the disorder is selected from the group comprising inflammation, cancer, rheumatic disorder, severe graft versus host disease, osteoarthritis, cardiovascular disorder, epithelial diseases, neurodegenerative disorders, autoimmune disorders, bone and cartilage disorders, osteoporosis, renal osteodystrophy, Paget's disease of bone, osteopetrosis, rickets, neurological disorders, intoxication, neuroendocrinology disorders, endocrinology disorders, genetic disorders, infectious diseases, dental disorders, cosmetic procedures, coagulation disorders, dermatoses, diabetes, age-associated disorders.

Also described herein is a method for treating or ameliorating a disorder comprising administering to a patient suffering from said disorder a therapeutically effective amount of a synthetic extracellular vesicle having a hydrodynamic radius between 70 nm and 5000 nm, comprising:

a lipid bilayer comprising at least two lipids selected from the group comprising:

a neutral lipid selected from the group comprising ceramide, sphingomyelin, cephalin, cholesterol, cerebrosides, diacylglycerols, phosphatidylcholines, lysophosphatidylcholines, phosphatidylethanolamines, lysophosphatidylethanolamine, lysoethanolamines, inverted headgroup lipids, sphingosins, sterol-modified phospholipids, ether ester lipids, diether lipids, vinyl ether (plasmalogen);

an anionic lipid selected from the group comprising phosphatidic acids, lysophosphatidic acid derivatives, phosphatidylglycerols, lysophosphatidylglycerols, phosphatidylserines, lysophosphatidylserines, phosphatidylinositols, phosphatidylinositolphosphates, cardiolipins, Bis(Monoacylglycero)Phosphate derivatives;

a cationic lipid selected from the group comprising diol-eyl-N,N-dimethylammonium chloride; N-(2,3-dioley-loxy)propyl)-N,N,N-trimethylammonium chloride; N,N-distearyl-N,N-dimethylammonium bromide; N-(2,3-dioleyloxy)propyl)-N,N,N-trimethylammo-nium chloride; 3β-(N-(N',N'-dimethylaminoethane)-carbamoyl)cholesterol; 1,2-dimyristyloxypropyl-3-di-methyl-hydroxy ethyl ammonium bromide; 2,3-dioleyloxy-N-[2(sperminecarboxamido)ethyl]-N,N-dimethyl-1-propanaminium trifluoroacetate; dioctadecylamidoglycyl carboxyspermine; N-(2,3-di-oleyloxy)propyl)-N,N-dimethylammonium chloride and 1,2-Dioleoyl-3-dimethylammonium-propane;

a pH-sensitive lipid selected from the group comprising lipid N-(4-carboxybenzyl)-N,N-dimethyl-2,3-bis (oleoyloxy)propan-1-aminium, 1,2-distearoyl-3-dim-ethylammonium-propane, 1,2-dipalmitoyl-sn-glycero-3-succinate, 1,2-dioleoyl-sn-glycero-3-succinate, N-palmitoyl homocysteine; a photoswitchable lipid;

acylglycine derivatives, prenol derivatives, prostaglan-dine derivatives, glycosylated diacyl glycerols, eico-sanoid derivatives, (palmitoyloxy)octadecanoic acid derivatives, diacetylene derivatives, diphytanoyl derivatives, fluorinated lipids, brominated lipids, lipopolysaccharides;

one of the aforementioned lipids coupled to a functional ligand selected from the group comprising biotin, N-hydroxysuccinimide ester, nitrilotriacetic acid-nickel, amine, carboxylic acid, maleimides, dithio-pyridinyl, pyridyl disulfide, pyridyldithiopropionate, N-benzylguanine, carboxyacyl, cyanur, folate, square, galloyl, glycan, thiol, arginylglycylaspartic acid, a fluo-rescent dye molecule, a magnetic resonance imaging reagent, a chelator;

one of the aforementioned lipids coupled to polyethyl-eneglycol with a molecular weight comprised between 350 and 50,000 g/mole;

one or more nucleic acid molecules selected from the group comprising DNA, cDNA, mRNA, siRNA, anti-sense nucleotides, shRNA, piRNA, snRNA, lncRNA, PNA, left handed DNA, Clustered Regularly Inter-spaced Short Palindromic Repeats (CRISPR) guide RNA, miRNA molecules; and one or more extracellular vesicle associated proteins selected from the group comprising tetraspanin pro-teins CD9, CD37, CD47, CD53, CD63, CD81, CD82, CD151, Tspan8, heterotrimeric G protein subunit alpha (GNA), integrin α-chains, integrin β-chains, transferrin receptor 1 (TfR1, CD71), transferrin receptor 2 (TFR2), lysosome associated membrane proteins (LAMP1, LAMP2), heparan sulfate proteoglycans, syndecans, extracellular matrix metalloproteinase inducer (EMMPRIN, BSG), A Disintegrin And Metal-loproteinase Domain 10 (ADAM10), CD3, CD11c, CD14, CD29, CD31, CD41, CD42a, CD44, CD45, CD50 (intercellular adhesion molecule 1, ICAM-1), CD55, CD59, CD73, CD80, CD86, CD90, sonic hedgehog (SHH), major histocompatibility complex I (MHCI), major histocompatibility complex II (MHCII), epidermal growth factor receptor 2 (ERBB2), epithelial cell adhesion molecule (EpCAM), Glycophorin A (GYPA); Acetylcholinesterase S and E (AChE-S, AChE-E), amyloid beta precursor protein (APP), multidrug resistance-associated protein 1 (ABCC1), stem cells antigen-1 (Sca-1), protein com-plexes endosomal sorting complexes required for trans-port ESCRT-I, ESCRT-II, and ESCRT-III, tumour susceptibility gene 101 (TSG101), charged multivesicular body protein (CHMP), Apoptosis-Linked Gene 2-In-teracting Protein X (ALIX), vacuolar protein sorting 4 homolog A 4A and 4B, arrestin domain-containing protein (ARRDC1), flotillin-1, flotillin-2; caveolins, EH-domain containing 1-4 (EHD1-EHD4), Ras homolog family member A (RHOA), annexins, heat shock proteins, ADP-ribosylation factor 6 (ARF6), syntenin, microtubule-associated protein Tau (MAPT), cytokines, growth factors, interleukins, milk fat glob-ule-EGF factor 8 protein (MFGE8), adhesion proteins, extracellular matrix proteins, nicotinamide phosphori-bosyltransferase, signal transduction proteins, Wnta, Wntb, Fas, Fas Ligand (FasL), RANK, RANK Ligand (RANKL), indolamin-2,3-dioxygenase, cytotoxic T-lymphocyte-associated protein 4-immunoglobulin fusion protein, tumor necrosis factor-related apoptosis-inducing ligand, histone proteins, lamin A/C, inner membrane mitochondrial protein (IMMT), cytochrome C-1 (CYC1), mitochondrial import receptor subunit TOM20, calnexin, heat shock protein 90 kDa beta (Grp94), member 1 (HSP90B1), heat shock 70 kDa protein 5 (HSPA5), Golgin A2 (GM130, GOLGA2), Autophagy Related 9A (ATG9A), actinin1, actinin4 (ACTN1, ACTN4), cytokeratin 18 (KRT18), or a frag-ment thereof;

wherein the disorder is selected from the group comprising inflammation, cancer, rheumatic disorder, severe graft ver-sus host disease, osteoarthritis, cardiovascular disorder, epi-thelial diseases, neurodegenerative disorders, autoimmune disorders, bone and cartilage disorders, osteoporosis, renal osteodystrophy, Paget's disease of bone, osteopetrosis, rick-ets, neurological disorders, intoxication, neuroendocrinol-ogy disorders, endocrinology disorders, genetic disorders, infectious diseases, dental disorders, cosmetic procedures, coagulation disorders, dermatoses, diabetes, age-associated disorders.

Also described herein is a method for treating or amelio-rating a disorder comprising administering to a patient suffering from said disorder a therapeutically effective amount of a synthetic extracellular vesicle as disclosed herein, wherein the disorder is selected from the group comprising inflammation, cancer, rheumatic disorder, severe graft versus host disease, osteoarthritis, cardiovascular dis-order, epithelial diseases, neurodegenerative disorders, auto-immune disorders, bone and cartilage disorders, osteoporo-sis, renal osteodystrophy, Paget's disease of bone, osteopetrosis, rickets, neurological disorders, intoxication, neuroendocrinology disorders, endocrinology disorders, genetic disorders, infectious diseases, dental disorders, cos-metic procedures, coagulation disorders, dermatoses, diabe-tes, age-associated disorders.

Also described herein is a method for treating or amelio-rating a disorder comprising administering to a patient suffering from said disorder a therapeutically effective amount of a synthetic extracellular vesicle having a hydro-dynamic radius between 70 nm and 5000 nm, comprising:

a lipid bilayer comprising at least two lipids selected from the group comprising:

a neutral lipid selected from the group comprising cer-amide, sphingomyelin, cephalin, cholesterol, cerebro-sides, diacylglycerols, phosphatidylcholines, lysophos-phatidylcholines, phosphatidylethanolamines, lysophosphatidylethanolamine, lysoethanolamines, inverted headgroup lipids, sphingosins, sterol-modified phospholipids, ether ester lipids, diether lipids, vinyl ether (plasmalogen);

an anionic lipid selected from the group comprising phosphatidic acids, lysophosphatidic acid derivatives, phosphatidylglycerols, lysophosphatidylglycerols, phosphatidylserines, lysophosphatidylserines, phosphatidylinositols, phosphatidylinositolphosphates, cardiolipins, Bis(Monoacylglycero)Phosphate derivatives;

a cationic lipid selected from the group comprising dioleyl-N,N-dimethylammonium chloride; N-(2,3-dioleyloxy)propyl)-N,N,N-trimethylammonium chloride; N,N-distearyl-N,N-dimethylammonium bromide; N-(2,3-dioleyloxy)propyl)-N,N,N-trimethylammonium chloride; 3β-(N-(N',N'-dimethylaminoethane)-carbamoyl)cholesterol; 1,2-dimyristyloxypropyl dimethyl-hydroxy ethyl ammonium bromide; 2,3-dioleyloxy-N-[2(sperminecarboxamido)ethyl]-N,N-dimethyl-1-propanaminium trifluoroacetate; dioctadecylamidoglycyl carboxyspermine; N-(2,3-dioleyloxy)propyl)-N,N-dimethylammonium chloride and 1,2-Dioleoyl dimethylammonium-propane;

a pH-sensitive lipid selected from the group comprising lipid N-(4-carboxybenzyl)-N,N-dimethyl-2,3-bis(oleoyloxy)propan-1-aminium, 1,2-distearoyl-3-dimethylammonium-propane, 1,2-dipalmitoyl-sn-glycero-3-succinate, 1,2-dioleoyl-sn-glycero-3-succinate, N-palmitoyl homocysteine;

a photoswitchable lipid;

acylglycine derivatives, prenol derivatives, prostaglandine derivatives, glycosylated diacyl glycerols, eicosanoid derivatives, (palmitoyloxy)octadecanoic acid derivatives, diacetylene derivatives, diphytanoyl derivatives, fluorinated lipids, brominated lipids, lipopolysaccharides;

one of the aforementioned lipids coupled to a functional ligand selected from the group comprising biotin, N-hydroxysuccinimide ester, nitrilotriacetic acid-nickel, amine, carboxylic acid, maleimides, dithiopyridinyl, pyridyl disulfide, pyridyldithiopropionate, N-benzylguanine, carboxyacyl, cyanur, folate, square, galloyl, glycan, thiol, arginylglycylaspartic acid, a fluorescent dye molecule, a magnetic resonance imaging reagent, a chelator;

one of the aforementioned lipids coupled to polyethyleneglycol with a molecular weight comprised between 350 and 50,000 g/mole; and one or more extracellular vesicle associated proteins selected from the group comprising tetraspanin proteins CD9, CD37, CD47, CD53, CD63, CD81, CD82, CD151, Tspan8, heterotrimeric G protein subunit alpha (GNA), integrin α-chains, integrin β-chains, transferrin receptor 1 (TfR1, CD71), transferrin receptor 2 (TFR2), lysosome associated membrane proteins (LAMP1, LAMP2), heparan sulfate proteoglycans, syndecans, extracellular matrix metalloproteinase inducer (EMMPRIN, BSG), A Disintegrin And Metalloproteinase Domain 10 (ADAM10), CD3, CD11c, CD14, CD29, CD31, CD41, CD42a, CD44, CD45, CD50 (intercellular adhesion molecule 1, ICAM-1), CD55, CD59, CD73, CD80, CD86, CD90, sonic hedgehog (SHH), major histocompatibility complex I (MHCI), major histocompatibility complex II (MHCII), epidermal growth factor receptor 2 (ERBB2), epithelial cell adhesion molecule (Ep-CAM), Glycophorin A (GYPA); Acetylcholinesterase S and E (AChE-S, AChE-E), amyloid beta precursor protein (APP), multidrug resistance-associated protein 1 (ABCC1), stem cells antigen-1 (Sca-1), protein complexes endosomal sorting complexes required for transport ESCRT-I, ESCRT-II, and ESCRT-III, tumour susceptibility gene 101 (TSG101), charged multivesicular body protein (CHMP), Apoptosis-Linked Gene 2-Interacting Protein X (ALIX), vacuolar protein sorting 4 homolog A 4A and 4B, arrestin domain-containing protein (ARRDC1), flotillin-1, flotillin-2; caveolins, EH-domain containing 1-4 (EHD1-EHD4), Ras homolog family member A (RHOA), annexins, heat shock proteins, ADP-ribosylation factor 6 (ARF6), syntenin, microtubule-associated protein Tau (MAPT), cytokines, growth factors, interleukins, milk fat globule-EGF factor 8 protein (MFGE8), adhesion proteins, extracellular matrix proteins, nicotinamide phosphoribosyltransferase, signal transduction proteins, Wnta, Wntb, Fas, Fas Ligand (FasL), RANK, RANK Ligand (RANKL), indolamin-2,3-dioxygenase, cytotoxic T-lymphocyte-associated protein 4-immunoglobulin fusion protein, tumor necrosis factor-related apoptosis-inducing ligand, histone proteins, lamin NC, inner membrane mitochondrial protein (IMMT), cytochrome C-1 (CYC1), mitochondrial import receptor subunit TOM20, calnexin, heat shock protein 90 kDa beta (Grp94), member 1 (HSP90B1), heat shock 70 kDa protein 5 (HSPA5), Golgin A2 (GM130, GOLGA2), Autophagy Related 9A (ATG9A), actinin1, actinin4 (ACTN1, ACTN4), cytokeratin 18 (KRT18), or a fragment thereof;

wherein the disorder is selected from the group comprising inflammation, cancer, rheumatic disorder, severe graft versus host disease, osteoarthritis, cardiovascular disorder, epithelial diseases, neurodegenerative disorders, autoimmune disorders, bone and cartilage disorders, osteoporosis, renal osteodystrophy, Paget's disease of bone, osteopetrosis, rickets, neurological disorders, intoxication, neuroendocrinology disorders, endocrinology disorders, genetic disorders, infectious diseases, dental disorders, cosmetic procedures, coagulation disorders, dermatoses, diabetes, age-associated disorders.

Also described herein is a method for treating or ameliorating a disorder comprising administering to a patient suffering from said disorder a therapeutically effective amount of a synthetic extracellular vesicle between 70 nm and 5000 nm with the composition described above and specifically comprising:

a lipid bilayer comprising cholesterol, N-stearoyl-D-erythro-sphingosylphosphorylcholine (SM), 1,2-dioleoyl-sn-glycero-3-phosphocholine (DOPC), 1,2-dioleoyl-sn-glycero-3-phospho-L-serine (DOPS), 1,2-dioleoyl-sn-glycero-3-phospho-ethanolamine (DOPE), 1,2-dioleoyl-sn-glycero-3-phospho-rac-(1-glycerol) (DOPG), 1,2-dioleoyl-sn-glycero-3-phosphate (sodium salt) (PA), diacylglycerol, phosphatidylinositol, 1,2-dioleoyl-sn-glycero phosphoethanolamine-N-(lissamine rhodamine B sulfonyl) (LissRhod PE), 1,2-dioleoyl-sn-glycero-3-[(N-(5-amino-1-carboxypentyl) iminodiacetic acid) succinyl] (nickel salt) (DGS-NTA (Ni$^{2+}$));

one or more nucleic acid molecules selected from the group comprising miRNA miR-21, miR-124, miR-125, miR-126, miR-130 and miR-132; and one or more transmembrane proteins selected from the group comprising tetraspanin proteins CD9, CD63 and CD81, or a fragment thereof;

wherein the disorder is selected from the group comprising inflammation, cancer, rheumatic disorder, severe graft versus host disease, osteoarthritis, cardiovascular disorder, epithelial diseases, neurodegenerative disorders, autoimmune disorders, bone and cartilage disorders, osteoporosis, renal osteodystrophy, Paget's disease of bone, osteopetrosis, rickets, neurological disorders, intoxication, neuroendocrinology disorders, endocrinology disorders, genetic disorders, infectious diseases, dental disorders, cosmetic procedures, coagulation disorders, dermatoses, diabetes, age-associated disorders.

Also described herein is a method for treating or ameliorating a disorder comprising administering to a patient suffering from said disorder a therapeutically effective amount of a synthetic extracellular vesicle between 70 nm and 5000 nm with the composition described above and specifically comprising:

one or more functional protein nicotinamide phosphoribosyltransferase, or a fragment thereof;

one or more transmembrane proteins selected from the group comprising tetraspanin proteins CD9, CD63 and CD81, or a fragment thereof;

one or more cytosolic proteins selected from the group comprising Apoptosis-Linked Gene 2-Interacting Protein X (ALIX), tumour susceptibility gene 101 protein (TSG101), or a fragment thereof; and wherein the synthetic extracellular vesicle does not comprise transferrin and albumin, or a fragment thereof;

wherein the disorder is selected from the group comprising inflammation, cancer, rheumatic disorder, severe graft versus host disease, osteoarthritis, cardiovascular disorder, epithelial diseases, neurodegenerative disorders, autoimmune disorders, bone and cartilage disorders, osteoporosis, renal osteodystrophy, Paget's disease of bone, osteopetrosis, rickets, neurological disorders, intoxication, neuroendocrinology disorders, endocrinology disorders, genetic disorders, infectious diseases, dental disorders, cosmetic procedures, coagulation disorders, dermatoses, diabetes, age-associated disorders.

Also described herein is a method for treating or ameliorating a disorder comprising administering to a patient suffering from said disorder a therapeutically effective amount of a synthetic extracellular vesicle between 70 nm and 5000 nm with the composition described above, and specifically comprising:

one or more transmembrane proteins selected from the group comprising MHCII, CD80, and CD86, or a fragment thereof;

optionally one or more transmembrane proteins selected from the group comprising CD11c, MHCI, integrin α-chains, integrin β-chains, ICAM-1, and CD71, or a fragment thereof; and one or more functional proteins selected from the group comprising cytokines, interleukins, interleukin 4, milk fat globule-EGF factor 8 protein (MFGE8), growth factors, Fas, Fas ligand (FasL), indolamin-2,3-dioxygenase, cytotoxic T-lymphocyte-associated protein 4-immunoglobulin fusion protein (CTLA4-Ig), tumor necrosis factor-related apoptosis-inducing ligand (Apo2L, TRAIL), or a fragment thereof;

wherein the disorder is selected from the group comprising inflammation, cancer, rheumatic disorder, severe graft versus host disease, osteoarthritis, cardiovascular disorder, epithelial diseases, neurodegenerative disorders, autoimmune disorders, bone and cartilage disorders, osteoporosis, renal osteodystrophy, Paget's disease of bone, osteopetrosis, rickets, neurological disorders, intoxication, neuroendocrinology disorders, endocrinology disorders, genetic disorders, infectious diseases, dental disorders, cosmetic procedures, coagulation disorders, dermatoses, diabetes, age-associated disorders.

Also described herein is a method for treating or ameliorating a disorder comprising administering to a patient suffering from said disorder a therapeutically effective amount of a synthetic extracellular vesicle between 70 nm and 5000 nm with the composition described above, and specifically comprising:

a lipid bilayer comprising 1,2-dioleoyl-sn-glycero-3-phosphocholine (DOPC), 1,2-dioleoyl-sn-glycero-3-phospho-rac-(1-glycerol) (DOPG), 1,2-dioleoyl-sn-glycero-3-phosphoethanolamine-N-(lissamine rhodamine B sulfonyl) (LissRhod PE), 1,2-dioleoyl-sn-glycero-3-[(N-(5-amino-1-carboxypentyl)iminodiacetic acid) succinyl] (nickel salt) (DGS-NTA(Ni$^{2+}$)); functional protein Fas Ligand, or a fragment thereof; and optionally functional protein intercellular adhesion protein-1, or a fragment thereof;

wherein the disorder is selected from the group comprising inflammation, cancer, rheumatic disorder, severe graft versus host disease, osteoarthritis, cardiovascular disorder, epithelial diseases, neurodegenerative disorders, autoimmune disorders, bone and cartilage disorders, osteoporosis, renal osteodystrophy, Paget's disease of bone, osteopetrosis, rickets, neurological disorders, intoxication, neuroendocrinology disorders, endocrinology disorders, genetic disorders, infectious diseases, dental disorders, cosmetic procedures, coagulation disorders, dermatoses, diabetes, age-associated disorders.

Also described herein is a method for treating or ameliorating a disorder comprising administering to a patient suffering from said disorder a therapeutically effective amount of a synthetic extracellular vesicle between 70 nm and 5000 nm with the composition described above, and specifically comprising:

one or more transmembrane proteins selected from the group comprising CD29, CD44, CD90, CD73, CD44, Sca-1, or a fragment thereof;

one or more functional proteins selected from the group comprising Wnta and Wntb, or a fragment thereof;

at least one nucleic acid molecule selected from the group comprising miR-140-5p, miR-92a-3p-e;

one or more transmembrane proteins selected from the group comprising tetraspanin proteins CD9, CD63, and CD81, or a fragment thereof;

one or more nucleic acid molecules selected from the group comprising miR-17, miR-18a, miR-19a, miR-19b-1, miR-20a, miR-92a, let-7a, miR-21, miR124, miR126, miR-133b, miR-191, miR-222, miR-494, miR-6087, miR-30d-5p; and optionally one or more nucleic acid molecules selected from the group comprising miR-33b, miR-451, miR-575, miR-630, miR-638, miR-1202, miR-1207-5p, miR-1225-5p, miR-1268, miR-K12-3;

wherein the disorder is selected from the group comprising inflammation, cancer, rheumatic disorder, severe graft versus host disease, osteoarthritis, cardiovascular disorder, epithelial diseases, neurodegenerative disorders, autoimmune disorders, bone and cartilage disorders, osteoporosis, renal osteodystrophy, Paget's disease of bone, osteopetrosis, rickets, neurological disorders, intoxication, neuroendocrinology disorders, endocrinology disorders, genetic disorders, infectious diseases, dental disorders, cosmetic procedures, coagulation disorders, dermatoses, diabetes, age-associated disorders.

Further described herein is a method for treating or ameliorating a disorder comprising administering to a patient suffering from said disorder a therapeutically effective amount of a synthetic extracellular vesicle between 70 nm and 5000 nm with the composition described above, and specifically comprising:

a lipid bilayer comprising 1,2-dioleoyl-sn-glycero-3-phosphocholine (DOPC), 1,2-dioleoyl-sn-glycero-3-phospho-rac-(1-glycerol) (DOPG), 1,2-dioleoyl-sn-glycero-3-phosphoethanolamine-N-(lissamine rhodamine B sulfonyl) (LissRhod PE), 1,2-dioleoyl-sn-glycero-3-[(N-(5-amino-1-carboxypentyl)iminodi-acetic acid) succinyl] (nickel salt) (DGS-NTA(Ni$^{2+}$)); and functional protein RANK, or a fragment thereof;

wherein the disorder is selected from the group comprising inflammation, cancer, rheumatic disorder, severe graft versus host disease, osteoarthritis, cardiovascular disorder, epithelial diseases, neurodegenerative disorders, autoimmune disorders, bone and cartilage disorders, osteoporosis, renal osteodystrophy, Paget's disease of bone, osteopetrosis, rickets, neurological disorders, intoxication, neuroendocrinology disorders, endocrinology disorders, genetic disorders, infectious diseases, dental disorders, cosmetic procedures, coagulation disorders, dermatoses, diabetes, age-associated disorders.

"Disorder" is any condition that would benefit from treatment with a substance/molecule or method described herein.

"Cell proliferative disorder" and "proliferative disorder" refer to disorders that are associated with some degree of abnormal cell proliferation, such as cancer.

"Cancer" and "cancerous" refer to, or describe a physiological condition in mammals that is typically characterized by a cell proliferative disorder. Cancer generally can include, but is not limited to, carcinoma, lymphoma (e.g., Hodgkin's and non-Hodgkin's lymphoma), blastoma, sarcoma, and leukemia. More specific examples of cancer can include, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

"Tumour" refers to all neoplastic cell growth and proliferation, whether malignant or benign, and all pre-cancerous and cancerous cells and tissues. The terms "cancer", "cancerous", "cell proliferative disorder", "proliferative disorder", and "tumour" are not mutually exclusive as referred to herein.

"Cardiovascular disorders" include but are not limited to disorders of the heart and the vascular system like congestive heart failure, myocardial infarction, ischemic diseases of the heart, all kinds of atrial and ventricular arrhythmias, hypertensive vascular diseases, peripheral vascular diseases, and atherosclerosis.

"Metastasis" refers to the spread of cancer and/or tumour from its primary site to other places in the body of an individual.

The term "neurodegenerative disease" or "neurological disorder" or "neuroinflammatory disorder" refers to any disease, disorder, or condition affecting the central or peripheral nervous system. Preferred examples of neurodegenerative diseases and neuroinflammatory disorders are selected from the group comprising or consisting of: Alzheimer's disease, Parkinson's disease, Creutzfeldt Jakob disease (CJD), new variant of Creutzfeldt Jakobs disease (nvCJD), Hallervorden Spatz disease, Huntington's disease, multisystem atrophy, dementia, frontotemporal dementia, motor neuron disorders of multiple spontaneous or genetic background, amyotrophic lateral sclerosis (ALS), spinal muscular atrophy, spinocerebellar atrophies (SCAs), schizophrenia, affective disorders, major depression, meningoencephalitis, bacterial meningoencephalitis, viral meningoencephalitis, CNS autoimmune disorders, multiple sclerosis (MS), acute ischemic/hypoxic lesions, stroke, CNS and spinal cord trauma, head and spinal trauma, brain traumatic injuries, arteriosclerosis, atherosclerosis, microangiopathic dementia, Binswanger' disease (Leukoaraiosis), retinal degeneration, cochlear degeneration, macular degeneration, cochlear deafness, AIDS-related dementia, retinitis pigmentosa, fragile X-associated tremor/ataxia syndrome (FXTAS), progressive supranuclear palsy (PSP), striatonigral degeneration (SND), olivopontocerebellear degeneration (OPCD), Shy Drager syndrome (SDS), age dependant memory deficits, neurodevelopmental disorders associated with dementia, Down's Syndrome, synucleinopathies, superoxide dismutase mutations, trinucleotide repeat disorders as Huntington's Disease, trauma, hypoxia, vascular diseases, vascular inflammations, CNS-ageing. Also age dependant decrease of stem cell renewal may be addressed.

"Aging-associated disorders and diseases" are most often seen with increasing frequency with increasing senescence. Examples of aging-associated diseases are atherosclerosis and cardiovascular disease, cancer, arthritis, cataracts, osteoporosis, type 2 diabetes, hypertension and Alzheimer's disease. The incidence of all of these diseases increases exponentially with age.

"Rheumatic diseases" are characterized by inflammation that affects the connecting or supporting structures of the body; most commonly the joints, but also sometimes the tendons, ligaments, bones, and muscles. Some rheumatic diseases even affect the organs. These diseases can ultimately cause loss of function in those body parts. Preferred examples of rheumatic diseases and are selected from the group comprising or consisting of: osteoarthritis, rheumatoid arthritis, fibromyalgia, systemic lupus erythematosus, gout, juvenile idiopathic arthritis, arthritis, scleroderma.

"Epithelial diseases" include acne, atopic eczema, atopic dermatitis, contact dermatitis, impetigo, psoriasis, sunburn, sweating disorders, yeast infections of the mucous membranes.

"Endocrinology disorders" include diabetes, adrenal insufficiency, cushing's disease, gigantism, hyperthyroidism, hypothyroidism, hypopituitarism, polycystic ovary syndrome.

Neuroendocrine disorders are disorders that affect the interaction between the nervous system and the endocrine system. Examples of neuroendocrine disorders include diabetes insipidus, Kallman syndrome, neuroendocrine cancer, and neuroendocrine tumors (NETs), which are neoplasms that arise from cells of the endocrine and nervous systems.

"Bone and cartilage disorders" include diseases or injuries that affect human bones and cartilage.

"Osteoarthritis" is one of the leading causes of disability in adults worldwide. It is a degenerative disease of the joints secondary to many predisposing factors, most notably age, joint injury, altered mechanical stress, and obesity. All these processes cause a local chronic inflammatory response resulting in the progressive joint failure characteristic of osteoarthritis.

"Osteoporosis" is the result of cumulative bone loss during aging. Nevertheless, a wide variety of diseases, medications, and lifestyles can cause or contribute to the development of osteoporosis. In addition, the immune system participates in the regulation of bone homeostasis through production of cytokines and inflammatory mediators with subsequent activation of cartilage-degrading proteinases.

"Paget's disease" is a chronic skeletal disorder, caused by enhanced bone resorption followed by abnormal bone formation, in which a potential cross talk between the bone and the immune system takes place.

Other bone related disorders include renal osteodystrophy, osteopetrosis, rickets.

"Cartilage disorders" include osteoarthritis, costochondritis enchondromatosis, herniation, achondroplasia, relapsing polychondritis, chondroma, chondrosarcoma.

"Treatment", "treat" or "treating" refer to clinical intervention in an attempt to alter the natural course of a disorder in the individual being treated, and can be performed either for prophylaxis or during the course of clinical pathology. Desired results of treatment can include, but are not limited to, preventing occurrence or recurrence of the disorder, alleviation of symptoms, diminishment of any direct or indirect pathological consequences of the disorder, preventing metastasis, decreasing the rate of progression, amelioration or palliation of a disease state, and remission or improved prognosis. For example, treatment can include administration of a therapeutically effective amount of a pharmaceutical formulation comprising a synthetic extracellular vesicle disclosed herein to a subject to delay development or slow progression of a disorder, wherein the disorder is selected from the group comprising inflammation, cancer, rheumatic disorder, severe graft versus host disease, osteoarthritis, cardiovascular disorder, epithelial diseases, neurodegenerative disorders, autoimmune disorders, bone and cartilage disorders, osteoporosis, renal osteodystrophy, Paget's disease of bone, osteopetrosis, rickets, neurological disorders, intoxication, neuroendocrinology disorders, endocrinology disorders, genetic disorders, infectious diseases, dental disorders, cosmetic procedures, coagulation disorders, dermatoses, diabetes, age-associated disorders.

"Pharmaceutical formulation" refers to a preparation in a form that allows the biological activity of the active ingredient (s) to be effective, and which contain no additional components which are toxic to the subjects to which the formulation is administered.

"Pharmaceutically acceptable carrier" refers to an ingredient in a pharmaceutical formulation, other than an active ingredient, which is nontoxic to the subject to whom it is administered. A pharmaceutically acceptable carrier includes, but is not limited to, a buffer, excipient, stabilizer, or preservative.

"Therapeutically effective amount" refers to the amount of an active ingredient or agent (e.g., a pharmaceutical formulation) to achieve a desired therapeutic or prophylactic result, e.g., to treat or prevent a disease or disorder in a subject. In the case of a cancer, the therapeutically effective amount of the therapeutic agent is an amount that reduces the number of cancer cells; reduces the primary tumour size; inhibits (i.e. slows to some extent and preferably stop) cancer cell infiltration into peripheral organs; inhibits (i.e. slows to some extent and preferably stop) tumour metastasis; inhibits, to some extent, tumour growth; and/or relieves to some extent one or more of the symptoms associated with the cancer. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

"Individual" or "subject" refers to a mammal, including but not limited to, domesticated animals (e.g. cows, sheep, cats, dogs, and horses), primates (e.g. humans and non-human primates such as monkeys), rabbits, and rodents (e.g. mice and rats).

A "therapeutic agent" or "therapeutic molecule" includes a compound or molecule that, when present in an effective amount, produces a desired therapeutic effect, pharmacologic and/or physiologic effect on a subject in need thereof. It includes any compound, e.g. a small molecule drug, or a biologic (e.g., a polypeptide drug or a nucleic acid drug) that when administered to a subject has a measurable or conveyable effect on the subject, e.g., it alleviates or decreases a symptom of a disease, disorder or condition.

As used herein, the term "antibody" encompasses an immunoglobulin whether natural or partly or wholly synthetically produced, and fragments thereof. The term also covers any protein having a binding domain that is homologous to an immunoglobulin binding domain. "Antibody" further includes a polypeptide comprising a framework region from an immunoglobulin gene or fragments thereof that specifically binds and recognizes an antigen. Use of the term antibody is meant to include whole antibodies, polyclonal, monoclonal and recombinant antibodies, fragments thereof, and further includes single-chain antibodies, humanized antibodies, murine antibodies, chimeric, mouse-human, mouse-primate, primate-human monoclonal antibodies, anti-idiotype antibodies, antibody fragments, such as, e.g., scFv, (scFv)2, Fab, Fab', and F(ab')2, F(abl)2, Fv, dAb, and Fd fragments, diabodies, and antibody-related polypeptides. Antibody includes bispecific antibodies and multispecific antibodies so long as they exhibit the desired biological activity or function.

DESCRIPTION OF THE FIGURES

FIG. 22 shows stability of the extracellular vesicles after storage in human serum at 4° C., calculated as cellular fluorescence retention normalized to untreated control cells (retention=1). fsEV=fully synthetic extracellular vesicles.

EXAMPLES

Materials

Figure 1:
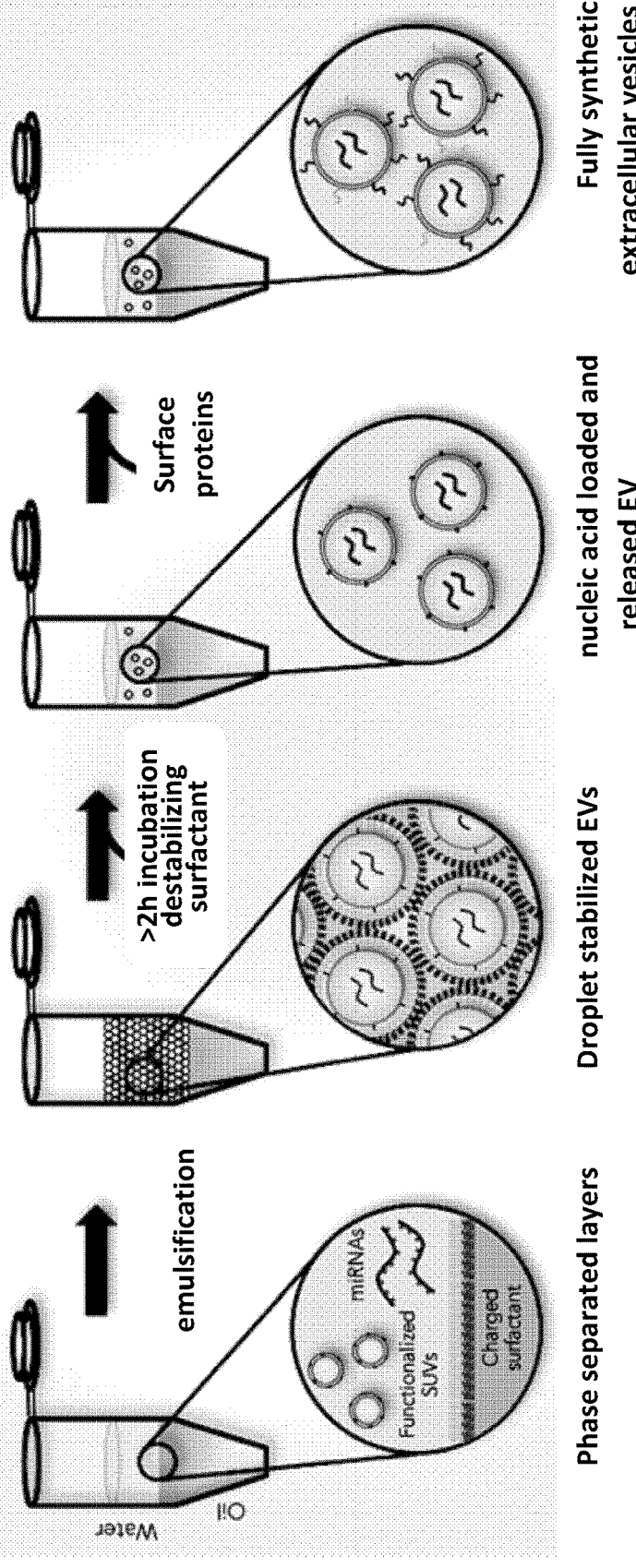
FIG. 1 shows a schematic representation of the production pipeline for bottom-up assembly of fully synthetic extracellular vesicles within a stabilizing polymer shell.

18:1 DOPG 1,2-dioleoyl-sn-glycero-3-phospho-(1'-rac-glycerol), 18:1 DOPC 1,2-dioleoyl-sn-glycero-3-phospho-cholesteroline, 18:1 DOPE 1,2-dioleoyl-sn-glycero-3-phosphoethanolamine, LissRhod PE 1,2-dioleoyl-sn-glycero-3-phosphoethanolamine-N-(lissamine rhodamine B sulfonyl), 18:1 DGS-NTA(Ni) 1,2-dioleoyl-sn-glycero-3-[(N-(5-amino-1-carboxypentyl)iminodiacetic acid)succinyl] (nickel salt), 18:1 1,2-dioleoyl-sn-glycero-3-phospho-(1'-myo-inositol) (ammonium salt), 18:1 1,2-di-(9Z-octadecenoyl)-sn-glycero-3-phospho-L-serine (sodium salt), 18:1 1,2-di-(9Z-octadecenoyl)-sn-glycero-3-phosphate (sodium salt), cholesterol, 18:1 1-2-di-(9Z-octadecenoyl)-sn-glycerol, 18:0 N-stearoyl-D-erythro-sphingosylphosphorylcholine and extrude set with 50 nm pore size polycarbonate filter membranes were purchased from Avanti Polar Lipids, USA. All lipids were stored in chloroform at −20° C. and used without further purification. Hoechst 33342, CellTracker Green CMFDA dye, wheat germ agglutinin (WGA)-AlexaFluor conjugates (obtained from Thermo Fisher scientific, Invitrogen), Dulbecco's Modified Eagle Medium (DMEM) high Glucose, heat inactivated as well as exosome depleted fetal bovine serum, recombinant N-terminal His-tagged human CD9 (amino acids 103-203), penicillin-streptomycin (10,000 U/mL), L-Glutamine (200 mM), Alexa Fluor 488 NHS Ester, trypsin-EDTA (0.05%) with phenol red and phosphate buffered saline were purchased from Thermo Fischer Scientific, Germany. 1H,1H,2H,2H-Perfluoro-1-octanol (PFO) de-emulsifier and human male plasma serum were purchased from Sigma Aldrich, Germany. Bovine albumin fraction V (BSA) was purchased from Carl Roth, Germany. HaCaT cells were obtained from CLS cell line service, Germany. A431, K562, MC 3T3, and BJ cell lines as well as Iscove's Modified Dulbecco's Medium were obtained from ATCC, USA. Atto488 conjugated 1,2-dipalmitoyl-sn-glycero-3-phosphoethanolamine was purchased from Atto-Tec GmbH, Germany. Caspase 8 (Cleaved Asp391) monoclonal antibody (clone S.147.8) was purchased from Thermo Fischer Scientific, Germany. Purified Mouse Anti-ERK1/2 (pT202/pY204) was purchased from BD biosciences (Cat. No. 612358). Recombinant N-terminal His-tagged human CD9 (protein ID P21926 amino acids 112-195) was purchased from Novus Biologicals, Germany. Recombinant N-terminal His-tagged human TSG101 (protein ID Q99816, amino acids 1-145) was purchased from Fitzgerald, USA. Recombinant N-terminal His-tagged human CD81 (protein ID P35762, amino acids 113-201) was purchased from MyBioSource, USA. Recombinant N-terminal His-tagged human CD63 (protein ID P08962, amino acids Ala 103-Val 203) was purchased from Thermo Fischer Scientific, Germany. Recombinant His-tagged RANK (protein ID O35305, amino acids 31-214) was obtained from Abcam, Germany. Recombinant his-tagged FasL amino acids N-Met-His8 (Pro134-Leu281) (protein ID NM_000639.1) was obtained from BioLegend, USA. His tagged ICAM-1 (protein ID P05362) recombinant human protein (Met 1-Glu 480), was obtained from Thermo Fischer Scientific, Germany. miRIDIAN micro RNA mimics (hsa-miR-21-5p, hsa-miR124-3p, hsa-miR-125b-5p, hsa-miR-126-5p, hsa-miR-130a-3p, hsa-miR-132-3p) were purchased from Horizon Dharmacon, USA. K562 exosomes (HBM-K562) were obtained from Hansa BioMed Lonza, Switzerland. 4-well cell exclusion inserts were purchased from Ibidi, Germany. Pre-wounded full thickness human organotypic skin cultures, respective culture media and histological sample preparation services were purchased from MatTek Cooperation, USA. FC-40 oil was purchased from Iolitec, Germany. ELISA kit for quantification of human pro-collagen I alpha was obtained from Abcam, UK.

Methods

Exosome Isolation from K562 Cell Cultures

K562 extracellular vesicles were isolated from conditioned cell culture medium by differential centrifugation. For this, K562 cells were cultured in 50 ml of Iscove's modified Dulbecco's Medium for 48 hours in suspension with 10% exosome free serum at 37° C. and 5% CO$_2$ atmosphere. The final cell concentration was 5×10$^5$ cells/ml. After incubation, the cell suspension was centrifuged at 300 g at 4° C. for 10 minutes to remove the cells. The supernatant was filtered through a 0.22 μm filter and centrifuged at 125,000 g at 4° C. for 75 min with a Beckmann Coulter Optima XE-100 ultracentrifuge in a JA-20 fixed angle rotor (k-factor 770). The pellet was washed with 50 ml ice-cold PBS and centrifuged again under the same conditions. The exosome pellet was resuspended in 1 ml PBS. The total protein concentration of this exosome suspension was assessed by measuring the absorbance at 280 nm with a Nanodrop ND-1000 spectrophotometer.

Confocal and Bright Field Microscopy

Confocal microscopy was performed with a laser scanning microscope LSM 800 (Carl Zeiss AG). Images were acquired with a 20× (Objective Plan-Apochromat 20×/0.8 M27, Carl Zeiss AG) and a 63× immersion oil objective (Plan-Apochromat 63×/1.40 Oil DIC, Carl Zeiss AG). Images were analyzed with ImageJ (NIH) and adjustments of image brightness and contrast or background corrections were performed always on the whole image and special care was taken not to obscure or eliminate any information from the original image. For bright field imaging a Leica DMi8 inverted fluorescent microscope equipped with a sCMOS camera and 10×HC PL Fluotar (NA 0.32, PH1) objective was used.

For analysis of extracellular vesicle uptake into HaCaT cells, rhodamine B labeled extracellular vesicles were incubated with HaCaT cells in Nunc LabTek 8-well chambers. Immediately after addition of the extracellular vesicles to the cells, 5 μg/ml of AlexaFluor (obtained from Thermo Fischer Scientific, Invitrogen) conjugated wheat germ agglutinin (WGA) was added to the medium. Cells were incubated for 24 hours and subsequently imaged by confocal laser scanning microscopy. WGA binds to specific sugar residues on the outer cell membrane and is endocytosed along with them during membrane turn-over and endocytotic processes, staining intracellular endosomal vesicles.

Alexa488 labelled CD9 was produced by incubating NHS functionalized Alexa488 with recombinant CD9 in a twofold molar excess for 2 hours at 37° C. in PBS. Subsequently, free NHS was quenched by adding a 10-fold molar excess of glycine.

Staining of HaCaT cells with CellTracker Green was performed by incubating 20 μM of cell Tracker Green CMFDA dye for 60 min. To remove excess dye and non-uptaken synthetic extracellular vesicles, cells were rinsed twice with PBS.

Transmission Electron Microscopy

For analysis of synthetic extracellular vesicles conjugated with recombinant extracellular domain of FasL (FIG. 18a), cryo-electron microscopy samples were prepared by applying 2.5 μL of vesicle solution onto a glow-discharged 200 mesh C-flat holey carbon-coated multihole grid. Subsequently, blotting was performed for 4 s. Plunge-freezing was performed in liquid ethane using a Vitrobot Mark IV at 100% humidity and grids were stored under liquid nitrogen. The samples were imaged with a FEI Tecnai G2 T20 twin transmission electron microscope operated at 200 kV. A FEI Eagle 4k HS, 200 kV CCD camera was used to record electron micrographs with a total dose of ≈40 electrons/A2.

The protein to lipid ratio on vesicle membranes (FIG. 23a) was evaluated through negative staining of gold nanoparticles on the vesicle membranes and transmission electron microscopy analysis. To this aim, vesicles were incubated with 6x-Histidine tagged Protein G for 15 min. Subsequently, gold nanoparticle conjugated antibodies (Anti-goat IgG (whole molecule)-gold antibody produced in rabbit; Sigma Aldrich #G5402). Vesicle solutions were subsequently prefixed with 0.5% osmium tetroxide. Subsequently a negative staining was performed using 1% uranyl acetate and imaging was performed with a Zeiss EM 10 CR transmission electron microscope. ImageJ (NIH) software was used to measure the total vesicle area from electron micrographs. Additionally, gold nanoparticles on the vesicles were manually counted.

Dynamic Light Scattering

Analysis of the hydrodynamic radius of vesicles was performed with a Malvern Zetasizer Nano ZS system. Samples were diluted to a final lipid concentration of 15 μM in PBS filtered with through a 0.22 μm filter. The temperature equilibration time was set to 300 s at 25° C. Three individual measurements for each sample were performed at a scattering angle of 173° based on the built-in automatic run-number selection. The material refractive index was set to 1.4233 and solvent properties were set to $\eta$=0.8882, n=1.33 and $\varepsilon$=79.0.

Polydispersion Index Determination

Size polydispersion index (PDI) was assessed from hydrodynamic radius measurements based on dynamic light scattering. A Malvern Zetasizer Nano ZS was used to perform dynamic light scattering (DLS) measurements and PDI was derived from the automatically calculated size distribution analysis.

Cell Culture

HaCaT, BJ and A431 cells were cultured in Dulbecco's Modified Eagle Medium supplemented with 4.5 g/l glucose, 1% L-glutamine, 1% penicillin/streptomycin and 10% fetal bovine serum. Cells were routinely cultured at 37° C. and 5% $CO_2$ atmosphere and passaged at approx. 80% confluency using 0.05% trypsin/EDTA treatment. K562 cells were cultured in suspension in Iscove's modified Dulbecco's Medium supplemented with 10% exosomes free fetal bovine serum. K562 cells were splitted every other day by transferring 3 ml of cell suspension to 10 ml of fresh cell culture medium.

To evaluate serum stability (FIG. 22), 100,000 HaCaT cells/well were seeded in 96-flat bottom transparent well plates. After 24 hours, synthetic extracellular vesicles harbouring fluorescent Rhodamine B lipids, preserved in serum at 4° C. for 2 days or 63 days, were added for 24 hours to the cells. Subsequently, fluorescence intensity in every well was measured by microplate-reader analysis. The cells were then washed 3 times with 100 μl PBS and remaining fluorescence intensity in each well (corresponding to the uptaken or strongly bound vesicles) was measured again by microplate reader. The fluorescence intensity after washing was divided by the fluorescence intensity before washing for each well and normalized to the untreated control value.

Assessment of Cell Proliferation

For proliferation analysis, a previously reported Hoechst 33342 intensity analysis was applied. To this end, HaCaT and A431 cells were seeded at a density of 15.000 cells/well in a flat-bottom transparent 96-well plate in 200 μl culture medium. Cells were seeded together with corresponding extracellular vesicles and incubated for 48 hours. Subsequently, cells were washed twice with 100 μl PBS and incubated for 10 min with icecold culture medium supplemented with 10 μM Hoechst 33342. After removal of the culture medium and 2x washing with PBS, Hoechst 33342 intensity was measured at four individual positions in each well using an Infinite M200 TECAN plate reader controlled by TECAN iControl software with an in-built gain optimization and excitation/emission setting adjusted to 380/460 nm. Measurements were performed in triplicates.

Cell Exclusion Assay

For in vitro 2D wound healing assays, 4-well silicone cell exclusion cell culture inserts with a gap width of 500 μm were used in 12-well plastic plates. Cells were seeded at a cell density of 40,000 cells/well and allowed to adhere overnight in 110 μl culture medium (2 ml of culture medium were added to the well outside of the inserts). Extracellular vesicles were incubated (at final lipid concentration of 10 μM) with the cell monolayer for 24 hours. Subsequently, the inserts were carefully removed using sterile tweezers and the wound was allowed to close for 16 hours. For quantification, culture medium was removed and cell layers were fixed with ice-cold 4% paraformaldehyde for a minimum of 20 min. The wound sides were then imaged by phase contract microscopy and the cell free area was quantified manually with ImageJ software.

Organotypic Dermal Cultures

For analysis of human organotypic full thickness skin models, pre-wounded human epidermal keratinocytes (obtained from neonatal-foreskin normal tissue of a single donor) and fibroblasts 3D cultures were obtained from a commercial distributer (MatTek corporation). Skins were cultured at an air-liquid interface following manufacturer's suggestions. For wound closure analysis, tissues were allowed to equilibrate for 16 hours after arrival at 37° C. in a 5% $CO_2$ atmosphere. Subsequently, 2 μl of the extracellular vesicle solution (or respective buffer controls) were pipetted onto the wound side and the wound was allowed to heal for 48 hours at 37° C. in a 5% $CO_2$ atmosphere. Tissues were then fixed with 10% formalin solution overnight at 4° C. Wound size was quantified from histological H/E slices. For each wound, six individual slices and three individual wounds were analyzed.

Protein Analysis by Gel-Electrophoresis

For gel-electrophoretic analysis of protein content of K562 exosomes and synthetic extracellular vesicles, a NuPAGE bold Bis-Tris 4-12% gradient gel was used with MES running buffer. Electrophoresis was performed at 200V for 35 min under denaturing conditions with a total of 3 μg (for natural exosomes) or 500 ng (for synthetic extracellular vesicles) of protein loaded onto each lane. Protein staining was performed with Coomassie R250. Line intensity profiles of the respective lanes were measured by ImageJ software.

Quantitative Assessment of Collagen Deposition

For quantification of in vitro collagen deposition, BJ dermal fibroblast were seeded in 96-well flat bottom transparent cell culture plates at a density of 20,000 cells/well. 24 hours after seeding, cells were washed twice with PBS and 200 µl of fresh cell culture medium was added together with synthetic extracellular vesicles (to a final lipids concentration of 10 µM) to the cells. Cells were incubated for 24 hours with synthetic extracellular vesicles. Subsequently human pro-collagen I alpha in the medium was quantified by enzyme-linked immunosorbent assay (Abcam ELISA Kit) following the manufacturer's instructions.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the scope of the invention as described in the following claims.

Example 1. Production of Biomimetic Fully Synthetic Extracellular Vesicles

Synthetic extracellular vesicles were produced by shear stress emulsification (FIG. 1). At first, a solution of small unilamellar vesicles was prepared as follows: lipids dissolved in chloroform stock solutions were mixed at the desired lipid ratio in glass vials and subsequently dried under a gentle nitrogen stream. The obtained lipid film was rehydrated to a final lipid concentration of 6 mM in PBS for 15 min and afterwards shaken for 5 min at 1000 rpm. This solution of small unilamellar vesicles was extruded at least 9 time through a 50 nm pore size filter.

The so obtained solution, representing the water phase of step a), was then diluted to a final concentration of 3 mM with PBS, or eventually PBS containing the desired miRID-IAN miRNA mimic components at concentration 40-145 nM.

In this example, polymer shell-stabilized extracellular vesicles were produced from small unilamellar vesicles containing 41 mol % cholesterol, 16 mol % SM, 15 mol % DOPC, 11 mol % DOPS, 6 mol % DOPE, 5 mol % DOPG, 2 mol % PA, 1 mol % DAG, 1 mol % PI, 1 mol % LissRhod PE, 1 mol % DGS-NTA(Ni$^{2+}$) in PBS containing miRID-IAN RNA (40-145 nM). This lipid composition resembles that of natural extracellular vesicles. However, the technology allows for the integration of an almost unrestricted number of possible lipid types into synthetic exosome membrane.

This water phase was then combined with an oil phase at a ratio 1:2. The oil phase consisted of FC-40 oil containing the fluorosurfactant triblock PEG2500-PFPE600-PEG2500 at a final concentration of 1.25 mM.

The combined water phase and oil phase was then emulsified using an Ultra Turrax IKA T10 basic emulsifier for, exemplarily, 60 sec at approx. 26,300 rpm. The resulting polymer shell stabilized synthetic extracellular vesicles were incubated for at least 2 hours at 4° C. in the dark.

Release of the polymer shell stabilized extracellular vesicles into an aqueous release buffer was performed by removing excess oil phase and adding the release buffer (PBS) and 1H,1H,2H,2H-perfluoro-1-octanol (PFO) to the mixture in a 1:1:1 ratio of aqueous release buffer:PFO. aqueous intraluminal buffer. After 30 min of equilibration, the layer containing the extracellular vesicles was transferred into a 2 ml microtube and PBS was added to a final volume of 2 ml.

This solution was centrifuged at >10,000 g for 15 min.

The supernatant was discarded and the extracellular vesicle pellet was resuspended in PBS. The extracellular vesicles were also released into PBS containing 0.1% BSA to block unspecific protein-lipid interactions In order to conjugate the released extracellular vesicles with CD peptides, the total amount of NTA(Ni$^{2+}$) functionalized lipids was calculated according to the lipid ratio. Thus, the His-tagged CD-peptides (CD9, TSG101, or CD63, or CD81) were added to the extracellular vesicle solution in a 1:2 excess and allowed to conjugate for 1 hour at 37° C. protected from light. After this phase, 500 nM Hoechst33342 was eventually added to the extracellular vesicles to visualize nucleic acids by confocal microscopy analysis.

The extracellular vesicle solution was subsequently centrifuged at >10,000 rpm for 15 min. The supernatant containing unbound peptides was disposed and the extracellular vesicle pellet resuspended in PBS.

In order to compare the lipid ratio of the formed extracellular vesicles, and that of the small unilamellar vesicles, the total lipid concentration of the extracellular vesicles was determined by quantifying the fluorescence from the integrated rhodamine B or Atto488 conjugated lipids, which was referenced to a small unilamellar vesicle standard dilution curve.

Figure 2:
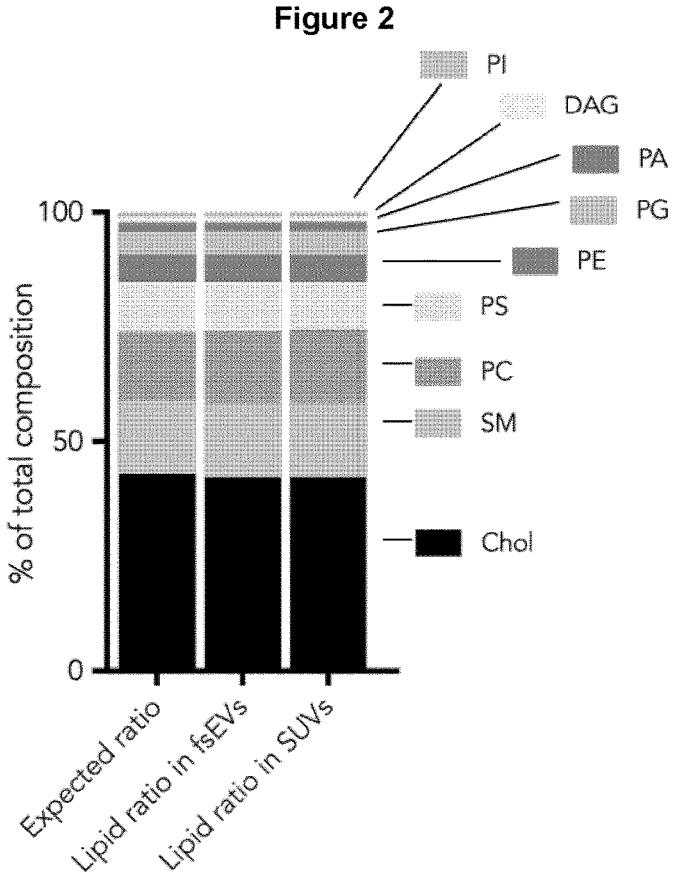
FIG. 2 shows quantification of lipid ratios (18:1 DOPI, 18:1 DAG, 18:1 PA, 18:1 DOPG, 18:1 DOPE, 18:1 DOPS, 18:1 DOPC, SM, Cholesterol) in the starting small unilamellar vesicles and in the produced synthetic extracellular vesicles as quantified by electrospray-ionization tandem mass spectrometry. These results are compared to the corresponding expected lipid ratio according to design of fully synthetic extracellular vesicles.

The results of quantitative electrospray-ionization tandem mass spectrometry revealed that fully synthetic extracellular vesicles had the lipid composition cholesterol:SM:DOPC:DOPS:DOPE:DOPG:PA:DAG:PI 43:16:15:11:6:5:2:1:1, resembling not only the lipid composition of natural extracellular vesicles, but also that of the original small unilamellar vesicles (FIG. 2), proving that no lipid ratio change occurs during the emulsification and release procedures. Therefore, the lipid composition of the extracellular vesicles can be easily fine-tuned by changing the lipid formulation of the original small unilamellar vesicles.

Example 2. Comparison with Exosomes Obtained by State of the Art Methods

The fully synthetic extracellular vesicles produced as described in Example 1 were compared to natural extracellular vesicles in term of purity, protein composition, dimension, and variability between different batches.

Figure 3:
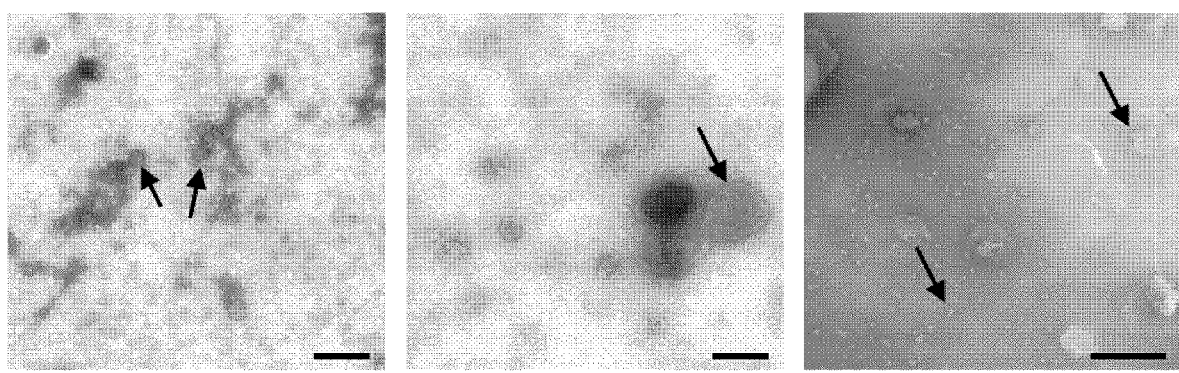
FIG. 3 shows transmission electron micrographs of uranyl acetate negative stained natural and synthetic vesicles. Left panel shows extracellular vesicles (black arrows) isolated from 48 hours conditioned K562 cell culture media by differential ultracentrifugation. Middle panel shows extracellular vesicles isolated from conditioned K562 media by a commercial distributer. Right panel shows fully synthetic extracellular vesicles produced with the lipid composition 70 mol % DOPC, 5 mol % DOPE, 20 mol % DOPG, 5 mol % DOPS according to one embodiment of the invention. Scale bars 100 nm, 100 nm and 1 μm, respectively.

Interestingly, the fully synthetic extracellular vesicles produced according to the invention contained considerably less contaminating aggregates and non-vesicular particles compared to exosomes isolated by differential centrifugation from conditioned K562 erythroleukemia cell media or commercially available exosomes from the same cell line (see FIG. 3).

Figure 4:
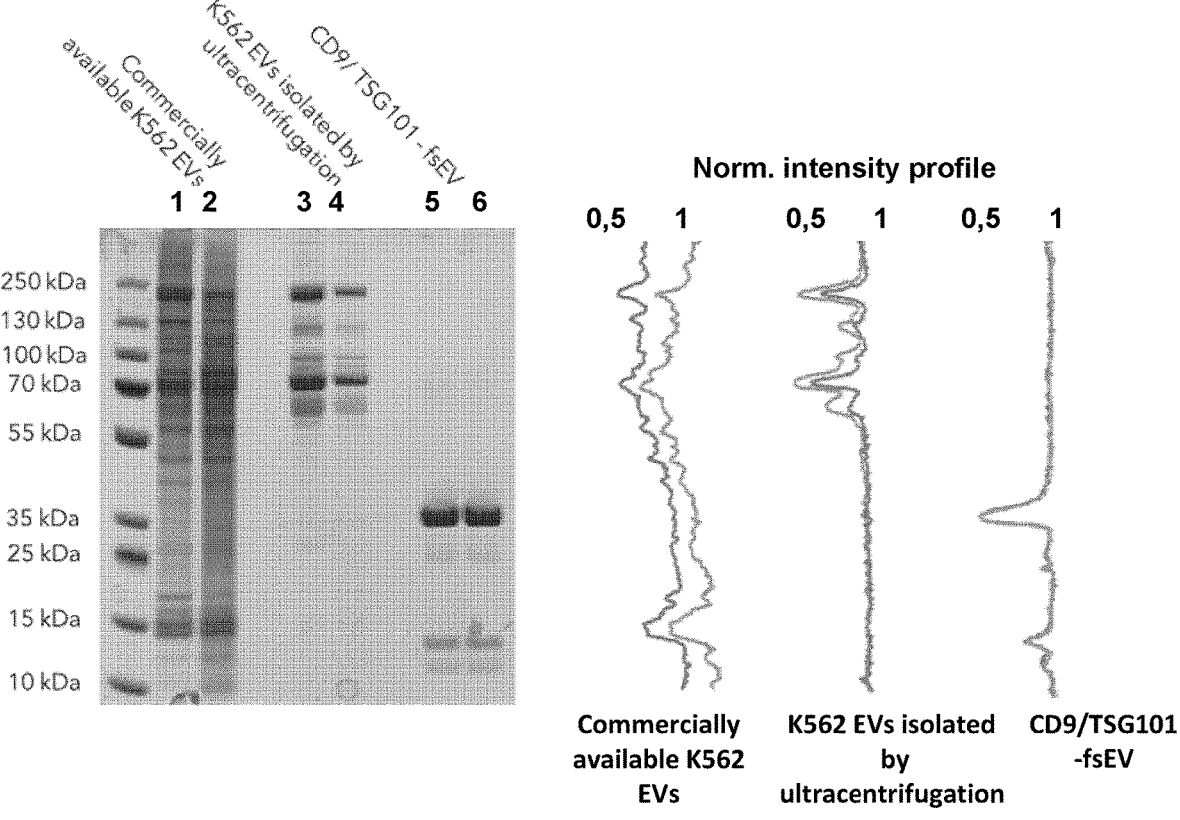
FIG. 4 shows denaturating SDS polyacrylamide gel electrophoretic characterization of synthetic extracellular vesicles protein content. 3 μg of two different production batches of K562 Extracellular vesicles isolated by a commercial distributer were loaded on lane 1 and 2. 3 μg extracellular vesicles from two separate isolations of K562 cells were loaded on lane 3 and 4. 500 ng of synthetic extracellular vesicles from two separate assemblies and decorated with the extracellular domains of CD9 (Ser112-Ile195) and TSG101 (Gly1-Pro145) were loaded on lane 5 and 6. Normalized Line profile intensities of respective lanes are shown on the right.

Moreover, when assessing the protein content of the respective vesicles by denaturating polyacrylamide gel-electrophoresis, it was found that exosomes isolated from conditioned K562 media and K562 commercial exosomes, differed greatly in their protein content, underscoring the degree of variation between different vesicle preparation methods (FIG. 4). Furthermore, when considering the variation between different exosome batches prepared with the same method (column 1 vs 2 and 3 vs 4 of FIG. 4), a substantial degree of variation in the protein composition could be observed. In contrast, fully synthetic extracellular vesicles equipped with purified recombinant human forms of exosome's surface markers CD9 and TSG101, attached by nitrilotriacetic acid (NTA)-poly histidine tag chemistry, appeared with a clearly defined band pattern and showed almost identical characteristics between separate preparations (column 5 vs 6 of FIG. 4). Thus, polymer shell stabilized extracellular vesicles can be considered as a more defined and robust platform for extracellular vesicles research that outperforms extracellular vesicles isolates from natural sources in terms of purity and reproducibility.

Additionally the biophysical similarity of fully synthetic extracellular vesicles to natural extracellular vesicles was evaluated by dynamic light scattering. The results showed that the size of polymer shell stabilized extracellular vesicles and therefore the hydrodynamic radius of fully synthetic extracellular vesicles can be fine-tuned by adjusting the shear stress used during emulsification, producing fully synthetic extracellular vesicles radii between 292 nm±12 nm, (CV=4.1%; n=3) by emulsification for 30 sec at 30,000 rpm, and radii between 627 nm±15 nm, (CV=2.4%; n=3) by emulsification for 30 sec at 14,000 rpm. The zeta potential of synthetic extracellular vesicles containing the above-mentioned lipid formulation was −12.3 mV (±0.7 mV, n=3). Thus, size and zeta potential of the fully synthetic extracellular vesicles are comparable to those of natural extracellular vesicles reported in literature (Vogel, R. et al. *High-Resolution Single Particle Zeta Potential Characterization of Biological Nanoparticles using Tunable Resistive Pulse Sensing, Scientific reports* 7, 2017).

Moreover, the hydrodynamic radius values of the synthetic extracellular vesicles were very similar to those of commercial K562 exosomes (468 nm±199 nm, CV=42.5%, and −11.8 mV±0.9 mV, n=3) and of exosomes isolated from conditioned K562 cell culture medium (240 nm±32 nm, CV=13.3%, and −11.3 mV±0.5 mV, n=3).

With respect to particle size distribution characterization, a parameter used to define the size range of the lipidic carrier systems is called the "polydispersity index" (PDI). PDI is basically a representation of the distribution of size populations within a given sample. The term "polydispersity" (or "dispersity" as recommended by IUPAC) is used to describe the degree of non-uniformity of a size distribution of particles (Danaei et al., *Pharmaceutics* 2018, 10, 57). Also known as the heterogeneity index, PDI is a number calculated from a two-parameter fit to the correlation data (the cumulants analysis). This index is dimensionless. The numerical value of PDI ranges from 0.0 (for a perfectly uniform sample with respect to the particle size) to 1.0 (for a highly polydisperse sample with multiple particle size populations). In drug delivery applications using lipid-based carriers, such as liposome and nanoliposome formulations, a PDI of 0.3 and below is considered to be acceptable and indicates a homogenous population of phospholipid vesicles.

Dynamic scattering analysis showed that the polydispersion index of an exemplary sample of fully synthetic extracellular vesicles is 0.098, demonstrating that the vesicles are homogenous in size.

Figure 22:
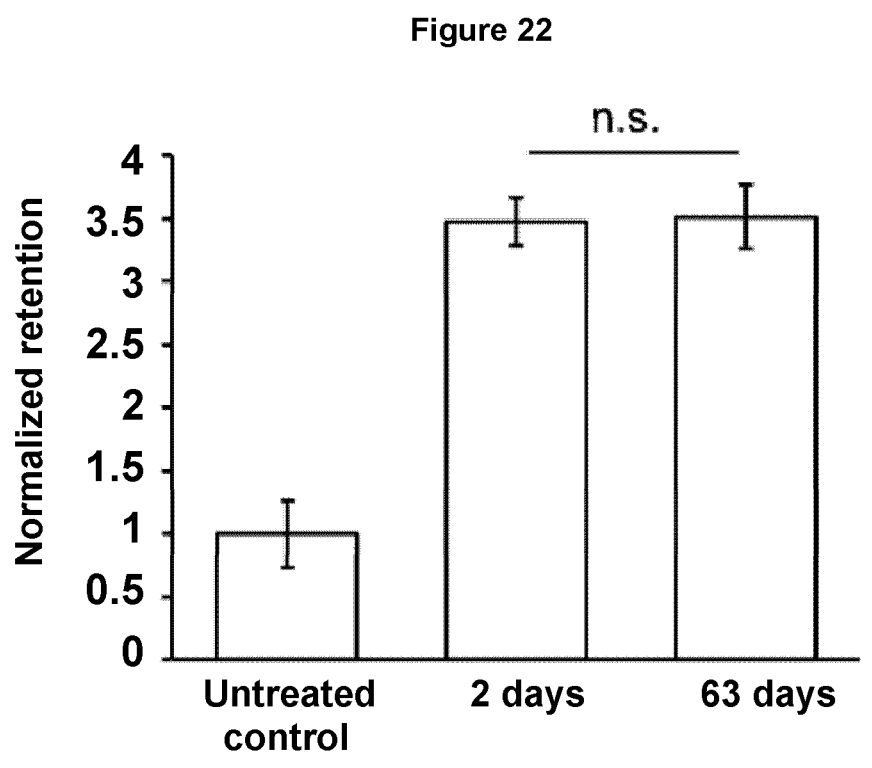

Vesicle stability was evaluated by measuring the uptake rate by target cells of two synthetic extracellular vesicle samples preserved for two different time intervals (FIG. 22). The two samples of fluorescently labeled vesicles (see Methods) were used after storage in 2% human serum at 4° C. for 2 days or 63 days. Vesicle uptake was measured as fluorescence retention normalized to untreated cells. The results show that no significant difference in the uptake of the synthetic extracellular vesicles by cells can be detected after 63 days of storage in serum.

These results confirm that fully synthetic extracellular vesicles can be assembled from individually adjustable synthetic lipid precursors to precisely match the lipid composition and therefore biophysical characteristic (membrane charge, dimensions) of natural extracellular vesicles. Importantly, the fully synthetic extracellular vesicles prepared according to the inventive method showed the technical advantage to be much more reproducible, pure, stable and homogenous in size (coefficient of variation and PDI) in comparison with the exosomes obtained according to prior art methods.

Example 3. Building of Fully Synthetic
Extracellular Vesicles Resembling the Protein and
Nucleic Acid Composition of Natural Exosomes Although lipids play an important role in extracellular vesicle communication, for therapeutic applications the main physiological functions of extracellular vesicles is commonly attributed to their micro RNA (miRNA) cargo and to the peripheral membrane proteins and receptor ligands on their surface.

The inventors have here produced synthetic exosomes miming fibrocyte-derived exosomes, in order to show the potential of the inventive method to produce synthetic exosomes for therapeutic application.

Natural fibrocyte-derived exosomes contain miRNAs including miR-21, miR-124, miR-125, miR-126, miR-130 and miR-132 and protein components including CD9, CD63 and CD81, and have been shown to promote wound-healing. Therefore, synthetic exosomes where prepared using synthetic miRIDIAN mimics of the miRNA described in the natural exosomes at a concentration typically found in natural exosomes (750 pg/1012 vesicles), by mixing the miRNA solution with the initial water phase containing the lipids (FIG. 1). Following the release of the synthetic exosomes from the surrounding polymer shell into an aqueous solution, synthetic exosomes were decorated with recombinant extracellular domains of human tetraspanins CD9, CD63 and CD81 via poly-Histidine-tag chemistry at a 1:100 protein to lipid ratio, at a similar protein to lipid ratio as described for natural exosomes.

Figure 5:
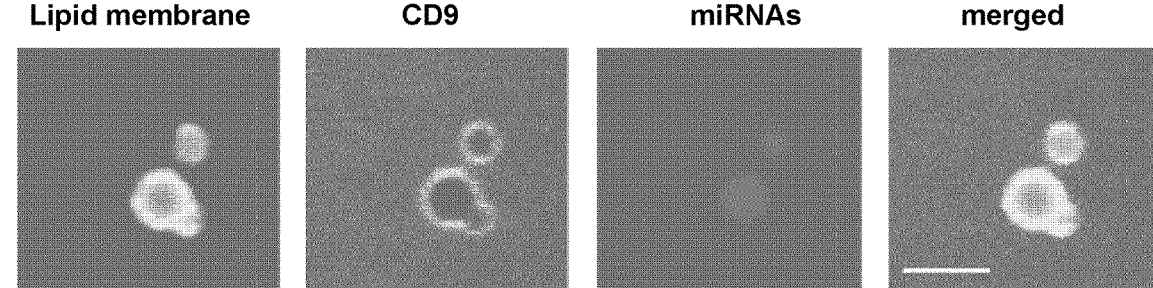
FIG. 5 shows representative confocal microscopy images of fully synthetic extracellular vesicles containing LissRhodamine B PE lipids, Alexa488 labeled CD9 (CD9) and Hoechst 33342 labeled miRNAs miR-21, miR-124, miR-125, miR-126, miR-130 and miR-132. Scale bar is 2 μm.

Confocal microscopy analysis of the prepared synthetic exosomes showed luminal distribution of the miRNAs and peripheral distribution of Alexa-488 labeled CD9, overlapping with the lipid fluorescence of Liss Rhodamin PE integrated into the lipid bilayer (FIG. 5), thus demonstrating the correct bottom-up assembly of miRNA loaded and protein decorated extracellular vesicles.

Figure 6:
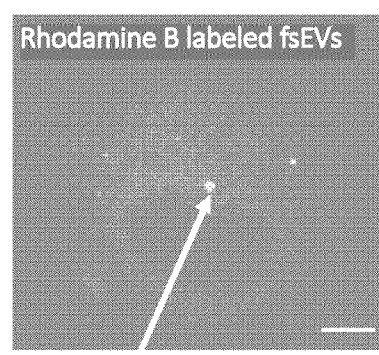
FIG. 6 shows single plan fluorescence confocal microscopy images of synthetic extracellular vesicles labelled with rhodamine B PE (left panel) and incubated with HaCaT keratynocytes stained with wheat germ agglutinin (WGA)-Alexa647 (middle panel) for 24 hours. Synthetic extracellular vesicles are internalized and co-localized with the WGA stained endosomes (right panel). Scale bar is 5 μm.
Figure 6:
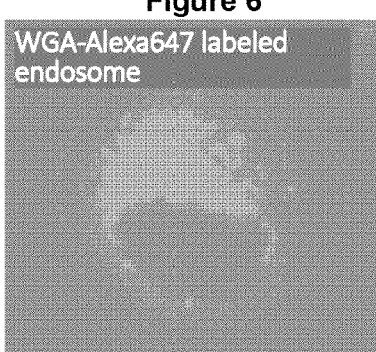
Figure 6:
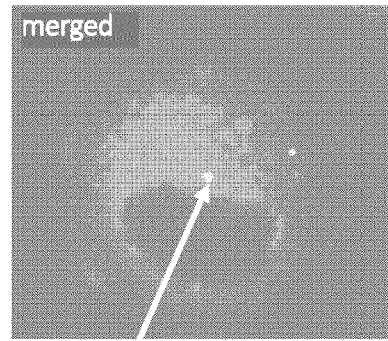

Example 4. Interaction Between Synthetic Extracellular Vesicles and Target Cells The interaction of fully synthetic extracellular vesicles synthetized as explained in Example 3 with target cells was analysed by incubating the keratinocytes HaCaT cells with said vesicles for 24 hours. These experiments showed that fluorescently labeled synthetic extracellular vesicles are internalized by HaCaT cells via an endosomal pathway (FIG. 6).

Importantly, these results suggest that the content of the fully synthetic extracellular vesicles is delivered into the target cells, so that they could be used for intracellular cargo delivery and for therapy of different disorders.

Example 5. Effect of Synthetic Extracellular Vesicles on Wound Healing

It has been shown that human fibrocyte-derived exosomes can have pro-proliferative effect, accelerates the collective migratory behavior of dermal keratinocytes and enhances collagen deposition of dermal fibroblasts, ultimately promoting wound closure in a diabetic mice model. Therefore, the wound healing effect of the synthetic extracellular vesicles synthetized as in Example 3 was tested studying their effect on cell proliferation, migration and collagen deposition, which is crucial for wound closure and healing.

The pro-proliferative effect on spontaneously immortalized keratinocytes Hacat cells, was assessed by quantifying keratinocyte number via nuclear staining after 48 h of incubation with the fully synthetic extracellular vesicles.

Figure 7:
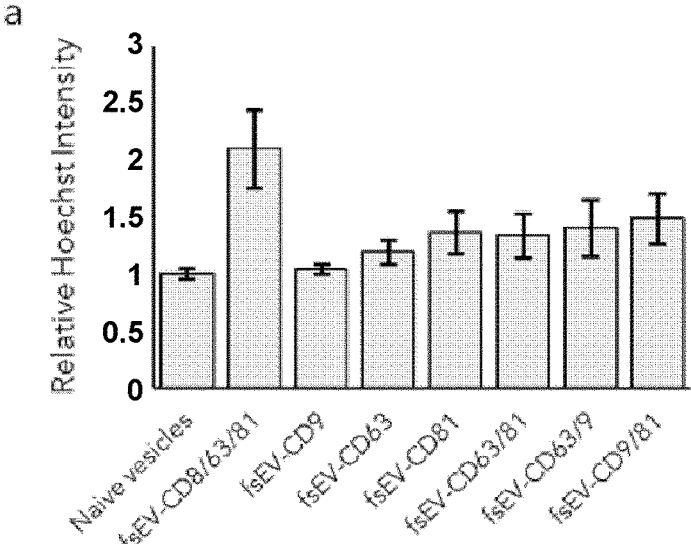
FIG. 7 shows (a and b) fluorescence intensity analysis of Hoechst 33342 stained HaCaT keratinocyte cultures to compare the effect of synthetic extracellular vesicles differing for the composition in tetraspanins or miRNAs, after treatment for 48 hours. Results are shown as mean±SD, n=3 technical replicates.
Figure 7:
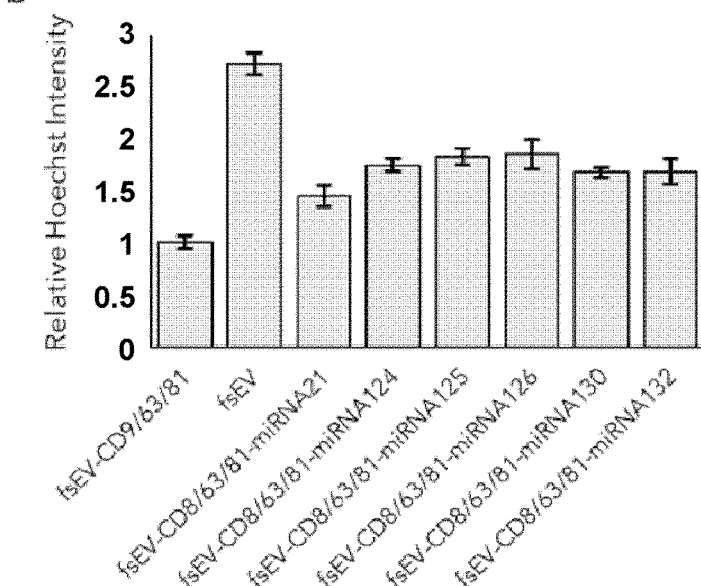

In order to decipher the contribution of the individual biomolecular components of the fully synthetic extracellular vesicles, fully synthetic extracellular vesicles lacking miRNAs, but decorated with the single tetraspanins or combinations of them were produced and analysed. Interestingly, co-presentation of CD9 and CD63 or CD9 and CD81 leaded to a synergistic effect on proliferation (FIG. 7a). However, the pro-proliferative effect was most pronounced when CD9, CD63 and CD81 where all co-presented, inducing a more than 2.7-fold increase compared to cultures treated with naive vesicles. The addition of the soluble tetraspanin protein variants alone to the HaCaT cells did not show a comparable effect. Therefore, these results reveal that the sole presentation of the CD9, CD63 and CD81 extracellular domain on synthetically assembled vesicles, has a pro-proliferative effect on keratinocytes, which can be considered as an essential requirement to promote wound healing.

The contribution of the single miRNAs was further evaluated by producing CD9, CD63 and CD81 biofunctionalized synthetic extracellular vesicles loaded with the individual human miRNA mimics (FIG. 7b). Interestingly, the results revealed that each individual miRNA enhanced to some extend the pro-proliferative effect. Slightly higher enhancement (1.7-fold) was observed in case of miR-125 or miR-126 loaded fully synthetic extracellular vesicles. However, the highest pro-proliferative effect (2.5-fold) was achieved when fully synthetic extracellular vesicles were loaded with a combination of all six miRNAs compared to non-loaded CD9, CD63, CD81-biofunctionalized fully synthetic extracellular vesicles. Generally, miRNAs modulate a broad spectrum of cell activities by translational regulation of intracellular signaling pathways.

Thus, these results show that fully synthetic extracellular vesicles can act as appropriate carriers to convey miRNA-based signaling information and thereby acting on post-transcriptional gene regulation by which they mirror a central mechanism of extracellular vesicle signaling.

Figure 8:
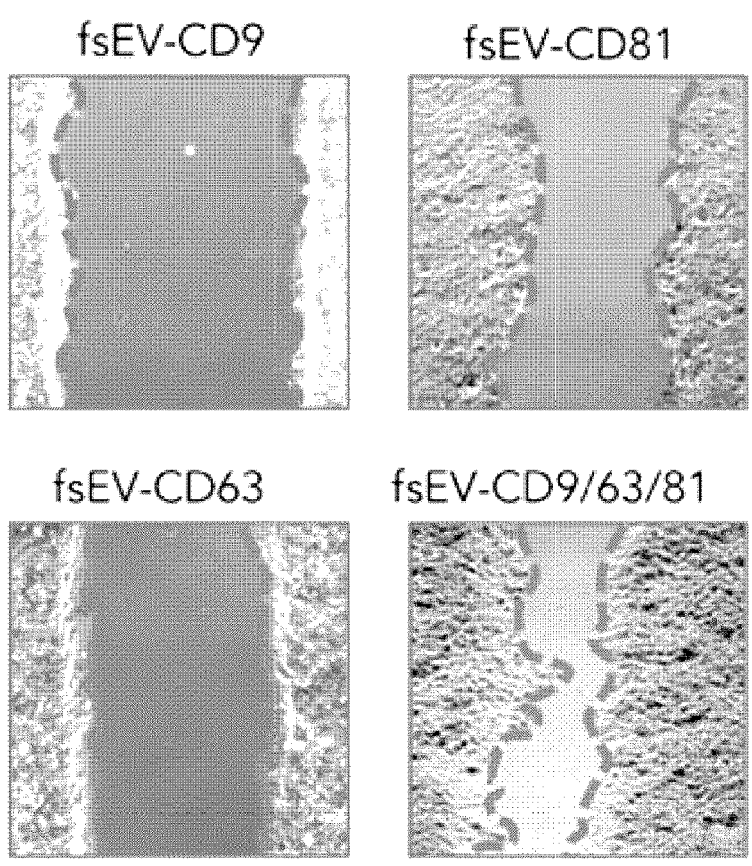
FIG. 8 shows phase contrast images of cell exclusion in vitro wound healing assays after 16 hours of migration of HaCaT monolayers pre-treated with the indicated different synthetic extracellular vesicles for 24 hours.
Figure 9:
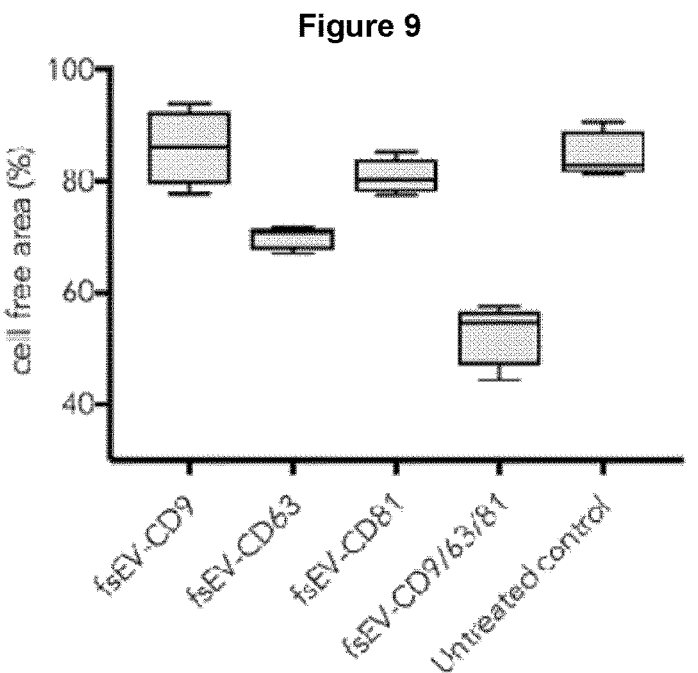
FIG. 9 shows in vitro quantification of wound healing migration assay of HaCaT keratinocyte monolayers treated for 24 hours with extracellular vesicles decorated with different tetraspanins, showed also in FIG. 7. Box-plots show mean values, 0.75 and 0.25 quantile values, whiskers show maximum and minimum values, n=4 artificial wound sides.
Figure 10:
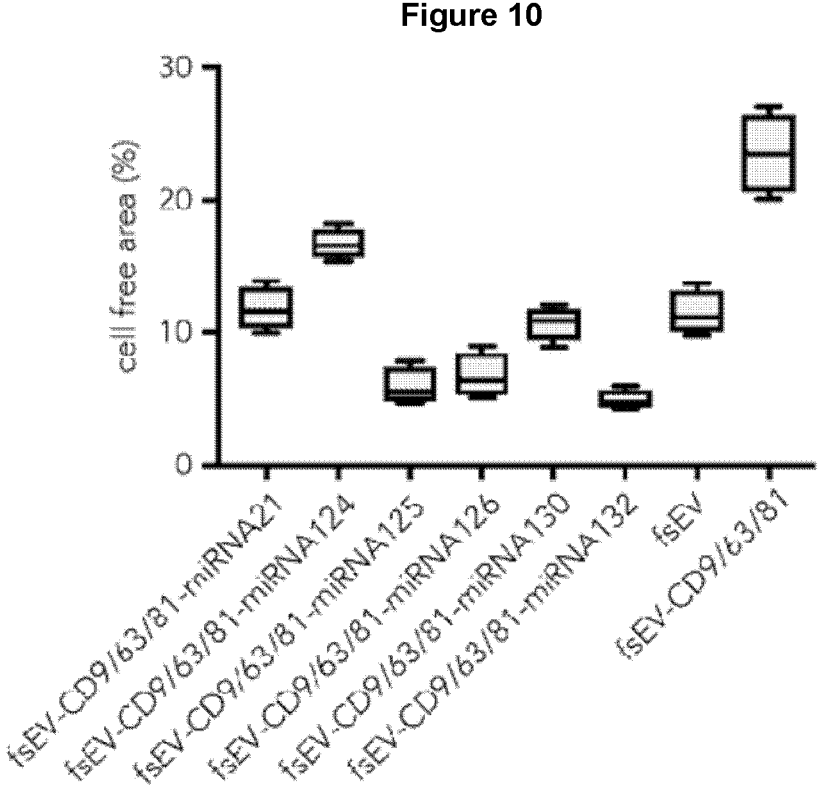
FIG. 10 shows in vitro quantification of wound healing migration assay of HaCaT keratinocyte monolayers treated for 24 hours with extracellular vesicles having different miRNAs, and showed also in FIG. 7. Box-plots show mean values, 0.75 and 0.25 quantile values, whiskers show maximum and minimum values, n=4 artificial wound sides.

The effect of extracellular vesicles on epithelial cell migration was assessed performing in vitro cell exclusion wound healing assays of collectively migrating keratinocyte monolayers treated for 24 h with the fully synthetic extracellular vesicles (FIG. 8). By quantifying the cell free area 16 hours after removal of the exclusion-inserts, the fully synthetic extracellular vesicles resulted able to promote keratinocyte migration into the cell free area and therefore closure of the artificial wound side (FIG. 9). Similarly to the results obtained for the pro-proliferative effect, co-presentation of all three tetraspanins on the fully synthetic extracellular vesicles showed a more pronounced enhancement of collective cell migration compared to single presentation of the proteins. When analyzing the effects of the individual miRNAs, miRNA132 resulted to especially improve the migratory behavior, and co-encapsulation of all six miRNAs could further increase collective cell migration compared to treatment with fully synthetic extracellular vesicles functionalized with CD9, CD63, CD81 only (FIG. 10).

Building on these observation, the ratios of the different miRNAs and tetraspanins could be varied, in order to assess the influence of individual signaling pathways.

Figure 11:
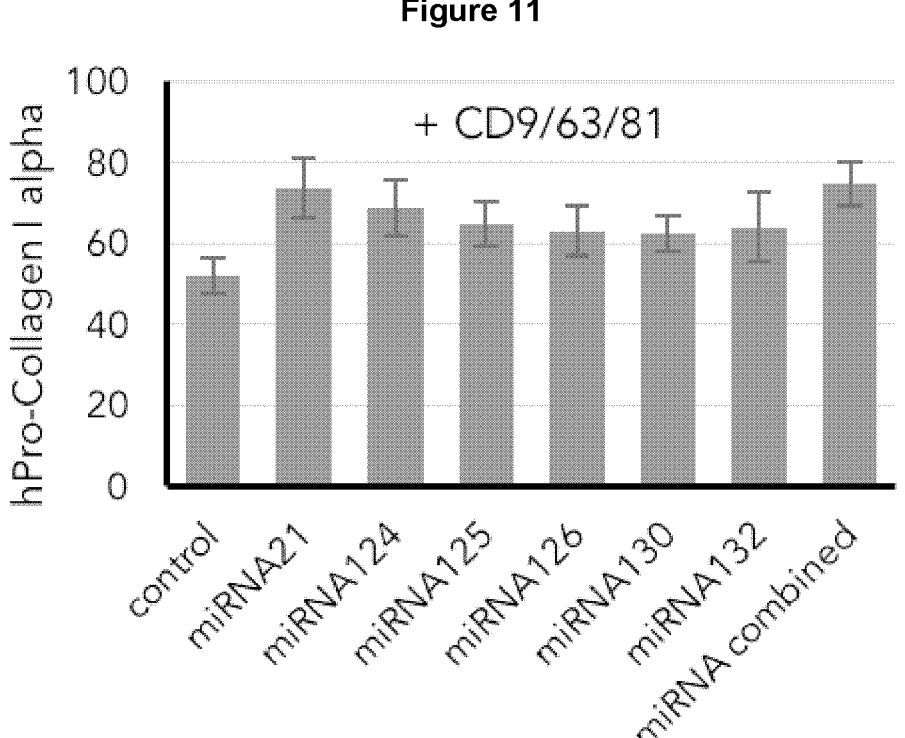
FIG. 11 shows enzyme-linked immunosorbent assay analysis of pro-collagen-la deposition of dermal fibroblasts after treatment for 24 hours with CD9, CD63 and CD81 decorated synthetic extracellular vesicles with different miRNA compositions. Results are shown as mean±SD, n=3 technical replicates.

The effect of fully synthetic extracellular vesicles on pro-collagen-la deposition of BJ dermal fibroblasts was assessed by enzyme-linked immunosorbent assay (ELISA) after a 24 hours treatment with the synthetic extracellular vesicles (FIG. 11). Although individual miRNA constituents showed no significant effect, a higher collagen deposition was obtained by treatment with fully synthetic extracellular vesicles containing all six miRNAs and tetraspanins.

Taken all these finding together, the in vitro assembled vesicles, like their natural equivalents, comprise the ability to boost three of the very fundamental processes critical for wound healing: proliferation, migration and collagen deposition.

Figure 12:
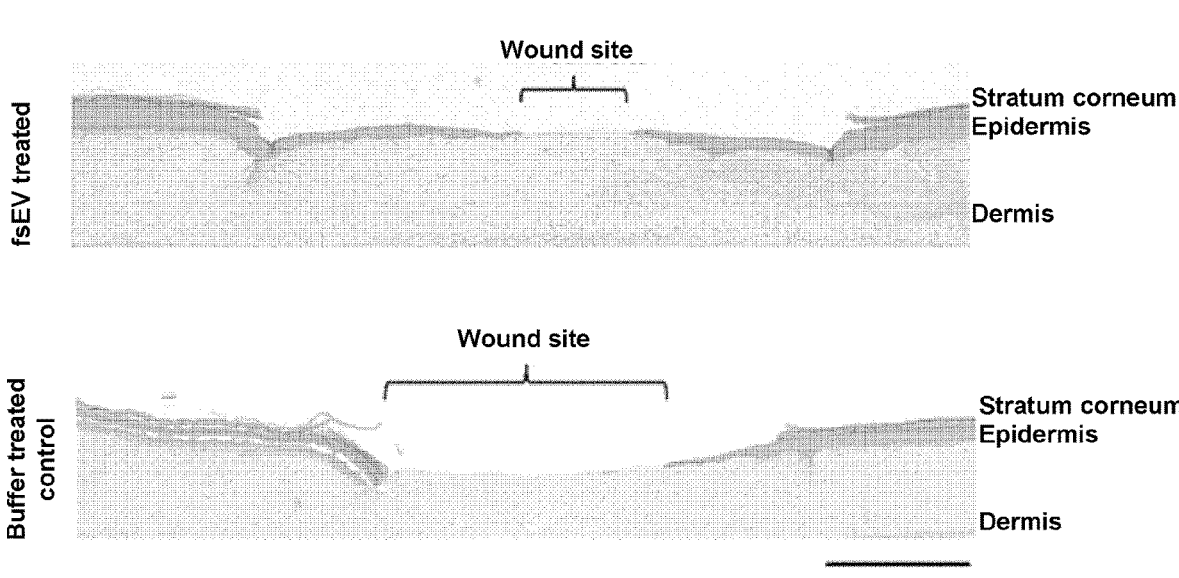
FIG. 12 shows hematoxilin/eosin stained histological sections of epidermal-wounded full thickness human organotypic skin models treated with the synthetic extracellular vesicles (fsEVs) or only the buffer control for 48 hours. Scale bar is 1 mm.
Figure 13:
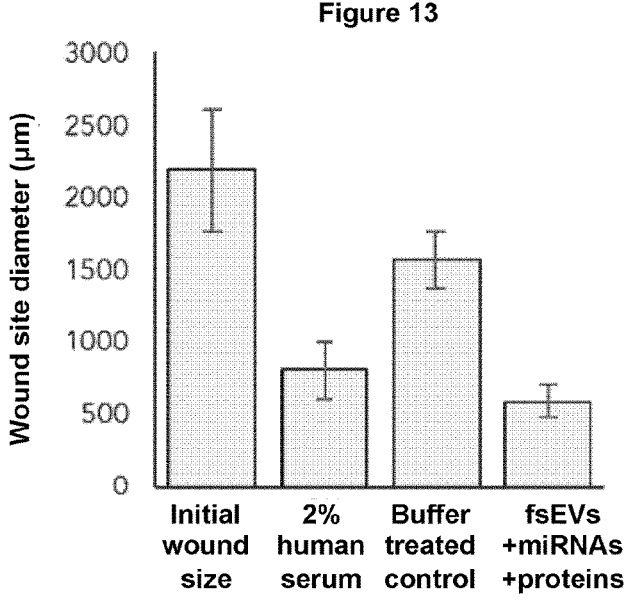
FIG. 13 shows quantification of epidermal wound-bed closure of full thickness human organotypic skin models from FIG. 11 treated with 2% human serum (positive control), buffer treated controls (negative control) and synthetic extracellular vesicles loaded with miRNAs miR-21, miR-124, miR-125, miR-126, miR-130 and miR-132 and decorated with CD9, CD63 and CD81. Results are shown as mean±SD, n=3 individual organotypic cultures.
Figure 14:
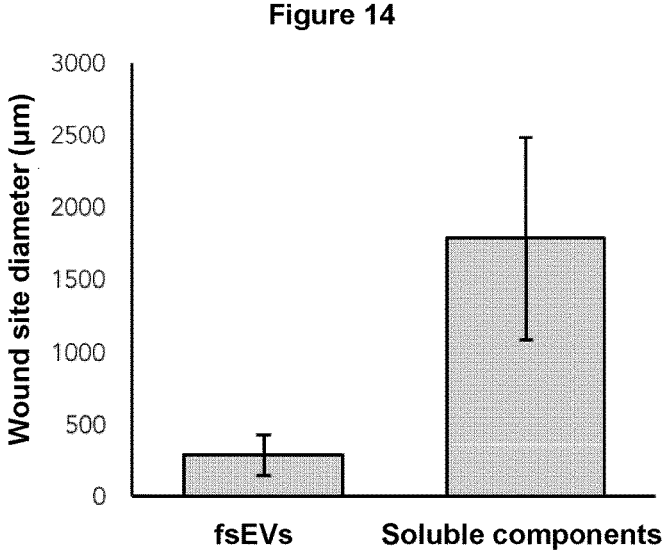
FIG. 14 shows quantification of epidermal wound-bed closure of full thickness human organotypic skin models treated with synthetic extracellular vesicles or only the soluble miRNA and tetraspanin components for 48 hours. Results are shown as mean±SD, n=3 individual organotypic cultures.

Example 6. Effect of Biomimetic Fully Synthetic Extracellular Vesicles on Epithelial Regeneration In order to assess the ability of fully synthetic extracellular vesicles to promote epithelial regeneration of wounded skin, wounded organotypic full-thickness human skin models (FIG. 12) were treated by applying synthetic extracellular vesicles for 48 hours on the wound site (see Methods). Closure of the 3 mm epidermal wound was assessed by quantification of the epithelial wound bed size from hematoxylin-eosin (H/E) stained histological samples (FIG. 13). The treatment with synthetic extracellular vesicles substantially augmented the healing processes compared to buffer treated controls and application of the single soluble constituents was not as effective as the fully synthetic extracellular vesicles (FIG. 14).

Example 7. Migration Promotion of Fully Synthetic Extracellular Vesicles

It is known that proliferation, migration and collagen deposition play a critical role in development and progression of epithelial carcinomas. Therefore, the effect of fully synthetic extracellular vesicles miming the fibrocyte derived vesicle was additionally tested on A431 human vulvar squamous carcinoma cells.

Figure 15:
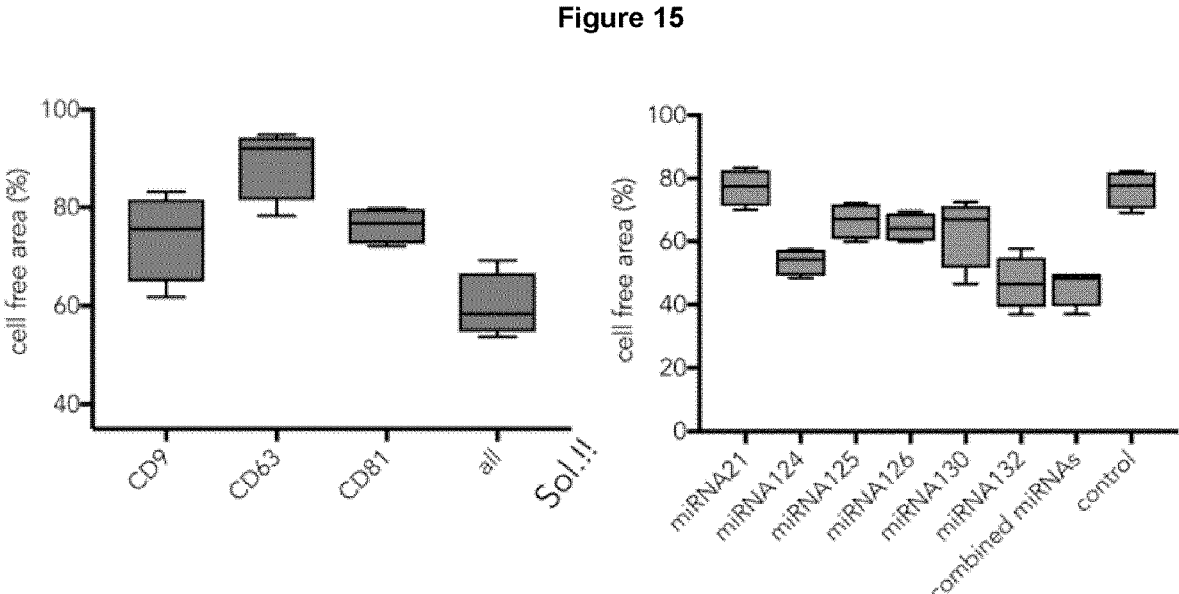
FIG. 15 shows effect of synthetic extracellular vesicles on migration of A431 carcinoma cells, analysed by an in vitro wound healing migration assay of A431 carcinoma monolayers treated for 24 hours with synthetic extracellular vesicle variants. Box-plots show mean, 0.75 and 0.25 quantile, whiskers show maximum and minimum values, n=4 artificial wound sides
Figures 16, 17:
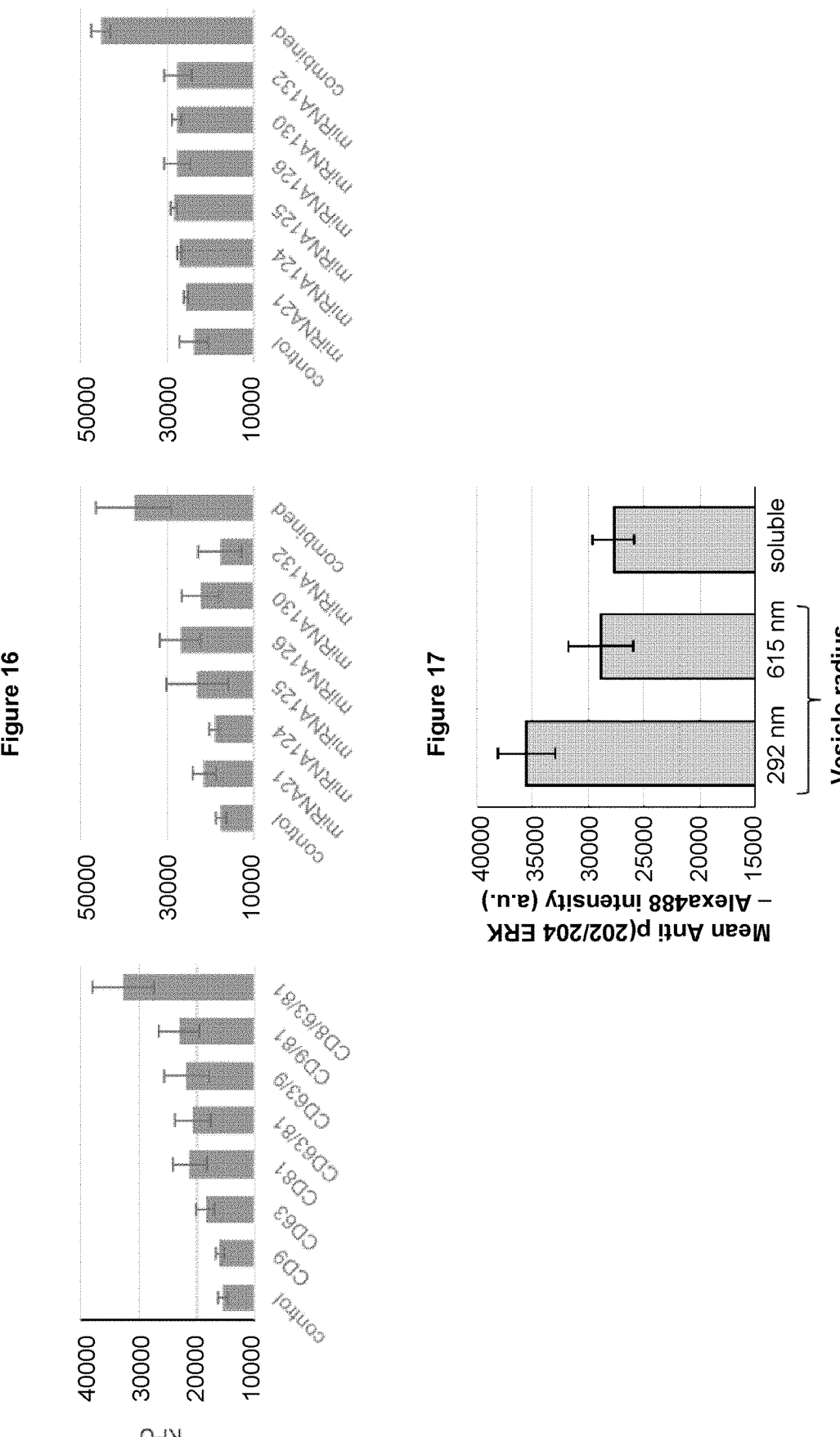
FIG. 16 shows effect of synthetic extracellular vesicles on proliferation of A431 carcinoma cells. Fluorescence intensity analysis of Hoechst 33342 stained A431 cells after treatment with synthetic extracellular vesicles of different composition for 48 hours. Results are shown as mean±SD, n=3 technical replicates.
FIG. 17 shows quantification of ERK phosphorylation at amino acids 202/204 in MC-3T3 cells after incubation for 24 hours with RANK presenting synthetic extracellular vesicles of different radii (292 nm, 615 nm) or soluble RANK alone. Bars represent mean values±SD, n=3 technical replicates.

The results revealed that A431 carcinoma cells responded to fully synthetic extracellular vesicle treatment by accelerated in vitro collective migration, a central requirement for tumor invasion and metastasis, but displayed an altered sensitivity for the respective fully synthetic extracellular vesicle surface proteins (FIG. 15). Moreover, the fully synthetic extracellular vesicles increased A431 cells proliferation of 1.8-fold (FIG. 16).

Example 8. Extracellular Vesicles for Age-Related Disorders

The inventive method was applied to produce synthetic extracellular vesicles containing a nicotinamide phosphoribosyltransferase intracellular protein, as previous studies showed that these vesicles play a role in treatment of age-related disorders, and increase of lifespan.

Therefore, the inventors have here produced synthetic extracellular vesicles according to the inventive method and specifically comprising the functional protein nicotinamide phosphoribosyltransferase, and cytosolic proteins such as Apoptosis-Linked Gene 2-Interacting Protein X (ALIX), tumour susceptibility gene 101 protein (TSG101). These synthetic extracellular vesicles did not comprise transferrin and albumin.

Example 9. Synthesis of Immunoregulatory Extracellular Vesicles

The inventors aimed to synthetize synthetic extracellular vesicles with immunoregulatory properties that could be used to treat immune disorders, autoimmune disorders, inflammatory disorders, such as rheumatoid arthritis, and cancer, e.g. by cancer immunotherapy.

This type of synthetic extracellular vesicles can comprise transmembrane proteins such as MHCII, CD80, CD86, CD11c, MHCI, integrin α-chains, integrin β-chains, ICAM-1, and CD71; functional proteins such as cytokines, interleukins, IL4, growth factors, milk fat globule-EGF factor 8 protein (MFGE8), Fas, Fas Ligand (FasL), RANK, RANK Ligand (RANKL), indolamin-2,3-dioxygenase, cytotoxic T-lymphocyte-associated protein 4-immunoglobulin fusion protein (CTLA4-Ig), tumor necrosis factor-related apoptosis-inducing ligand (Apo2L, TRAIL).

Fas (also named CD95, Apo-1) is a membrane receptor from the TNF family expressed on surface of almost all cells in the human body. Upon activation by Fas ligand (FasL), Fas induces apoptosis by activation of caspase signalling. Fas mediated apoptosis plays a major role in immunobiology, and especially by death induction of infected and cancerous cells mediated by cytotoxic T-cells and by natural killer cells (NK-cells). Moreover, Fas induced apoptosis is crucial for regulation of T-cell physiology in inflammatory diseases. Major producers of FasL are T-cells and NK-cells which release FasL primarily from intracellular reservoirs in a form bound to extracellular vesicles resembling exosomes.

Synthetic extracellular vesicles presenting FasL could therefore be useful not only to investigate further Fas-signalling, but also to provide new therapy option in immune disorders, inflammatory disorders, neurodegenerative disorders, or cancer.

Figure 18:
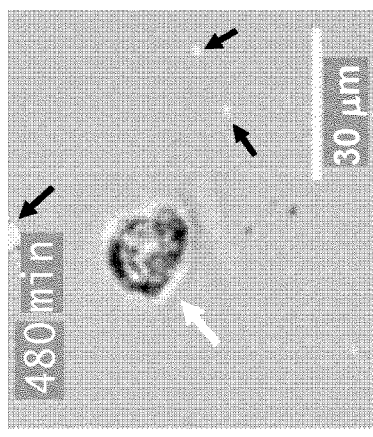
FIG. 18 shows bottom-up assembly of Fas Ligand (FasL) comprising synthetic extracellular vesicles. A) cryo-electron microscospy image of synthetic extracellular vesicles conjugated with recombinant extracellular domain of FasL. B) Live cell fluorescence time laps imaging of HaCaT cells incubated with FasL-synthetic extracellular vesicles (black arrow arrows). Upon contact formation with the synthetic extracellular vesicles (white arrow at 30 min), cells undergo progressive cells death, form blebs and stain positive for propidium iodide (white arrow at 480 min). C) Plate reader quantification of propidium iodide signals of Jurkat T-cells incubated with FasL-synthetic extracellular vesicles (vFasL), or with soluble FasL (sFasL), or left untreated as control. Bars represent mean values±SD, n=3 biological replicates.
Figure 18:
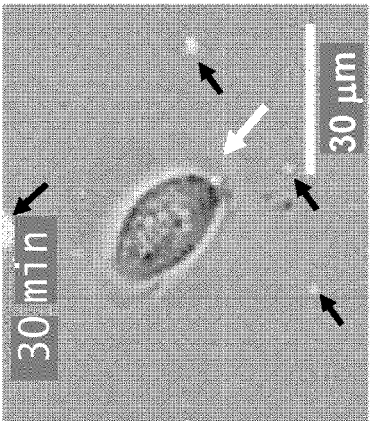
Figure 18:
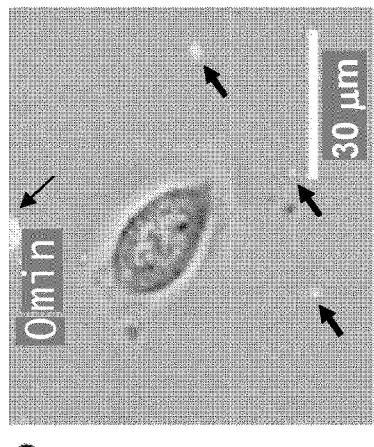
Figure 18:
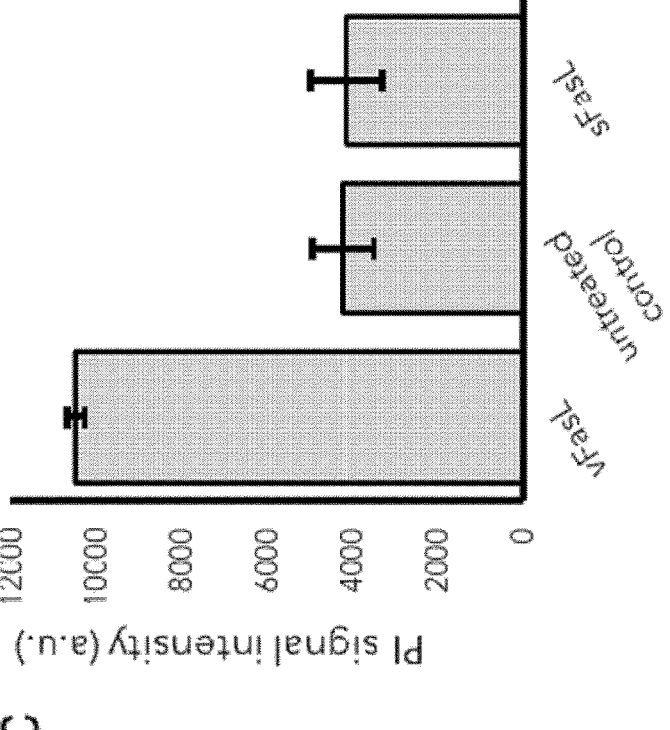
Figure 18:
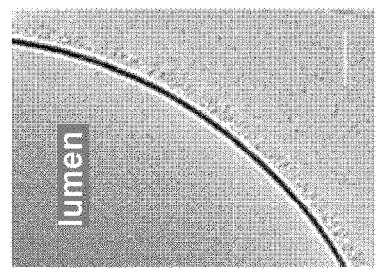

In order to produce synthetic extracellular vesicles presenting FasL, synthetic extracellular vesicles were produced by the inventive method based on mechanical emulsification at 14,000 rpm for 30 sec with the following composition: 20 mol % DOPG, 78 mol % DOPC, 1 mol % DGS-NTA(Ni²⁺) and 1 mol % LissRhod PE. Obtained synthetic extracellular vesicles had a mean hydrodynamic radius of 606 nm, as measured by dynamic light scattering (DLS). Recombinant his-tagged FasL amino acids N-Met-His8 (BioLegend, USA) was coupled on the surface of these synthetic extracellular vesicles by applying bio-orthogonal surface chemistry NTA-poly-histidine tag coupling. The FasL present on synthetic extracellular vesicles is referred to as vesicular FasL to differentiate from soluble FasL (sFasL). Cryo-electron microscopy analysis demonstrated correct coupling of FasL on vesicle surface (FIG. 18*a*). The pro-apoptotic activity of FasL-synthetic extracellular vesicles was then tested on human keratinocytes by following cell positivity for propidium iodide by live-cell time lapse imaging (FIG. 18*b*). Upon contact formation with the FasL presenting synthetic vesicles, target cells stained progressively positive for propidium iodide (PI), demonstrating the pro-apoptotic activity of FasL-synthetic vesicles on target cells.

FasL-synthetic vesicles were then tested for their pro-apoptotic activity on T-cells, which is important for therapy of inflammatory and autoimmune diseases. To this aim, Jurkat T-cells were incubated for 24 hours with FasL-synthetic vesicles and apoptotis was quantified by measuring propidium iodide (PI) staining intensity on a plate reader. Results showed that vesicle bound recombinant FasL is able to induce apoptosis in the T-cells, but not soluble FasL (FIG. 18*c*).

Figure 19:
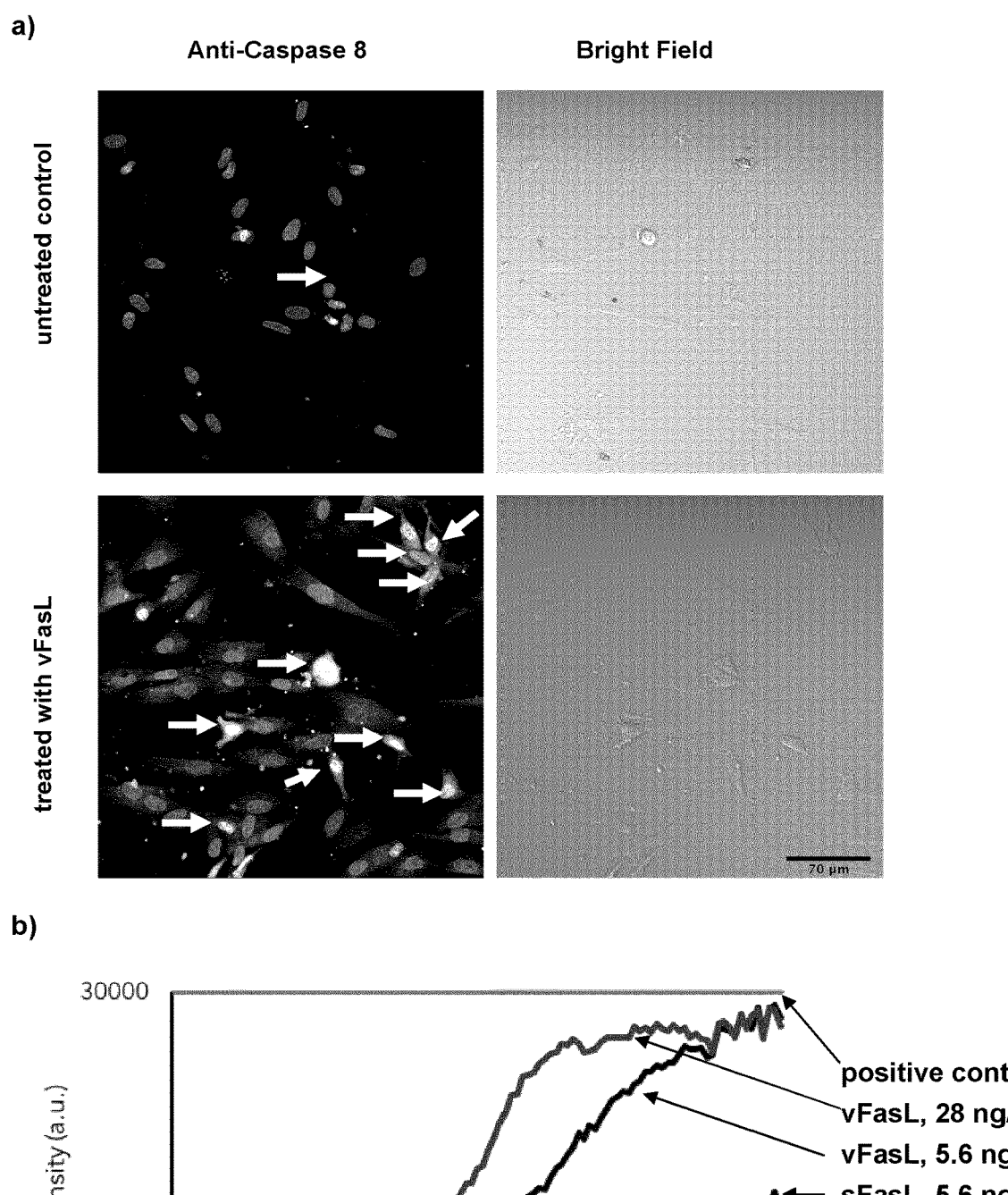
FIG. 19 shows caspase-8 activation in human dermal fibroblasts (BJ cells) incubated with Fas Ligand (FasL) comprising synthetic extracellular vesicles (vFasL). a) Analysis by fluorescence microscopy: left column shows staining for activated caspase 8, i.e. cleaved at Asp391 (white arrows), and DAPI stained nuclei. Right column shows corresponding bright field images. b) Time-analysis of staining intensity of propidium iodide of BJ cells incubated with FasL comprising synthetic extracellular vesicles (vFasL) at concentration 28 ng/ml and 5.6 ng/ml (amount of vesicular FasL/ml). c) Time-analysis of staining intensity of propidium iodide of BJ cells incubated with $10^7$ vesicles and $10^8$ vesicles of FasL comprising synthetic extracellular vesicles (vFasL).

Thereafter, FasL-synthetic vesicles were tested for their ability to activate caspase-8, which has been shown also for natural FasL-vesicles. To this aim, human dermal fibroblast BJ cells were incubated with FasL-synthetic vesicles for 2 hours and then stained with antibodies recognizing activated caspase-8, i.e. cleaved at Asp391 (FIG. 19). The results confirmed activation of caspase 8 in the BJ cells treated with FasL-synthetic vesicles. Activation of caspase-8 was directly proportional to the vesicle concentration (FIG. 19*c*), and to the concentration of vesicular FasL in solution after a given time (FIG. 19*b*). The concentration of FasL is calculated in these experiments as the total amount of FasL in the vesicle sample/ml, considering that FasL molar concentration is the same as that of NTA(Ni²⁺) lipids in the membrane (i.e. both 1 mol %=10 μM).

Figure 21:
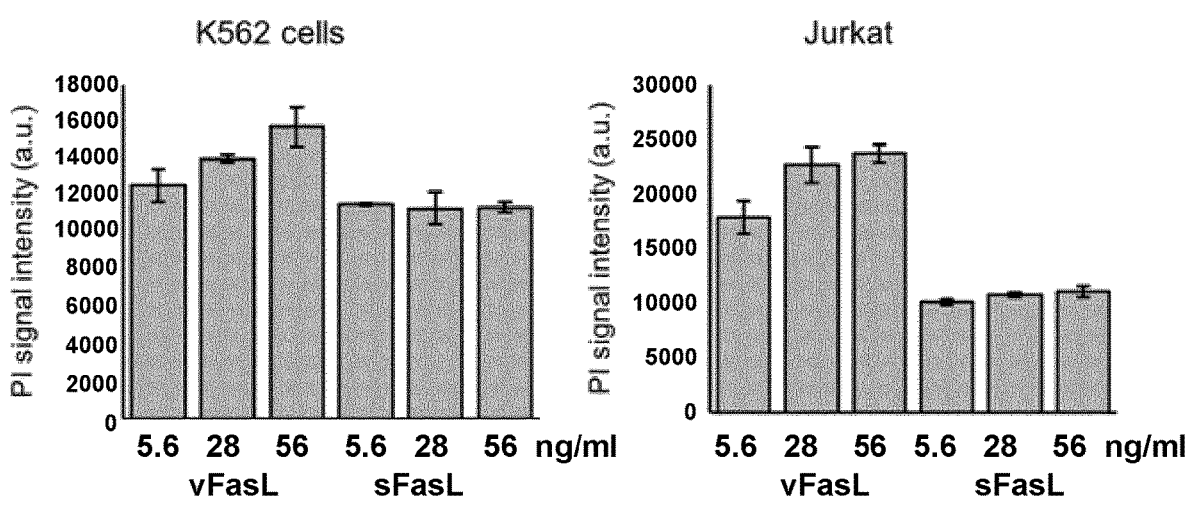
FIG. 21 shows assessment of FasL cytotoxicity on Jurkat and K562 cells at different concentrations of Fas Ligand (FasL) comprising synthetic extracellular vesicles (vFasL) or soluble FasL (sFasL). Cells were incubated with the different preparations and propidium iodide staining intensity was quantified after 24 hours.

We further evaluated the pro-apoptotic concentration range of FasL presenting synthetic vesicles on Jurkat T-cells and on K562 granulocytic cells, which are frequently used to assess FasL mediated apoptosis on NK cells. We again found that the addition of soluble FasL (sFasL) did not display any cytotoxic effect at all tested concentrations (FIG. 21). However, FasL bound on synthetic vesicle surface could induce substantial cell death in both cell line, at the lowest tested amount of 5.6 ng/ml. Highest pro-apoptotic efficiency could be observed for the highest tested amount of 56 ng/ml FasL presenting synthetic vesicle.

Figure 20:
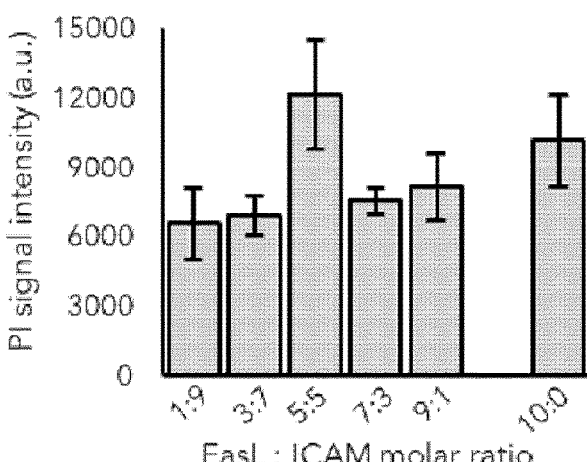
FIG. 20 Optimization of FasL-ICAM ratio present on surface of synthetic extracellular vesicles. Jurkat T-cells were incubated with synthetic extracellular vesicles having the different indicated FasL-ICAM ratios for 24 hours and cell death was quantified by propidium iodide (PI) staining. Bars represent mean values±SD, n=3 biological replicates.

Thereafter, the inventive method was used to assemble pro-apoptotic synthetic vesicles exposing not only FasL but also the intercellular adhesion molecule ICAM-1, which is presented on natural occurring extracellular vesicles with immunological activity. Synthetic extracellular vesicles presenting FasL and ICAM-1, were produced as described above by mechanical emulsification at 14,000 rpm for 30 sec. Obtained synthetic extracellular vesicles had a mean hydrodynamic radius of 606 nm. The pro-apoptotic potential of these vesicles was tested on Jurkat T-cells using different FasL to ICAM-1 ratios, and measuring cell death by propidium iodide (PI) staining It was found that the killing efficiency of the synthetic vesicles depends on the FasL to ICAM-1 ratio (FIG. 20). Such quantitative optimization of protein composition in extracellular vesicles is not feasible using natural derived extracellular vesicles. It was found that a FasL to ICAM-1 ratio of 5:5 is optimal and can induce cells apoptosis at a similar level as vesicles presenting only FasL (10:0=double as much FasL on the vesicle surface). In other words, we could increase pro-apoptotic signalling by a factor of 2 through this initial optimization. Interestingly, ICAM-1 is not cytotoxic by itself but when present as adhesion protein on cell derived vesicles. This demonstrates that adhesion proteins like ICAM-1 can further increase the cytotoxicity of FasL exposing vesicles, probably because they mediate and facilitate the adhesion of the vesicles to the target cells.

Moreover, in order to analyse the effect of vesicle membrane density of FasL on the pro-apoptotic potential, vesicles harbouring 5 mol % DGS-NTA(Ni$^{2+}$) were compared to vesicles with 1 mol % DGS-NTA(Ni$^{2+}$). Jurkat cells were incubated with FasL-extracellular vesicles (vFasL) with 1 mol % DGS-NTA(Ni$^{2+}$) at $1\times10^8$ vesicles/ml or vFasL) with 5 mol % DGS-NTA(Ni$^{2+}$) at $2\times10^7$ vesicles/ml, in order to have the same final FasL concentration in the two samples. Results showed that vesicles with higher FasL density (5 mol % DGS-NTA(Ni$^{2+}$)) displayed reduced killing-efficiency.

Figure 23:
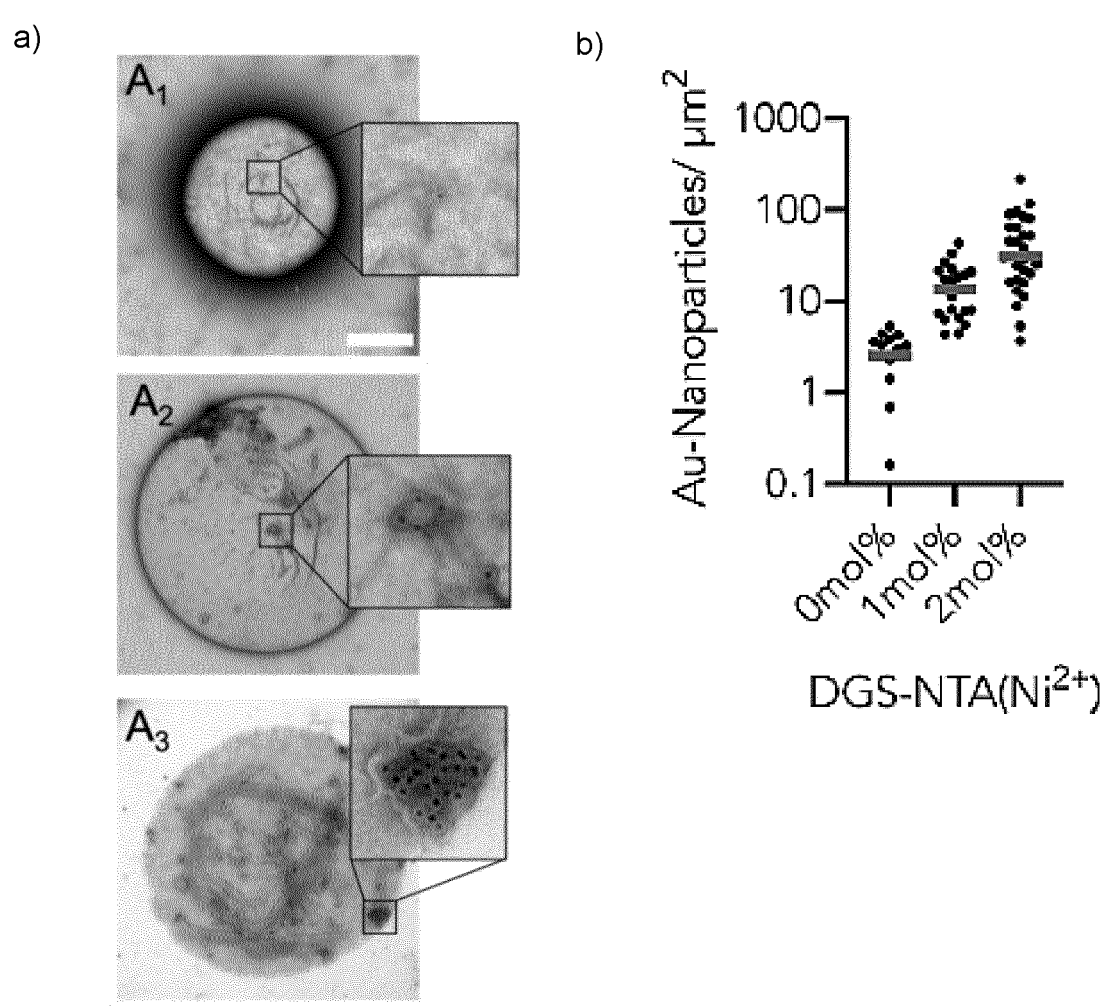
FIG. 23 shows assessment of NTA(Ni$^{2+}$) directed protein density on vesicle membranes. a) Representative transmission electron microscopy images of uranyl acetate negative stained vesicles harboring different NTA(Ni$^{2+}$) concentrations and incubated with histidine-tagged protein G immobilized IgG conjugated to gold-nanoparticles. Scale bar is 500 nm. A1=0 mol % NTA(Ni$^{2+}$), A2=1 mol % NTA(Ni$^{2+}$), A3=2 mol % NTA(Ni$^{2+}$). Black points are the gold nanoparticles. b) Quantification of the gold nanoparticle density on the surface of vesicles harboring different NTA(Ni$^{2+}$) concentrations. c) Quantification of PI staining intensity in Jurkat cell cultures treated with 28 ng/ml vFasL on vesicles harbouring 1 mol % and 5 mol % DGS-NTA(Ni$^{2+}$) after 24 h of incubation. Results are shown as mean±SD from three biological triplicates.
Figure 23:
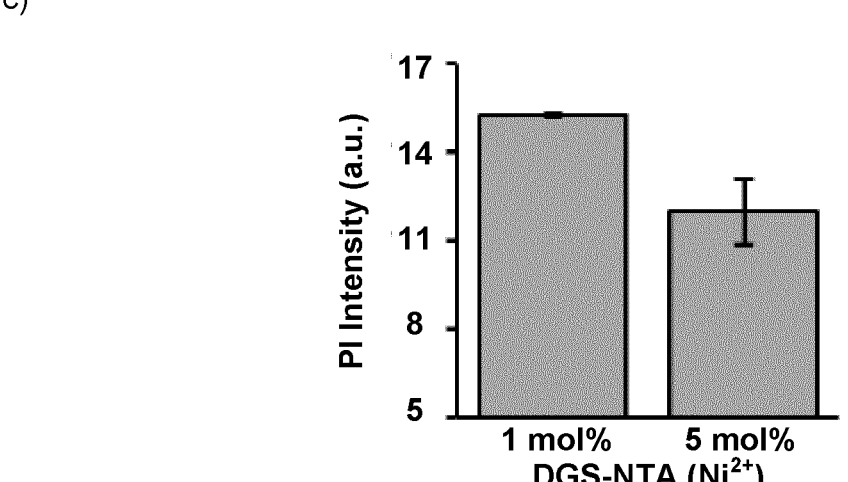

The molar percentage of DGS-NTA(Ni$^{2+}$) is a measure of the density of FasL on the vesicles as confirmed by labelling the vesicles with gold-nanoparticle conjugated antibodies and subsequent transmission electron microscopy imaging (FIG. 23a, 23b).

Example 10. Synthetic Extracellular Vesicles Resembling Mesenchymal Stem-Cell Derived Extracellular Vesicles The inventive method was applied to produce synthetic extracellular vesicles resembling those derived from mesenchymal stem cells. Natural extracellular vesicles derived from mesenchymal stem cells have been shown to have a wide range of potential therapeutic effects, such as alleviation of severe graft versus host disease, osteoarthritis and promotion of cartilage extracellular matrix homeostasis.

The synthetic extracellular vesicles resembling those of mesenchymal stem cell origin were prepared with transmembrane proteins such as CD29, CD44, CD90, CD73, Sca-1, tetraspanin proteins CD9, CD63, and CD81, functional proteins such as Wnta and Wntb, nucleic acid molecules such as miR-140-5p, miR-92a-3p-e, nucleic acid molecules such as miRNAs miR-33b, miR-451, miR-575, miR-630, miR-638, miR-1202, miR-1207-5p, miR-1225-5p, miR-1268, miR-K12-3.

Example 11. Synthetic Extracellular Vesicles for Treatment of Stroke, Angiogenesis, and Other Cardiovascular Disorders Emerging evidence suggests that stem cell derived exosomes and their microRNA cargo mediate cell therapy derived neurorestorative effects in patients after stroke. In particular, these exosomes can play a role in angiogenesis, neurogenesis, vascular remodeling, white matter remodeling, and also modulate inflammatory and immune responses at the local and systemic level.

In order to reproduce exosomes with such properties, the inventive method was applied to produce synthetic extracellular vesicle specifically comprising: transmembrane proteins such as CD29, CD44, CD90, CD73, CD44, Sca-1, tetraspanin proteins CD9, CD63, and CD81; nucleic acid molecules such as miR-17, miR-18a, miR-19a, miR-19b-1, miR-20a, miR-92a, let-7a, miR-21, miR124, miR126, miR-133b, miR-191, miR-222, miR-494, miR-6087, miR-30d-5p; miR-33b, miR-451, miR-575, miR-630, miR-638, miR-1202, miR-1207-5p, miR-1225-5p, miR-1268, miR-K12-3.

Example 12. Synthetic Extracellular Vesicles for Treatment of Osteoporosis and Other Bone Diseases Osteoclast to osteoblast signalling is crucial for bone homeostasis in order to assure correct bone formation and resorption. Receptor activator of nuclear factor-κB (RANK) is pivotal for this interaction. It has been shown, that maturing osteoclasts secrete vesicles presenting RANK on their surface, which then binds to RANKL on osteoblast surface, thus boosting mineralization of osteoblasts by activation of "reverse signalling". After RANK ligand (RANKL)-RANK binding, downstream MAP-kinase signalling is activated. The RANK-exposing vesicles have been shown to be crucial for physiological signalling and represent potential therapeutic targets to treat bone diseases such as osteoporosis.

Therefore, synthetic extracellular vesicles exposing RANK on their surface were produced applying the inventive method based on emulsification using a mechanic emulsifier, and tested for their activating effect on pre-osteoblast cells.

Synthetic extracellular vesicles were produced the following lipid composition: 20 mol % DOPG, 78 mol % DOPC, 1 mol % DGS-NTA(Ni$^{2+}$) and 1 mol % LissRhod PE. Recombinant His-tagged RANK (amino acids 31-214) (protein ID O35305) was coupled on the surface of these synthetic extracellular vesicles by applying bio-orthogonal surface chemistry NTA-poly-histidine tag coupling, at a protein lipid (LissRhodPE) ratio of 1:100. Two samples of such synthetic extracellular vesicles were produced having hydrodynamic radii of 292 nm (emulsification at 30,000 rpm, 30 sec) and 615 nm (emulsification at 14,000 rpm, 30 sec), respectively, in order to optimize the vesicle dimension for maximal functionality. Synthetic extracellular vesicles were incubated with MC 3T3 cells, a model of pre-osteoblast cells, for 24 hours in 96 well plates at concentration 10 μM (vesicle lipid moles/medium volume). Cell samples were subsequently stained for p(202/204) ERK with an anti-p(202/204) ERK1/2-Alexa488 conjugated antibody and staining intensity was quantified using an Infinite M200 TECAN plate reader controlled by TECAN iControl software with an in-built gain optimization and excitation/emission setting adjusted to 488/512 nm. Here, phosphorylation of ERK at amino acids 202/204 was quantified as a measure of vesicular RANK potency in specific pre-osteoblast cell activation. As a control, soluble RANK was added to control cells at the same concentration as used to produce vesicular RANK (soluble or vesicle RANK/medium volume=100 ng/ml).

The results revealed that RANK exposed on synthetic extracellular vesicles can induce RANK signalling more strongly compared to soluble RANK (FIG. 17). Moreover, we found that smaller RANK vesicles are stronger inducers compared to large vesicles. These data demonstrate that RANK presenting synthetic extracellular vesicles could be used for bone remodelling therapy in bone diseases such as osteoporosis. Moreover, the inventive RANK presenting synthetic extracellular vesicles could be used to further investigate the physiology of bone formation and remodeling.

TABLE 3

| | Suitable miRNA molecules | | | | |
|---|---|---|---|---|---|
| MIRNA ID | ENTREZ ID | MIRNA ID | ENTREZ ID | MIRNA ID | ENTREZ ID |
| let-7a | 406881 | miR-30c-2* | 407032 | miR-141 | 406933 |
| let-7b | 406884 | miR-30d | 407033 | miR-143 | 406935 |
| let-7c | 406885 | miR-30e | 407034 | miR-145 | 406937 |
| let-7d | 406886 | miR-30e-3p | 407034 | miR-146a | 406938 |
| let-7e | 406887 | miR-31 | 407035 | miR-146b | 574447 |
| let-7f | 406888 | miR-32 | 407036 | miR-147 | 406939 |
| let-7g | 406890 | miR-33a | 407039 | miR-148a | 406940 |
| let-7i | 406891 | miR-33b | 693120 | miR-148b | 442892 |
| miR-1 | 406952 | miR-34a | 407040 | miR-149 | 406941 |
| miR-7-1* | 407043 | miR-34B | 407041 | miR-150 | 406942 |
| miR-10a | 406902 | miR-92a-1 | 407048 | miR-151 | 442893 |
| miR-10b | 406903 | miR-92A2 | 407049 | miR-152 | 406943 |
| miR-15a | 406948 | miR-92b | 693235 | miR-153-1 | 406944 |
| miR-15b | 406949 | miR-93 | 407050 | miR-153-2 | 406945 |
| miR-16 | 51573 | miR-95 | 407052 | miR-154 | 406946 |
| miR-16-1 | 406950 | miR-96 | 407053 | miR-155 | 406947 |
| miR-16-2 | 406951 | miR-98 | 407054 | miR-181a-2 | 406954 |
| miR-17 | 406952 | miR-99a | 407055 | miR-181a-1 | 406995 |
| miR-17-3p | 406952 | miR-99b | 407056 | miR-181B2 | 406956 |
| miR-17-5p | 406952 | miR-17-92a-1 | 407975 | miR-181c | 406957 |
| miR-18a | 406953 | miR-100 | 406892 | miR-181d | 574457 |
| miR-18b | 574033 | miR-101 | 406893 | miR-182 | 406958 |
| miR-19a | 406979 | miR-103A1 | 406895 | miR-183 | 406959 |
| miR-19b | 406980 | miR-103A2 | 406896 | miR-184 | 406960 |
| miR-19b-1* | 406980 | miR-103b-1 | 100302238 | miR-185 | 406961 |
| miR-19B2 | 406981 | miR-103b-2 | 100302282 | miR-186 | 406962 |
| miR-20a | 406982 | miR-105-1 | 406897 | miR-187 | 406963 |
| miR-20b | 574032 | miR-105-2 | 406898 | miR-188 | 406964 |
| miR-21 | 406991 | miR-106a | 406899 | miR-190 | 406965 |
| miR-22 | 407004 | miR-106b | 406900 | miR-190A | 406965 |
| miR-23a | 407010 | miR-107 | 406901 | miR-191 | 406966 |
| miR-23b | 407011 | miR-122 | 406906 | miR-192 | 406967 |
| miR-24 | 407012 | miR-125a | 406910 | miR-193a | 406968 |
| miR-24 | 407013 | miR-125B1 | 406911 | miR-193b | 574455 |
| miR-25 | 407014 | miR-125B2 | 406912 | miR-194 | 406969 |
| miR-26a | 407015 | miR-126 | 406913 | miR-194-2 | 406970 |
| miR-26A1 | 407015 | miR-128-1 | 406915 | miR-195 | 406971 |
| miR-26A2 | 407016 | miR-128-2 | 406916 | miR-196a | 406972 |
| miR-26b | 407017 | miR-130a | 406919 | miR-196A2 | 406973 |
| miR-27a | 407018 | miR-130b | 406920 | miR-196b | 442920 |
| miR-27b | 407019 | miR-132 | 406921 | miR-197 | 406974 |
| miR-28 | 407020 | miR-133a | 128826 | miR-198 | 406975 |
| miR-29a | 407021 | miR-134 | 406924 | miR-199A2 | 406977 |
| miR-29b | 407024 | miR-135a-1 | 406925 | miR-199B | 406978 |
| miR-29b-2 | 407025 | miR-135a-2 | 406926 | miR-200a | 406983 |
| miR-29B1 | 407024 | miR-135b | 442891 | miR-200b | 406984 |
| miR-29c | 407026 | miR-136 | 406927 | miR-200c | 406985 |
| miR-30a | 407029 | miR-137 | 406928 | miR-202 | 574448 |
| miR-30a-3p | 407029 | miR-138 | 406929 | miR-203 | 406986 |
| miR-30a-5p | 407029 | miR-138-2 | 406930 | miR-204 | 406987 |
| miR-30b | 407030 | miR-139 | 406931 | miR-205 | 406988 |
| miR-30C1 | 407031 | miR-140 | 406932 | miR-2052 | 100302260 |
| miR-206 | 406989 | miR-373 | 442918 | miR-500 | 574502 |
| miR-210 | 406992 | miR-374a | 442919 | miR-500A | 574502 |
| miR-214 | 406996 | miR-374b | 100126317 | miR-501 | 574503 |
| miR-215 | 406997 | miR-375 | 494324 | miR-502 | 574504 |
| miR-217 | 406999 | miR-376A1 | 494325 | miR-503 | 574506 |
| miR-218-1 | 407000 | miR-376C | 442913 | miR-504 | 574507 |
| miR-219-1 | 407002 | miR-377 | 494326 | miR-505 | 574508 |
| miR-219b | 100616335 | miR-378 | 494327 | miR-507 | 574512 |
| miR-221 | 407006 | miR-378A | 494327 | miR-510 | 574515 |
| miR-222 | 407007 | miR-379 | 494328 | miR-511 | 574445 |
| miR-223 | 407008 | miR-380 | 494329 | miR-513 | 574510 |
| miR-224 | 407009 | miR-380-3p | 494329 | miR-513b | 100313822 |
| miR-296 | 407022 | miR-381 | 494330 | miR-513c | 100302114 |
| miR-297 | 100126354 | miR-382 | 494331 | miR-516b-2 | 574485 |
| miR-299 | 407023 | miR-383 | 494332 | miR-516b-1 | 574490 |
| miR-301a | 407027 | miR-384 | 494333 | miR-517c | 574492 |
| miR-301b | 100126318 | miR-409 | 574413 | miR-5189 | 100847057 |
| miR-302a | 407028 | miR-410 | 574434 | miR-518c* | 574477 |
| miR-320b-1 | 100302117 | miR-411 | 693121 | miR-518d-3p | 574489 |
| miR-320c-1 | 100302135 | miR-412 | 574433 | miR-518e* | 574487 |
| miR-320d-2 | 100302169 | miR-421 | 693122 | miR-518f | 574472 |
| miR-320c-2 | 100302195 | miR-422a | 494334 | miR-519b | 574469 |
| miR-320b-2 | 100313769 | miR-423 | 494335 | miR-520b | 574473 |
| miR-320d-1 | 100313896 | miR-424 | 494336 | miR-520e | 574461 |

TABLE 3-continued

Suitable miRNA molecules

| MIRNA ID | ENTREZ ID | MIRNA ID | ENTREZ ID | MIRNA ID | ENTREZ ID |
| --- | --- | --- | --- | --- | --- |
| miR-320A | 407037 | miR-425 | 494337 | miR-521 | 574481 |
| miR-323A | 442897 | miR-429 | 554210 | miR-521 | 574494 |
| miR-323B | 574410 | miR-431* | 574038 | miR-522 | 574495 |
| miR-324 | 442898 | miR-432 | 574451 | miR-526a | 574475 |
| miR-324-3p | 442898 | miR-433 | 574034 | miR-526a | 574486 |
| miR-324-5p | 442898 | miR-448 | 554212 | miR-527 | 574497 |
| miR-325 | 442899 | miR-449a | 554213 | miR-532 | 693124 |
| miR-326 | 442900 | miR-450a-1 | 554214 | miR-539 | 664612 |
| miR-328 | 442901 | miR-450a-2 | 574505 | miR-541 | 100126308 |
| miR-331 | 442903 | miR-450B | 100126302 | miR-542 | 664617 |
| miR-335 | 442904 | miR-451 | 574411 | miR-543 | 100126335 |
| miR-335-5p | 442904 | miR-452 | 574412 | miR-548c-5p | 693129 |
| miR-337 | 442905 | miR-323b | 574410 | miR-548d-5p | 693130 |
| miR-338 | 442906 | miR-454 | 768216 | miR-548d-5p | 693131 |
| miR-339 | 442907 | miR-455 | 619556 | miR-550* | 693133 |
| miR-340 | 442908 | miR-483 | 619552 | miR-550a-1 | 693133 |
| miR-342 | 442909 | miR-484 | 619553 | miR-550a-2 | 693134 |
| miR-342-3p | 442909 | miR-485 | 574436 | miR-551b | 693136 |
| miR-345 | 442910 | miR-486 | 619554 | miR-557 | 693142 |
| miR-346 | 442911 | miR-486-5p | 619554 | miR-561 | 693146 |
| miR-361 | 494323 | miR-487A | 619555 | miR-564 | 693149 |
| miR-362 | 574030 | miR-487b | 664616 | miR-571 | 693156 |
| miR-363 | 574031 | miR-492 | 574449 | miR-573 | 693158 |
| miR-365 | 100126355 | miR-493 | 574450 | miR-574 | 693159 |
| miR-369 | 442914 | miR-494 | 574452 | miR-574-3p | 693159 |
| miR-369-3p | 442914 | miR-495 | 574453 | miR-575 | 693160 |
| miR-370 | 442915 | miR-496 | 574454 | miR-577 | 693162 |
| miR-371 | 442916 | miR-498 | 574460 | miR-578 | 693163 |
| miR-581 | 693166 | miR-671 | 768213 | miR-1276 | 100302121 |
| miR-582 | 693167 | miR-708 | 100126333 | miR-1278 | 100302163 |
| miR-583 | 693168 | miR-718 | 100313781 | miR-1279 | 100302182 |
| miR-584 | 693169 | miR-744 | 100126313 | miR-1284 | 100302112 |
| miR-585 | 693170 | miR-758 | 768212 | miR-1286 | 100302118 |
| miR-588 | 693173 | miR-760 | 100126348 | miR-1288 | 100302124 |
| miR-589 | 693174 | miR-762 | 100313837 | miR-1287 | 100302133 |
| miR-590 | 693175 | miR-765 | 768220 | miR-1281 | 100302237 |
| miR-592 | 693177 | miR-766 | 768218 | miR-1282 | 100302254 |
| miR-593 | 693178 | miR-769 | 768217 | miR-1281 | 100302237 |
| miR-595 | 693180 | miR-770 | 768222 | miR-1295a | 100302178 |
| miR-598 | 693183 | miR-874 | 100126343 | miR-1290 | 100302276 |
| miR-601 | 693186 | miR-877 | 100126314 | miR-1291 | 100302221 |
| miR-603 | 693188 | miR-887 | 100126347 | miR-1293 | 100302220 |
| miR-609 | 693194 | miR-889 | 100126345 | miR-1294 | 100302181 |
| miR-610 | 693195 | miR-890 | 100126303 | miR-1296 | 100302150 |
| miR-612 | 693197 | miR-892b | 100126307 | miR-1297 | 100302187 |
| miR-615 | 693200 | miR-921 | 100126349 | miR-1298 | 100302153 |
| miR-617 | 693202 | miR-924 | 100126323 | miR-1299 | 100302167 |
| miR-618 | 693203 | miR-935 | 100126325 | miR-1301 | 100302246 |
| miR-622 | 693207 | miR-936 | 100126326 | miR-1305 | 100302270 |
| miR-623 | 693208 | miR-939 | 100126351 | miR-1321 | 100302171 |
| miR-624* | 693209 | miR-940 | 100126328 | miR-1322 | 100302166 |
| miR-625 | 693210 | miR-942 | 100126331 | miR-1323 | 100302255 |
| miR-627 | 693212 | miR-943 | 100126332 | miR-1343 | 100616437 |
| miR-628 | 693213 | miR-1180 | 100302256 | miR-1468 | 100302115 |
| miR-629 | 693214 | miR-1181 | 100302213 | miR-1471 | 100302126 |
| miR-630 | 693215 | miR-1182 | 100302132 | miR-1537 | 100302139 |
| miR-631 | 693216 | miR-1183 | 100302122 | miR-1538 | 100302119 |
| miR-632 | 693217 | miR-1185-1 | 100302157 | miR-1539 | 100302257 |
| miR-634 | 693219 | miR-1193 | 100422837 | miR-1587 | 100616251 |
| miR-637 | 693222 | miR-1197 | 100302250 | miR-1825 | 100302183 |
| miR-638 | 693223 | miR-1200 | 100302113 | miR-1827 | 100302217 |
| miR-639 | 693224 | miR-1202 | 100302259 | miR-1908 | 100302263 |
| miR-641 | 693226 | miR-1204 | 100302185 | miR-1910 | 100302261 |
| miR-642 | 693227 | miR-1205 | 100302161 | miR-1912 | 100302144 |
| miR-645 | 693230 | miR-1208 | 100302281 | miR-1913 | 100302141 |
| miR-647 | 693232 | miR-1225-5p | 100188847 | miR-1976 | 100302190 |
| miR-648 | 693233 | miR-1226* | 100302232 | miR-2110 | 100302224 |
| miR-649 | 693234 | miR-122a | 406906 | miR-2113 | 100302164 |
| miR-651 | 723779 | miR-1231 | 100302158 | miR-2116 | 100313886 |
| miR-652 | 724022 | miR-1244 | 100302285 | miR-2117 | 100313779 |
| miR-654 | 724024 | miR-1246 | 100302142 | miR-2278 | 100313780 |
| miR-655 | 724025 | miR-1248 | 100302143 | miR-2355 | 100423036 |
| miR-656 | 724026 | miR-1249 | 100302149 | miR-2467 | 100616360 |
| miR-657 | 724027 | miR-1251 | 100302289 | miR-2861 | 100422910 |
| miR-658 | 724028 | miR-1254 | 100302273 | miR-3115 | 100422866 |
| miR-659 | 724029 | miR-1261 | 100302228 | miR-3117 | 100422871 |

TABLE 3-continued

Suitable miRNA molecules

| MIRNA ID | ENTREZ ID | MIRNA ID | ENTREZ ID | MIRNA ID | ENTREZ ID |
|---|---|---|---|---|---|
| miR-660 | 724030 | miR-1262 | 100302279 | miR-3125 | 100422986 |
| miR-662 | 724032 | miR-1264 | 100302251 | miR-3137 | 100422926 |
| miR-663 | 724033 | miR-1270 | 100302179 | miR-3138 | 100423011 |
| miR-665 | 100126315 | miR-1275 | 100302123 | miR-3143 | 100422934 |
| miR-3146 | 100422967 | miR-4279 | 100422874 | miR-6087 | 102464835 |
| miR-3147 | 100422939 | miR-4281 | 100422962 | miR-6131 | 102465138 |
| miR-3149 | 100422921 | miR-4286 | 100422982 | miR-7112 | 102465906 |
| miR-3152 | 100422869 | miR-4290 | 100422963 | miR-7704 | 102465802 |
| miR-3155A | 100422989 | miR-4292 | 100422860 | miR-7705 | 102466854 |
| miR-3161 | 100423000 | miR-4297 | 100422873 | miR-7706 | 102465803 |
| miR-3168 | 100422878 | miR-4303 | 100422924 | miR-7974 | 102465856 |
| miR-3169 | 100422973 | miR-4306 | 100422861 | | |
| miR-3170 | 100422881 | miR-4311 | 100422905 | | |
| miR-3174 | 100422841 | miR-4312 | 100422971 | | |
| miR-3175 | 100422995 | miR-4316 | 100422851 | | |
| miR-3176 | 100423037 | miR-4317 | 100422840 | | |
| miR-3182 | 100422853 | miR-4322 | 100422925 | | |
| miR-3188 | 100422833 | miR-4323 | 100422980 | | |
| miR-3198 | 100423025 | miR-4325 | 100422883 | | |
| miR-3200 | 100422912 | miR-4326 | 100422945 | | |
| miR-3605 | 100500853 | miR-4327 | 100422891 | | |
| miR-3609 | 100500819 | miR-4424 | 100616328 | | |
| miR-3615 | 100500847 | miR-4429 | 100616469 | | |
| miR-3621 | 100500811 | miR-4443 | 100616407 | | |
| miR-3648 | 100500862 | miR-4447 | 100616485 | | |
| miR-3652 | 100500842 | miR-4448 | 100616127 | | |
| miR-3653 | 100500833 | miR-4454 | 100616234 | | |
| miR-3655 | 100500820 | miR-4455 | 100616111 | | |
| miR-3656 | 100500840 | miR-4461 | 100616209 | | |
| miR-3657 | 100500889 | miR-4467 | 100616367 | | |
| miR-3661 | 100500905 | miR-4482-1 | 100616323 | | |
| miR-3662 | 100500880 | miR-4485 | 100616263 | | |
| miR-3686 | 100500839 | miR-4488 | 100616470 | | |
| miR-3687 | 100500815 | miR-4492 | 100616376 | | |
| miR-3691 | 100500900 | miR-4497 | 100616454 | | |
| miR-3714 | 100500913 | miR-4508 | 100616275 | | |
| miR-3907 | 100500835 | miR-4520-1 | 100616401 | | |
| miR-3909 | 100500826 | miR-4520-2 | 100616466 | | |
| miR-3911 | 100500872 | miR-4524a | 100616316 | | |
| miR-3912 | 100500831 | miR-4536-1 | 100616155 | | |
| miR-3924 | 100500834 | miR-4644 | 100616430 | | |
| miR-3928 | 100500901 | miR-4645 | 100616285 | | |
| miR-3937 | 100500822 | miR-4657 | 100616393 | | |
| miR-3939 | 100500857 | miR-4710 | 100616300 | | |
| miR-3943 | 100500829 | miR-4785 | 100616364 | | |
| miR-3945 | 100500818 | miR-4792 | 100616448 | | |
| miR-3960 | 100616250 | miR-5000 | 100846995 | | |
| miR-3972 | 100616188 | miR-5094 | 100847059 | | |
| miR-4253 | 100422914 | miR-5100 | 100847014 | | |
| miR-4254 | 100423028 | miR-5190 | 100847080 | | |
| miR-4257 | 100422997 | miR-5192 | 100847087 | | |
| miR-4258 | 100423020 | miR-5572 | 100847042 | | |
| miR-4259 | 100422852 | miR-5690 | 100847048 | | |
| miR-4265 | 100422863 | miR-5698 | 100847024 | | |
| miR-4268 | 100422959 | miR-5704 | 100847040 | | |
| miR-4274 | 100422826 | miR-6089 | 102464837 | | |

TABLE 4

Suitable extracellular vesicle associated proteins

| Gene Name | Gene Symbol |
|---|---|
| alpha-1-B glycoprotein | A1BG |
| alpha-2-macroglobulin | A2M |
| alpha-2-macroglobulin-like 1 | A2ML1 |
| achalasia, adrenocortical insufficiency, alacrimia | AAAS |
| acetoacetyl-CoA synthetase | AACS |
| AAR2 splicing factor homolog (*S. cerevisiae*) | AAR2 |
| alanyl-tRNA synthetase | AARS |
| alanyl-tRNA synthetase domain containing 1 | AARSD1 |

TABLE 4-continued

| Suitable extracellular vesicle associated proteins | |
| --- | --- |
| Gene Name | Gene Symbol |
| aminoadipate-semialdehyde dehydrogenase-phosphopantetheinyl transferase | AASDHPPT |
| ATP-binding cassette, sub-family A (ABC1), member 7 | ABCA7 |
| ATP-binding cassette, sub-family B (MDR/TAP), member 1 | ABCB1 |
| ATP-binding cassette, sub-family B (MDR/TAP), member 11 | ABCB11 |
| ATP-binding cassette, sub-family B (MDR/TAP), member 4 | ABCB4 |
| ATP-binding cassette, sub-family B (MDR/TAP), member 6 (Langereis blood group) | ABCB6 |
| ATP-binding cassette, sub-family C (CFTR/MRP), member 1 | ABCC1 |
| ATP-binding cassette, sub-family C (CFTR/MRP), member 11 | ABCC11 |
| ATP-binding cassette, sub-family C (CFTR/MRP), member 2 | ABCC2 |
| ATP-binding cassette, sub-family C (CFTR/MRP), member 4 | ABCC4 |
| ATP-binding cassette, sub-family C (CFTR/MRP), member 5 | ABCC5 |
| ATP-binding cassette, sub-family C (CFTR/MRP), member 9 | ABCC9 |
| ATP-binding cassette, sub-family D (ALD), member 2 | ABCD2 |
| ATP-binding cassette, sub-family E (OABP), member 1 | ABCE1 |
| ATP-binding cassette, sub-family F (GCN20), member 1 | ABCF1 |
| ATP-binding cassette, sub-family F (GCN20), member 2 | ABCF2 |
| ATP-binding cassette, sub-family F (GCN20), member 3 | ABCF3 |
| ATP-binding cassette, sub-family G (WHITE), member 2 (Junior blood group) | ABCG2 |
| abhydrolase domain containing 11 | ABHD11 |
| abhydrolase domain containing 14B | ABHD14B |
| abhydrolase domain containing 16A | ABHD16A |
| abhydrolase domain containing 17A | ABHD17A |
| abhydrolase domain containing 17B | ABHD17B |
| abl-interactor 1 | ABH |
| abl-interactor 2 | ABI2 |
| ABI family, member 3 | ABI3 |
| ABI family, member 3 (NESH) binding protein | ABI3BP |
| activator of basal transcription 1 | ABT1 |
| acetyl-CoA acyltransferase 1 | ACAA1 |
| acetyl-CoA acyltransferase 2 | ACAA2 |
| acetyl-CoA carboxylase alpha | ACACA |
| acetyl-CoA carboxylase beta | ACACB |
| acyl-CoA dehydrogenase family, member 8 | ACAD8 |
| acyl-CoA dehydrogenase, C-4 to C-12 straight chain | ACADM |
| ArfGAP with coiled-coil, ankyrin repeat and PH domains 1 | ACAP1 |
| acetyl-CoA acetyltransferase 1 | ACAT1 |
| acetyl-CoA acetyltransferase 2 | ACAT2 |
| acyl-CoA binding domain containing 3 | ACBD3 |
| angiotensin I converting enzyme | ACE |
| angiotensin I converting enzyme 2 | ACE2 |
| ATP citrate lyase | ACLY |
| aconitase 1, soluble | ACO1 |
| aconitase 2, mitochondrial | ACO2 |
| acyl-CoA thioesterase 1 | ACOT1 |
| acyl-CoA thioesterase 11 | ACOT11 |
| acyl-CoA thioesterase 7 | ACOT7 |
| acid phosphatase 1, soluble | ACP1 |
| acid phosphatase 2, lysosomal | ACP2 |
| acid phosphatase, prostate | ACPP |
| acyl-CoA synthetase long-chain family member 1 | ACSL1 |
| acyl-CoA synthetase long-chain family member 3 | ACSL3 |

TABLE 4-continued

Suitable extracellular vesicle associated proteins

| Gene Name | Gene Symbol |
| --- | --- |
| acyl-CoA synthetase long-chain family member 4 | ACSL4 |
| acyl-CoA synthetase long-chain family member 5 | ACSL5 |
| acyl-CoA synthetase long-chain family member 6 | ACSL6 |
| acyl-CoA synthetase medium-chain family member 1 | ACSM1 |
| acyl-CoA synthetase short-chain family member 2 | ACSS2 |
| actin, alpha 1, skeletal muscle | ACTA1 |
| actin, alpha 2, smooth muscle, aorta | ACTA2 |
| actin, beta | ACTB |
| actin, beta-like 2 | ACTBL2 |
| actin, alpha, cardiac muscle 1 | ACTC1 |
| actin gamma 1 | ACTG1 |
| actin, gamma 2, smooth muscle, enteric | ACTG2 |
| actin-like 6A | ACTL6A |
| actinin, alpha 1 | ACTN1 |
| actinin, alpha 2 | ACTN2 |
| actinin, alpha 3 (gene/pseudogene) | ACTN3 |
| actinin, alpha 4 | ACTN4 |
| actin-related protein 10 homolog (*S. cerevisiae*) | ACTR10 |
| ARP1 actin-related protein 1 homolog A, centractin alpha (yeast) | ACTR1A |
| ARP1 actin-related protein 1 homolog B, centractin beta (yeast) | ACTR1B |
| ARP2 actin-related protein 2 homolog (yeast) | ACTR2 |
| ARP3 actin-related protein 3 homolog (yeast) | ACTR3 |
| ARP3 actin-related protein 3 homolog B (yeast) | ACTR3B |
| ARP3 actin-related protein 3 homolog C (yeast) | ACTR3C |
| ARP5 actin-related protein 5 homolog (yeast) | ACTR5 |
| ARP8 actin-related protein 8 homolog (yeast) | ACTR8 |
| activin A receptor, type I | ACVR1 |
| activin A receptor, type IB | ACVR1B |
| aminoacylase 1 | ACY1 |
| aminoacylase 3 | ACY3 |
| adenosine deaminase | ADA |
| ADAM metallopeptidase domain 10 | ADAM10 |
| ADAM metallopeptidase domain 15 | ADAM15 |
| ADAM metallopeptidase domain 17 | ADAM17 |
| ADAM metallopeptidase domain 30 | ADAM30 |
| ADAM metallopeptidase domain 9 | ADAM9 |
| ADAM metallopeptidase with thrombospondin type 1 motif, 1 | ADAMTS1 |
| ADAM metallopeptidase with thrombospondin type 1 motif, 12 | ADAMTS12 |
| ADAM metallopeptidase with thrombospondin type 1 motif, 13 | ADAMTS13 |
| ADAM metallopeptidase with thrombospondin type 1 motif, 2 | ADAMTS2 |
| ADAM metallopeptidase with thrombospondin type 1 motif, 3 | ADAMTS3 |
| adenosine deaminase, RNA-specific | ADAR |
| adenylate cyclase 1 (brain) | ADCY1 |
| adenylate cyclase 6 | ADCY6 |
| adenylate cyclase 9 | ADCY9 |
| adducin 1 (alpha) | ADD1 |
| adducin 2 (beta) | ADD2 |
| adhesion G protein-coupled receptor E5 | ADGRE5 |
| adhesion G protein-coupled receptor G1 | ADGRG1 |
| adhesion G protein-coupled receptor G2 | ADGRG2 |
| adhesion G protein-coupled receptor G4 | ADGRG4 |
| adhesion G protein-coupled receptor G6 | ADGRG6 |
| adhesion G protein-coupled receptor L2 | ADGRL2 |
| adhesion G protein-coupled receptor L3 | ADGRL3 |
| adhesion G protein-coupled receptor V1 | ADGRV1 |
| alcohol dehydrogenase 1A (class I), alpha polypeptide | ADH1A |

TABLE 4-continued

| Suitable extracellular vesicle associated proteins | |
| --- | --- |
| Gene Name | Gene Symbol |
| alcohol dehydrogenase 1B (class I), beta polypeptide | ADH1B |
| alcohol dehydrogenase 1C (class I), gamma polypeptide | ADH1C |
| alcohol dehydrogenase 5 (class III), chi polypeptide | ADH5 |
| alcohol dehydrogenase 6 (class V) | ADH6 |
| adipogenesis regulatory factor | ADIRF |
| adenosine kinase | ADK |
| ADP-ribosylhydrolase like 2 | ADPRHL2 |
| adrenergic, beta, receptor kinase 1 | ADRBK1 |
| adhesion regulating molecule 1 | ADRM1 |
| adenylosuccinate lyase | ADSL |
| adenylosuccinate synthase | ADSS |
| AE binding protein 1 | AEBP1 |
| afamin | AFM |
| alpha-fetoprotein | AFP |
| ATP/GTP binding protein-like 3 | AGBL3 |
| acylglycerol kinase | AGK |
| amylo-alpha-1,6-glucosidase, 4-alpha-glucanotransferase | AGL |
| argonaute RISC catalytic component 2 | AGO2 |
| alkylglycerone phosphate synthase | AGPS |
| anterior gradient 2 | AGR2 |
| anterior gradient 3 | AGR3 |
| agrin | AGRN |
| angiotensinogen (serpin peptidase inhibitor, clade A, member 8) | AGT |
| angiotensin II receptor-associated protein | AGTRAP |
| AT hook containing transcription factor 1 | AHCTF1 |
| adenosylhomocysteinase | AHCY |
| adenosylhomocysteinase-like 1 | AHCYL1 |
| adenosylhomocysteinase-like 2 | AHCYL2 |
| AHNAK nucleoprotein | AHNAK |
| AHNAK nucleoprotein 2 | AHNAK2 |
| aryl-hydrocarbon receptor repressor | AHRR |
| AHA1, activator of heat shock 90 kDa protein ATPase homolog 1 (yeast) | AHSA1 |
| alpha-2-HS-glycoprotein | AHSG |
| axin interactor, dorsalization associated | AIDA |
| allograft inflammatory factor 1-like | AIF1L |
| apoptosis-inducing factor, mitochondrion-associated, 2 | AIFM2 |
| aminoacyl tRNA synthetase complex-interacting multifunctional protein 1 | AIMP1 |
| aminoacyl tRNA synthetase complex-interacting multifunctional protein 2 | AIMP2 |
| adenylate kinase 1 | AK1 |
| adenylate kinase 2 | AK2 |
| adenylate kinase 4 | AK4 |
| A kinase (PRKA) anchor protein 12 | AKAP12 |
| A kinase (PRKA) anchor protein 9 | AKAP9 |
| aldo-keto reductase family 1, member A1 (aldehyde reductase) | AKR1A1 |
| aldo-keto reductase family 1, member B1 (aldose reductase) | AKR1B1 |
| aldo-keto reductase family 1, member B10 (aldose reductase) | AKR1B10 |
| aldo-keto reductase family 1, member C1 | AKR1C1 |
| aldo-keto reductase family 1, member C3 | AKR1C3 |
| aldo-keto reductase family 1, member E2 | AKR1E2 |
| aldo-keto reductase family 7, member A2 (aflatoxin aldehyde reductase) | AKR7A2 |
| aldo-keto reductase family 7, member A3 (aflatoxin aldehyde reductase) | AKR7A3 |
| aldo-keto reductase family 7-like (gene/pseudogene) | AKR7L |
| v-akt murine thymoma viral oncogene homolog 1 | AKT1 |
| v-akt murine thymoma viral oncogene homolog 2 | AKT2 |
| aminolevulinate dehydratase | ALAD |
| albumin | ALB |
| activated leukocyte cell adhesion molecule | ALCAM |
| aldehyde dehydrogenase 16 family, member A1 | ALDH16A1 |

TABLE 4-continued

| Suitable extracellular vesicle associated proteins | |
|---|---|
| Gene Name | Gene Symbol |
| aldehyde dehydrogenase 18 family, member A1 | ALDH18A1 |
| aldehyde dehydrogenase 1 family, member A1 | ALDH1A1 |
| aldehyde dehydrogenase 1 family, member A3 | ALDH1A3 |
| aldehyde dehydrogenase 1 family, member L1 | ALDH1L1 |
| aldehyde dehydrogenase 2 family (mitochondrial) | ALDH2 |
| aldehyde dehydrogenase 3 family, member A1 | ALDH3A1 |
| aldehyde dehydrogenase 3 family, member A2 | ALDH3A2 |
| aldehyde dehydrogenase 3 family, member B1 | ALDH3B1 |
| aldehyde dehydrogenase 5 family, member A1 | ALDH5A1 |
| aldehyde dehydrogenase 6 family, member A1 | ALDH6A1 |
| aldehyde dehydrogenase 7 family, member A1 | ALDH7A1 |
| aldehyde dehydrogenase 8 family, member A1 | ALDH8A1 |
| aldehyde dehydrogenase 9 family, member A1 | ALDH9A1 |
| aldolase A, fructose-bisphosphate | ALDOA |
| aldolase B, fructose-bisphosphate | ALDOB |
| aldolase C, fructose-bisphosphate | ALDOC |
| anaplastic lymphoma receptor tyrosine kinase | ALK |
| AlkB family member 5, RNA demethylase | ALKBH5 |
| arachidonate 12-lipoxygenase | ALOX12 |
| arachidonate 12-lipoxygenase pseudogene 2 | ALOX12P2 |
| alkaline phosphatase, liver/bone/kidney | ALPL |
| alkaline phosphatase, placental | ALPP |
| alkaline phosphatase, placental-like 2 | ALPPL2 |
| Aly/REF export factor | ALYREF |
| alpha-1-microglobulin/bikunin precursor | AMBP |
| amnion associated transmembrane protein | AMN |
| antagonist of mitotic exit network 1 homolog (S. cerevisiae) | AMN1 |
| adenosine monophosphate deaminase 2 | AMPD2 |
| amylase, alpha 1A (salivary) | AMY1A |
| amylase, alpha 1B (salivary) | AMY1B |
| amylase, alpha 1C (salivary) | AMY1C |
| amylase, alpha 2A (pancreatic) | AMY2A |
| amylase, alpha 2B (pancreatic) | AMY2B |
| anaphase promoting complex subunit 1 | ANAPC1 |
| anaphase promoting complex subunit 2 | ANAPC2 |
| anaphase promoting complex subunit 5 | ANAPC5 |
| anaphase promoting complex subunit 7 | ANAPC7 |
| angiogenin, ribonuclease, RNase A family, 5 | ANG |
| angiopoietin 1 | ANGPT1 |
| angiopoietin-like 1 | ANGPTL1 |
| angiopoietin-like 2 | ANGPTL2 |
| angiopoietin-like 3 | ANGPTL3 |
| angiopoietin-like 4 | ANGPTL4 |
| angiopoietin-like 7 | ANGPTL7 |
| ankyrin 1, erythrocytic | ANK1 |
| ankyrin repeat and FYVE domain containing 1 | ANKFY1 |
| ANKH inorganic pyrophosphate transport regulator | ANKH |
| ankyrin repeat domain 13A | ANKRD13A |
| ankyrin repeat domain 18B | ANKRD18B |
| ankyrin repeat domain 23 | ANKRD23 |
| ankyrin repeat domain 24 | ANKRD24 |
| ankyrin repeat domain 26 | ANKRD26 |
| ankyrin repeat domain 28 | ANKRD28 |
| ankyrin repeat domain 36 | ANKRD36 |
| ankyrin repeat domain 44 | ANKRD44 |
| ankyrin repeat and sterile alpha motif domain containing 1A | ANKS1A |

TABLE 4-continued

Suitable extracellular vesicle associated proteins

| Gene Name | Gene Symbol |
|---|---|
| ankyrin repeat and sterile alpha motif domain containing 1B | ANKS1B |
| anillin, actin binding protein | ANLN |
| anoctamin 1, calcium activated chloride channel | ANO1 |
| anoctamin 6 | ANO6 |
| acidic (leucine-rich) nuclear phosphoprotein 32 family, member A | ANP32A |
| acidic (leucine-rich) nuclear phosphoprotein 32 family, member B | ANP32B |
| acidic (leucine-rich) nuclear phosphoprotein 32 family, member E | ANP32E |
| alanyl (membrane) aminopeptidase | ANPEP |
| anthrax toxin receptor 1 | ANTXR1 |
| anthrax toxin receptor 2 | ANTXR2 |
| annexin A1 | ANXA1 |
| annexin A11 | ANXA11 |
| annexin A13 | ANXA13 |
| annexin A2 | ANXA2 |
| annexin A2 pseudogene 1 | ANXA2P1 |
| annexin A2 pseudogene 2 | ANXA2P2 |
| annexin A3 | ANXA3 |
| annexin A4 | ANXA4 |
| annexin A5 | ANXA5 |
| annexin A6 | ANXA6 |
| annexin A7 | ANXA7 |
| annexin A8 | ANXA8 |
| amine oxidase, copper containing 1 | AOC1 |
| aldehyde oxidase 1 | AOX1 |
| adaptor-related protein complex 1, beta 1 subunit | AP1B1 |
| adaptor-related protein complex 1, gamma 1 subunit | AP1G1 |
| adaptor-related protein complex 1, mu 1 subunit | AP1M1 |
| adaptor-related protein complex 1, mu 2 subunit | AP1M2 |
| adaptor-related protein complex 1, sigma 1 subunit | AP1S1 |
| adaptor-related protein complex 2, alpha 1 subunit | AP2A1 |
| adaptor-related protein complex 2, alpha 2 subunit | AP2A2 |
| adaptor-related protein complex 2, beta 1 subunit | AP2B1 |
| adaptor-related protein complex 2, mu 1 subunit | AP2M1 |
| adaptor-related protein complex 2, sigma 1 subunit | AP2S1 |
| adaptor-related protein complex 3, beta 1 subunit | AP3B1 |
| adaptor-related protein complex 3, delta 1 subunit | AP3D1 |
| adaptor-related protein complex 3, mu 1 subunit | AP3M1 |
| adaptor-related protein complex 3, sigma 2 subunit | AP3S2 |
| adaptor-related protein complex 4, mu 1 subunit | AP4M1 |
| adaptor-related protein complex 5, beta 1 subunit | AP5B1 |
| adaptor-related protein complex 5, mu 1 subunit | AP5M1 |
| adaptor-related protein complex 5, zeta 1 subunit | AP5Z1 |
| apoptotic peptidase activating factor 1 | APAF1 |
| amyloid beta (A4) precursor protein-binding, family B, member 1 interacting protein | APBB1IP |
| amyloid P component, serum | APCS |
| acylaminoacyl-peptide hydrolase | APEH |
| APEX nuclease (multifunctional DNA repair enzyme) 1 | APEX1 |
| APH1A gamma secretase subunit | APH1A |
| apoptosis inhibitor 5 | API5 |
| amyloid beta (A4) precursor-like protein 2 | APLP2 |

TABLE 4-continued

| Suitable extracellular vesicle associated proteins | |
|---|---|
| Gene Name | Gene Symbol |
| adipocyte plasma membrane associated protein | APMAP |
| apolipoprotein A-I | APOA1 |
| apolipoprotein A-II | APOA2 |
| apolipoprotein A-IV | APOA4 |
| apolipoprotein A-V | APOA5 |
| apolipoprotein B | APOB |
| apolipoprotein B mRNA editing enzyme, catalytic polypeptide-like 3A | APOBEC3A |
| APOBEC3A and APOBEC3B deletion hybrid | APOBEC3A_B |
| apolipoprotein B mRNA editing enzyme, catalytic polypeptide-like 3B | APOBEC3B |
| apolipoprotein B mRNA editing enzyme, catalytic polypeptide-like 3C | APOBEC3C |
| apolipoprotein C-II | APOC2 |
| apolipoprotein C-III | APOC3 |
| apolipoprotein D | APOD |
| apolipoprotein E | APOE |
| apolipoprotein H (beta-2-glycoprotein I) | APOH |
| apolipoprotein L, 1 | APOL1 |
| apolipoprotein L, 2 | APOL2 |
| apolipoprotein M | APOM |
| amyloid beta (A4) precursor protein | APP |
| adaptor protein, phosphotyrosine interaction, PH domain and leucine zipper containing 1 | APPL1 |
| adaptor protein, phosphotyrosine interaction, PH domain and leucine zipper containing 2 | APPL2 |
| adenine phosphoribosyltransferase | APRT |
| aquaporin 1 (Colton blood group) | AQP1 |
| aquaporin 2 (collecting duct) | AQP2 |
| aquaporin 5 | AQP5 |
| aquarius intron-binding spliceosomal factor | AQR |
| androgen receptor | AR |
| A-Raf proto-oncogene, serine/threonine kinase | ARAF |
| ArfGAP with RhoGAP domain, ankyrin repeat and PH domain 1 | ARAP1 |
| ArfGAP with RhoGAP domain, ankyrin repeat and PH domain 3 | ARAP3 |
| archain 1 | ARCN1 |
| amphiregulin | AREG |
| ADP-ribosylation factor 1 | ARF1 |
| ADP-ribosylation factor 3 | ARF3 |
| ADP-ribosylation factor 4 | ARF4 |
| ADP-ribosylation factor 5 | ARF5 |
| ADP-ribosylation factor 6 | ARF6 |
| ADP-ribosylation factor GTPase activating protein 3 | ARFGAP3 |
| ADP-ribosylation factor guanine nucleotide-exchange factor 2 (brefeldin A-inhibited) | ARFGEF2 |
| ADP-ribosylation factor interacting protein 1 | ARFIP1 |
| arginase 1 | ARG1 |
| Rho GTPase activating protein 1 | ARHGAP1 |
| Rho GTPase activating protein 15 | ARHGAP15 |
| Rho GTPase activating protein 18 | ARHGAP18 |
| Rho GTPase activating protein 23 | ARHGAP23 |
| Rho GTPase activating protein 26 | ARHGAP26 |
| Rho GTPase activating protein 33 | ARHGAP33 |
| Rho GTPase activating protein 35 | ARHGAP35 |
| Rho GTPase activating protein 4 | ARHGAP4 |
| Rho GTPase activating protein 6 | ARHGAP6 |
| Rho GTPase activating protein 8 | ARHGAP8 |
| Rho GTPase activating protein 9 | ARHGAP9 |
| Rho GDP dissociation inhibitor (GDI) alpha | ARHGDIA |
| Rho GDP dissociation inhibitor (GDI) beta | ARHGDIB |
| Rho guanine nucleotide exchange factor (GEF) 1 | ARHGEF1 |
| Rho guanine nucleotide exchange factor (GEF) 12 | ARHGEF12 |
| Rho guanine nucleotide exchange factor (GEF) 16 | ARHGEF16 |

TABLE 4-continued

| Suitable extracellular vesicle associated proteins | |
| --- | --- |
| Gene Name | Gene Symbol |
| Rho guanine nucleotide exchange factor (GEF) 17 | ARHGEF17 |
| Rho/Rac guanine nucleotide exchange factor (GEF) 18 | ARHGEF18 |
| Rho/Rac guanine nucleotide exchange factor (GEF) 2 | ARHGEF2 |
| Rho guanine nucleotide exchange factor (GEF) 39 | ARHGEF39 |
| Rac/Cdc42 guanine nucleotide exchange factor (GEF) 6 | ARHGEF6 |
| Rho guanine nucleotide exchange factor (GEF) 7 | ARHGEF7 |
| AT rich interactive domain 1A (SWI-like) | ARID1A |
| AT rich interactive domain 5B (MRF1-like) | ARID5B |
| ADP-ribosylation factor-like 1 | ARL1 |
| ADP-ribosylation factor-like 15 | ARL15 |
| ADP-ribosylation factor-like 2 | ARL2 |
| ADP-ribosylation factor-like 3 | ARL3 |
| ADP-ribosylation factor-like 6 | ARL6 |
| ADP-ribosylation factor-like 6 interacting protein 1 | ARL6IP1 |
| ADP-ribosylation factor-like 6 interacting protein 5 | ARL6IP5 |
| ADP-ribosylation factor-like 8A | ARL8A |
| ADP-ribosylation factor-like 8B | ARL8B |
| armadillo repeat containing 3 | ARMC3 |
| armadillo repeat containing 5 | ARMC5 |
| armadillo repeat containing 6 | ARMC6 |
| armadillo repeat containing 8 | ARMC8 |
| armadillo repeat containing 9 | ARMC9 |
| age-related maculopathy susceptibility 2 | ARMS2 |
| acidic residue methyltransferase 1 | ARMT1 |
| actin related protein 2/3 complex, subunit 1A, 41 kDa | ARPC1A |
| actin related protein 2/3 complex, subunit 1B, 41 kDa | ARPC1B |
| actin related protein 2/3 complex, subunit 2, 34 kDa | ARPC2 |
| actin related protein 2/3 complex, subunit 3, 21 kDa | ARPC3 |
| actin related protein 2/3 complex, subunit 4, 20 kDa | ARPC4 |
| ARPC4-TTLL3 readthrough | ARPC4-TTLL3 |
| actin related protein 2/3 complex, subunit 5, 16 kDa | ARPC5 |
| actin related protein 2/3 complex, subunit 5-like | ARPC5L |
| cAMP-regulated phosphoprotein, 19 kDa | ARPP19 |
| arrestin 3, retinal (X-arrestin) | ARR3 |
| arrestin domain containing 1 | ARRDC1 |
| arrestin domain containing 3 | ARRDC3 |
| arylsulfatase B | ARSB |
| arylsulfatase E (chondrodysplasia punctata 1) | ARSE |
| arylsulfatase F | ARSF |
| armadillo repeat gene deleted in velocardiofacial syndrome | ARVCF |
| N-acylsphingosine amidohydrolase (acid ceramidase) 1 | ASAH1 |
| ArfGAP with SH3 domain, ankyrin repeat and PH domain 1 | ASAP1 |
| ArfGAP with SH3 domain, ankyrin repeat and PH domain 2 | ASAP2 |
| ankyrin repeat and SOCS box containing 15 | ASB15 |
| activating signal cointegrator 1 complex subunit 3 | ASCC3 |
| ash1 (absent, small, or homeotic)-like (*Drosophila*) | ASH1L |
| argininosuccinate lyase | ASL |
| acetylserotonin O-methyltransferase-like | ASMTL |
| arsA arsenite transporter, ATP-binding, homolog 1 (bacterial) | ASNA1 |
| asparagine synthetase (glutamine-hydrolyzing) | ASNS |
| aspartate beta-hydroxylase | ASPH |

TABLE 4-continued

| Suitable extracellular vesicle associated proteins | |
| --- | --- |
| Gene Name | Gene Symbol |
| asporin | ASPN |
| argininosuccinate synthase 1 | ASS1 |
| ATPase family, AAA domain containing 2 | ATAD2 |
| ATPase family, AAA domain containing 2B | ATAD2B |
| ATPase family, AAA domain containing 3A | ATAD3A |
| ATPase family, AAA domain containing 3B | ATAD3B |
| ATPase family, AAA domain containing 3C | ATAD3C |
| autophagy related 3 | ATG3 |
| autophagy related 7 | ATG7 |
| autophagy related 9A | ATG9A |
| 5-aminoimidazole-4-carboxamide ribonucleotide formyltransferase/IMP cyclohydrolase | ATIC |
| atlastin GTPase 2 | ATL2 |
| atlastin GTPase 3 | ATL3 |
| ATPase, class V, type 10A | ATP10A |
| ATPase, class V, type 10D | ATP10D |
| ATPase, class VI, type 11A | ATP11A |
| ATPase, class VI, type 11C | ATP11C |
| ATPase, H+/K+ transporting, nongastric, alpha polypeptide | ATP12A |
| ATPase type 13A3 | ATP13A3 |
| ATPase, Na+/K+ transporting, alpha 1 polypeptide | ATP1A1 |
| ATPase, Na+/K+ transporting, alpha 2 polypeptide | ATP1A2 |
| ATPase, Na+/K+ transporting, alpha 3 polypeptide | ATP1A3 |
| ATPase, Na+/K+ transporting, alpha 4 polypeptide | ATP1A4 |
| ATPase, Na+/K+ transporting, beta 1 polypeptide | ATP1B1 |
| ATPase, Na+/K+ transporting, beta 3 polypeptide | ATP1B3 |
| ATPase, Ca++ transporting, cardiac muscle, slow twitch 2 | ATP2A2 |
| ATPase, Ca++ transporting, ubiquitous | ATP2A3 |
| ATPase, Ca++ transporting, plasma membrane 1 | ATP2B1 |
| ATPase, Ca++ transporting, plasma membrane 2 | ATP2B2 |
| ATPase, Ca++ transporting, plasma membrane 3 | ATP2B3 |
| ATPase, Ca++ transporting, plasma membrane 4 | ATP2B4 |
| ATPase, Ca++ transporting, type 2C, member 1 | ATP2C1 |
| ATPase, H+/K+ exchanging, alpha polypeptide | ATP4A |
| ATP synthase, H+ transporting, mitochondrial F1 complex, alpha subunit 1, cardiac muscle | ATP5A1 |
| ATP synthase, H+ transporting, mitochondrial F1 complex, beta polypeptide | ATP5B |
| ATP synthase, H+ transporting, mitochondrial F1 complex, gamma polypeptide 1 | ATP5C1 |
| ATP synthase, H+ transporting, mitochondrial F1 complex, delta subunit | ATP5D |
| ATP synthase, H+ transporting, mitochondrial Fo complex, subunit d | ATP5H |
| ATP synthase, H+ transporting, mitochondrial Fo complex, subunit E | ATP5I |
| ATP synthase, H+ transporting, mitochondrial Fo complex, subunit G | ATP5L |
| ATP synthase, H+ transporting, mitochondrial F1 complex, O subunit | ATP5O |
| ATPase, H+ transporting, lysosomal accessory protein 1 | ATP6AP1 |
| ATPase, H+ transporting, lysosomal accessory protein 2 | ATP6AP2 |
| ATPase, H+ transporting, lysosomal V0 subunit a1 | ATP6V0A1 |
| ATPase, H+ transporting, lysosomal V0 subunit a2 | ATP6V0A2 |

TABLE 4-continued

| Suitable extracellular vesicle associated proteins | |
| --- | --- |
| Gene Name | Gene Symbol |
| ATPase, H+ transporting, lysosomal V0 subunit a4 | ATP6V0A4 |
| ATPase, H+ transporting, lysosomal 16 kDa, V0 subunit c | ATP6V0C |
| ATPase, H+ transporting, lysosomal 38 kDa, V0 subunit d1 | ATP6V0D1 |
| ATPase, H+ transporting, lysosomal 38 kDa, V0 subunit d2 | ATP6V0D2 |
| ATPase, H+ transporting, lysosomal 70 kDa, V1 subunit A | ATP6V1A |
| ATPase, H+ transporting, lysosomal 56/58 kDa, V1 subunit B1 | ATP6V1B1 |
| ATPase, H+ transporting, lysosomal 56/58 kDa, V1 subunit B2 | ATP6V1B2 |
| ATPase, H+ transporting, lysosomal 42 kDa, V1 subunit C1 | ATP6V1C1 |
| ATPase, H+ transporting, lysosomal 42 kDa, V1 subunit C2 | ATP6V1C2 |
| ATPase, H+ transporting, lysosomal 34 kDa, V1 subunit D | ATP6V1D |
| ATPase, H+ transporting, lysosomal 31 kDa, V1 subunit E1 | ATP6V1E1 |
| ATPase, H+ transporting, lysosomal 14 kDa, V1 subunit F | ATP6V1F |
| ATPase, H+ transporting, lysosomal 13 kDa, V1 subunit G1 | ATP6V1G1 |
| ATPase, H+ transporting, lysosomal 50/57 kDa, V1 subunit H | ATP6V1H |
| ATPase, Cu++ transporting, alpha polypeptide | ATP7A |
| ATPase, Cu++ transporting, beta polypeptide | ATP7B |
| ATPase, aminophospholipid transporter (APLT), class I, type 8A, member 1 | ATP8A1 |
| ATPase, aminophospholipid transporter, class I, type 8A, member 2 | ATP8A2 |
| ATPase, aminophospholipid transporter, class I, type 8B, member 1 | ATP8B1 |
| ATPase, aminophospholipid transporter, class I, type 8B, member 3 | ATP8B3 |
| ATPase, class II, type 9A | ATP9A |
| ATPase, class II, type 9B | ATP9B |
| attractin | ATRN |
| ataxin 1 | ATXN1 |
| ataxin 10 | ATXN10 |
| ataxin 2-like | ATXN2L |
| AXL receptor tyrosine kinase | AXL |
| alpha-2-glycoprotein 1, zinc-binding | AZGP1 |
| alpha-2-glycoprotein 1, zinc-binding pseudogene 1 | AZGP1P1 |
| azurocidin 1 | AZU1 |
| beta-2-microglobulin | B2M |
| beta-1,3-glucuronyltransferase 3 | B3GAT3 |
| UDP-GlcNAc: betaGal beta-1,3-N-acetylglucosaminyltransferase 2 | B3GNT2 |
| UDP-Gal: betaGlcNAc beta 1,4-galactosyltransferase, polypeptide 1 | B4GALT1 |
| UDP-Gal: betaGlcNAc beta 1,4-galactosyltransferase, polypeptide 3 | B4GALT3 |
| UDP-Gal: betaGlcNAc beta 1,4-galactosyltransferase, polypeptide 4 | B4GALT4 |
| UDP-Gal: betaGlcNAc beta 1,4-galactosyltransferase, polypeptide 5 | B4GALT5 |
| xylosylprotein beta 1,4-galactosyltransferase, polypeptide 7 | B4GALT7 |
| BRISC and BRCA1 A complex member 1 | BABAM1 |
| beta-site APP-cleaving enzyme 2 | BACE2 |
| BTB and CNC homology 1, basic leucine zipper transcription factor 2 | BACH2 |
| BCL2-associated athanogene | BAG1 |
| BCL2-associated athanogene 2 | BAG2 |
| BCL2-associated athanogene 5 | BAG5 |
| BCL2-associated athanogene 6 | BAG6 |
| BAI1-associated protein 2 | BAIAP2 |
| BAI1-associated protein 2-like 1 | BAIAP2L1 |
| BAI1-associated protein 2-like 2 | BAIAP2L2 |

TABLE 4-continued

| Suitable extracellular vesicle associated proteins | |
| --- | --- |
| Gene Name | Gene Symbol |
| barrier to autointegration factor 1 | BANF1 |
| brain abundant, membrane attached signal protein 1 | BASP1 |
| BCL2-associated X protein | BAX |
| bromodomain adjacent to zinc finger domain, 1B | BAZ1B |
| butyrobetaine (gamma), 2-oxoglutarate dioxygenase (gamma-butyrobetaine hydroxylase) 1 | BBOX1 |
| Bardet-Biedl syndrome 4 | BBS4 |
| basal cell adhesion molecule (Lutheran blood group) | BCAM |
| B-cell receptor-associated protein 31 | BCAP31 |
| breast carcinoma amplified sequence 2 | BCAS2 |
| branched chain amino-acid transaminase 1, cytosolic | BCAT1 |
| BRCA2 and CDKN1A interacting protein | BCCIP |
| butyrylcholinesterase | BCHE |
| B-cell CLL/lymphoma 11A (zinc finger protein) | BCL11A |
| BCL2-like 12 (proline rich) | BCL2L12 |
| breakpoint cluster region | BCR |
| 3-hydroxybutyrate dehydrogenase, type 2 | BDH2 |
| brain-derived neurotrophic factor | BDNF |
| BEN domain containing 7 | BEND7 |
| biglycan | BGN |
| basic helix-loop-helix domain containing, class B, 9 | BHLHB9 |
| betaine--homocysteine S-methyltransferase | BHMT |
| betaine--homocysteine S-methyltransferase 2 | BHMT2 |
| BicC family RNA binding protein 1 | BICC1 |
| bridging integrator 1 | BIN1 |
| bridging integrator 2 | BIN2 |
| BLK proto-oncogene, Src family tyrosine kinase | BLK |
| Bloom syndrome, RecQ helicase-like | BLM |
| bleomycin hydrolase | BLMH |
| biogenesis of lysosomal organelles complex-1, subunit 5, muted | BLOC1S5 |
| biliverdin reductase A | BLVRA |
| biliverdin reductase B | BLVRB |
| bone morphogenetic protein 15 | BMP15 |
| bone morphogenetic protein 3 | BMP3 |
| bone morphogenetic protein 4 | BMP4 |
| bone morphogenetic protein 7 | BMP7 |
| bone morphogenetic protein receptor, type II (serine/threonine kinase) | BMPR2 |
| bolA family member 2 | BOLA2 |
| bolA family member 2B | BOLA2B |
| block of proliferation 1 | BOP1 |
| bactericidal/permeability-increasing protein | BPI |
| BPI fold containing family A, member 1 | BPIFA1 |
| BPI fold containing family A, member 2 | BPIFA2 |
| BPI fold containing family B, member 1 | BPIFB1 |
| 3'(2'),5'-bisphosphate nucleotidase 1 | BPNT1 |
| BRCA1-associated ATM activator 1 | BRAT1 |
| breast cancer 2, early onset | BRCA2 |
| bromodomain containing 4 | BRD4 |
| brain and reproductive organ-expressed (TNFRSF1A modulator) | BRE |
| BRI3 binding protein | BRI3BP |
| BRX1, biogenesis of ribosomes | BRIX1 |
| BRICK1, SCAR/WAVE actin-nucleating complex subunit | BRK1 |
| breast cancer metastasis suppressor 1 | BRMS1 |
| BRO1 domain and CAAX motif containing | BROX |
| basigin (Ok blood group) | BSG |
| bone marrow stromal cell antigen 1 | BST1 |
| bone marrow stromal cell antigen 2 | BST2 |
| BTAF1 RNA polymerase II, B-TFIID transcription factor-associated, 170 kDa | BTAF1 |
| basic transcription factor 3 | BTF3 |
| B-cell translocation gene 1, anti-proliferative | BTG1 |

TABLE 4-continued

| Suitable extracellular vesicle associated proteins | |
| --- | --- |
| Gene Name | Gene Symbol |
| BTG family, member 2 | BTG2 |
| Bruton agammaglobulinemia tyrosine kinase | BTK |
| butyrophilin, subfamily 1, member A1 | BTN1A1 |
| butyrophilin, subfamily 2, member A1 | BTN2A1 |
| butyrophilin, subfamily 3, member A1 | BTN3A1 |
| butyrophilin, subfamily 3, member A2 | BTN3A2 |
| butyrophilin, subfamily 3, member A3 | BTN3A3 |
| BUB3 mitotic checkpoint protein | BUB3 |
| basic leucine zipper and W2 domains 1 | BZW1 |
| basic leucine zipper and W2 domains 2 | BZW2 |
| chromosome 10 open reading frame 54 | C10orf54 |
| chromosome 10 open reading frame 90 | C10orf90 |
| chromosome 11 open reading frame 52 | C11orf52 |
| chromosome 11 open reading frame 54 | C11orf54 |
| chromosome 12 open reading frame 10 | C12orf10 |
| chromosome 12 open reading frame 57 | C12orf57 |
| chromosome 14 open reading frame 1 | C14orf1 |
| chromosome 14 open reading frame 166 | C14orf166 |
| chromosome 15 open reading frame 52 | C15orf52 |
| chromosome 16 open reading frame 13 | C16orf13 |
| chromosome 16 open reading frame 54 | C16orf54 |
| chromosome 16 open reading frame 62 | C16orf62 |
| chromosome 16 open reading frame 87 | C16orf87 |
| chromosome 16 open reading frame 89 | C16orf89 |
| chromosome 17 open reading frame 75 | C17orf75 |
| chromosome 17 open reading frame 80 | C17orf80 |
| chromosome 19 open reading frame 18 | C19orf18 |
| C1GALT1-specific chaperone 1 | C1GALT1C1 |
| chromosome 1 open reading frame 116 | C1orf116 |
| chromosome 1 open reading frame 198 | C1orf198 |
| complement component 1, q subcomponent, A chain | C1QA |
| complement component 1, q subcomponent, B chain | C1QB |
| complement component 1, q subcomponent binding protein | C1QBP |
| complement component 1, q subcomponent, C chain | C1QC |
| C1q and tumor necrosis factor related protein 1 | C1QTNF1 |
| C1q and tumor necrosis factor related protein 3 | C1QTNF3 |
| complement component 1, r subcomponent | C1R |
| complement component 1, r subcomponent-like | C1RL |
| complement component 1, s subcomponent | C1S |
| chromosome 21 open reading frame 59 | C21orf59 |
| C2 calcium-dependent domain containing 5 | C2CD5 |
| chromosome 2 open reading frame 16 | C2orf16 |
| chromosome 2 open reading frame 74 | C2orf74 |
| chromosome 2 open reading frame 88 | C2orf88 |
| complement component 3 | C3 |
| complement component 4A (Rodgers blood group) | C4A |
| complement component 4B (Chido blood group) | C4B |
| complement component 4 binding protein, alpha | C4BPA |
| complement component 4 binding protein, beta | C4BPB |
| complement component 5 | C5 |
| chromosome 5 open reading frame 15 | C5orf15 |
| chromosome 5 open reading frame 24 | C5orf24 |
| chromosome 5 open reading frame 46 | C5orf46 |
| chromosome 5 open reading frame 51 | C5orf51 |
| complement component 6 | C6 |
| chromosome 6 open reading frame 10 | C6orf10 |
| chromosome 6 open reading frame 163 | C6orf163 |
| complement component 7 | C7 |
| chromosome 7 open reading frame 50 | C7orf50 |
| complement component 8, alpha polypeptide | C8A |

TABLE 4-continued

| Suitable extracellular vesicle associated proteins | |
| --- | --- |
| Gene Name | Gene Symbol |
| complement component 8, gamma polypeptide | C8G |
| chromosome 8 open reading frame 33 | C8orf33 |
| complement component 9 | C9 |
| chromosome 9 open reading frame 64 | C9orf64 |
| chromosome 9 open reading frame 91 | C9orf91 |
| carbonic anhydrase I | CA1 |
| carbonic anhydrase XII | CA12 |
| carbonic anhydrase XIV | CA14 |
| carbonic anhydrase II | CA2 |
| carbonic anhydrase IV | CA4 |
| carbonic anhydrase VI | CA6 |
| carbonic anhydrase IX | CA9 |
| calcium binding protein 39 | CAB39 |
| calcium binding protein 39-like | CAB39L |
| calcium binding protein 1 | CABP1 |
| calcium channel, voltage-dependent, R type, alpha 1E subunit | CACNA1E |
| calcium channel, voltage-dependent, L type, alpha 1S subunit | CACNA1S |
| calcium channel, voltage-dependent, alpha 2/delta subunit 1 | CACNA2D1 |
| calcium channel, voltage-dependent, alpha 2/delta subunit 2 | CACNA2D2 |
| calcium channel, voltage-dependent, alpha 2/delta subunit 4 | CACNA2D4 |
| calcyclin binding protein | CACYBP |
| carbamoyl-phosphate synthetase 2, aspartate transcarbamylase, and dihydroorotase | CAD |
| cell adhesion molecule 1 | CADM1 |
| cell adhesion molecule 4 | CADM4 |
| calbindin 1, 28 kDa | CALB1 |
| calmodulin 1 (phosphorylase kinase, delta) | CALM1 |
| calmodulin 2 (phosphorylase kinase, delta) | CALM2 |
| calmodulin 3 (phosphorylase kinase, delta) | CALM3 |
| calmodulin-like 3 | CALML3 |
| calmodulin-like 5 | CALML5 |
| calreticulin | CALR |
| calumenin | CALU |
| calcium/calmodulin-dependent protein kinase II delta | CAMK2D |
| calcium/calmodulin-dependent protein kinase II gamma | CAMK2G |
| calcium/calmodulin-dependent protein kinase IV | CAMK4 |
| calcium/calmodulin-dependent protein kinase kinase 2, beta | CAMKK2 |
| CaM kinase-like vesicle-associated | CAMKV |
| cathelicidin antimicrobial peptide | CAMP |
| calmodulin binding transcription activator 1 | CAMTA1 |
| cullin-associated and neddylation-dissociated 1 | CAND1 |
| cullin-associated and neddylation-dissociated 2 (putative) | CAND2 |
| calcium activated nucleotidase 1 | CANT1 |
| calnexin | CANX |
| CAP, adenylate cyclase-associated protein 1 (yeast) | CAP1 |
| capping protein (actin filament), gelsolin-like | CAPG |
| calpain 1, (mu/I) large subunit | CAPN1 |
| calpain 2, (m/II) large subunit | CAPN2 |
| calpain 5 | CAPN5 |
| calpain 7 | CAPN7 |
| calpain, small subunit 1 | CAPNS1 |
| calpain, small subunit 2 | CAPNS2 |
| cell cycle associated protein 1 | CAPRIN1 |
| calcyphosine | CAPS |
| calcyphosine 2 | CAPS2 |
| capping protein (actin filament) muscle Z-line, alpha 1 | CAPZA1 |
| capping protein (actin filament) muscle Z-line, alpha 2 | CAPZA2 |
| capping protein (actin filament) muscle Z-line, beta | CAPZB |

TABLE 4-continued

| Suitable extracellular vesicle associated proteins | |
| --- | --- |
| Gene Name | Gene Symbol |
| caspase recruitment domain family, member 9 | CARD9 |
| calcium regulated heat stable protein 1, 24 kDa | CARHSP1 |
| carbohydrate kinase domain containing | CARKD |
| cysteinyl-tRNA synthetase | CARS |
| cancer susceptibility candidate 4 | CASC4 |
| calcium/calmodulin-dependent serine protein kinase (MAGUK family) | CASK |
| caspase 14, apoptosis-related cysteine peptidase | CASP14 |
| caspase 3, apoptosis-related cysteine peptidase | CASP3 |
| caspase 6, apoptosis-related cysteine peptidase | CASP6 |
| caspase 9, apoptosis-related cysteine peptidase | CASP9 |
| catalase | CAT |
| caveolin 1, caveolae protein, 22 kDa | CAV1 |
| caveolin 2 | CAV2 |
| Cbl proto-oncogene, E3 ubiquitin protein ligase | CBL |
| carbonyl reductase 1 | CBR1 |
| carbonyl reductase 3 | CBR3 |
| cystathionine-beta-synthase | CBS |
| chromobox homolog 1 | CBX1 |
| chromobox homolog 3 | CBX3 |
| chromobox homolog 5 | CBX5 |
| chromobox homolog 8 | CBX8 |
| coiled-coil and C2 domain containing 1A | CC2D1A |
| coiled-coil and C2 domain containing 1B | CC2D1B |
| cell division cycle and apoptosis regulator 1 | CCAR1 |
| cell cycle and apoptosis regulator 2 | CCAR2 |
| cysteine conjugate-beta lyase 2 | CCBL2 |
| coiled-coil domain containing 105 | CCDC105 |
| coiled-coil domain containing 115 | CCDC115 |
| coiled-coil domain containing 129 | CCDC129 |
| coiled-coil domain containing 132 | CCDC132 |
| coiled-coil domain containing 158 | CCDC158 |
| coiled-coil domain containing 171 | CCDC171 |
| coiled-coil domain containing 175 | CCDC175 |
| coiled-coil domain containing 22 | CCDC22 |
| coiled-coil domain containing 25 | CCDC25 |
| coiled-coil domain containing 33 | CCDC33 |
| coiled-coil domain containing 47 | CCDC47 |
| coiled-coil domain containing 50 | CCDC50 |
| coiled-coil domain containing 64B | CCDC64B |
| coiled-coil domain containing 88B | CCDC88B |
| coiled-coil domain containing 93 | CCDC93 |
| chemokine (C-C motif) ligand 2 | CCL2 |
| chemokine (C-C motif) ligand 20 | CCL20 |
| chemokine (C-C motif) ligand 22 | CCL22 |
| chemokine (C-C motif) ligand 28 | CCL28 |
| chemokine (C-C motif) ligand 7 | CCL7 |
| cerebral cavernous malformation 2 | CCM2 |
| cyclin D-type binding-protein 1 | CCNDBP1 |
| cyclin Y | CCNY |
| cyclin Y-like 1 | CCNYL1 |
| cell cycle progression 1 | CCPG1 |
| chemokine (C-C motif) receptor 4 | CCR4 |
| chemokine (C-C motif) receptor 5 (gene/pseudogene) | CCR5 |
| copper chaperone for superoxide dismutase | CCS |
| chaperonin containing TCP1, subunit 2 (beta) | CCT2 |
| chaperonin containing TCP1, subunit 3 (gamma) | CCT3 |
| chaperonin containing TCP1, subunit 4 (delta) | CCT4 |
| chaperonin containing TCP1, subunit 5 (epsilon) | CCT5 |
| chaperonin containing TCP1, subunit 6A (zeta 1) | CCT6A |

TABLE 4-continued

| Suitable extracellular vesicle associated proteins | |
| --- | --- |
| Gene Name | Gene Symbol |
| chaperonin containing TCP1, subunit 6B (zeta 2) | CCT6B |
| chaperonin containing TCP1, subunit 7 (eta) | CCT7 |
| chaperonin containing TCP1, subunit 8 (theta) | CCT8 |
| CD101 molecule | CD101 |
| CD109 molecule | CD109 |
| CD14 molecule | CD14 |
| CD151 molecule (Raph blood group) | CD151 |
| CD163 molecule | CD163 |
| CD163 molecule-like 1 | CD163L1 |
| CD19 molecule | CD19 |
| CD1a molecule | CD1A |
| CD1b molecule | CD1B |
| CD1c molecule | CD1C |
| CD2 molecule | CD2 |
| CD200 molecule | CD200 |
| CD209 molecule | CD209 |
| CD22 molecule | CD22 |
| CD226 molecule | CD226 |
| CD24 molecule | CD24 |
| CD247 molecule | CD247 |
| CD248 molecule, endosialin | CD248 |
| CD274 molecule | CD274 |
| CD276 molecule | CD276 |
| CD2-associated protein | CD2AP |
| CD2 (cytoplasmic tail) binding protein 2 | CD2BP2 |
| CD300a molecule | CD300A |
| CD320 molecule | CD320 |
| CD33 molecule | CD33 |
| CD36 molecule (thrombospondin receptor) | CD36 |
| CD37 molecule | CD37 |
| CD38 molecule | CD38 |
| CD3d molecule, delta (CD3-TCR complex) | CD3D |
| CD3e molecule, epsilon (CD3-TCR complex) | CD3E |
| CD3g molecule, gamma (CD3-TCR complex) | CD3G |
| CD4 molecule | CD4 |
| CD40 molecule, TNF receptor superfamily member 5 | CD40 |
| CD40 ligand | CD40LG |
| CD44 molecule (Indian blood group) | CD44 |
| CD46 molecule, complement regulatory protein | CD46 |
| CD47 molecule | CD47 |
| CD48 molecule | CD48 |
| CD5 molecule | CD5 |
| CD53 molecule | CD53 |
| CD55 molecule, decay accelerating factor for complement (Cromer blood group) | CD55 |
| CD58 molecule | CD58 |
| CD59 molecule, complement regulatory protein | CD59 |
| CD5 molecule-like | CD5L |
| CD6 molecule | CD6 |
| CD63 molecule | CD63 |
| CD68 molecule | CD68 |
| CD70 molecule | CD70 |
| CD74 molecule, major histocompatibility complex, class II invariant chain | CD74 |
| CD79b molecule, immunoglobulin-associated beta | CD79B |
| CD80 molecule | CD80 |
| CD81 molecule | CD81 |
| CD82 molecule | CD82 |
| CD84 molecule | CD84 |
| CD86 molecule | CD86 |
| CD8a molecule | CD8A |
| CD8b molecule | CD8B |
| CD9 molecule | CD9 |
| CD99 molecule | CD99 |
| CD99 molecule-like 2 | CD99L2 |
| cell division cycle 16 | CDC16 |
| cell division cycle 23 | CDC23 |

TABLE 4-continued

| Suitable extracellular vesicle associated proteins | |
| --- | --- |
| Gene Name | Gene Symbol |
| cell division cycle 25B | CDC25B |
| cell division cycle 27 | CDC27 |
| cell division cycle 37 | CDC37 |
| cell division cycle 42 | CDC42 |
| CDC42 binding protein kinase alpha (DMPK-like) | CDC42BPA |
| CDC42 binding protein kinase beta (DMPK-like) | CDC42BPB |
| CDC42 binding protein kinase gamma (DMPK-like) | CDC42BPG |
| cell division cycle 42 pseudogene 6 | CDC42P6 |
| CDC42 small effector 2 | CDC42SE2 |
| cell division cycle 5-like | CDC5L |
| cell division cycle associated 3 | CDCA3 |
| cell division cycle associated 8 | CDCA8 |
| CUB domain containing protein 1 | CDCP1 |
| cadherin 1, type 1, E-cadherin (epithelial) | CDH1 |
| cadherin 11, type 2, OB-cadherin (osteoblast) | CDH11 |
| cadherin 13 | CDH13 |
| cadherin 17, LI cadherin (liver-intestine) | CDH17 |
| cadherin 2, type 1, N-cadherin (neuronal) | CDH2 |
| cadherin-related 23 | CDH23 |
| cadherin 3, type 1, P-cadherin (placental) | CDH3 |
| cadherin 6, type 2, K-cadherin (fetal kidney) | CDH6 |
| cadherin 9, type 2 (T1-cadherin) | CDH9 |
| cadherin-related family member 2 | CDHR2 |
| cadherin-related family member 5 | CDHR5 |
| CDP-diacylglycerol--inositol 3-phosphatidyltransferase | CDIPT |
| cyclin-dependent kinase 1 | CDK1 |
| cyclin-dependent kinase 11B | CDK11B |
| cyclin-dependent kinase 12 | CDK12 |
| cyclin-dependent kinase 13 | CDK13 |
| cyclin-dependent kinase 14 | CDK14 |
| cyclin-dependent kinase 16 | CDK16 |
| cyclin-dependent kinase 17 | CDK17 |
| cyclin-dependent kinase 18 | CDK18 |
| cyclin-dependent kinase 2 | CDK2 |
| cyclin-dependent kinase 3 | CDK3 |
| cyclin-dependent kinase 4 | CDK4 |
| cyclin-dependent kinase 5 | CDK5 |
| cyclin-dependent kinase 5, regulatory subunit 2 (p39) | CDK5R2 |
| CDK5 regulatory subunit associated protein 2 | CDK5RAP2 |
| cyclin-dependent kinase 6 | CDK6 |
| cyclin-dependent kinase 9 | CDK9 |
| CDP-diacylglycerol synthase (phosphatidate cytidylyltransferase) 2 | CDS2 |
| corneodesmosin | CDSN |
| CDV3 homolog (mouse) | CDV3 |
| carcinoembryonic antigen-related cell adhesion molecule 1 (biliary glycoprotein) | CEACAM1 |
| carcinoembryonic antigen-related cell adhesion molecule 5 | CEACAM5 |
| carcinoembryonic antigen-related cell adhesion molecule 8 | CEACAM8 |
| cat eye syndrome chromosome region, candidate 5 | CECR5 |
| carboxyl ester lipase | CEL |
| CUGBP, Elav-like family member 1 | CELF1 |
| CUGBP, Elav-like family member 2 | CELF2 |
| cell migration inducing protein, hyaluronan binding | CEMIP |
| centromere protein E, 312 kDa | CENPE |
| centromere protein V | CENPV |
| centrosomal protein 131 kDa | CEP131 |
| centrosomal protein 250 kDa | CEP250 |
| centrosomal protein 350 kDa | CEP350 |
| centrosomal protein 55 kDa | CEP55 |
| centrosomal protein 97 kDa | CEP97 |
| ceramide synthase 1 | CERS1 |
| carboxylesterase 2 | CES2 |
| carboxylesterase 3 | CES3 |

TABLE 4-continued

| Suitable extracellular vesicle associated proteins | |
|---|---|
| Gene Name | Gene Symbol |
| cholesteryl ester transfer protein, plasma | CETP |
| cilia and flagella associated protein 20 | CFAP20 |
| cilia and flagella associated protein 43 | CFAP43 |
| cilia and flagella associated protein 44 | CFAP44 |
| cilia and flagella associated protein 58 | CFAP58 |
| cilia and flagella associated protein 70 | CFAP70 |
| complement factor B | CFB |
| complement factor D (adipsin) | CFD |
| complement factor H | CFH |
| complement factor H-related 3 | CFHR3 |
| complement factor I | CFI |
| cofilin 1 (non-muscle) | CFL1 |
| cofilin 2 (muscle) | CFL2 |
| cystic fibrosis transmembrane conductance regulator (ATP-binding cassette sub-family C, member 7) | CFTR |
| coiled-coil-helix-coiled-coil-helix domain containing 3 | CHCHD3 |
| chromodomain helicase DNA binding protein 1-like | CHD1L |
| chromodomain helicase DNA binding protein 4 | CHD4 |
| chromodomain helicase DNA binding protein 6 | CHD6 |
| chromodomain helicase DNA binding protein 9 | CHD9 |
| chitinase domain containing 1 | CHID1 |
| charged multivesicular body protein 1A | CHMP1A |
| charged multivesicular body protein 1B | CHMP1B |
| charged multivesicular body protein 2A | CHMP2A |
| charged multivesicular body protein 2B | CHMP2B |
| charged multivesicular body protein 3 | CHMP3 |
| charged multivesicular body protein 4A | CHMP4A |
| charged multivesicular body protein 4B | CHMP4B |
| charged multivesicular body protein 4C | CHMP4C |
| charged multivesicular body protein 5 | CHMP5 |
| charged multivesicular body protein 6 | CHMP6 |
| cysteine and histidine-rich domain (CHORD) containing 1 | CHORDC1 |
| calcineurin-like EF-hand protein 1 | CHP1 |
| chordin-like 2 | CHRDL2 |
| cholinergic receptor, nicotinic, alpha 3 (neuronal) | CHRNA3 |
| carbohydrate (keratan sulfate Gal-6) sulfotransferase 1 | CHST1 |
| carbohydrate (chondroitin 4) sulfotransferase 12 | CHST12 |
| carbohydrate (N-acetylgalactosamine 4-0) sulfotransferase 14 | CHST14 |
| CTF18, chromosome transmission fidelity factor 18 homolog (*S. cerevisiae*) | CHTF18 |
| conserved helix-loop-helix ubiquitous kinase | CHUK |
| cytosolic iron-sulfur assembly component 1 | CIAO1 |
| calcium and integrin binding 1 (calmyrin) | CIB1 |
| cold inducible RNA binding protein | CIRBP |
| CDGSH iron sulfur domain 2 | CISD2 |
| citron rho-interacting serine/threonine kinase | CIT |
| Cbp/p300-interacting transactivator, with Glu/Asp-rich carboxy-terminal domain, 1 | CITED1 |
| cytoskeleton-associated protein 4 | CKAP4 |
| cytoskeleton associated protein 5 | CKAP5 |
| creatine kinase, brain | CKB |
| creatine kinase, mitochondrial 1A | CKMT1A |
| creatine kinase, mitochondrial 1B | CKMT1B |
| cytoplasmic linker associated protein 1 | CLASP1 |
| cytoplasmic linker associated protein 2 | CLASP2 |
| Charcot-Leyden crystal galectin | CLC |
| chloride channel accessory 4 | CLCA4 |
| chloride channel, voltage-sensitive 3 | CLCN3 |
| chloride channel, voltage-sensitive 4 | CLCN4 |
| chloride channel, voltage-sensitive 5 | CLCN5 |
| chloride channel, voltage-sensitive 7 | CLCN7 |
| claudin 1 | CLDN1 |
| claudin 12 | CLDN12 |

TABLE 4-continued

Suitable extracellular vesicle associated proteins

| Gene Name | Gene Symbol |
|---|---|
| claudin 18 | CLDN18 |
| claudin 2 | CLDN2 |
| claudin 3 | CLDN3 |
| claudin 4 | CLDN4 |
| claudin 5 | CLDN5 |
| claudin 6 | CLDN6 |
| claudin 7 | CLDN7 |
| claudin domain containing 1 | CLDND1 |
| C-type lectin domain family 11, member A | CLEC11A |
| C-type lectin domain family 1, member B | CLEC1B |
| C-type lectin domain family 3, member B | CLEC3B |
| chloride intracellular channel 1 | CLIC1 |
| chloride intracellular channel 2 | CLIC2 |
| chloride intracellular channel 3 | CLIC3 |
| chloride intracellular channel 4 | CLIC4 |
| chloride intracellular channel 5 | CLIC5 |
| chloride intracellular channel 6 | CLIC6 |
| clathrin interactor 1 | CLINT1 |
| CAP-GLY domain containing linker protein 2 | CLIP2 |
| ceroid-lipofuscinosis, neuronal 3 | CLN3 |
| chloride channel, nucleotide-sensitive, 1A | CLNS1A |
| caseinolytic mitochondrial matrix peptidase chaperone subunit | CLPX |
| clarin 3 | CLRN3 |
| calsyntenin 1 | CLSTN1 |
| clathrin, light chain A | CLTA |
| clathrin, light chain B | CLTB |
| clathrin, heavy chain (Hc) | CLTC |
| clathrin, heavy chain-like 1 | CLTCL1 |
| clusterin | CLU |
| clustered mitochondria (cluA/CLU1) homolog | CLUH |
| clavesin 2 | CLVS2 |
| carboxymethylenebutenolidase homolog (Pseudomonas) | CMBL |
| c-Maf inducing protein | CMIP |
| cytidine monophosphate (UMP-CMP) kinase 1, cytosolic | CMPK1 |
| cytidine monophosphate (UMP-CMP) kinase 2, mitochondrial | CMPK2 |
| cap methyltransferase 1 | CMTR1 |
| cardiomyopathy associated 5 | CMYA5 |
| CNDP dipeptidase 2 (metallopeptidase M20 family) | CNDP2 |
| cyclic nucleotide gated channel beta 1 | CNGB1 |
| connector enhancer of kinase suppressor of Ras 2 | CNKSR2 |
| CNKSR family member 3 | CNKSR3 |
| calponin 1, basic, smooth muscle | CNN1 |
| calponin 2 | CNN2 |
| calponin 3, acidic | CNN3 |
| cyclin and CBS domain divalent metal cation transport mediator 2 | CNNM2 |
| cyclin and CBS domain divalent metal cation transport mediator 3 | CNNM3 |
| cyclin and CBS domain divalent metal cation transport mediator 4 | CNNM4 |
| CCR4-NOT transcription complex, subunit 1 | CNOT1 |
| CCR4-NOT transcription complex, subunit 11 | CNOT11 |
| CCR4-NOT transcription complex, subunit 7 | CNOT7 |
| 2',3'-cyclic nucleotide 3' phosphodiesterase | CNP |
| canopy FGF signaling regulator 2 | CNPY2 |
| ciliary neurotrophic factor receptor | CNTFR |
| centlein, centrosomal protein | CNTLN |
| contactin 1 | CNTN1 |
| contactin 5 | CNTN5 |
| contactin associated protein-like 4 | CNTNAP4 |
| CoA synthase | COASY |
| cordon-bleu WH2 repeat protein-like 1 | COBLL1 |
| cochlin | COCH |
| component of oligomeric golgi complex 1 | COG1 |
| component of oligomeric golgi complex 2 | COG2 |

TABLE 4-continued

| Suitable extracellular vesicle associated proteins | |
| --- | --- |
| Gene Name | Gene Symbol |
| component of oligomeric golgi complex 3 | COG3 |
| component of oligomeric golgi complex 4 | COG4 |
| component of oligomeric golgi complex 5 | COG5 |
| component of oligomeric golgi complex 6 | COG6 |
| component of oligomeric golgi complex 7 | COG7 |
| collagen, type XI, alpha 1 | COL11A1 |
| collagen, type XII, alpha 1 | COL12A1 |
| collagen, type XIV, alpha 1 | COL14A1 |
| collagen, type XV, alpha 1 | COL15A1 |
| collagen, type XVI, alpha 1 | COL16A1 |
| collagen, type XVIII, alpha 1 | COL18A1 |
| collagen, type I, alpha 1 | COL1A1 |
| collagen, type I, alpha 2 | COL1A2 |
| collagen, type XXI, alpha 1 | COL21A1 |
| collagen, type XXIV, alpha 1 | COL24A1 |
| collagen, type II, alpha 1 | COL2A1 |
| collagen, type III, alpha 1 | COL3A1 |
| collagen, type IV, alpha 1 | COL4A1 |
| collagen, type IV, alpha 2 | COL4A2 |
| collagen, type IV, alpha 3 (Goodpasture antigen) | COL4A3 |
| collagen, type V, alpha 1 | COL5A1 |
| collagen, type V, alpha 2 | COL5A2 |
| collagen, type VI, alpha 1 | COL6A1 |
| collagen, type VI, alpha 2 | COL6A2 |
| collagen, type VI, alpha 3 | COL6A3 |
| collagen, type VII, alpha 1 | COL7A1 |
| collectin sub-family member 10 (C-type lectin) | COLEC10 |
| collectin sub-family member 12 | COLEC12 |
| collagen beta(1-O)galactosyltransferase 1 | COLGALT1 |
| COMM domain containing 3 | COMMD3 |
| cartilage oligomeric matrix protein | COMP |
| catechol-O-methyltransferase | COMT |
| coatomer protein complex, subunit alpha | COPA |
| coatomer protein complex, subunit beta 1 | COPB1 |
| coatomer protein complex, subunit beta 2 (beta prime) | COPB2 |
| coatomer protein complex, subunit epsilon | COPE |
| coatomer protein complex, subunit gamma 1 | COPG1 |
| coatomer protein complex, subunit gamma 2 | COPG2 |
| COP9 signalosome subunit 2 | COPS2 |
| COP9 signalosome subunit 3 | COPS3 |
| COP9 signalosome subunit 4 | COPS4 |
| COP9 signalosome subunit 5 | COPS5 |
| COP9 signalosome subunit 6 | COPS6 |
| COP9 signalosome subunit 8 | COPS8 |
| coatomer protein complex, subunit zeta 1 | COPZ1 |
| coenzyme Q6 monooxygenase | COQ6 |
| coronin, actin binding protein, 1A | CORO1A |
| coronin, actin binding protein, 1B | CORO1B |
| coronin, actin binding protein, 1C | CORO1C |
| coronin 7 | CORO7 |
| CORO7-PAM16 readthrough | CORO7-PAM16 |
| coactosin-like F-actin binding protein 1 | COTL1 |
| cytochrome c oxidase subunit IV isoform 1 | COX4I1 |
| cytochrome c oxidase subunit Vb | COX5B |
| ceruloplasmin (ferroxidase) | CP |
| carboxypeptidase A1 (pancreatic) | CPA1 |
| carboxypeptidase B1 (tissue) | CPB1 |
| carboxypeptidase D | CPD |
| carboxypeptidase M | CPM |
| carboxypeptidase N, polypeptide 2 | CPN2 |
| copine I | CPNE1 |
| copine II | CPNE2 |
| copine III | CPNE3 |
| copine V | CPNE5 |
| copine VI (neuronal) | CPNE6 |
| copine VIII | CPNE8 |
| coproporphyrinogen oxidase | CPOX |
| carbamoyl-phosphate synthase 1, mitochondrial | CPS1 |
| cleavage and polyadenylation specific factor 1, 160 kDa | CPSF1 |
| cleavage and polyadenylation specific factor 3, 73 kDa | CPSF3 |

TABLE 4-continued

| Suitable extracellular vesicle associated proteins | |
|---|---|
| Gene Name | Gene Symbol |
| cleavage and polyadenylation specific factor 3-like | CPSF3L |
| cleavage and polyadenylation specific factor 6, 68 kDa | CPSF6 |
| cleavage and polyadenylation specific factor 7, 59 kDa | CPSF7 |
| carboxypeptidase, vitellogenic-like | CPVL |
| complement component (3b/4b) receptor 1 (Knops blood group) | CR1 |
| complement component (3d/Epstein Barr virus) receptor 2 | CR2 |
| cellular retinoic acid binding protein 2 | CRABP2 |
| crumbs family member 2 | CRB2 |
| crumbs family member 3 | CRB3 |
| cAMP responsive element binding protein 5 | CREB5 |
| cellular repressor of E1A-stimulated genes 1 | CREG1 |
| cysteine-rich protein 2 | CRIP2 |
| cysteine-rich PDZ-binding protein | CRIPT |
| cysteine-rich secretory protein LCCL domain containing 1 | CRISPLD1 |
| v-crk avian sarcoma virus CT10 oncogene homolog | CRK |
| v-crk avian sarcoma virus CT10 oncogene homolog-like | CRKL |
| cytokine receptor-like factor 3 | CRLF3 |
| collapsin response mediator protein 1 | CRMP1 |
| crooked neck pre-mRNA splicing factor 1 | CRNKL1 |
| cornulin | CRNN |
| ciliary rootlet coiled-coil, rootletin | CROCC |
| ciliary rootlet coiled-coil, rootletin family member 2 | CROCC2 |
| cartilage associated protein | CRTAP |
| CREB regulated transcription coactivator 2 | CRTC2 |
| crystallin, alpha A | CRYAA |
| crystallin, alpha B | CRYAB |
| crystallin, lambda 1 | CRYL1 |
| crystallin, mu | CRYM |
| crystallin, zeta (quinone reductase) | CRYZ |
| crystallin, zeta (quinone reductase)-like 1 | CRYZL1 |
| citrate synthase | CS |
| cold shock domain containing E1, RNA-binding | CSDE1 |
| CSE1 chromosome segregation 1-like (yeast) | CSE1L |
| colony stimulating factor 1 (macrophage) | CSF1 |
| colony stimulating factor 2 (granulocyte-macrophage) | CSF2 |
| colony stimulating factor 3 (granulocyte) | CSF3 |
| c-src tyrosine kinase | CSK |
| CUB and Sushi multiple domains 2 | CSMD2 |
| casein alpha s1 | CSN1S1 |
| casein beta | CSN2 |
| casein kappa | CSN3 |
| casein kinase 1, alpha 1 | CSNK1A1 |
| casein kinase 1, delta | CSNK1D |
| casein kinase 1, gamma 1 | CSNK1G1 |
| casein kinase 1, gamma 3 | CSNK1G3 |
| casein kinase 2, alpha 1 polypeptide | CSNK2A1 |
| casein kinase 2, alpha prime polypeptide | CSNK2A2 |
| casein kinase 2, beta polypeptide | CSNK2B |
| chondroitin sulfate proteoglycan 4 | CSPG4 |
| chondroitin sulfate proteoglycan 5 (neuroglycan C) | CSPG5 |
| cysteine and glycine-rich protein 1 | CSRP1 |
| cysteine and glycine-rich protein 2 | CSRP2 |
| cystatin C | CST3 |
| cystatin S | CST4 |
| cystatin D | CST5 |
| cystatin A (stefin A) | CSTA |
| cystatin B (stefin B) | CSTB |
| cleavage stimulation factor, 3' pre-RNA, subunit 1, 50 kDa | CSTF1 |
| cleavage stimulation factor, 3' pre-RNA, subunit 3, 77 kDa | CSTF3 |
| C-terminal binding protein 1 | CTBP1 |
| C-terminal binding protein 2 | CTBP2 |

TABLE 4-continued

| Suitable extracellular vesicle associated proteins | |
|---|---|
| Gene Name | Gene Symbol |
| CTD nuclear envelope phosphatase 1 | CTDNEP1 |
| CTD (carboxy-terminal domain, RNA polymerase II, polypeptide A) small phosphatase 1 | CTDSP1 |
| CTD (carboxy-terminal domain, RNA polymerase II, polypeptide A) small phosphatase-like | CTDSPL |
| cystathionine gamma-lyase | CTH |
| cytotoxic T-lymphocyte-associated protein 4-immunoglobulin fusion protein | CTLA4-Ig |
| catenin (cadherin-associated protein), alpha 1, 102 kDa | CTNNA1 |
| catenin (cadherin-associated protein), alpha 2 | CTNNA2 |
| catenin (cadherin-associated protein), beta 1, 88 kDa | CTNNB1 |
| catenin (cadherin-associated protein), delta 1 | CTNND1 |
| catenin (cadherin-associated protein), delta 2 | CTNND2 |
| cystinosin, lysosomal cystine transporter | CTNS |
| CTP synthase 1 | CTPS1 |
| CTP synthase 2 | CTPS2 |
| CTR9, Paf1/RNA polymerase II complex component | CTR9 |
| cathepsin A | CTSA |
| cathepsin B | CTSB |
| cathepsin C | CTSC |
| cathepsin D | CTSD |
| cathepsin G | CTSG |
| cathepsin H | CTSH |
| cathepsin L | CTSL |
| cathepsin V | CTSV |
| cathepsin Z | CTSZ |
| cortactin | CTTN |
| cubilin (intrinsic factor-cobalamin receptor) | CUBN |
| cullin 1 | CUL1 |
| cullin 2 | CUL2 |
| cullin 3 | CUL3 |
| cullin 4A | CUL4A |
| cullin 4B | CUL4B |
| cullin 5 | CUL5 |
| cutA divalent cation tolerance homolog (E. coli) | CUTA |
| cut-like homeobox 2 | CUX2 |
| CWC25 spliceosome-associated protein homolog (S. cerevisiae) | CWC25 |
| CWF19-like 1, cell cycle control (S. pombe) | CWF19L1 |
| coxsackie virus and adenovirus receptor | CXADR |
| chemokine (C-X-C motif) ligand 16 | CXCL16 |
| chemokine (C-X-C motif) ligand 2 | CXCL2 |
| chemokine (C-X-C motif) ligand 8 | CXCL8 |
| chemokine (C-X-C motif) receptor 4 | CXCR4 |
| cytochrome b5 type A (microsomal) | CYB5A |
| cytochrome b5 type B (outer mitochondrial membrane) | CYB5B |
| cytochrome b5 reductase 1 | CYB5R1 |
| cytochrome b5 reductase 3 | CYB5R3 |
| cytochrome b-245, beta polypeptide | CYBB |
| cytochrome b reductase 1 | CYBRD1 |
| cytochrome c-1 | CYC1 |
| cytoplasmic FMR1 interacting protein 1 | CYFIP1 |
| cytoplasmic FMR1 interacting protein 2 | CYFIP2 |
| cytochrome P450, family 17, subfamily A, polypeptide 1 | CYP17A1 |
| cytochrome P450, family 2, subfamily D, polypeptide 6 | CYP2D6 |
| cysteine-rich, angiogenic inducer, 61 | CYR61 |
| cysteine-rich tail protein 1 | CYSRT1 |
| cysteine-rich transmembrane module containing 1 | CYSTM1 |
| cytohesin 2 | CYTH2 |
| cytohesin 3 | CYTH3 |
| dishevelled associated activator of morphogenesis 1 | DAAM1 |
| Dab, mitogen-responsive phosphoprotein, homolog 2 (Drosophila) | DAB2 |
| dishevelled-binding antagonist of beta- | DACT1 |

TABLE 4-continued

| Suitable extracellular vesicle associated proteins | |
| --- | --- |
| Gene Name | Gene Symbol |
| catenin 1 | |
| defender against cell death 1 | DAD1 |
| dystroglycan 1 (dystrophin-associated glycoprotein 1) | DAG1 |
| dual adaptor of phosphotyrosine and 3-phosphoinositides | DAPP1 |
| aspartyl-tRNA synthetase | DARS |
| DBF4 zinc finger B | DBF4B |
| dopamine beta-hydroxylase (dopamine beta-monooxygenase) | DBH |
| diazepam binding inhibitor (GABA receptor modulator, acyl-CoA binding protein) | DBI |
| drebrin 1 | DBN1 |
| drebrin-like | DBNL |
| DDB1 and CUL4 associated factor 7 | DCAF7 |
| discoidin, CUB and LCCL domain containing 2 | DCBLD2 |
| dermcidin | DCD |
| dachsous cadherin-related 2 | DCHS2 |
| deoxycytidine kinase | DCK |
| doublecortin-like kinase 1 | DCLK1 |
| doublecortin-like kinase 2 | DCLK2 |
| decorin | DON |
| dopachrome tautomerase | DOT |
| dynactin 1 | DCTN1 |
| dynactin 2 (p50) | DCTN2 |
| dynactin 3 (p22) | DCTN3 |
| dCTP pyrophosphatase 1 | DCTPP1 |
| DCN1, defective in cullin neddylation 1, domain containing 3 | DCUN1D3 |
| dicarbonyl/L-xylulose reductase | DCXR |
| dimethylarginine dimethylaminohydrolase 1 | DDAH1 |
| dimethylarginine dimethylaminohydrolase 2 | DDAH2 |
| damage-specific DNA binding protein 1, 127 kDa | DDB1 |
| dopa decarboxylase (aromatic L-amino acid decarboxylase) | DDC |
| dendrin | DDN |
| dolichyl-diphosphooligosaccharide--protein glycosyltransferase subunit (non-catalytic) | DDOST |
| discoidin domain receptor tyrosine kinase 1 | DDR1 |
| discoidin domain receptor tyrosine kinase 2 | DDR2 |
| DDRGK domain containing 1 | DDRGK1 |
| D-dopachrome tautomerase | DDT |
| DEAD (Asp-Glu-Ala-Asp) box helicase 1 | DDX1 |
| DEAD (Asp-Glu-Ala-Asp) box helicase 17 | DDX17 |
| DEAD (Asp-Glu-Ala-Asp) box polypeptide 18 | DDX18 |
| DEAD (Asp-Glu-Ala-Asp) box polypeptide 19A | DDX19A |
| DEAD (Asp-Glu-Ala-Asp) box polypeptide 19B | DDX19B |
| DEAD (Asp-Glu-Ala-Asp) box helicase 21 | DDX21 |
| DEAD (Asp-Glu-Ala-Asp) box polypeptide 23 | DDX23 |
| DEAD (Asp-Glu-Ala-Asp) box polypeptide 27 | DDX27 |
| DEAD (Asp-Glu-Ala-Asp) box polypeptide 39A | DDX39A |
| DEAD (Asp-Glu-Ala-Asp) box polypeptide 39B | DDX39B |
| DEAD (Asp-Glu-Ala-Asp) box helicase 3, X-linked | DDX3X |
| DEAD (Asp-Glu-Ala-Asp) box helicase 3, Y-linked | DDX3Y |
| DEAD (Asp-Glu-Ala-Asp) box polypeptide 4 | DDX4 |
| DEAD (Asp-Glu-Ala-Asp) box polypeptide 46 | DDX46 |
| DEAD (Asp-Glu-Ala-Asp) box polypeptide 47 | DDX47 |
| DEAD (Asp-Glu-Ala-Asp) box polypeptide 49 | DDX49 |
| DEAD (Asp-Glu-Ala-Asp) box helicase 5 | DDX5 |
| DEAD (Asp-Glu-Ala-Asp) box polypeptide 50 | DDX50 |
| DEAD (Asp-Glu-Ala-Asp) box polypeptide 58 | DDX58 |
| DEAD (Asp-Glu-Ala-Asp) box helicase 6 | DDX6 |
| DEAD (Asp-Glu-Ala-Asp) box polypeptide 60 | DDX60 |
| 2,4-dienoyl CoA reductase 1, mitochondrial | DECR1 |
| differentially expressed in FDCP 6 homolog (mouse) | DEF6 |
| defensin, alpha 1 | DEFA1 |
| defensin, alpha 1B | DEFA1B |
| defensin, alpha 3, neutrophil-specific | DEFA3 |
| DEK proto-oncogene | DEK |
| DENN/MADD domain containing 3 | DENND3 |
| DENN/MADD domain containing 6A | DENND6A |
| density-regulated protein | DENR |
| DEP domain containing 1B | DEPDC1B |

TABLE 4-continued

| Suitable extracellular vesicle associated proteins | |
|---|---|
| Gene Name | Gene Symbol |
| deoxyribose-phosphate aldolase (putative) | DERA |
| derlin 1 | DERL1 |
| desmin | DES |
| deafness, autosomal dominant 5 | DFNA5 |
| diacylglycerol kinase, alpha 80 kDa | DGKA |
| 24-dehydrocholesterol reductase | DHCR24 |
| 7-dehydrocholesterol reductase | DHCR7 |
| dihydrofolate reductase | DHFR |
| dehydrogenase/reductase (SDR family) member 1 | DHRS1 |
| dehydrogenase/reductase (SDR family) member 7 | DHRS7 |
| DEAH (Asp-Glu-Ala-His) box helicase 15 | DHX15 |
| DEAH (Asp-Glu-Ala-His) box polypeptide 16 | DHX16 |
| DEAH (Asp-Glu-Ala-His) box helicase 30 | DHX30 |
| DEAH (Asp-Glu-Ala-His) box polypeptide 34 | DHX34 |
| DEAH (Asp-Glu-Ala-His) box polypeptide 36 | DHX36 |
| DEAH (Asp-Glu-Ala-His) box helicase 9 | DHX9 |
| diaphanous-related formin 1 | DIAPH1 |
| diaphanous-related formin 3 | DIAPH3 |
| DIM1 dimethyladenosine transferase 1 homolog (*S. cerevisiae*) | DIMT1 |
| DIP2 disco-interacting protein 2 homolog A (*Drosophila*) | DIP2A |
| DIP2 disco-interacting protein 2 homolog B (*Drosophila*) | DIP2B |
| DIP2 disco-interacting protein 2 homolog C (*Drosophila*) | DIP2C |
| DIRAS family, GTP-binding RAS-like 2 | DIRAS2 |
| DIS3 exosome endoribonuclease and 3'-5' exoribonuclease | DIS3 |
| DIS3 like 3'-5' exoribonuclease 2 | DIS3L2 |
| disrupted in schizophrenia 1 | DISC1 |
| dyskeratosis congenita 1, dyskerin | DKC1 |
| dickkopf WNT signaling pathway inhibitor 1 | DKK1 |
| dickkopf WNT signaling pathway inhibitor 3 | DKK3 |
| dihydrolipoamide S-acetyltransferase | DLAT |
| DLC1 Rho GTPase activating protein | DLC1 |
| dihydrolipoamide dehydrogenase | DLD |
| discs, large homolog 1 (*Drosophila*) | DLG1 |
| discs, large homolog 2 (*Drosophila*) | DLG2 |
| discs, large homolog 3 (*Drosophila*) | DLG3 |
| dihydrolipoamide S-succinyltransferase (E2 component of 2-oxo-glutarate complex) | DLST |
| DNA methyltransferase 1 associated protein 1 | DMAP1 |
| deleted in malignant brain tumors 1 | DMBT1 |
| dystrophin | DMD |
| dynein, axonemal, assembly factor 5 | DNAAF5 |
| dynein, axonemal, heavy chain 12 | DNAH12 |
| dynein, axonemal, heavy chain 17 | DNAH17 |
| dynein, axonemal, heavy chain 2 | DNAH2 |
| dynein, axonemal, heavy chain 5 | DNAH5 |
| dynein, axonemal, heavy chain 7 | DNAH7 |
| dynein, axonemal, heavy chain 8 | DNAH8 |
| DnaJ (Hsp40) homolog, subfamily A, member 1 | DNAJA1 |
| DnaJ (Hsp40) homolog, subfamily A, member 2 | DNAJA2 |
| DnaJ (Hsp40) homolog, subfamily B, member 1 | DNAJB1 |
| DnaJ (Hsp40) homolog, subfamily B, member 11 | DNAJB11 |
| DnaJ (Hsp40) homolog, subfamily B, member 3 | DNAJB3 |
| DnaJ (Hsp40) homolog, subfamily B, member 6 | DNAJB6 |
| DnaJ (Hsp40) homolog, subfamily B, member 9 | DNAJB9 |
| DnaJ (Hsp40) homolog, subfamily C, member 10 | DNAJC10 |
| DnaJ (Hsp40) homolog, subfamily C, member 13 | DNAJC13 |
| DnaJ (Hsp40) homolog, subfamily C, member 19 | DNAJC19 |

TABLE 4-continued

Suitable extracellular vesicle associated proteins

| Gene Name | Gene Symbol |
| --- | --- |
| DnaJ (Hsp40) homolog, subfamily C, member 2 | DNAJC2 |
| DnaJ (Hsp40) homolog, subfamily C, member 3 | DNAJC3 |
| DnaJ (Hsp40) homolog, subfamily C, member 5 | DNAJC5 |
| DnaJ (Hsp40) homolog, subfamily C, member 7 | DNAJC7 |
| DnaJ (Hsp40) homolog, subfamily C, member 8 | DNAJC8 |
| DnaJ (Hsp40) homolog, subfamily C, member 9 | DNAJC9 |
| deoxyribonuclease l-like 1 | DNASE1L1 |
| dynamin 1 | DNM1 |
| dynamin 1-like | DNM1L |
| dynamin 2 | DNM2 |
| dynamin 3 | DNM3 |
| DNA (cytosine-5-)-methyltransferase 1 | DNMT1 |
| DNA (cytosine-5-)-methyltransferase 3 alpha | DNMT3A |
| aspartyl aminopeptidase | DNPEP |
| 2'-deoxynucleoside 5'-phosphate N-hydrolase 1 | DNPH1 |
| DNA nucleotidylexotransferase | DNTT |
| dedicator of cytokinesis 1 | DOCK1 |
| dedicator of cytokinesis 10 | DOCK10 |
| dedicator of cytokinesis 11 | DOCK11 |
| dedicator of cytokinesis 2 | DOCK2 |
| dedicator of cytokinesis 5 | DOCK5 |
| dedicator of cytokinesis 7 | DOCK7 |
| dedicator of cytokinesis 8 | DOCK8 |
| dedicator of cytokinesis 9 | DOCK9 |
| docking protein 1, 62 kDa (downstream of tyrosine kinase 1) | DOK1 |
| docking protein 2, 56 kDa | DOK2 |
| docking protein 3 | DOK3 |
| docking protein 7 | DOK7 |
| dopey family member 2 | DOPEY2 |
| dipeptidase 1 (renal) | DPEP1 |
| dipeptidase 3 | DPEP3 |
| dipeptidyl-peptidase 3 | DPP3 |
| dipeptidyl-peptidase 4 | DPP4 |
| dipeptidyl-peptidase 7 | DPP7 |
| dpy-30 homolog (*C. elegans*) | DPY30 |
| dihydropyrimidinase | DPYS |
| dihydropyrimidinase-like 2 | DPYSL2 |
| dihydropyrimidinase-like 3 | DPYSL3 |
| developmentally regulated GTP binding protein 1 | DRG1 |
| developmentally regulated GTP binding protein 2 | DRG2 |
| desmocollin 1 | DSC1 |
| desmocollin 2 | DSC2 |
| desmocollin 3 | DSC3 |
| Down syndrome critical region 3 | DSCR3 |
| desmoglein 1 | DSG1 |
| desmoglein 2 | DSG2 |
| desmoglein 3 | DSG3 |
| DSN1, MIS12 kinetochore complex component | DSN1 |
| desmoplakin | DSP |
| dystonin | DST |
| destrin (actin depolymerizing factor) | DSTN |
| deltex 3 like, E3 ubiquitin ligase | DTX3L |
| deoxythymidylate kinase (thymidylate kinase) | DTYMK |
| dual oxidase 2 | DUOX2 |
| dihydrouridine synthase 3-like (*S. cerevisiae*) | DUS3L |
| dual specificity phosphatase 26 (putative) | DUSP26 |
| dual specificity phosphatase 3 | DUSP3 |
| deoxyuridine triphosphatase | DUT |
| dynein, cytoplasmic 1, heavy chain 1 | DYNC1H1 |
| dynein, cytoplasmic 1, intermediate chain 2 | DYNC1I2 |
| dynein, cytoplasmic 1, light intermediate chain 1 | DYNC1LI1 |

TABLE 4-continued

| Suitable extracellular vesicle associated proteins | |
| --- | --- |
| Gene Name | Gene Symbol |
| dynein, cytoplasmic 1, light intermediate chain 2 | DYNC1LI2 |
| dynein, cytoplasmic 2, heavy chain 1 | DYNC2H1 |
| dynein, light chain, LC8-type 1 | DYNLL1 |
| dynein, light chain, roadblock-type 1 | DYNLRB1 |
| dynein, light chain, Tctex-type 1 | DYNLT1 |
| dysferlin | DYSF |
| dystrotelin | DYTN |
| EBNA1 binding protein 2 | EBNA1BP2 |
| endothelin converting enzyme 1 | ECE1 |
| enoyl CoA hydratase 1, peroxisomal | ECH1 |
| ethylmalonyl-CoA decarboxylase 1 | ECHDC1 |
| enoyl CoA hydratase, short chain, 1, mitochondrial | ECHS1 |
| extracellular matrix protein 1 | ECM1 |
| enhancer of mRNA decapping 3 | EDC3 |
| enhancer of mRNA decapping 4 | EDC4 |
| endothelial differentiation-related factor 1 | EDF1 |
| EGF-like repeats and discoidin l-like domains 3 | EDIL3 |
| endothelin receptor type B | EDNRB |
| early endosome antigen 1 | EEA1 |
| eukaryotic translation elongation factor 1 alpha 1 | EEF1A1 |
| eukaryotic translation elongation factor 1 alpha 1 pseudogene 5 | EEF1A1P5 |
| eukaryotic translation elongation factor 1 alpha 2 | EEF1A2 |
| eukaryotic translation elongation factor 1 beta 2 | EEF1B2 |
| eukaryotic translation elongation factor 1 delta (guanine nucleotide exchange protein) | EEF1D |
| eukaryotic translation elongation factor 1 epsilon 1 | EEF1E1 |
| eukaryotic translation elongation factor 1 gamma | EEF1G |
| eukaryotic translation elongation factor 2 | EEF2 |
| eukaryotic elongation factor, selenocysteine-tRNA-specific | EEFSEC |
| EF-hand calcium binding domain 5 | EFCAB5 |
| EGF containing fibulin-like extracellular matrix protein 1 | EFEMP1 |
| EGF containing fibulin-like extracellular matrix protein 2 | EFEMP2 |
| EF-hand domain family, member D2 | EFHD2 |
| ephrin-B1 | EFNB1 |
| EFR3 homolog A (S. cerevisiae) | EFR3A |
| elongation factor Tu GTP binding domain containing 1 | EFTUD1 |
| elongation factor Tu GTP binding domain containing 2 | EFTUD2 |
| epidermal growth factor | EGF |
| EGF-like-domain, multiple 7 | EGFL7 |
| epidermal growth factor receptor | EGFR |
| EH domain binding protein 1-like 1 | EHBP1L1 |
| EH-domain containing 1 | EHD1 |
| EH-domain containing 2 | EHD2 |
| EH-domain containing 3 | EHD3 |
| EH-domain containing 4 | EHD4 |
| enoyl-CoA, hydratase/3-hydroxyacyl CoA dehydrogenase | EHHADH |
| euchromatic histone-lysine N-methyltransferase 2 | EHMT2 |
| eukaryotic translation initiation factor 1A, Y-linked | EIF1AY |
| eukaryotic translation initiation factor 2A, 65 kDa | EIF2A |
| eukaryotic translation initiation factor 2-alpha kinase 2 | EIF2AK2 |
| eukaryotic translation initiation factor 2B, subunit 1 alpha, 26 kDa | EIF2B1 |
| eukaryotic translation initiation factor 2B, subunit 2 beta, 39 kDa | EIF2B2 |

TABLE 4-continued

| Suitable extracellular vesicle associated proteins | |
| --- | --- |
| Gene Name | Gene Symbol |
| eukaryotic translation initiation factor 2B, subunit 3 gamma, 58 kDa | EIF2B3 |
| eukaryotic translation initiation factor 2B, subunit 4 delta, 67 kDa | EIF2B4 |
| eukaryotic translation initiation factor 2B, subunit 5 epsilon, 82 kDa | EIF2B5 |
| eukaryotic translation initiation factor 2D | EIF2D |
| eukaryotic translation initiation factor 2, subunit 1 alpha, 35 kDa | EIF2S1 |
| eukaryotic translation initiation factor 2, subunit 2 beta, 38 kDa | EIF2S2 |
| eukaryotic translation initiation factor 2, subunit 3 gamma, 52 kDa | EIF2S3 |
| eukaryotic translation initiation factor 3, subunit A | EIF3A |
| eukaryotic translation initiation factor 3, subunit B | EIF3B |
| eukaryotic translation initiation factor 3, subunit C | EIF3C |
| eukaryotic translation initiation factor 3, subunit C-like | EIF3CL |
| eukaryotic translation initiation factor 3, subunit D | EIF3D |
| eukaryotic translation initiation factor 3, subunit E | EIF3E |
| eukaryotic translation initiation factor 3, subunit F | EIF3F |
| eukaryotic translation initiation factor 3, subunit G | EIF3G |
| eukaryotic translation initiation factor 3, subunit H | EIF3H |
| eukaryotic translation initiation factor 3, subunit I | EIF3I |
| eukaryotic translation initiation factor 3, subunit J | EIF3J |
| eukaryotic translation initiation factor 3, subunit K | EIF3K |
| eukaryotic translation initiation factor 3, subunit L | EIF3L |
| eukaryotic translation initiation factor 3, subunit M | EIF3M |
| eukaryotic translation initiation factor 4A1 | EIF4A1 |
| eukaryotic translation initiation factor 4A2 | EIF4A2 |
| eukaryotic translation initiation factor 4A3 | EIF4A3 |
| eukaryotic translation initiation factor 4B | EIF4B |
| eukaryotic translation initiation factor 4E | EIF4E |
| eukaryotic translation initiation factor 4 gamma, 1 | EIF4G1 |
| eukaryotic translation initiation factor 4H | EIF4H |
| eukaryotic translation initiation factor 5 | EIF5 |
| eukaryotic translation initiation factor 5A | EIF5A |
| eukaryotic translation initiation factor 5A2 | EIF5A2 |
| eukaryotic translation initiation factor 5A-like 1 | EIF5AL1 |
| eukaryotic translation initiation factor 5B | EIF5B |
| eukaryotic translation initiation factor 6 | EIF6 |
| elastase, neutrophil expressed | ELANE |
| ELAV like RNA binding protein 1 | ELAVL1 |
| engulfment and cell motility 1 | ELMO1 |
| engulfment and cell motility 2 | ELMO2 |
| engulfment and cell motility 3 | ELMO3 |
| elongator acetyltransferase complex subunit 2 | ELP2 |
| elongator acetyltransferase complex subunit 3 | ELP3 |
| embigin | EMB |
| emerin | EMD |
| essential meiotic structure-specific endonuclease subunit 2 | EME2 |
| EMG1 N1-specific pseudouridine methyltransferase | EMG1 |

TABLE 4-continued

| Suitable extracellular vesicle associated proteins | |
| --- | --- |
| Gene Name | Gene Symbol |
| elastin microfibril interfacer 1 | EMILIN1 |
| elastin microfibril interfacer 2 | EMILIN2 |
| echinoderm microtubule associated protein like 3 | EML3 |
| echinoderm microtubule associated protein like 4 | EML4 |
| echinoderm microtubule associated protein like 5 | EML5 |
| enabled homolog (*Drosophila*) | ENAH |
| endonuclease domain containing 1 | ENDOD1 |
| endoglin | ENG |
| endo-beta-N-acetylglucosaminidase | ENGASE |
| enolase 1, (alpha) | ENO1 |
| enolase 2 (gamma, neuronal) | ENO2 |
| enolase 3 (beta, muscle) | ENO3 |
| glutamyl aminopeptidase (aminopeptidase A) | ENPEP |
| ectonucleotide pyrophosphatase/phosphodiesterase 1 | ENPP1 |
| ectonucleotide pyrophosphatase/phosphodiesterase 3 | ENPP3 |
| ectonucleotide pyrophosphatase/phosphodiesterase 4 (putative) | ENPP4 |
| ectonucleotide pyrophosphatase/phosphodiesterase 6 | ENPP6 |
| ectonucleotide pyrophosphatase/phosphodiesterase 7 | ENPP7 |
| ectonucleoside triphosphate diphosphohydrolase 1 | ENTPD1 |
| ectonucleoside triphosphate diphosphohydrolase 2 | ENTPD2 |
| ectonucleoside triphosphate diphosphohydrolase 4 | ENTPD4 |
| erythrocyte membrane protein band 4.1 | EPB41 |
| erythrocyte membrane protein band 4.1-like 1 | EPB41L1 |
| erythrocyte membrane protein band 4.1-like 2 | EPB41L2 |
| erythrocyte membrane protein band 4.1-like 3 | EPB41L3 |
| erythrocyte membrane protein band 4.1 like 4B | EPB41L4B |
| erythrocyte membrane protein band 4.1 like 5 | EPB41L5 |
| erythrocyte membrane protein band 4.2 | EPB42 |
| epithelial cell adhesion molecule | EPCAM |
| EPH receptor A1 | EPHA1 |
| EPH receptor A2 | EPHA2 |
| EPH receptor A3 | EPHA3 |
| EPH receptor A4 | EPHA4 |
| EPH receptor A5 | EPHA5 |
| EPH receptor B1 | EPHB1 |
| EPH receptor B2 | EPHB2 |
| EPH receptor B3 | EPHB3 |
| EPH receptor B4 | EPHB4 |
| epoxide hydrolase 1, microsomal (xenobiotic) | EPHX1 |
| epoxide hydrolase 2, cytoplasmic | EPHX2 |
| epsin 2 | EPN2 |
| epsin 3 | EPN3 |
| erythropoietin | EPO |
| epiplakin 1 | EPPK1 |
| glutamyl-prolyl-tRNA synthetase | EPRS |
| epidermal growth factor receptor pathway substrate 15 | EPS15 |
| epidermal growth factor receptor pathway substrate 15-like 1 | EPS15L1 |
| epidermal growth factor receptor pathway substrate 8 | EPS8 |
| EPS8-like 1 | EPS8L1 |
| EPS8-like 2 | EPS8L2 |
| EPS8-like 3 | EPS8L3 |
| eosinophil peroxidase | EPX |
| endoplasmic reticulum aminopeptidase 1 | ERAP1 |
| erb-b2 receptor tyrosine kinase 2 | ERBB2 |
| erbb2 interacting protein | ERBB2IP |

TABLE 4-continued

| Suitable extracellular vesicle associated proteins | |
|---|---|
| Gene Name | Gene Symbol |
| erb-b2 receptor tyrosine kinase 3 | ERBB3 |
| erb-b2 receptor tyrosine kinase 4 | ERBB4 |
| excision repair cross-complementation group 2 | ERCC2 |
| endoplasmic reticulum-golgi intermediate compartment (ERGIC) 1 | ERGIC1 |
| ERGIC and golgi 2 | ERGIC2 |
| ER lipid raft associated 1 | ERLIN1 |
| ER lipid raft associated 2 | ERLIN2 |
| erythroblast membrane-associated protein (Scianna blood group) | ERMAP |
| ermin, ERM-like protein | ERMN |
| endoplasmic reticulum metallopeptidase 1 | ERMP1 |
| ERO1-like (*S. cerevisiae*) | ERO1L |
| endoplasmic reticulum protein 29 | ERP29 |
| endoplasmic reticulum protein 44 | ERP44 |
| endogenous retrovirus group FRD, member 2 | ERVFRD-2 |
| endogenous retrovirus group K, member 6 | ERVK-6 |
| endothelial cell adhesion molecule | ESAM |
| esterase D | ESD |
| endothelial cell-specific molecule 1 | ESM1 |
| epithelial splicing regulatory protein 1 | ESRP1 |
| epithelial splicing regulatory protein 2 | ESRP2 |
| extended synaptotagmin-like protein 1 | ESYT1 |
| extended synaptotagmin-like protein 2 | ESYT2 |
| eukaryotic translation termination factor 1 | ETF1 |
| electron-transfer-flavoprotein, alpha polypeptide | ETFA |
| electron-transfer-flavoprotein, beta polypeptide | ETFB |
| ethylmalonic encephalopathy 1 | ETHE1 |
| eva-1 homolog A (*C. elegans*) | EVA1A |
| eva-1 homolog B (*C. elegans*) | EVA1B |
| ecotropic viral integration site 2B | EVI2B |
| Enah/Vasp-like | EVL |
| envoplakin | EVPL |
| exocyst complex component 1 | EXOC1 |
| exocyst complex component 2 | EXOC2 |
| exocyst complex component 3 | EXOC3 |
| exocyst complex component 3-like 4 | EXOC3L4 |
| exocyst complex component 4 | EXOC4 |
| exocyst complex component 5 | EXOC5 |
| exocyst complex component 6 | EXOC6 |
| exocyst complex component 6B | EXOC6B |
| exocyst complex component 7 | EXOC7 |
| exocyst complex component 8 | EXOC8 |
| exosome component 1 | EXOSC1 |
| exosome component 3 | EXOSC3 |
| exosome component 4 | EXOSC4 |
| exosome component 5 | EXOSC5 |
| exosome component 6 | EXOSC6 |
| exosome component 7 | EXOSC7 |
| exostosin glycosyltransferase 2 | EXT2 |
| exostosin-like glycosyltransferase 2 | EXTL2 |
| eyes shut homolog (*Drosophila*) | EYS |
| ezrin | EZR |
| coagulation factor X | F10 |
| coagulation factor XI | F11 |
| F11 receptor | F11R |
| coagulation factor XIII, A1 polypeptide | F13A1 |
| coagulation factor II (thrombin) | F2 |
| coagulation factor II (thrombin) receptor | F2R |
| coagulation factor II (thrombin) receptor-like 3 | F2RL3 |
| coagulation factor III (thromboplastin, tissue factor) | F3 |
| coagulation factor V (proaccelerin, labile factor) | F5 |
| coagulation factor VII (serum prothrombin conversion accelerator) | F7 |
| coagulation factor VIII, procoagulant component | F8 |
| coagulation factor IX | F9 |
| fatty acid binding protein 1, liver | FABP1 |
| fatty acid binding protein 3, muscle and | FABP3 |

TABLE 4-continued

| Suitable extracellular vesicle associated proteins | |
| --- | --- |
| Gene Name | Gene Symbol |
| heart | |
| fatty acid binding protein 5 (psoriasis-associated) | FABP5 |
| fatty acid binding protein 5 pseudogene 7 | FABP5P7 |
| Fas (TNFRSF6)-associated via death domain | FADD |
| Fas (TNFRSF6) associated factor 1 | FAF1 |
| fumarylacetoacetate hydrolase (fumarylacetoacetase) | FAH |
| fumarylacetoacetate hydrolase domain containing 2A | FAHD2A |
| family with sequence similarity 104, member A | FAM104A |
| family with sequence similarity 120A | FAM120A |
| family with sequence similarity 120B | FAM120B |
| family with sequence similarity 129, member A | FAM129A |
| family with sequence similarity 129, member B | FAM129B |
| family with sequence similarity 151, member A | FAM151A |
| family with sequence similarity 160, member A2 | FAM160A2 |
| family with sequence similarity 171, member A1 | FAM171A1 |
| family with sequence similarity 171, member A2 | FAM171A2 |
| family with sequence similarity 174, member A | FAM174A |
| family with sequence similarity 174, member B | FAM174B |
| family with sequence similarity 175, member B | FAM175B |
| family with sequence similarity 177, member A1 | FAM177A1 |
| family with sequence similarity 178, member B | FAM178B |
| family with sequence similarity 179, member B | FAM179B |
| family with sequence similarity 184, member A | FAM184A |
| family with sequence similarity 186, member A | FAM186A |
| family with sequence similarity 193, member B | FAM193B |
| family with sequence similarity 208, member B | FAM208B |
| family with sequence similarity 209, member A | FAM209A |
| family with sequence similarity 20, member A | FAM20A |
| family with sequence similarity 20, member C | FAM20C |
| family with sequence similarity 213, member A | FAM213A |
| family with sequence similarity 213, member B | FAM213B |
| family with sequence similarity 3, member B | FAM3B |
| family with sequence similarity 3, member C | FAM3C |
| family with sequence similarity 49, member A | FAM49A |
| family with sequence similarity 49, member B | FAM49B |
| family with sequence similarity 63, member A | FAM63A |
| family with sequence similarity 63, member B | FAM63B |
| family with sequence similarity 64, member A | FAM64A |

TABLE 4-continued

| Suitable extracellular vesicle associated proteins | |
| --- | --- |
| Gene Name | Gene Symbol |
| family with sequence similarity 65, member A | FAM65A |
| family with sequence similarity 65, member C | FAM65C |
| family with sequence similarity 71, member F1 | FAM71F1 |
| family with sequence similarity 83, member F | FAM83F |
| family with sequence similarity 83, member H | FAM83H |
| family with sequence similarity 84, member B | FAM84B |
| family with sequence similarity 91, member A1 | FAM91A1 |
| family with sequence similarity 98, member A | FAM98A |
| family with sequence similarity 98, member B | FAM98B |
| Fanconi anemia, complementation group I | FANCI |
| Fanconi anemia, complementation group M | FANCM |
| fibroblast activation protein, alpha | FAP |
| FERM, RhoGEF (ARHGEF) and pleckstrin domain protein 1 (chondrocyte-derived) | FARP1 |
| phenylalanyl-tRNA synthetase, alpha subunit | FARSA |
| phenylalanyl-tRNA synthetase, beta subunit | FARSB |
| Fas cell surface death receptor | FAS |
| Fas ligand (TNF superfamily, member 6) | FASLG |
| fatty acid synthase | FASN |
| FAT atypical cadherin 1 | FAT1 |
| FAT atypical cadherin 2 | FAT2 |
| FAT atypical cadherin 4 | FAT4 |
| fibrillarin | FBL |
| fibulin 1 | FBLN1 |
| fibulin 2 | FBLN2 |
| fibrillin 1 | FBN1 |
| fibrillin 2 | FBN2 |
| fibrillin 3 | FBN3 |
| fructose-1,6-bisphosphatase 1 | FBP1 |
| fructose-1,6-bisphosphatase 2 | FBP2 |
| F-box and leucine-rich repeat protein 12 | FBXL12 |
| F-box and leucine-rich repeat protein 20 | FBXL20 |
| F-box and leucine-rich repeat protein 4 | FBXL4 |
| F-box and leucine-rich repeat protein 8 | FBXL8 |
| F-box protein 15 | FBXO15 |
| F-box protein 17 | FBXO17 |
| F-box protein 2 | FBXO2 |
| F-box protein 22 | FBXO22 |
| F-box protein 45 | FBXO45 |
| F-box protein 6 | FBXO6 |
| F-box and WD repeat domain containing 8 | FBXW8 |
| Fc fragment of IgE, high affinity I, receptor for; gamma polypeptide | FCER1G |
| Fc fragment of IgE, low affinity II, receptor for (CD23) | FCER2 |
| Fc fragment of IgG binding protein | FCGBP |
| Fc fragment of IgG, low affinity IIa, receptor (CD32) | FCGR2A |
| Fc fragment of IgG, low affinity IIc, receptor for (CD32) (gene/pseudogene) | FCGR2C |
| Fc fragment of IgG, receptor, transporter, alpha | FCGRT |
| ficolin (collagen/fibrinogen domain containing) 1 | FCN1 |
| ficolin (collagen/fibrinogen domain containing lectin) 2 | FCN2 |
| ficolin (collagen/fibrinogen domain containing) 3 | FCN3 |
| Fc receptor-like A | FCRLA |
| farnesyl-diphosphate farnesyltransferase 1 | FDFT1 |
| farnesyl diphosphate synthase | FDPS |
| flap structure-specific endonuclease 1 | FEN1 |
| fermitin family member 2 | FERMT2 |
| fermitin family member 3 | FERMT3 |
| FES proto-oncogene, tyrosine kinase | FES |

TABLE 4-continued

| Suitable extracellular vesicle associated proteins | |
| --- | --- |
| Gene Name | Gene Symbol |
| fibrinogen alpha chain | FGA |
| fibrinogen beta chain | FGB |
| FYVE, RhoGEF and PH domain containing 2 | FGD2 |
| FYVE, RhoGEF and PH domain containing 4 | FGD4 |
| fibroblast growth factor 16 | FGF16 |
| fibroblast growth factor 18 | FGF18 |
| fibroblast growth factor 19 | FGF19 |
| fibroblast growth factor binding protein 1 | FGFBP1 |
| fibroblast growth factor receptor 1 | FGFR1 |
| fibroblast growth factor receptor 2 | FGFR2 |
| fibroblast growth factor receptor 3 | FGFR3 |
| fibroblast growth factor receptor 4 | FGFR4 |
| fibroblast growth factor receptor-like 1 | FGFRL1 |
| fibrinogen gamma chain | FGG |
| fibrinogen-like 2 | FGL2 |
| FGR proto-oncogene, Src family tyrosine kinase | FGR |
| fumarate hydratase | FH |
| forkhead-associated (FHA) phosphopeptide binding domain 1 | FHAD1 |
| four and a half LIM domains 1 | FHL1 |
| four and a half LIM domains 5 | FHL5 |
| formin homology 2 domain containing 1 | FHOD1 |
| fidgetin-like 1 | FIGNL1 |
| FK506 binding protein 15, 133 kDa | FKBP15 |
| FK506 binding protein 1A, 12 kDa | FKBP1A |
| FK506 binding protein 3, 25 kDa | FKBP3 |
| FK506 binding protein 4, 59 kDa | FKBP4 |
| FK506 binding protein 5 | FKBP5 |
| filaggrin family member 2 | FLG2 |
| flightless I homolog (*Drosophila*) | FLII |
| filamin A, alpha | FLNA |
| filamin B, beta | FLNB |
| filamin C, gamma | FLNC |
| flotillin 1 | FLOT1 |
| flotillin 2 | FLOT2 |
| fms-related tyrosine kinase 1 | FLT1 |
| feline leukemia virus subgroup C cellular receptor 1 | FLVCR1 |
| formin 1 | FMN1 |
| formin-like 1 | FMNL1 |
| formin-like 2 | FMNL2 |
| formin-like 3 | FMNL3 |
| fibromodulin | FMOD |
| fibronectin 1 | FN1 |
| fructosamine 3 kinase | FN3K |
| fructosamine 3 kinase related protein | FN3KRP |
| formin binding protein 1-like | FNBP1L |
| fibronectin type III domain containing 1 | FNDC1 |
| farnesyltransferase, CAAX box, alpha | FNTA |
| folate hydrolase (prostate-specific membrane antigen) 1 | FOLH1 |
| folate receptor 1 (adult) | FOLR1 |
| forkhead box F1 | FOXF1 |
| fucose-1-phosphate guanylyltransferase | FPGT |
| frequently rearranged in advanced T-cell lymphomas 1 | FRAT1 |
| FRAS1 related extracellular matrix protein 2 | FREM2 |
| FRAS1 related extracellular matrix 3 | FREM3 |
| fyn-related Src family tyrosine kinase | FRK |
| FERM domain containing 5 | FRMD5 |
| FERM domain containing 8 | FRMD8 |
| FERM and PDZ domain containing 3 | FRMPD3 |
| FRY-like | FRYL |
| fascin actin-bundling protein 1 | FSCN1 |
| fibronectin type III and SPRY domain containing 2 | FSD2 |
| fibrous sheath interacting protein 2 | FSIP2 |
| follistatin | FST |
| formimidoyltransferase cyclodeaminase | FTCD |
| ferritin, heavy polypeptide 1 | FTH1 |
| ferritin, light polypeptide | FTL |
| ferritin, light polypeptide pseudogene 3 | FTLP3 |
| FtsJ homolog 3 (*E. coli*) | FTSJ3 |
| far upstream element (FUSE) binding protein 1 | FUBP1 |

TABLE 4-continued

Suitable extracellular vesicle associated proteins

| Gene Name | Gene Symbol |
| --- | --- |
| far upstream element (FUSE) binding protein 3 | FUBP3 |
| fucosidase, alpha-L-1, tissue | FUCA1 |
| fucosidase, alpha-L-2, plasma | FUCA2 |
| fucokinase | FUK |
| furin (paired basic amino acid cleaving enzyme) | FURIN |
| FUS RNA binding protein | FUS |
| fucosyltransferase 2 (secretor status included) | FUT2 |
| fucosyltransferase 3 (galactoside 3(4)-L-fucosyltransferase, Lewis blood group) | FUT3 |
| fucosyltransferase 6 (alpha (1,3) fucosyltransferase) | FUT6 |
| fucosyltransferase 8 (alpha (1,6) fucosyltransferase) | FUT8 |
| fuzzy planar cell polarity protein | FUZ |
| fragile X mental retardation, autosomal homolog 1 | FXR1 |
| fragile X mental retardation, autosomal homolog 2 | FXR2 |
| FXYD domain containing ion transport regulator 2 | FXYD2 |
| FXYD domain containing ion transport regulator 3 | FXYD3 |
| FYN binding protein | FYB |
| FYVE and coiled-coil domain containing 1 | FYCO1 |
| FYN proto-oncogene, Src family tyrosine kinase | FYN |
| frizzled class receptor 2 | FZD2 |
| frizzled class receptor 6 | FZD6 |
| frizzled class receptor 7 | FZD7 |
| GTPase activating protein (SH3 domain) binding protein 1 | G3BP1 |
| GTPase activating protein (SH3 domain) binding protein 2 | G3BP2 |
| glucose-6-phosphate dehydrogenase | G6PD |
| glucosidase, alpha; acid | GAA |
| GABA(A) receptor-associated protein-like 2 | GABARAPL2 |
| GA binding protein transcription factor, alpha subunit 60 kDa | GABPA |
| gamma-aminobutyric acid (GABA) A receptor, beta 2 | GABRB2 |
| cyclin G associated kinase | GAK |
| galactose-3-O-sulfotransferase 4 | GAL3ST4 |
| UDP-galactose-4-epimerase | GALE |
| galactokinase 1 | GALK1 |
| galactose mutarotase (aldose 1-epimerase) | GALM |
| polypeptide N-acetylgalactosaminyltransferase 13 | GALNT13 |
| polypeptide N-acetylgalactosaminyltransferase 2 | GALNT2 |
| polypeptide N-acetylgalactosaminyltransferase 3 | GALNT3 |
| polypeptide N-acetylgalactosaminyltransferase 4 | GALNT4 |
| polypeptide N-acetylgalactosaminyltransferase 5 | GALNT5 |
| polypeptide N-acetylgalactosaminyltransferase 7 | GALNT7 |
| glucosidase, alpha; neutral AB | GANAB |
| glyceraldehyde-3-phosphate dehydrogenase | GAPDH |
| glyceraldehyde-3-phosphate dehydrogenase, spermatogenic | GAPDHS |
| GAR1 ribonucleoprotein | GAR1 |
| glycyl-tRNA synthetase | GARS |
| phosphoribosylglycinamide formyltransferase, phosphoribosylglycinamide synthetase, phosphoribosylaminoimidazole synthetase | GART |
| growth arrest-specific 6 | GAS6 |
| GATS protein-like 3 | GATSL3 |
| glucosidase, beta, acid | GBA |
| glucan (1,4-alpha-), branching enzyme 1 | GBE1 |

TABLE 4-continued

| Suitable extracellular vesicle associated proteins | |
| --- | --- |
| Gene Name | Gene Symbol |
| golgi brefeldin A resistant guanine nucleotide exchange factor 1 | GBF1 |
| guanylate binding protein 1, interferon-inducible | GBP1 |
| guanylate binding protein family, member 6 | GBP6 |
| group-specific component (vitamin D binding protein) | GC |
| grancalcin, EF-hand calcium binding protein | GCA |
| glutamate-cysteine ligase, modifier subunit | GCLM |
| GCN1 general control of amino-acid synthesis 1-like 1 (yeast) | GCN1L1 |
| glucosaminyl (N-acetyl) transferase 2, I-branching enzyme (I blood group) | GCNT2 |
| glucosaminyl (N-acetyl) transferase 3, mucin type | GCNT3 |
| guanine deaminase | GDA |
| growth differentiation factor 1 | GDF1 |
| growth differentiation factor 11 | GDF11 |
| growth differentiation factor 15 | GDF15 |
| growth differentiation factor 2 | GDF2 |
| growth differentiation factor 3 | GDF3 |
| growth differentiation factor 5 | GDF5 |
| growth differentiation factor 9 | GDF9 |
| GDP dissociation inhibitor 1 | GDI1 |
| GDP dissociation inhibitor 2 | GDI2 |
| glycerophosphodiester phosphodiesterase domain containing 3 | GDPD3 |
| glycerophosphodiester phosphodiesterase domain containing 5 | GDPD5 |
| gem (nuclear organelle) associated protein 2 | GEMIN2 |
| gem (nuclear organelle) associated protein 4 | GEMIN4 |
| gem (nuclear organelle) associated protein 5 | GEMIN5 |
| golgi to ER traffic protein 4 homolog (S. cerevisiae) | GET4 |
| glial fibrillary acidic protein | GFAP |
| G elongation factor, mitochondrial 1 | GFM1 |
| G elongation factor, mitochondrial 2 | GFM2 |
| glutamine--fructose-6-phosphate transaminase 1 | GFPT1 |
| glutamine-fructose-6-phosphate transaminase 2 | GFPT2 |
| GDNF family receptor alpha 1 | GFRA1 |
| GDNF family receptor alpha 3 | GFRA3 |
| golgi-associated, gamma adaptin ear containing, ARF binding protein 1 | GGA1 |
| golgi-associated, gamma adaptin ear containing, ARF binding protein 3 | GGA3 |
| gamma-glutamylamine cyclotransferase | GGACT |
| gamma-glutamylcyclotransferase | GGCT |
| gamma-glutamyl hydrolase (conjugase, folylpolygammaglutamyl hydrolase) | GGH |
| gamma-glutamyltransferase 1 | GGT1 |
| gamma-glutamyltransferase 2 | GGT2 |
| gamma-glutamyltransferase 3 pseudogene | GGT3P |
| gamma-glutamyltransferase light chain 1 | GGTLC1 |
| gamma-glutamyltransferase light chain 2 | GGTLC2 |
| growth hormone inducible transmembrane protein | GHITM |
| GID complex subunit 8 | GID8 |
| GTPase, IMAP family member 4 | GIMAP4 |
| GTPase, IMAP family member 8 | GIMAP8 |
| GIPC PDZ domain containing family, member 1 | GIPC1 |
| GIPC PDZ domain containing family, member 2 | GIPC2 |
| gap junction protein, alpha 1, 43 kDa | GJA1 |
| gap junction protein, beta 1, 32 kDa | GJB1 |
| gap junction protein, gamma 1, 45 kDa | GJC1 |
| glycerol kinase 2 | GK2 |
| galactosidase, alpha | GLA |
| galactosidase, beta 1 | GLB1 |
| glycine dehydrogenase (decarboxylating) | GLDC |
| golgi glycoprotein 1 | GLG1 |
| GLI pathogenesis-related 2 | GLIPR2 |
| glomulin, FKBP associated protein | GLMN |

TABLE 4-continued

| Gene Name | Gene Symbol |
| --- | --- |
| Suitable extracellular vesicle associated proteins | |
| glyoxalase I | GLO1 |
| glutaredoxin (thioltransferase) | GLRX |
| glutaredoxin 3 | GLRX3 |
| glutaminase | GLS |
| glycosyltransferase 8 domain containing 1 | GLT8D1 |
| glutamate dehydrogenase 1 | GLUD1 |
| glutamate-ammonia ligase | GLUL |
| glyoxylate reductase 1 homolog (Arabidopsis) | GLYR1 |
| GM2 ganglioside activator | GM2A |
| GDP-mannose 4,6-dehydratase | GMDS |
| glia maturation factor, gamma | GMFG |
| GDP-mannose pyrophosphorylase A | GMPPA |
| GDP-mannose pyrophosphorylase B | GMPPB |
| guanosine monophosphate reductase 2 | GMPR2 |
| guanine monophosphate synthase | GMPS |
| guanine nucleotide binding protein (G protein), alpha 11 (Gq class) | GNA11 |
| guanine nucleotide binding protein (G protein) alpha 12 | GNA12 |
| guanine nucleotide binding protein (G protein), alpha 13 | GNA13 |
| guanine nucleotide binding protein (G protein), alpha 14 | GNA14 |
| guanine nucleotide binding protein (G protein), alpha 15 (Gq class) | GNAW |
| guanine nucleotide binding protein (G protein), alpha inhibiting activity polypeptide 1 | GNAI1 |
| guanine nucleotide binding protein (G protein), alpha inhibiting activity polypeptide 2 | GNAI2 |
| guanine nucleotide binding protein (G protein), alpha inhibiting activity polypeptide 3 | GNAI3 |
| guanine nucleotide binding protein (G protein), alpha activating activity polypeptide, olfactory type | GNAL |
| guanine nucleotide binding protein (G protein), alpha activating activity polypeptide O | GNAO1 |
| guanine nucleotide binding protein (G protein), q polypeptide | GNAQ |
| GNAS complex locus | GNAS |
| guanine nucleotide binding protein (G protein), alpha transducing activity polypeptide 1 | GNAT1 |
| guanine nucleotide binding protein (G protein), alpha transducing activity polypeptide 2 | GNAT2 |
| guanine nucleotide binding protein, alpha transducing 3 | GNAT3 |
| guanine nucleotide binding protein (G protein), alpha z polypeptide | GNAZ |
| guanine nucleotide binding protein (G protein), beta polypeptide 1 | GNB1 |
| guanine nucleotide binding protein (G protein), beta polypeptide 1-like | GNB1L |
| guanine nucleotide binding protein (G protein), beta polypeptide 2 | GNB2 |
| guanine nucleotide binding protein (G protein), beta polypeptide 2-like 1 | GNB2L1 |
| guanine nucleotide binding protein (G protein), beta polypeptide 3 | GNB3 |
| guanine nucleotide binding protein (G protein), beta polypeptide 4 | GNB4 |
| guanine nucleotide binding protein (G protein), beta 5 | GNB5 |
| glucosamine (UDP-N-acetyl)-2-epimerase/N-acetylmannosamine kinase | GNE |
| guanine nucleotide binding protein (G protein), gamma 10 | GNG10 |
| guanine nucleotide binding protein (G protein), gamma 11 | GNG11 |
| guanine nucleotide binding protein (G protein), gamma 12 | GNG12 |

TABLE 4-continued

| Suitable extracellular vesicle associated proteins | |
| --- | --- |
| Gene Name | Gene Symbol |
| guanine nucleotide binding protein (G protein), gamma 2 | GNG2 |
| guanine nucleotide binding protein (G protein), gamma 5 | GNG5 |
| guanine nucleotide binding protein (G protein), gamma 7 | GNG7 |
| guanine nucleotide binding protein-like 1 | GNL1 |
| guanine nucleotide binding protein-like 2 (nucleolar) | GNL2 |
| guanine nucleotide binding protein-like 3 (nucleolar) | GNL3 |
| glucosamine-6-phosphate deaminase 1 | GNPDA1 |
| glucosamine-6-phosphate deaminase 2 | GNPDA2 |
| glucosamine-phosphate N-acetyltransferase 1 | GNPNAT1 |
| N-acetylglucosamine-1-phosphate transferase, gamma subunit | GNPTG |
| glucosamine (N-acetyl)-6-sulfatase | GNS |
| golgin A2 | GOLGA2 |
| golgin A3 | GOLGA3 |
| golgin A5 | GOLGA5 |
| golgin A7 | GOLGA7 |
| golgin B1 | GOLGB1 |
| golgi integral membrane protein 4 | GOLIM4 |
| golgi membrane protein 1 | GOLM1 |
| golgi phosphoprotein 3 (coat-protein) | GOLPH3 |
| golgin, RAB6-interacting | GORAB |
| golgi reassembly stacking protein 2, 55 kDa | GORASP2 |
| golgi SNAP receptor complex member 1 | GOSR1 |
| glutamic-oxaloacetic transaminase 1, soluble | GOT1 |
| glutamic-oxaloacetic transaminase 2, mitochondrial | GOT2 |
| glycoprotein Ib (platelet), alpha polypeptide | GP1BA |
| glycoprotein Ib (platelet), beta polypeptide | GP1BB |
| glycoprotein V (platelet) | GP5 |
| glycoprotein VI (platelet) | GP6 |
| glycoprotein IX (platelet) | GP9 |
| glycoprotein A33 (transmembrane) | GPA33 |
| glypican 1 | GPC1 |
| glypican 3 | GPC3 |
| glypican 4 | GPC4 |
| glypican 5 | GPC5 |
| glypican 6 | GPC6 |
| glycerol-3-phosphate dehydrogenase 1 (soluble) | GPD1 |
| glycerol-3-phosphate dehydrogenase 1-like | GPD1L |
| glucose-6-phosphate isomerase | GPI |
| glycoprotein M6A | GPM6A |
| glycoprotein (transmembrane) nmb | GPNMB |
| G protein-coupled receptor 107 | GPR107 |
| G protein-coupled receptor 143 | GPR143 |
| G protein-coupled receptor 155 | GPR155 |
| G protein-coupled receptor 176 | GPR176 |
| G protein-coupled receptor 179 | GPR179 |
| G protein-coupled receptor, class C, group 5, member A | GPRC5A |
| G protein-coupled receptor, class C, group 5, member B | GPRC5B |
| G protein-coupled receptor, class C, group 5, member C | GPRC5C |
| G protein pathway suppressor 1 | GPS1 |
| glutamic-pyruvate transaminase (alanine aminotransferase) | GPT |
| glutathione peroxidase 1 | GPX1 |
| glutathione peroxidase 2 | GPX2 |
| glutathione peroxidase 3 | GPX3 |
| glutathione peroxidase 4 | GPX4 |
| GRB2-related adaptor protein 2 | GRAP2 |
| growth factor receptor-bound protein 2 | GRB2 |
| gremlin 1, DAN family BMP antagonist | GREM1 |
| glyoxylate reductase/hydroxypyruvate reductase | GRHPR |
| glutamate receptor, ionotropic, delta 1 | GRID1 |
| glutamate receptor, ionotropic, N-methyl D-aspartate 1 | GRIN1 |

TABLE 4-continued

| Suitable extracellular vesicle associated proteins | |
| --- | --- |
| Gene Name | Gene Symbol |
| glutamate receptor interacting protein 2 | GRIP2 |
| GRIP1 associated protein 1 | GRIPAP1 |
| G protein-coupled receptor kinase 5 | GRK5 |
| G protein-coupled receptor kinase 6 | GRK6 |
| glutamate receptor, metabotropic 2 | GRM2 |
| glutamate receptor, metabotropic 3 | GRM3 |
| glutamate receptor, metabotropic 7 | GRM7 |
| granulin | GRN |
| growth hormone regulated TBC protein 1 | GRTP1 |
| glutamate-rich WD repeat containing 1 | GRWD1 |
| gasdermin A | GSDMA |
| gasdermin D | GSDMD |
| Gse1 coiled-coil protein | GSE1 |
| glycogen synthase kinase 3 alpha | GSK3A |
| glycogen synthase kinase 3 beta | GSK3B |
| gelsolin | GSN |
| G1 to S phase transition 1 | GSPT1 |
| G1 to S phase transition 2 | GSPT2 |
| glutathione reductase | GSR |
| glutathione synthetase | GSS |
| glutathione S-transferase alpha 1 | GSTA1 |
| glutathione S-transferase alpha 2 | GSTA2 |
| glutathione S-transferase alpha 3 | GSTA3 |
| glutathione S-transferase alpha 5 | GSTA5 |
| glutathione S-transferase, C-terminal domain containing | GSTCD |
| glutathione S-transferase kappa 1 | GSTK1 |
| glutathione S-transferase mu 1 | GSTM1 |
| glutathione S-transferase mu 2 (muscle) | GSTM2 |
| glutathione S-transferase mu 3 (brain) | GSTM3 |
| glutathione S-transferase mu 5 | GSTM5 |
| glutathione S-transferase omega 1 | GSTO1 |
| glutathione S-transferase omega 2 | GSTO2 |
| glutathione S-transferase pi 1 | GSTP1 |
| general transcription factor IIB | GTF2B |
| general transcription factor IIi | GTF2I |
| general transcription factor IIIC, polypeptide 5, 63 kDa | GTF3C5 |
| GTP binding protein 1 | GTPBP1 |
| GTP binding protein 2 | GTPBP2 |
| G-2 and S-phase expressed 1 | GTSE1 |
| glucuronidase, beta | GUSB |
| glycosyltransferase-like 1B | GYLTL1B |
| glycophorin C (Gerbich blood group) | GYPC |
| glycogen synthase 1 (muscle) | GYS1 |
| glycogen synthase 2 (liver) | GYS2 |
| granzyme A (granzyme 1, cytotoxic T-lymphocyte-associated serine esterase 3) | GZMA |
| H1 histone family, member 0 | H1F0 |
| H1 histone family, member O, oocyte-specific | H1FOO |
| H1 histone family, member X | H1FX |
| H2A histone family, member J | H2AFJ |
| H2A histone family, member V | H2AFV |
| H2A histone family, member X | H2AFX |
| H2A histone family, member Y | H2AFY |
| H2A histone family, member Y2 | H2AFY2 |
| H2A histone family, member Z | H2AFZ |
| H3 histone, family 3A | H3F3A |
| H3 histone, family 3B (H3.3B) | H3F3B |
| H3 histone, family 3C | H3F3C |
| 3-hydroxyacyl-CoA dehydratase 3 | HACD3 |
| hydroxyacyl-CoA dehydrogenase | HADH |
| hydroxyacyl-CoA dehydrogenase/3-ketoacyl-CoA thiolase/enoyl-CoA hydratase (trifunctional protein), alpha subunit | HADHA |
| hydroxyacyl-CoA dehydrogenase/3-ketoacyl-CoA thiolase/enoyl-CoA hydratase (trifunctional protein), beta subunit | HADHB |
| histidine ammonia-lyase | HAL |
| hyaluronan and proteoglycan link protein 1 | HAPLN1 |
| hyaluronan and proteoglycan link protein 3 | HAPLN3 |
| histidyl-tRNA synthetase | HARS |
| histidyl-tRNA synthetase 2, mitochondrial | HARS2 |

TABLE 4-continued

| Suitable extracellular vesicle associated proteins | |
| --- | --- |
| Gene Name | Gene Symbol |
| hyaluronan synthase 1 | HAS1 |
| histone acetyltransferase 1 | HAT1 |
| HAUS augmin-like complex, subunit 5 | HAUS5 |
| hemoglobin, alpha 1 | HBA1 |
| hemoglobin, alpha 2 | HBA2 |
| hemoglobin, beta | HBB |
| hemoglobin, delta | HBD |
| hemoglobin, epsilon 1 | HBE1 |
| hemoglobin, gamma A | HBG1 |
| hemoglobin, gamma G | HBG2 |
| HBS1-like translational GTPase | HBS1L |
| host cell factor C1 | HCFC1 |
| HCK proto-oncogene, Src family tyrosine kinase | HCK |
| hyperpolarization activated cyclic nucleotide gated potassium channel 3 | HCN3 |
| histone deacetylase 1 | HDAC1 |
| histone deacetylase 2 | HDAC2 |
| histone deacetylase 3 | HDAC3 |
| histone deacetylase 5 | HDAC5 |
| histone deacetylase 6 | HDAC6 |
| hepatoma-derived growth factor | HDGF |
| haloacid dehalogenase-like hydrolase domain containing 2 | HDHD2 |
| high density lipoprotein binding protein | HDLBP |
| heme binding protein 1 | HEBP1 |
| heme binding protein 2 | HEBP2 |
| HECT domain containing E3 ubiquitin protein ligase 3 | HECTD3 |
| HECT domain containing E3 ubiquitin protein ligase 4 | HECTD4 |
| heart development protein with EGF-like domains 1 | HEG1 |
| helicase, lymphoid-specific | HELLS |
| hephaestin | HEPH |
| HECT and RLD domain containing E3 ubiquitin protein ligase 5 | HERC5 |
| hexosaminidase A (alpha polypeptide) | HEXA |
| hexosaminidase B (beta polypeptide) | HEXB |
| homogentisate 1,2-dioxygenase | HGD |
| hepatocyte growth factor (hepapoietin A; scatter factor) | HGF |
| HGF activator | HGFAC |
| hepatocyte growth factor-regulated tyrosine kinase substrate | HGS |
| hypermethylated in cancer 2 | HIC2 |
| HID1 domain containing | HID1 |
| histidine triad nucleotide binding protein 1 | HINT1 |
| histidine triad nucleotide binding protein 3 | HINT3 |
| histone cluster 1, H1a | HIST1H1A |
| histone cluster 1, H1b | HIST1H1B |
| histone cluster 1, H1c | HIST1H1C |
| histone cluster 1, H1d | HIST1H1D |
| histone cluster 1, H1e | HIST1H1E |
| histone cluster 1, H1t | HIST1H1T |
| histone cluster 1, H2aa | HIST1H2AA |
| histone cluster 1, H2ab | HIST1H2AB |
| histone cluster 1, H2ac | HIST1H2AC |
| histone cluster 1, H2ad | HIST1H2AD |
| histone cluster 1, H2ae | HIST1H2AE |
| histone cluster 1, H2ag | HIST1H2AG |
| histone cluster 1, H2ah | HIST1H2AH |
| histone cluster 1, H2ai | HIST1H2AI |
| histone cluster 1, H2aj | HIST1H2AJ |
| histone cluster 1, H2ak | HIST1H2AK |
| histone cluster 1, H2al | HIST1H2AL |
| histone cluster 1, H2am | HIST1H2AM |
| histone cluster 1, H2ba | HIST1H2BA |
| histone cluster 1, H2bb | HIST1H2BB |
| histone cluster 1, H2bc | HIST1H2BC |
| histone cluster 1, H2bd | HIST1H2BD |
| histone cluster 1, H2be | HIST1H2BE |
| histone cluster 1, H2bf | HIST1H2BF |
| histone cluster 1, H2bg | HIST1H2BG |
| histone cluster 1, H2bh | HIST1H2BH |
| histone cluster 1, H2bi | HIST1H2BI |

TABLE 4-continued

| Suitable extracellular vesicle associated proteins | |
| --- | --- |
| Gene Name | Gene Symbol |
| histone cluster 1, H2bj | HIST1H2BJ |
| histone cluster 1, H2bk | HIST1H2BK |
| histone cluster 1, H2bl | HIST1H2BL |
| histone cluster 1, H2bm | HIST1H2BM |
| histone cluster 1, H2bn | HIST1H2BN |
| histone cluster 1, H2bo | HIST1H2BO |
| histone cluster 1, H3a | HIST1H3A |
| histone cluster 1, H3b | HIST1H3B |
| histone cluster 1, H3c | HIST1H3C |
| histone cluster 1, H3d | HIST1H3D |
| histone cluster 1, H3e | HIST1H3E |
| histone cluster 1, H3f | HIST1H3F |
| histone cluster 1, H3g | HIST1H3G |
| histone cluster 1, H3h | HIST1H3H |
| histone cluster 1, H3i | HIST1H3I |
| histone cluster 1, H3j | HIST1H3J |
| histone cluster 1, H4a | HIST1H4A |
| histone cluster 1, H4b | HIST1H4B |
| histone cluster 1, H4c | HIST1H4C |
| histone cluster 1, H4d | HIST1H4D |
| histone cluster 1, H4e | HIST1H4E |
| histone cluster 1, H4f | HIST1H4F |
| histone cluster 1, H4g | HIST1H4G |
| histone cluster 1, H4h | HIST1H4H |
| histone cluster 1, H4i | HIST1H4I |
| histone cluster 1, H4j | HIST1H4J |
| histone cluster 1, H4k | HIST1H4K |
| histone cluster 1, H4I | HIST1H4L |
| histone cluster 2, H2aa3 | HIST2H2AA3 |
| histone cluster 2, H2aa4 | HIST2H2AA4 |
| histone cluster 2, H2ab | HIST2H2AB |
| histone cluster 2, H2ac | HIST2H2AC |
| histone cluster 2, H2bc (pseudogene) | HIST2H2BC |
| histone cluster 2, H2be | HIST2H2BE |
| histone cluster 2, H2bf | HIST2H2BF |
| histone cluster 2, H3a | HIST2H3A |
| histone cluster 2, H3c | HIST2H3C |
| histone cluster 2, H3d | HIST2H3D |
| histone cluster 2, H4a | HIST2H4A |
| histone cluster 2, H4b | HIST2H4B |
| histone cluster 3, H2a | HIST3H2A |
| histone cluster 3, H2bb | HIST3H2BB |
| histone cluster 3, H3 | HIST3H3 |
| histone cluster 4, H4 | HIST4H4 |
| human immunodeficiency virus type I enhancer binding protein 1 | HIVEP1 |
| human immunodeficiency virus type I enhancer binding protein 3 | HIVEP3 |
| hexokinase 1 | HK1 |
| major histocompatibility complex, class I, A | HLA-A |
| major histocompatibility complex, class I, B | HLA-B |
| major histocompatibility complex, class I, C | HLA-C |
| major histocompatibility complex, class II, DM beta | HLA-DMB |
| major histocompatibility complex, class II, DP beta 1 | HLA-DPB1 |
| major histocompatibility complex, class II, DQ alpha 1 | HLA-DQA1 |
| major histocompatibility complex, class II, DQ beta 1 | HLA-DQB1 |
| major histocompatibility complex, class II, DR alpha | HLA-DRA |
| major histocompatibility complex, class II, DR beta 1 | HLA-DRB1 |
| major histocompatibility complex, class II, DR beta 3 | HLA-DRB3 |
| major histocompatibility complex, class II, DR beta 5 | HLA-DRB5 |
| major histocompatibility complex, class I, E | HLA-E |
| major histocompatibility complex, class I, G | HLA-G |
| major histocompatibility complex, class I, H (pseudogene) | HLA-H |
| histocompatibility (minor) 13 | HM13 |
| hydroxymethylbilane synthase | HMBS |
| hemicentin 1 | HMCN1 |
| high mobility group AT-hook 1 | HMGA1 |

TABLE 4-continued

| Suitable extracellular vesicle associated proteins | |
| --- | --- |
| Gene Name | Gene Symbol |
| high mobility group AT-hook 2 | HMGA2 |
| high mobility group box 1 | HMGB1 |
| high mobility group box 2 | HMGB2 |
| high mobility group box 3 | HMGB3 |
| 3-hydroxy-3-methylglutaryl-CoA synthase 1 (soluble) | HMGCS1 |
| 3-hydroxy-3-methylglutaryl-CoA synthase 2 (mitochondrial) | HMGCS2 |
| histocompatibility (minor) HA-1 | HMHA1 |
| heme oxygenase 2 | HMOX2 |
| hematological and neurological expressed 1 | HN1 |
| hematological and neurological expressed 1-like | HN1L |
| histamine N-methyltransferase | HNMT |
| heterogeneous nuclear ribonucleoprotein A0 | HNRNPA0 |
| heterogeneous nuclear ribonucleoprotein A1 | HNRNPA1 |
| heterogeneous nuclear ribonucleoprotein A2/B1 | HNRNPA2B1 |
| heterogeneous nuclear ribonucleoprotein A3 | HNRNPA3 |
| heterogeneous nuclear ribonucleoprotein A/B | HNRNPAB |
| heterogeneous nuclear ribonucleoprotein C (C1/C2) | HNRNPC |
| heterogeneous nuclear ribonucleoprotein C-like 1 | HNRNPCL1 |
| heterogeneous nuclear ribonucleoprotein C-like 2 | HNRNPCL2 |
| heterogeneous nuclear ribonucleoprotein C-like 3 | HNRNPCL3 |
| heterogeneous nuclear ribonucleoprotein C-like 4 | HNRNPCL4 |
| heterogeneous nuclear ribonucleoprotein D (AU-rich element RNA binding protein 1, 37 kDa) | HNRNPD |
| heterogeneous nuclear ribonucleoprotein D-like | HNRNPDL |
| heterogeneous nuclear ribonucleoprotein F | HNRNPF |
| heterogeneous nuclear ribonucleoprotein H1 (H) | HNRNPH1 |
| heterogeneous nuclear ribonucleoprotein H2 (H') | HNRNPH2 |
| heterogeneous nuclear ribonucleoprotein H3 (2H9) | HNRNPH3 |
| heterogeneous nuclear ribonucleoprotein K | HNRNPK |
| heterogeneous nuclear ribonucleoprotein L | HNRNPL |
| heterogeneous nuclear ribonucleoprotein M | HNRNPM |
| heterogeneous nuclear ribonucleoprotein R | HNRNPR |
| heterogeneous nuclear ribonucleoprotein U (scaffold attachment factor A) | HNRNPU |
| heterogeneous nuclear ribonucleoprotein U-like 1 | HNRNPUL1 |
| heterogeneous nuclear ribonucleoprotein U-like 2 | HNRNPUL2 |
| homer scaffolding protein 3 | HOMER3 |
| homeobox B3 | HOXB3 |
| homeobox B7 | HOXB7 |
| haptoglobin | HP |
| heterochromatin protein 1, binding protein 3 | HP1BP3 |
| hippocalcin | HPCA |
| hippocalcin-like 1 | HPCAL1 |
| 4-hydroxyphenylpyruvate dioxygenase | HPD |
| 4-hydroxyphenylpyruvate dioxygenase-like | HPDL |
| hydroxyprostaglandin dehydrogenase 15-(NAD) | HPGD |
| haptoglobin-related protein | HPR |
| hypoxanthine phosphoribosyltransferase 1 | HPRT1 |
| Hermansky-Pudlak syndrome 6 | HPS6 |
| heparanase | HPSE |
| hemopexin | HPX |
| Harvey rat sarcoma viral oncogene homolog | HRAS |
| histidine-rich glycoprotein | HRG |
| hornerin | HRNR |
| heat-responsive protein 12 | HRSP12 |
| heparan sulfate 2-O-sulfotransferase 1 | HS2ST1 |
| hydroxysteroid (17-beta) dehydrogenase 10 | HSD17B10 |
| hydroxysteroid (17-beta) dehydrogenase 12 | HSD17B12 |
| hydroxysteroid (17-beta) dehydrogenase 4 | HSD17B4 |
| hydroxysteroid dehydrogenase like 2 | HSDL2 |

TABLE 4-continued

| Suitable extracellular vesicle associated proteins | |
|---|---|
| Gene Name | Gene Symbol |
| hematopoietic SH2 domain containing | HSH2D |
| heat shock protein 90 kDa alpha (cytosolic), class A member 1 | HSP90AA1 |
| heat shock protein 90 kDa alpha (cytosolic), class A member 2, pseudogene | HSP90AA2P |
| heat shock protein 90 kDa alpha (cytosolic), class A member 4, pseudogene | HSP90AA4P |
| heat shock protein 90 kDa alpha (cytosolic), class B member 1 | HSP90AB1 |
| heat shock protein 90 kDa alpha (cytosolic), class B member 2, pseudogene | HSP90AB2P |
| heat shock protein 90 kDa alpha (cytosolic), class B member 3, pseudogene | HSP90AB3P |
| heat shock protein 90 kDa alpha (cytosolic), class B member 6, pseudogene | HSP90AB6P |
| heat shock protein 90 kDa beta (Grp94), member 1 | HSP90B1 |
| heat shock 70 kDa protein 12A | HSPA12A |
| heat shock 70 kD protein 12B | HSPA12B |
| heat shock protein 70 kDa family, member 13 | HSPA13 |
| heat shock 70 kDa protein 1A | HSPA1A |
| heat shock 70 kDa protein 1B | HSPA1B |
| heat shock 70 kDa protein 1-like | HSPA1L |
| heat shock 70 kDa protein 2 | HSPA2 |
| heat shock 70 kDa protein 4 | HSPA4 |
| heat shock 70 kDa protein 4-like | HSPA4L |
| heat shock 70 kDa protein 5 (glucose-regulated protein, 78 kDa) | HSPA5 |
| heat shock 70 kDa protein 6 (HSP70B') | HSPA6 |
| heat shock 70 kDa protein 7 (HSP70B) | HSPA7 |
| heat shock 70 kDa protein 8 | HSPA8 |
| heat shock 70 kDa protein 9 (mortalin) | HSPA9 |
| heat shock 27 kDa protein 1 | HSPB1 |
| heat shock 27 kDa protein 1 pseudogene 1 | HSPB1P1 |
| heat shock 22 kDa protein 8 | HSPB8 |
| heat shock 60 kDa protein 1 (chaperonin) | HSPD1 |
| heat shock 60 kDa protein 1 (chaperonin) pseudogene 1 | HSPD1P1 |
| heat shock 60 kDa protein 1 (chaperonin) pseudogene 4 | HSPD1P4 |
| heat shock 60 kDa protein 1 (chaperonin) pseudogene 5 | HSPD1P5 |
| heat shock 60 kDa protein 1 (chaperonin) pseudogene 6 | HSPD1P6 |
| heat shock 10 kDa protein 1 | HSPE1 |
| heparan sulfate proteoglycan 2 | HSPG2 |
| heat shock 105 kDa/110 kDa protein 1 | HSPH1 |
| HIV-1 Tat interactive protein 2, 30 kDa | HTATIP2 |
| HIV-1 Tat specific factor 1 | HTATSF1 |
| HtrA serine peptidase 1 | HTRA1 |
| HtrA serine peptidase 3 | HTRA3 |
| huntingtin | HTT |
| HECT, UBA and WWE domain containing 1, E3 ubiquitin protein ligase | HUWE1 |
| hyaluronoglucosaminidase 2 | HYAL2 |
| hydroxypyruvate isomerase (putative) | HYI |
| hypoxia up-regulated 1 | HYOU1 |
| isoleucyl-tRNA synthetase | IARS |
| inhibitor of Bruton agammaglobulinemia tyrosine kinase | IBTK |
| intercellular adhesion molecule 1 | ICAM1 |
| intercellular adhesion molecule 2 | ICAM2 |
| intercellular adhesion molecule 3 | ICAM3 |
| intercellular adhesion molecule 5, telencephalin | ICAM5 |
| insulin-degrading enzyme | IDE |
| isocitrate dehydrogenase 1 (NADP+), soluble | IDH1 |
| isocitrate dehydrogenase 2 (NADP+), mitochondrial | IDH2 |
| isocitrate dehydrogenase 3 (NAD+) alpha | IDH3A |
| isocitrate dehydrogenase 3 (NAD+) beta | IDH3B |
| isopentenyl-diphosphate delta isomerase 1 | IDI1 |
| idnK, gluconokinase homolog (E. coli) | IDNK |
| indolamin-2,3-dioxygenase | IDO |
| interferon, gamma-inducible protein 16 | IFI16 |

TABLE 4-continued

| Suitable extracellular vesicle associated proteins | |
| --- | --- |
| Gene Name | Gene Symbol |
| interferon-induced protein with tetratricopeptide repeats 1 | IFIT1 |
| interferon-induced protein with tetratricopeptide repeats 3 | IFIT3 |
| interferon-induced protein with tetratricopeptide repeats 5 | IFIT5 |
| interferon induced transmembrane protein 1 | IFITM1 |
| interferon induced transmembrane protein 2 | IFITM2 |
| interferon induced transmembrane protein 3 | IFITM3 |
| interferon, gamma | IFNG |
| interferon gamma receptor 1 | IFNGR1 |
| interferon-related developmental regulator 1 | IFRD1 |
| intraflagellar transport 140 | IFT140 |
| insulin-like growth factor 1 receptor | IGF1R |
| insulin-like growth factor 2 | IGF2 |
| insulin-like growth factor 2 mRNA binding protein 2 | IGF2BP2 |
| insulin-like growth factor 2 mRNA binding protein 3 | IGF2BP3 |
| insulin-like growth factor 2 receptor | IGF2R |
| insulin-like growth factor binding protein, acid labile subunit | IGFALS |
| insulin-like growth factor binding protein 2, 36 kDa | IGFBP2 |
| insulin-like growth factor binding protein 3 | IGFBP3 |
| insulin-like growth factor binding protein 4 | IGFBP4 |
| insulin-like growth factor binding protein 6 | IGFBP6 |
| insulin-like growth factor binding protein 7 | IGFBP7 |
| IGF-like family member 1 | IGFL1 |
| immunoglobulin heavy locus | IGH |
| immunoglobulin heavy constant alpha 1 | IGHA1 |
| immunoglobulin heavy constant alpha 2 (A2m marker) | IGHA2 |
| immunoglobulin heavy constant gamma 1 (G1m marker) | IGHG1 |
| immunoglobulin heavy constant gamma 2 (G2m marker) | IGHG2 |
| immunoglobulin heavy constant gamma 3 (G3m marker) | IGHG3 |
| immunoglobulin heavy constant gamma 4 (G4m marker) | IGHG4 |
| immunoglobulin heavy constant mu | IGHM |
| immunoglobulin heavy variable 3-11 (gene/pseudogene) | IGHV3-11 |
| immunoglobulin heavy variable 3-7 | IGHV3-7 |
| immunoglobulin heavy variable 4-31 | IGHV4-31 |
| immunoglobulin kappa locus | IGK |
| immunoglobulin kappa constant | IGKC |
| immunoglobulin kappa variable 1-5 | IGKV1-5 |
| immunoglobulin kappa variable 2-24 | IGKV2-24 |
| immunoglobulin kappa variable 3-20 | IGKV3-20 |
| immunoglobulin kappa variable 3D-15 (gene/pseudogene) | IGKV3D-15 |
| immunoglobulin kappa variable 4-1 | IGKV4-1 |
| immunoglobulin lambda locus | IGL |
| immunoglobulin lambda constant 1 (Mcg marker) | IGLC1 |
| immunoglobulin lambda constant 2 (Kern-Oz-marker) | IGLC2 |
| immunoglobulin lambda constant 3 (Kern-Oz+ marker) | IGLC3 |
| immunoglobulin lambda constant 6 (Kern + Oz-marker, gene/pseudogene) | IGLC6 |
| immunoglobulin lambda constant 7 | IGLC7 |
| immunoglobulin lambda-like polypeptide 5 | IGLL5 |
| immunoglobulin lambda variable 1-40 | IGLV1-40 |
| immunoglobulin lambda variable 1-44 | IGLV1-44 |
| immunoglobulin lambda variable 2-11 | IGLV2-11 |
| immunoglobulin lambda variable 3-21 | IGLV3-21 |
| immunoglobulin lambda variable 4-3 | IGLV4-3 |
| immunoglobulin superfamily, member 3 | IGSF3 |
| immunoglobulin superfamily, member 8 | IGSF8 |
| inhibitor of kappa light polypeptide gene enhancer in B-cells, kinase complex-associated protein | IKBKAP |

TABLE 4-continued

| Suitable extracellular vesicle associated proteins | |
| --- | --- |
| Gene Name | Gene Symbol |
| inhibitor of kappa light polypeptide gene enhancer in B-cells, kinase beta | IKBKB |
| inhibitor of kappa light polypeptide gene enhancer in B-cells, kinase gamma | IKBKG |
| IKAROS family zinc finger 5 (Pegasus) | IKZF5 |
| interleukin 10 | IL10 |
| interleukin 11 | IL11 |
| interleukin 13 | IL13 |
| interleukin 13 receptor, alpha 2 | IL13RA2 |
| interleukin 15 receptor, alpha | IL15RA |
| interleukin 17B | IL17B |
| interleukin 17 receptor C | IL17RC |
| interleukin 19 | IL19 |
| interleukin 1 receptor accessory protein | IL1RAP |
| interleukin 1 receptor accessory protein-like 1 | IL1RAPL1 |
| interleukin 1 receptor-like 2 | IL1RL2 |
| interleukin 1 receptor antagonist | IL1RN |
| interleukin 22 receptor, alpha 1 | IL22RA1 |
| interleukin 23, alpha subunit p19 | IL23A |
| interleukin 27 receptor, alpha | IL27RA |
| interleukin 3 | IL3 |
| interleukin 36, gamma | IL36G |
| interleukin 4 induced 1 | IL4I1 |
| interleukin 5 | IL5 |
| interleukin 6 signal transducer | IL6ST |
| interleukin 7 | IL7 |
| immunoglobulin-like domain containing receptor 1 | ILDR1 |
| interleukin enhancer binding factor 2 | ILF2 |
| interleukin enhancer binding factor 3, 90 kDa | ILF3 |
| integrin-linked kinase | ILK |
| integrin-linked kinase-associated serine/threonine phosphatase | ILKAP |
| inner membrane protein, mitochondrial | IMMT |
| IMP3, U3 small nucleolar ribonucleoprotein | IMP3 |
| inositol(myo)-1(or 4)-monophosphatase 1 | IMPA1 |
| inositol(myo)-1(or 4)-monophosphatase 2 | IMPA2 |
| inositol monophosphatase domain containing 1 | IMPAD1 |
| IMP (inosine 5'-monophosphate) dehydrogenase 1 | IMPDH1 |
| IMP (inosine 5'-monophosphate) dehydrogenase 2 | IMPDH2 |
| internexin neuronal intermediate filament protein, alpha | INA |
| InaD-like (*Drosophila*) | INADL |
| inverted formin, FH2 and WH2 domain containing | INF2 |
| inhibin, beta A | INHBA |
| inhibin, beta B | INHBB |
| INO80 complex subunit B | INO80B |
| inositol polyphosphate-1-phosphatase | INPP1 |
| inositol polyphosphate-4-phosphatase, type I, 107 kDa | INPP4A |
| inositol polyphosphate-5-phosphatase, 40 kDa | INPP5A |
| inositol polyphosphate-5-phosphatase, 75 kDa | INPP5B |
| inositol polyphosphate-5-phosphatase, 145 kDa | INPP5D |
| inositol polyphosphate phosphatase-like 1 | INPPL1 |
| insulin | INS |
| insulinoma-associated 2 | INSM2 |
| insulin receptor | INSR |
| insulin receptor-related receptor | INSRR |
| integrator complex subunit 1 | INTS1 |
| integrator complex subunit 3 | INTS3 |
| importin 11 | IPO11 |
| importin 4 | IPO4 |
| importin 5 | IPO5 |
| importin 7 | IPO7 |
| importin 8 | IPO8 |
| importin 9 | IPO9 |
| IQ motif containing G | IQCG |

TABLE 4-continued

Suitable extracellular vesicle associated proteins

| Gene Name | Gene Symbol |
| --- | --- |
| IQ motif containing GTPase activating protein 1 | IQGAP1 |
| IQ motif containing GTPase activating protein 2 | IQGAP2 |
| IQ motif containing GTPase activating protein 3 | IQGAP3 |
| interleukin-1 receptor-associated kinase 1 binding protein 1 | IRAK1BP1 |
| interferon regulatory factor 6 | IRF6 |
| insulin receptor substrate 2 | IRS2 |
| insulin receptor substrate 4 | IRS4 |
| iron-sulfur cluster assembly enzyme | ISCU |
| ISG15 ubiquitin-like modifier | ISG15 |
| interferon stimulated exonuclease gene 20 kDa-like 2 | ISG20L2 |
| increased sodium tolerance 1 homolog (yeast) | IST1 |
| ISY1 splicing factor homolog (*S. cerevisiae*) | ISY1 |
| ISY1-RAB43 readthrough | ISY1-RAB43 |
| inositol-3-phosphate synthase 1 | ISYNA1 |
| itchy E3 ubiquitin protein ligase | ITCH |
| integrin alpha FG-GAP repeat containing 3 | ITFG3 |
| integrin, alpha 1 | ITGA1 |
| integrin, alpha 11 | ITGA11 |
| integrin, alpha 2 (CD49B, alpha 2 subunit of VLA-2 receptor) | ITGA2 |
| integrin, alpha 2b (platelet glycoprotein IIb of IIb/IIIa complex, antigen CD41) | ITGA2B |
| integrin, alpha 3 (antigen CD49C, alpha 3 subunit of VLA-3 receptor) | ITGA3 |
| integrin, alpha 4 (antigen CD49D, alpha 4 subunit of VLA-4 receptor) | ITGA4 |
| integrin, alpha 5 (fibronectin receptor, alpha polypeptide) | ITGA5 |
| integrin, alpha 6 | ITGA6 |
| integrin, alpha 9 | ITGA9 |
| integrin, alpha L (antigen CD11A (p180), lymphocyte function-associated antigen 1; alpha polypeptide) | ITGAL |
| integrin, alpha M (complement component 3 receptor 3 subunit) | ITGAM |
| integrin, alpha V | ITGAV |
| integrin, alpha X (complement component 3 receptor 4 subunit) | ITGAX |
| integrin, beta 1 (fibronectin receptor, beta polypeptide, antigen CD29 includes MDF2, MSK12) | ITGB1 |
| integrin, beta 2 (complement component 3 receptor 3 and 4 subunit) | ITGB2 |
| integrin, beta 3 (platelet glycoprotein IIIa, antigen CD61) | ITGB3 |
| integrin, beta 4 | ITGB4 |
| integrin, beta 5 | ITGB5 |
| integrin, beta 6 | ITGB6 |
| integrin, beta 7 | ITGB7 |
| integrin, beta 8 | ITGB8 |
| inter-alpha-trypsin inhibitor heavy chain 1 | ITIH1 |
| inter-alpha-trypsin inhibitor heavy chain 2 | ITIH2 |
| inter-alpha-trypsin inhibitor heavy chain 3 | ITIH3 |
| inter-alpha-trypsin inhibitor heavy chain family, member 4 | ITIH4 |
| IL2-inducible T-cell kinase | ITK |
| intelectin 1 (galactofuranose binding) | ITLN1 |
| integral membrane protein 2B | ITM2B |
| integral membrane protein 2C | ITM2C |
| inosine triphosphatase (nucleoside triphosphate pyrophosphatase) | ITPA |
| inositol 1,4,5-trisphosphate receptor, type 2 | ITPR2 |
| inositol 1,4,5-trisphosphate receptor, type 3 | ITPR3 |
| inositol 1,4,5-trisphosphate receptor interacting protein-like 2 | ITPRIPL2 |
| intersectin 1 (SH3 domain protein) | ITSN1 |
| intersectin 2 | ITSN2 |
| involucrin | IVL |
| jade family PHD finger 2 | JADE2 |

TABLE 4-continued

Suitable extracellular vesicle associated proteins

| Gene Name | Gene Symbol |
| --- | --- |
| jagged 1 | JAG1 |
| Janus kinase 1 | JAK1 |
| Janus kinase 2 | JAK2 |
| Janus kinase 3 | JAK3 |
| janus kinase and microtubule interacting protein 1 | JAKMIP1 |
| junctional adhesion molecule 3 | JAM3 |
| joining chain of multimeric IgA and IgM | JCHAIN |
| jumonji domain containing 1C | JMJD1C |
| junctophilin 3 | JPH3 |
| junction plakoglobin | JUP |
| kalirin, RhoGEF kinase | KALRN |
| lysyl-tRNA synthetase | KARS |
| katanin p60 subunit A-like 2 | KATNAL2 |
| kelch repeat and BTB (POZ) domain containing 11 | KBTBD11 |
| potassium channel, voltage gated subfamily A regulatory beta subunit 2 | KCNAB2 |
| potassium channel, voltage gated modifier subfamily G, member 2 | KCNG2 |
| potassium channel, calcium activated intermediate/small conductance subfamily N alpha, member 4 | KCNN4 |
| potassium voltage-gated channel, modifier subfamily S, member 3 | KCNS3 |
| potassium channel, sodium activated subfamily T, member 1 | KCNT1 |
| potassium channel tetramerization domain containing 12 | KCTD12 |
| potassium channel tetramerization domain containing 14 | KCTD14 |
| potassium channel tetramerization domain containing 21 | KCTD21 |
| KDEL (Lys-Asp-Glu-Leu) endoplasmic reticulum protein retention receptor 2 | KDELR2 |
| lysine (K)-specific demethylase 1A | KDM1A |
| lysine (K)-specific demethylase 6B | KDM6B |
| KH domain containing, RNA binding, signal transduction associated 1 | KHDRBS1 |
| ketohexokinase (fructokinase) | KHK |
| KH-type splicing regulatory protein | KHSRP |
| KIAA0020 | KIAA0020 |
| KIAA0195 | KIAA0195 |
| KIAA0196 | KIAA0196 |
| KIAA0319-like | KIAA0319L |
| KIAA0368 | KIAA0368 |
| KIAA0513 | KIAA0513 |
| KIAA1033 | KIAA1033 |
| KIAA1161 | KIAA1161 |
| KIAA1217 | KIAA1217 |
| KIAA1324 | KIAA1324 |
| KIAA1468 | KIAA1468 |
| KIAA1522 | KIAA1522 |
| KIAA1524 | KIAA1524 |
| KIAA1598 | KIAA1598 |
| KIAA2013 | KIAA2013 |
| kinase D-interacting substrate, 220 kDa | KIDINS220 |
| kinesin family member 12 | KIF12 |
| kinesin family member 13A | KIF13A |
| kinesin family member 13B | KIF13B |
| kinesin family member 15 | KIF15 |
| kinesin family member 17 | KIF17 |
| kinesin family member 18B | KIF18B |
| kinesin family member 1B | KIF1B |
| KIF1 binding protein | KIF1BP |
| kinesin family member 21A | KIF21A |
| kinesin family member 23 | KIF23 |
| kinesin family member 26A | KIF26A |
| kinesin heavy chain member 2A | KIF2A |
| kinesin family member 3A | KIF3A |
| kinesin family member 3B | KIF3B |
| kinesin family member 3C | KIF3C |
| kinesin family member 4A | KIF4A |
| kinesin family member 5A | KIF5A |
| kinesin family member 5B | KIF5B |
| kinesin family member 5C | KIF5C |

TABLE 4-continued

Suitable extracellular vesicle associated proteins

| Gene Name | Gene Symbol |
| --- | --- |
| kinesin family member 6 | KIF6 |
| kinesin family member 9 | KIF9 |
| kinesin family member C1 | KIFC1 |
| kinesin family member C3 | KIFC3 |
| kin of IRRE like (*Drosophila*) | KIRREL |
| v-kit Hardy-Zuckerman 4 feline sarcoma viral oncogene homolog | KIT |
| klotho | KL |
| kinesin light chain 1 | KLC1 |
| kinesin light chain 2 | KLC2 |
| kinesin light chain 4 | KLC4 |
| KLF3 antisense RNA 1 | KLF3-AS1 |
| kelch domain containing 10 | KLHDC10 |
| kelch-like family member 14 | KLHL14 |
| kelch-like family member 22 | KLHL22 |
| kallikrein 1 | KLK1 |
| kallikrein-related peptidase 10 | KLK10 |
| kallikrein-related peptidase 11 | KLK11 |
| kallikrein-related peptidase 5 | KLK5 |
| kallikrein-related peptidase 6 | KLK6 |
| kallikrein-related peptidase 7 | KLK7 |
| kallikrein-related peptidase 8 | KLK8 |
| kallikrein B, plasma (Fletcher factor) 1 | KLKB1 |
| killer cell lectin-like receptor subfamily G, member 2 | KLRG2 |
| lysine (K)-specific methyltransferase 2C | KMT2C |
| lysine (K)-specific methyltransferase 2D | KMT2D |
| kininogen 1 | KNG1 |
| karyopherin alpha 1 (importin alpha 5) | KPNA1 |
| karyopherin alpha 2 (RAG cohort 1, importin alpha 1) | KPNA2 |
| karyopherin alpha 4 (importin alpha 3) | KPNA4 |
| karyopherin alpha 6 (importin alpha 7) | KPNA6 |
| karyopherin (importin) beta 1 | KPNB1 |
| keratinocyte proline-rich protein | KPRP |
| Kirsten rat sarcoma viral oncogene homolog | KRAS |
| KRIT1, ankyrin repeat containing | KRIT1 |
| KRR1, small subunit (SSU) processome component, homolog (yeast) | KRR1 |
| keratin 1, type II | KRT1 |
| keratin 10, type I | KRT10 |
| keratin 12, type I | KRT12 |
| keratin 13, type I | KRT13 |
| keratin 14, type I | KRT14 |
| keratin 15, type I | KRT15 |
| keratin 16, type I | KRT16 |
| keratin 16 pseudogene 2 | KRT16P2 |
| keratin 17, type I | KRT17 |
| keratin 17 pseudogene 3 | KRT17P3 |
| keratin 18, type I | KRT18 |
| keratin 18 pseudogene 19 | KRT18P19 |
| keratin 19, type I | KRT19 |
| keratin 2, type II | KRT2 |
| keratin 20, type I | KRT20 |
| keratin 24, type I | KRT24 |
| keratin 25, type I | KRT25 |
| keratin 27, type I | KRT27 |
| keratin 28, type I | KRT28 |
| keratin 3, type II | KRT3 |
| keratin 31, type I | KRT31 |
| keratin 33B, type I | KRT33B |
| keratin 36, type I | KRT36 |
| keratin 37, type I | KRT37 |
| keratin 38, type I | KRT38 |
| keratin 4, type II | KRT4 |
| keratin 5, type II | KRT5 |
| keratin 6A, type II | KRT6A |
| keratin 6B, type II | KRT6B |
| keratin 6C, type II | KRT6C |
| keratin 7, type II | KRT7 |
| keratin 71, type II | KRT71 |
| keratin 72, type II | KRT72 |
| keratin 73, type II | KRT73 |
| keratin 74, type II | KRT74 |
| keratin 75, type II | KRT75 |

TABLE 4-continued

| Suitable extracellular vesicle associated proteins | |
| --- | --- |
| Gene Name | Gene Symbol |
| keratin 76, type II | KRT76 |
| keratin 77, type II | KRT77 |
| keratin 78, type II | KRT78 |
| keratin 79, type II | KRT79 |
| keratin 8, type II | KRT8 |
| keratin 80, type II | KRT80 |
| keratin 84, type II | KRT84 |
| keratin 8 pseudogene 45 | KRT8P45 |
| keratin 8 pseudogene 9 | KRT8P9 |
| keratin 9, type I | KRT9 |
| keratinocyte differentiation-associated protein | KRTDAP |
| kinectin 1 (kinesin receptor) | KTN1 |
| L1 cell adhesion molecule | L1CAM |
| lacritin | LACRT |
| ladinin 1 | LAD1 |
| laminin, alpha 1 | LAMA1 |
| laminin, alpha 3 | LAMA3 |
| laminin, alpha 4 | LAMA4 |
| laminin, alpha 5 | LAMA5 |
| laminin, beta 1 | LAMB1 |
| laminin, beta 2 (laminin S) | LAMB2 |
| laminin, beta 3 | LAMB3 |
| laminin, gamma 1 (formerly LAMB2) | LAMC1 |
| laminin, gamma 2 | LAMC2 |
| lysosomal-associated membrane protein 1 | LAMP1 |
| lysosomal-associated membrane protein 2 | LAMP2 |
| late endosomal/lysosomal adaptor, MAPK and MTOR activator 1 | LAMTOR1 |
| late endosomal/lysosomal adaptor, MAPK and MTOR activator 3 | LAMTOR3 |
| late endosomal/lysosomal adaptor, MAPK and MTOR activator 4 | LAMTOR4 |
| LanC lantibiotic synthetase component C-like 1 (bacterial) | LANCL1 |
| LanC lantibiotic synthetase component C-like 2 (bacterial) | LANCL2 |
| leucine aminopeptidase 3 | LAP3 |
| lysosomal protein transmembrane 5 | LAPTM5 |
| La ribonucleoprotein domain family, member 7 | LARP7 |
| leucyl-tRNA synthetase | LARS |
| LAS1-like (S. cerevisiae) | LAS1L |
| LIM and SH3 protein 1 | LASP1 |
| linker for activation of T cells | LAT |
| linker for activation of T cells family, member 2 | LAT2 |
| lipopolysaccharide binding protein | LBP |
| lamin B receptor | LBR |
| LCK proto-oncogene, Src family tyrosine kinase | LCK |
| leucine carboxyl methyltransferase 1 | LCMT1 |
| lipocalin 1 | LCN1 |
| lipocalin 1 pseudogene 1 | LCN1P1 |
| lipocalin 2 | LCN2 |
| lymphocyte cytosolic protein 1 (L-plastin) | LCP1 |
| lymphocyte cytosolic protein 2 (SH2 domain containing leukocyte protein of 76 kDa) | LCP2 |
| lactate dehydrogenase A | LDHA |
| lactate dehydrogenase A-like 6B | LDHAL6B |
| lactate dehydrogenase B | LDHB |
| low density lipoprotein receptor | LDLR |
| leptin receptor | LEPR |
| leptin receptor overlapping transcript-like 1 | LEPROTL1 |
| leucine zipper-EF-hand containing transmembrane protein 1 | LETM1 |
| LFNG O-fucosylpeptide 3-beta-N-acetylglucosaminyltransferase | LFNG |
| lectin, galactoside-binding, soluble, 1 | LGALS1 |
| lectin, galactoside-binding, soluble, 3 | LGALS3 |
| lectin, galactoside-binding, soluble, 3 binding protein | LGALS3BP |
| lectin, galactoside-binding, soluble, 4 | LGALS4 |
| lectin, galactoside-binding, soluble, 7 | LGALS7 |
| lectin, galactoside-binding, soluble, 7B | LGALS7B |

TABLE 4-continued

| Suitable extracellular vesicle associated proteins | |
| --- | --- |
| Gene Name | Gene Symbol |
| lectin, galactoside-binding, soluble, 8 | LGALS8 |
| lectin, galactoside-binding, soluble, 9B | LGALS9B |
| lectin, galactoside-binding-like | LGALSL |
| leucine-rich repeat containing G protein-coupled receptor 4 | LGR4 |
| leucine-rich repeat containing G protein-coupled receptor 6 | LGR6 |
| lipoma HMGIC fusion partner-like 2 | LHFPL2 |
| leukemia inhibitory factor | LIF |
| ligase I, DNA, ATP-dependent | LIG1 |
| ligase III, DNA, ATP-dependent | LIG3 |
| LIM domain and actin binding 1 | LIMA1 |
| Lck interacting transmembrane adaptor 1 | LIME1 |
| LIM and senescent cell antigen-like domains 1 | LIMS1 |
| LIM and senescent cell antigen-like domains 2 | LIMS2 |
| LIM and senescent cell antigen-like domains 3-like | LIMS3L |
| lin-7 homolog A (C. elegans) | LIN7A |
| lin-7 homolog C (C. elegans) | LIN7C |
| long intergenic non-protein coding RNA 488 | LINC00488 |
| leucine rich repeat and Ig domain containing 1 | LINGO1 |
| lethal giant larvae homolog 1 (Drosophila) | LLGL1 |
| lethal giant larvae homolog 2 (Drosophila) | LLGL2 |
| lectin, mannose-binding, 1 | LMAN1 |
| lectin, mannose-binding 2 | LMAN2 |
| LMBR1 domain containing 1 | LMBRD1 |
| LIM and cysteine-rich domains 1 | LMCD1 |
| lamin A/C | LMNA |
| lamin B1 | LMNB1 |
| lamin B2 | LMNB2 |
| leucyl/cystinyl aminopeptidase | LNPEP |
| small nuclear ribonucleoprotein Sm D1 pseudogene | LOC100129492 |
| Ig kappa chain V-l region Walker-like | LOC100130100 |
| related RAS viral (r-ras) oncogene homolog 2 pseudogene | LOC100133211 |
| LOC100499484-C9orf174 readthrough | LOC100499484-C9ORF174 |
| uncharacterized LOC100996720 | LOC100996720 |
| uncharacterized LOC100996740 | LOC100996740 |
| uncharacterized LOC101060400 | LOC101060400 |
| DNA-directed RNA polymerase III subunit RPC5 | LOC101060521 |
| 40S ribosomal protein S26 | LOC101929876 |
| uroplakin-3b-like protein-like | LOC102724187 |
| histone H2B type F—S-like | LOC102724334 |
| cystathionine beta-synthase | LOC102724560 |
| splicing factor U2AF 35 kDa subunit | LOC102724594 |
| alpha-crystallin A chain | LOC102724652 |
| 40S ribosomal protein S8 pseudogene | LOC102724737 |
| immunoglobulin superfamily member 3-like | LOC102724844 |
| pyridoxal-dependent decarboxylase domain-containing protein 1 | LOC102724985 |
| peptidylprolyl isomerase A (cyclophilin A) pseudogene | LOC128192 |
| heat shock 70 kDa protein 5 (glucose-regulated protein, 78 kDa) pseudogene | LOC400750 |
| uncharacterized LOC440786 | LOC440786 |
| vitamin K epoxide reductase complex, subunit 1-like 1 pseudogene | LOC441241 |
| uncharacterized LOC442497 | LOC442497 |
| uncharacterized LOC642441 | LOC642441 |
| telomeric repeat-binding factor 1 pseudogene | LOC646127 |
| IST1 homolog | LOC728533 |
| exonuclease NEF-sp | LOC81691 |
| Ion peptidase 1, mitochondrial | LONP1 |
| lysyl oxidase-like 2 | LOXL2 |
| lysyl oxidase-like 4 | LOXL4 |
| lipoprotein, Lp(a) | LPA |
| lysophosphatidylcholine acyltransferase 3 | LPCAT3 |
| lysophosphatidylglycerol acyltransferase 1 | LPGAT1 |
| lipin 3 | LPIN3 |

TABLE 4-continued

| Suitable extracellular vesicle associated proteins | |
| --- | --- |
| Gene Name | Gene Symbol |
| lipoprotein lipase | LPL |
| lactoperoxidase | LPO |
| LIM domain containing preferred translocation partner in lipoma | LPP |
| LPS-responsive vesicle trafficking, beach and anchor containing | LRBA |
| leucine-rich alpha-2-glycoprotein 1 | LRG1 |
| low density lipoprotein receptor-related protein 1 | LRP1 |
| low density lipoprotein receptor-related protein 10 | LRP10 |
| low density lipoprotein receptor-related protein 1B | LRP1B |
| low density lipoprotein receptor-related protein 2 | LRP2 |
| low density lipoprotein receptor-related protein 4 | LRP4 |
| low density lipoprotein receptor-related protein 5 | LRP5 |
| low density lipoprotein receptor-related protein 6 | LRP6 |
| leucine-rich pentatricopeptide repeat containing | LRPPRC |
| leucine rich repeat containing 1 | LRRC1 |
| leucine rich repeat containing 15 | LRRC15 |
| leucine rich repeat containing 16A | LRRC16A |
| leucine rich repeat containing 26 | LRRC26 |
| leucine rich repeat containing 32 | LRRC32 |
| leucine rich repeat containing 47 | LRRC47 |
| leucine rich repeat containing 57 | LRRC57 |
| leucine rich repeat containing 59 | LRRC59 |
| leucine rich repeat containing 75A | LRRC75A |
| leucine rich repeat containing 8 family, member A | LRRC8A |
| leucine rich repeat containing 8 family, member C | LRRC8C |
| leucine rich repeat containing 8 family, member D | LRRC8D |
| leucine rich repeat containing 8 family, member E | LRRC8E |
| leucine rich repeat (in FLII) interacting protein 1 | LRRFIP1 |
| leucine rich repeat (in FLII) interacting protein 2 | LRRFIP2 |
| leucine-rich repeat kinase 2 | LRRK2 |
| leucine rich repeat and sterile alpha motif containing 1 | LRSAM1 |
| LSM12 homolog (*S. cerevisiae*) | LSM12 |
| LSM2 homolog, U6 small nuclear RNA associated (*S. cerevisiae*) | LSM2 |
| LSM3 homolog, U6 small nuclear RNA associated (*S. cerevisiae*) | LSM3 |
| LSM6 homolog, U6 small nuclear RNA associated (*S. cerevisiae*) | LSM6 |
| lymphocyte-specific protein 1 | LSP1 |
| lipolysis stimulated lipoprotein receptor | LSR |
| lanosterol synthase (2,3-oxidosqualene-lanosterol cyclase) | LSS |
| leukocyte specific transcript 1 | LST1 |
| leukotriene A4 hydrolase | LTA4H |
| leukotriene B4 receptor | LTB4R |
| latent transforming growth factor beta binding protein 1 | LTBP1 |
| latent transforming growth factor beta binding protein 2 | LTBP2 |
| latent transforming growth factor beta binding protein 3 | LTBP3 |
| latent transforming growth factor beta binding protein 4 | LTBP4 |
| lactotransferrin | LTF |
| leukocyte receptor tyrosine kinase | LTK |
| listerin E3 ubiquitin protein ligase 1 | LTN1 |
| LUC7-like (*S. cerevisiae*) | LUC7L |
| lumican | LUM |

TABLE 4-continued

| Suitable extracellular vesicle associated proteins | |
| --- | --- |
| Gene Name | Gene Symbol |
| lymphocyte antigen 6 complex, locus G6F | LY6G6F |
| lymphocyte antigen 75 | LY75 |
| LY75-CD302 readthrough | LY75-CD302 |
| lymphocyte antigen 9 | LY9 |
| Ly1 antibody reactive | LYAR |
| LYN proto-oncogene, Src family tyrosine kinase | LYN |
| LY6/PLAUR domain containing 3 | LYPD3 |
| lysophospholipase I | LYPLA1 |
| lysophospholipase II | LYPLA2 |
| lysophospholipase-like 1 | LYPLAL1 |
| lysozyme | LYZ |
| leucine-zipper-like transcription regulator 1 | LZTR1 |
| mannose-6-phosphate receptor (cation dependent) | M6PR |
| microtubule-actin crosslinking factor 1 | MACF1 |
| MAP-kinase activating death domain | MADD |
| melanoma antigen family A4 | MAGEA4 |
| melanoma antigen family B17 | MAGEB17 |
| melanoma antigen family B2 | MAGEB2 |
| melanoma antigen family D2 | MAGED2 |
| membrane associated guanylate kinase, WW and PDZ domain containing 3 | MAGI3 |
| mago-nashi homolog B (*Drosophila*) | MAGOHB |
| magnesium transporter 1 | MAGT1 |
| mal, T-cell differentiation protein 2 (gene/pseudogene) | MAL2 |
| MALT1 paracaspase | MALT1 |
| MAM domain containing 2 | MAMDC2 |
| mannosidase, alpha, class 1A, member 1 | MAN1A1 |
| mannosidase, alpha, class 1A, member 2 | MAN1A2 |
| mannosidase, alpha, class 1B, member 1 | MAN1B1 |
| mannosidase, alpha, class 2A, member 1 | MAN2A1 |
| mannosidase, alpha, class 2B, member 1 | MAN2B1 |
| mesencephalic astrocyte-derived neurotrophic factor | MANF |
| microtubule-associated protein 1A | MAP1A |
| microtubule-associated protein 1B | MAP1B |
| microtubule-associated protein 1S | MAP1S |
| microtubule-associated protein 2 | MAP2 |
| microtubule-associated protein Tau | MAPT |
| mitogen-activated protein kinase kinase 1 | MAP2K1 |
| mitogen-activated protein kinase kinase 2 | MAP2K2 |
| mitogen-activated protein kinase kinase 3 | MAP2K3 |
| mitogen-activated protein kinase kinase 4 | MAP2K4 |
| mitogen-activated protein kinase kinase 6 | MAP2K6 |
| mitogen-activated protein kinase kinase 7 | MAP2K7 |
| mitogen-activated protein kinase kinase kinase 1, E3 ubiquitin protein ligase | MAP3K1 |
| mitogen-activated protein kinase kinase kinase 19 | MAP3K19 |

TABLE 4-continued

| Suitable extracellular vesicle associated proteins | |
| --- | --- |
| Gene Name | Gene Symbol |
| microtubule-associated protein 4 | MAP4 |
| mitogen-activated protein kinase kinase kinase kinase 4 | MAP4K4 |
| microtubule-associated protein 7 | MAP7 |
| mitogen-activated protein kinase 1 | MAPK1 |
| mitogen-activated protein kinase 14 | MAPK14 |
| mitogen-activated protein kinase 1 interacting protein 1-like | MAPK1IP1L |
| mitogen-activated protein kinase 3 | MAPK3 |
| mitogen-activated protein kinase 8 | MAPK8 |
| mitogen-activated protein kinase 8 interacting protein 1 | MAPK8IP1 |
| mitogen-activated protein kinase 9 | MAPK9 |
| mitogen-activated protein kinase-activated protein kinase 2 | MAPKAPK2 |
| microtubule-associated protein, RP/EB family, member 1 | MAPRE1 |
| microtubule-associated protein, RP/EB family, member 2 | MAPRE2 |
| myristoylated alanine-rich protein kinase C substrate | MARCKS |
| MARCKS-like 1 | MARCKSL1 |
| MAP/microtubule affinity-regulating kinase 2 | MARK2 |
| MAP/microtubule affinity-regulating kinase 3 | MARK3 |
| methionyl-tRNA synthetase | MARS |
| MARVEL domain containing 2 | MARVELD2 |
| mannan-binding lectin serine peptidase 1 (C4/C2 activating component of Ra-reactive factor) | MASP1 |
| mannan-binding lectin serine peptidase 2 | MASP2 |
| methionine adenosyltransferase I, alpha | MAT1A |
| methionine adenosyltransferase II, alpha | MAT2A |
| methionine adenosyltransferase II, beta | MAT2B |
| matrilin 2 | MATN2 |
| matrin 3 | MATR3 |
| mitochondrial antiviral signaling protein | MAVS |
| methyl-CpG binding domain protein 3 | MBD3 |
| methyl-CpG binding domain protein 3-like 5 | MBD3L5 |
| methyl-CpG binding domain protein 5 | MBD5 |
| mannose-binding lectin (protein C) 2, soluble | MBL2 |
| metallo-beta-lactamase domain containing 2 | MBLAC2 |
| muscleblind-like splicing regulator 1 | MBNL1 |
| melanocortin 1 receptor (alpha melanocyte stimulating hormone receptor) | MC1R |
| melanoma cell adhesion molecule | MCAM |
| mutated in colorectal cancers | MCC |
| methylcrotonoyl-CoA carboxylase 1 (alpha) | MCCC1 |

TABLE 4-continued

Suitable extracellular vesicle associated proteins

| Gene Name | Gene Symbol |
| --- | --- |
| MCF.2 cell line derived transforming sequence-like 2 | MCF2L2 |
| minichromosome maintenance complex component 10 | MCM10 |
| minichromosome maintenance complex component 2 | MCM2 |
| minichromosome maintenance complex component 3 | MCM3 |
| minichromosome maintenance complex component 4 | MCM4 |
| minichromosome maintenance complex component 5 | MCM5 |
| minichromosome maintenance complex component 6 | MCM6 |
| minichromosome maintenance complex component 7 | MCM7 |
| minichromosome maintenance complex binding protein | MCMBP |
| mucolipin 1 | MCOLN1 |
| malignant T cell amplified sequence 1 | MCTS1 |
| malate dehydrogenase 1, NAD (soluble) | MDH1 |
| malate dehydrogenase 2, NAD (mitochondrial) | MDH2 |
| midkine (neurite growth-promoting factor 2) | MDK |
| MDN1, midasin homolog (yeast) | MDN1 |
| magnesium-dependent phosphatase 1 | MDP1 |
| malic enzyme 1, NADP(+)-dependent, cytosolic | ME1 |
| malic enzyme 3, NADP(+)-dependent, mitochondrial | ME3 |
| methyl CpG binding protein 2 | MECP2 |
| mediator complex subunit 20 | MED20 |
| mediator complex subunit 23 | MED23 |
| multiple EGF-like-domains 10 | MEGF10 |
| multiple EGF-like-domains 8 | MEGF8 |
| mediator of cell motility 1 | MEMO1 |
| multiple endocrine neoplasia I | MEN1 |
| meprin A, alpha (PABA peptide hydrolase) | MEP1A |
| meprin A, beta | MEP1B |
| mesoderm specific transcript | MEST |
| MET proto-oncogene, receptor tyrosine kinase | MET |
| methionyl aminopeptidase 2 | METAP2 |
| meteorin, glial cell differentiation regulator-like | METRNL |
| methyltransferase like 13 | METTL13 |
| methyltransferase like 16 | METTL16 |
| mex-3 RNA binding family member B | MEX3B |
| microfibrillar-associated protein 4 | MFAP4 |
| milk fat globule-EGF factor 8 protein | MFGE8 |
| antigen p97 (melanoma associated) identified by monoclonal antibodies 133.2 and 96.5 | MFI2 |
| major facilitator superfamily domain containing 1 | MFSD1 |
| major facilitator superfamily domain containing 2B | MFSD2B |
| maltase-glucoamylase | MGAM |

TABLE 4-continued

| Suitable extracellular vesicle associated proteins | |
| --- | --- |
| Gene Name | Gene Symbol |
| mannosyl (alpha-1,3-)-glycoprotein beta-1,2-N-acetylglucosaminyltransferase | MGAT1 |
| mannosyl (alpha-1,3-)-glycoprotein beta-1,4-N-acetylglucosaminyltransferase, isozyme A | MGAT4A |
| mannosyl (alpha-1,6-)-glycoprotein beta-1,6-N-acetyl-glucosaminyltransferase | MGAT5 |
| monoglyceride lipase | MGLL |
| O-6-methylguanine-DNA methyltransferase | MGMT |
| matrix Gla protein | MGP |
| mahogunin ring finger 1, E3 ubiquitin protein ligase | MGRN1 |
| microsomal glutathione S-transferase 2 | MGST2 |
| microsomal glutathione S-transferase 3 | MGST3 |
| mindbomb E3 ubiquitin protein ligase 2 | MIB2 |
| MHO class I polypeptide-related sequence A | MICA |
| microtubule associated monooxygenase, calponin and LIM domain containing 1 | MICAL1 |
| midline 2 | MID2 |
| mesoderm induction early response 1, family member 3 | MIER3 |
| macrophage migration inhibitory factor (glycosylation-inhibiting factor) | MIF |
| MIF antisense RNA 1 | MIF-AS1 |
| misshapen-like kinase 1 | MINK1 |
| mitotic spindle positioning | MISP |
| MIT, microtubule interacting and transport, domain containing 1 | MITD1 |
| makorin ring finger protein 1 | MKRN1 |
| melan-A | MLANA |
| megalencephalic leukoencephalopathy with subcortical cysts 1 | MLC1 |
| malectin | MLEC |
| myeloid leukemia factor 2 | MLF2 |
| mutL homolog 1 | MLH1 |
| myeloid/lymphoid or mixed-lineage leukemia (trithorax homolog, Drosophila); translocated to, 3 | MLLT3 |
| myeloid/lymphoid or mixed-lineage leukemia (trithorax homolog, Drosophila); translocated to, 4 | MLLT4 |
| MTOR associated protein, LST8 homolog (*S. cerevisiae*) | MLST8 |
| membrane metallo-endopeptidase | MME |
| matrix metallopeptidase 1 | MMP1 |
| matrix metallopeptidase 10 | MMP10 |
| matrix metallopeptidase 14 (membrane-inserted) | MMP14 |
| matrix metallopeptidase 15 (membrane-inserted) | MMP15 |
| matrix metallopeptidase 2 | MMP2 |
| matrix metallopeptidase 24 (membrane-inserted) | MMP24 |
| matrix metallopeptidase 25 | MMP25 |
| matrix metallopeptidase 3 | MMP3 |
| matrix metallopeptidase 7 | MMP7 |
| matrix metallopeptidase 9 | MMP9 |
| multimerin 1 | MMRN1 |
| multimerin 2 | MMRN2 |
| MMS19 nucleotide excision | MMS19 |

TABLE 4-continued

| Gene Name | Gene Symbol |
|-----------|-------------|
| repair homolog (*S. cerevisiae*) | |
| myeloid cell nuclear differentiation antigen | MNDA |
| MOB kinase activator 1A | MOB1A |
| MOB kinase activator 1B | MOB1B |
| MOB kinase activator 2 | MOB2 |
| molybdenum cofactor synthesis 3 | MOCS3 |
| mannosyl-oligosaccharide glucosidase | MOGS |
| MON2 homolog (*S. cerevisiae*) | MON2 |
| MORC family CW-type zinc finger 3 | MORC3 |
| v-mos Moloney murine sarcoma viral oncogene homolog | MOS |
| Mov10 RISC complex RNA helicase | MOV10 |
| monooxygenase, DBH-like 1 | MOXD1 |
| mannose phosphate isomerase | MPI |
| MPL proto-oncogene, thrombopoietin receptor | MPL |
| myeloperoxidase | MPO |
| membrane protein, palmitoylated 1, 55 kDa | MPP1 |
| membrane protein, palmitoylated 5 (MAGUK p55 subfamily member 5) | MPP5 |
| membrane protein, palmitoylated 6 (MAGUK p55 subfamily member 6) | MPP6 |
| membrane protein, palmitoylated 7 (MAGUK p55 subfamily member 7) | MPP7 |
| metallophosphoesterase 1 | MPPE1 |
| mercaptopyruvate sulfurtransferase | MPST |
| myelin protein zero-like 1 | MPZL1 |
| myelin protein zero-like 2 | MPZL2 |
| mannose receptor, C type 2 | MRC2 |
| MRE11 meiotic recombination 11 homolog A (*S. cerevisiae*) | MRE11A |
| methylthioribose-1-phosphate isomerase 1 | MRI1 |
| maestro heat-like repeat family member 1 | MROH1 |
| mitochondrial ribosomal protein S17 | MRPS17 |
| mitochondrial ribosomal protein S22 | MRPS22 |
| mRNA turnover 4 homolog (*S. cerevisiae*) | MRTO4 |
| murine retrovirus integration site 1 homolog | MRVI1 |
| membrane-spanning 4-domains, subfamily A, member 1 | MS4A1 |
| mutS homolog 2 | MSH2 |
| mutS homolog 3 | MSH3 |
| mutS homolog 6 | MSH6 |
| musashi RNA-binding protein 2 | MSI2 |
| male-specific lethal 1 homolog (*Drosophila*) | MSL1 |
| mesothelin | MSLN |
| methylsterol monooxygenase 1 | MSMO1 |
| microseminoprotein, prostate associated | MSMP |
| moesin | MSN |
| methionine sulfoxide reductase A | MSRA |
| macrophage stimulating 1 receptor | MST1R |

TABLE 4-continued

| Gene Name | Gene Symbol |
| --- | --- |
| Suitable extracellular vesicle associated proteins | |
| metastasis associated 1 family, member 2 | MTA2 |
| metastasis associated 1 family, member 3 | MTA3 |
| methylthioadenosine phosphorylase | MTAP |
| mitochondrial carrier 2 | MTCH2 |
| methylenetetrahydrofolate dehydrogenase (NADP+ dependent) 1, methenyltetrahydrofolate cyclohydrolase, formyltetrahydrofolate synthetase | MTHFD1 |
| methylenetetrahydrofolate dehydrogenase (NADP+ dependent) 1-like | MTHFD1L |
| myotubularin related protein 10 | MTMR10 |
| myotubularin related protein 12 | MTMR12 |
| mechanistic target of rapamycin (serine/threonine kinase) | MTOR |
| myotrophin | MTPN |
| metastasis suppressor 1 | MTSS1 |
| microsomal triglyceride transfer protein | MTTP |
| microtubule associated tumor suppressor candidate 2 | MTUS2 |
| mucin 1, cell surface associated | MUC1 |
| mucin 13, cell surface associated | MUC13 |
| mucin 16, cell surface associated | MUC16 |
| mucin 17, cell surface associated | MUC17 |
| mucin 4, cell surface associated | MUC4 |
| mucin 5AC, oligomeric mucus/gel-forming | MUC5AC |
| mucin 6, oligomeric mucus/gel-forming | MUC6 |
| mucin 7, secreted | MUC7 |
| melanoma associated antigen (mutated) 1-like 1 | MUM1L1 |
| multivesicular body subunit 12A | MVB12A |
| multivesicular body subunit 12B | MVB12B |
| mevalonate (diphospho) decarboxylase | MVD |
| mevalonate kinase | MVK |
| major vault protein | MVP |
| MX dynamin-like GTPase 1 | MX1 |
| MX dynamin-like GTPase 2 | MX2 |
| matrix-remodelling associated 5 | MXRA5 |
| matrix-remodelling associated 8 | MXRA8 |
| myeloid-associated differentiation marker | MYADM |
| MYB binding protein (P160) 1a | MYBBP1A |
| myosin binding protein C, fast type | MYBPC2 |
| MYC binding protein 2, E3 ubiquitin protein ligase | MYCBP2 |
| MYCBP associated protein | MYCBPAP |
| myc target 1 | MYCT1 |
| myeloid differentiation primary response 88 | MYD88 |
| myeloid-derived growth factor | MYDGF |
| myosin, heavy chain 10, non-muscle | MYH10 |
| myosin, heavy chain 11, smooth muscle | MYH11 |
| myosin, heavy chain 13, skeletal muscle | MYH13 |
| myosin, heavy chain 14, non-muscle | MYH14 |
| myosin, heavy chain 3, skeletal muscle, embryonic | MYH3 |

TABLE 4-continued

| Suitable extracellular vesicle associated proteins | |
| --- | --- |
| Gene Name | Gene Symbol |
| myosin, heavy chain 7, cardiac muscle, beta | MYH7 |
| myosin, heavy chain 8, skeletal muscle, perinatal | MYH8 |
| myosin, heavy chain 9, non-muscle | MYH9 |
| myosin, light chain 1, alkali; skeletal, fast | MYL1 |
| myosin, light chain 12A, regulatory, non-sarcomeric | MYL12A |
| myosin, light chain 12B, regulatory | MYL12B |
| myosin, light chain 3, alkali; ventricular, skeletal, slow | MYL3 |
| myosin, light chain 6, alkali, smooth muscle and non-muscle | MYL6 |
| myosin, light chain 6B, alkali, smooth muscle and non-muscle | MYL6B |
| myosin, light chain 9, regulatory | MYL9 |
| myosin light chain kinase | MYLK |
| myosin light chain kinase 2 | MYLK2 |
| myosin light chain kinase 3 | MYLK3 |
| myosin XVA | MYO15A |
| myosin XVI | MYO16 |
| myosin XVIIIA | MYO18A |
| myosin IA | MYO1A |
| myosin IB | MYO1B |
| myosin IC | MYO1C |
| myosin ID | MYO1D |
| myosin IE | MYO1E |
| myosin IF | MYO1F |
| myosin IG | MYO1G |
| myosin IIIB | MYO3B |
| myosin VA (heavy chain 12, myoxin) | MYO5A |
| myosin VB | MYO5B |
| myosin VI | MYO6 |
| myosin VIIA | MYO7A |
| myosin IXB | MYO9B |
| myocilin, trabecular meshwork inducible glucocorticoid response | MYOC |
| myoferlin | MYOF |
| myozenin 2 | MYOZ2 |
| NEDD4 binding protein 2-like 2 | N4BP2L2 |
| N(alpha)-acetyltransferase 10, NatA catalytic subunit | NAA10 |
| N(alpha)-acetyltransferase 15, NatA auxiliary subunit | NAA15 |
| N(alpha)-acetyltransferase 16, NatA auxiliary subunit | NAA16 |
| N(alpha)-acetyltransferase 50, NatE catalytic subunit | NAA50 |
| N-acetylated alpha-linked acidic dipeptidase 2 | NAALAD2 |
| NGFI-A binding protein 2 (EGR1 binding protein 2) | NAB2 |
| nascent polypeptide-associated complex alpha subunit | NACA |
| nascent polypeptide-associated complex alpha subunit 2 | NACA2 |
| NEDD8 activating enzyme E1 subunit 1 | NAE1 |
| N-acetylgalactosaminidase, alpha- | NAGA |
| N-acetylglucosamine kinase | NAGK |
| N-acetylglucosaminidase, alpha | NAGLU |
| nicotinamide phosphoribosyltransferase | NAMPT |

TABLE 4-continued

| Suitable extracellular vesicle associated proteins | |
| --- | --- |
| Gene Name | Gene Symbol |
| N-acetylneuraminic acid synthase | NANS |
| nucleosome assembly protein 1-like 1 | NAP1L1 |
| nucleosome assembly protein 1-like 4 | NAP1L4 |
| N-ethylmaleimide-sensitive factor attachment protein, alpha | NAPA |
| N-acyl phosphatidylethanolamine phospholipase D | NAPEPLD |
| N-ethylmaleimide-sensitive factor attachment protein, gamma | NAPG |
| Nicotinate phosphoribosyltransferase | NAPRT |
| napsin A aspartic peptidase | NAPSA |
| asparaginyl-tRNA synthetase | NARS |
| nuclear autoantigenic sperm protein (histone-binding) | NASP |
| N-acetyltransferase 1 (arylamine N-acetyltransferase) | NAT1 |
| N-acetyltransferase 10 (GCN5-related) | NAT10 |
| N-acetyltransferase 8-like (GCN5-related, putative) | NAT8L |
| neuron navigator 1 | NAV1 |
| neurobeachin-like 2 | NBEAL2 |
| neuroblastoma 1, DAN family BMP antagonist | NBL1 |
| neighbor of BRCA1 gene 1 | NBR1 |
| neurocalcin delta | NCALD |
| neural cell adhesion molecule 1 | NCAM1 |
| non-SMC condensin I complex, subunit D2 | NCAPD2 |
| non-SMC condensin I complex, subunit G | NCAPG |
| non-SMC condensin II complex, subunit G2 | NCAPG2 |
| non-SMC condensin I complex, subunit H | NCAPH |
| nuclear cap binding protein subunit 1, 80 kDa | NCBP1 |
| nuclear cap binding protein subunit 2, 20 kDa | NCBP2 |
| non-specific cytotoxic cell receptor protein 1 homolog (zebrafish) | NCCRP1 |
| neutral cholesterol ester hydrolase 1 | NCEH1 |
| neutrophil cytosolic factor 2 | NCF2 |
| neutrophil cytosolic factor 4, 40 kDa | NCF4 |
| NCK adaptor protein 1 | NCK1 |
| NCK adaptor protein 2 | NCK2 |
| NCK-associated protein 1 | NCKAP1 |
| NCK-associated protein 1-like | NCKAP1L |
| nucleolin | NCL |
| nuclear receptor coactivator 4 | NCOA4 |
| neuronal calcium sensor 1 | NCS1 |
| nicastrin | NCSTN |
| nudE neurodevelopment protein 1 | NDE1 |
| necdin-like 2 | NDNL2 |
| N-myc downstream regulated 1 | NDRG1 |
| NDRG family member 2 | NDRG2 |
| NDRG family member 3 | NDRG3 |
| NADH dehydrogenase (ubiquinone) Fe&endash;S protein 2, 49 kDa (NADH-coenzyme Q reductase) | NDUFS2 |
| nebulin | NEB |

TABLE 4-continued

Suitable extracellular vesicle associated proteins

| Gene Name | Gene Symbol |
| --- | --- |
| nebulette | NEBL |
| neural precursor cell expressed, developmentally down-regulated 1 | NEDD1 |
| neural precursor cell expressed, developmentally down-regulated 4, E3 ubiquitin protein ligase | NEDD4 |
| neural precursor cell expressed, developmentally down-regulated 4-like, E3 ubiquitin protein ligase | NEDD4L |
| neural precursor cell expressed, developmentally down-regulated 8 | NEDD8 |
| neural precursor cell expressed, developmentally down-regulated 9 | NEDD9 |
| neurofilament, heavy polypeptide | NEFH |
| neurofilament, light polypeptide | NEFL |
| neurofilament, medium polypeptide | NEFM |
| NIMA-related kinase 10 | NEK10 |
| NIMA-related kinase 7 | NEK7 |
| NIMA-related kinase 9 | NEK9 |
| negative elongation factor complex member B | NELFB |
| negative elongation factor complex member C/D | NELFCD |
| negative elongation factor complex member E | NELFE |
| neogenin 1 | NEO1 |
| nestin | NES |
| sialidase 1 (lysosomal sialidase) | NEU1 |
| neurofibromin 1 | NF1 |
| neurofibromin 2 (merlin) | NF2 |
| nuclear factor of activated T-cells, cytoplasmic, calcineurin-dependent 1 | NFATC1 |
| nuclear factor of activated T-cells, cytoplasmic, calcineurin-dependent 4 | NFATC4 |
| nuclear factor I/A | NFIA |
| nuclear factor, interleukin 3 regulated | NFIL3 |
| nuclear factor of kappa light polypeptide gene enhancer in B-cells 2 (p49/p100) | NFKB2 |
| nerve growth factor receptor | NGFR |
| N-glycanase 1 | NGLY1 |
| NHL repeat containing 2 | NHLRC2 |
| NHP2 ribonucleoprotein | NHP2 |
| NHP2 non-histone chromosome protein 2-like 1 (*S. cerevisiae*) | NHP2L1 |
| Nance-Horan syndrome (congenital cataracts and dental anomalies) | NHS |
| nidogen 1 | NID1 |
| nidogen 2 (osteonidogen) | NID2 |
| NIF3 NGG1 interacting factor 3-like 1 (*S. cerevisiae*) | NIF3L1 |
| nucleolar protein interacting with the FHA domain of MKI67 | NIFK |
| ninein (GSK3B interacting protein) | NIN |
| ninjurin 1 | NINJ1 |
| Nipped-B homolog (Drosophila) | NIPBL |
| nipsnap homolog 1 (C. elegans) | NIPSNAP1 |
| nischarin | NISCH |

TABLE 4-continued

| Suitable extracellular vesicle associated proteins | |
| --- | --- |
| Gene Name | Gene Symbol |
| nitrilase 1 | NIT1 |
| nitrilase family, member 2 | NIT2 |
| NFKB repressing factor | NKRF |
| NK6 homeobox 1 | NKX6-1 |
| NLR family, pyrin domain containing 8 | NLRP8 |
| NMD3 ribosome export adaptor | NMD3 |
| NME/NM23 nucleoside diphosphate kinase 1 | NME1 |
| NME1-NME2 readthrough | NME1-NME2 |
| NME/NM23 nucleoside diphosphate kinase 2 | NME2 |
| NME/NM23 nucleoside diphosphate kinase 2 pseudogene 1 | NME2P1 |
| NmrA-like family domain containing 1 | NMRAL1 |
| N-myristoyltransferase 1 | NMT1 |
| N-myristoyltransferase 2 | NMT2 |
| nucleotide-binding oligomerization domain containing 1 | NOD1 |
| nucleolar protein 9 | NOL9 |
| nucleolar and coiled-body phosphoprotein 1 | NOLC1 |
| NODAL modulator 1 | NOMO1 |
| NODAL modulator 2 | NOMO2 |
| NODAL modulator 3 | NOMO3 |
| non-POU domain containing, octamer-binding | NONO |
| NOP10 ribonucleoprotein | NOP10 |
| NOP14 nucleolar protein | NOP14 |
| NOP16 nucleolar protein | NOP16 |
| NOP2 nucleolar protein | NOP2 |
| NOP56 ribonucleoprotein | NOP56 |
| NOP58 ribonucleoprotein | NOP58 |
| NOP9 nucleolar protein | NOP9 |
| nitric oxide synthase trafficking | NOSTRIN |
| notch 1 | NOTCH1 |
| notch 2 | NOTCH2 |
| NADPH oxidase 3 | NOX3 |
| Niemann-Pick disease, type C1 | NPC1 |
| aminopeptidase puromycin sensitive | NPEPPS |
| nephrosis 1, congenital, Finnish type (nephrin) | NPHS1 |
| nephrosis 2, idiopathic, steroid-resistant (podocin) | NPHS2 |
| nuclear protein localization 4 homolog (*S. cerevisiae*) | NPLOC4 |
| nucleophosmin (nucleolar phosphoprotein B23, numatrin) | NPM1 |
| nucleophosmin/nucleoplasmin 3 | NPM3 |
| nephronectin | NPNT |
| natriuretic peptide receptor 1 | NPR1 |
| natriuretic peptide receptor 3 | NPR3 |
| neuroplastin | NPTN |
| NAD(P)H dehydrogenase, quinone 1 | NQO1 |
| NAD(P)H dehydrogenase, quinone 2 | NQO2 |
| nuclear receptor subfamily 3, group C, member 1 (glucocorticoid receptor) | NR3C1 |
| neuroblastoma RAS viral (v-ras) oncogene homolog | NRAS |
| nuclear respiratory factor 1 | NRF1 |
| neuregulin 2 | NRG2 |
| neuropilin 1 | NRP1 |
| neuropilin 2 | NRP2 |
| NAD(P) dependent steroid dehydrogenase-like | NSDHL |

TABLE 4-continued

| Suitable extracellular vesicle associated proteins | |
| --- | --- |
| Gene Name | Gene Symbol |
| N-ethylmaleimide-sensitive factor | NSF |
| NSFL1 (p97) cofactor (p47) | NSFL1C |
| NOP2/Sun RNA methyltransferase family, member 2 | NSUN2 |
| 5',3'-nucleotidase, cytosolic | NT5C |
| 5'-nucleotidase, cytosolic II | NT5C2 |
| 5'-nucleotidase domain containing 1 | NT5DC1 |
| 5'-nucleotidase, ecto (CD73) | NT5E |
| N-terminal Xaa-Pro-Lys N-methyltransferase 1 | NTMT1 |
| nucleoside-triphosphatase, cancer-related | NTPCR |
| neurotrophic tyrosine kinase, receptor, type 2 | NTRK2 |
| negative regulator of ubiquitin-like proteins 1 | NUB1 |
| nucleotide binding protein 2 | NUBP2 |
| nucleobindin 1 | NUCB1 |
| nucleobindin 2 | NUCB2 |
| nuclear casein kinase and cyclin-dependent kinase substrate 1 | NUCKS1 |
| nudC nuclear distribution protein | NUDC |
| NudC domain containing 1 | NUDCD1 |
| NudC domain containing 2 | NUDCD2 |
| nudix (nucleoside diphosphate linked moiety X)-type motif 16-like 1 | NUDT16L1 |
| nudix (nucleoside diphosphate linked moiety X)-type motif 21 | NUDT21 |
| nudix (nucleoside diphosphate linked moiety X)-type motif 4 | NUDT4 |
| nudix (nucleoside diphosphate linked moiety X)-type motif 5 | NUDT5 |
| nudix (nucleoside diphosphate linked moiety X)-type motif 9 | NUDT9 |
| nuclear mitotic apparatus protein 1 | NUMA1 |
| numb homolog (*Drosophila*) | NUMB |
| numb homolog (*Drosophila*)-like | NUMBL |
| nucleoporin 160 kDa | NUP160 |
| nucleoporin 205 kDa | NUP205 |
| nucleoporin 210 kDa | NUP210 |
| nucleoporin 43 kDa | NUP43 |
| nucleoporin 88 kDa | NUP88 |
| nucleoporin 93 kDa | NUP93 |
| nucleoporin like 2 | NUPL2 |
| nucleolar and spindle associated protein 1 | NUSAP1 |
| nuclear transport factor 2 | NUTF2 |
| nuclear RNA export factor 1 | NXF1 |
| nucleoredoxin | NXN |
| neurexophilin and PC-esterase domain family, member 4 | NXPE4 |
| O-acyl-ADP-ribose deacylase 1 | OARD1 |
| 2'-5'-oligoadenylate synthetase 2, 69/71 kDa | OAS2 |
| 2'-5'-oligoadenylate synthetase 3, 100 kDa | OAS3 |
| ornithine aminotransferase | OAT |
| oligonucleotide/oligosaccharide-binding fold containing 1 | OBFC1 |
| odorant binding protein 2A | OBP2A |
| obscurin, cytoskeletal calmodulin and titin-interacting RhoGEF | OBSCN |

TABLE 4-continued

| Suitable extracellular vesicle associated proteins | |
| --- | --- |
| Gene Name | Gene Symbol |
| OCIA domain containing 2 | OCIAD2 |
| occludin | OCLN |
| oculocerebrorenal syndrome of Lowe | OCRL |
| oral-facial-digital syndrome 1 | OFD1 |
| opioid growth factor receptor | OGFR |
| osteoglycin | OGN |
| O-linked N-acetylglucosamine (GlcNAc) transferase | OGT |
| oncoprotein induced transcript 3 | OIT3 |
| Obg-like ATPase 1 | OLA1 |
| olfactomedin 4 | OLFM4 |
| olfactomedin-like 3 | OLFML3 |
| oxidized low density lipoprotein (lectin-like) receptor 1 | OLR1 |
| optic atrophy 1 (autosomal dominant) | OPA1 |
| optic atrophy 3 (autosomal recessive, with chorea and spastic paraplegia) | OPA3 |
| opiate receptor-like 1 | OPRL1 |
| opioid receptor, mu 1 | OPRM1 |
| optineurin | OPTN |
| olfactory receptor, family 11, subfamily L, member 1 | OR11L1 |
| olfactory receptor, family 2, subfamily A, member 4 | OR2A4 |
| olfactory receptor, family 2, subfamily T, member 8 | OR2T8 |
| ORAI calcium release-activated calcium modulator 1 | ORAI1 |
| orosomucoid 1 | ORM1 |
| ORMDL sphingolipid biosynthesis regulator 1 | ORMDL1 |
| ORMDL sphingolipid biosynthesis regulator 2 | ORMDL2 |
| ORMDL sphingolipid biosynthesis regulator 3 | ORMDL3 |
| osteosarcoma amplified 9, endoplasmic reticulum lectin | OS9 |
| oxysterol binding protein | OSBP |
| oxysterol binding protein-like 1A | OSBPL1A |
| O-sialoglycoprotein endopeptidase | OSGEP |
| oncostatin M | OSM |
| oncostatin M receptor | OSMR |
| oligosaccharyltransferase complex subunit (non-catalytic) | OSTC |
| osteoclast stimulating factor 1 | OSTF1 |
| ornithine carbamoyltransferase | OTC |
| OTU deubiquitinase, ubiquitin aldehyde binding 1 | OTUB1 |
| OTU deubiquitinase 7A | OTUD7A |
| OTU deubiquitinase 7B | OTUD7B |
| oxidoreductase NAD-binding domain containing 1 | OXNAD1 |
| oxidative stress responsive 1 | OXSR1 |
| oxytocin receptor | OXTR |
| purinergic receptor P2X, ligand gated ion channel, 1 | P2RX1 |
| purinergic receptor P2X, ligand gated ion channel, 4 | P2RX4 |
| purinergic receptor P2X, ligand gated ion channel, 5 | P2RX5 |
| purinergic receptor P2Y, G-protein coupled, 12 | P2RY12 |
| purinergic receptor P2Y, G-protein coupled, 2 | P2RY2 |
| prolyl 3-hydroxylase 1 | P3H1 |

TABLE 4-continued

| Suitable extracellular vesicle associated proteins | |
| --- | --- |
| Gene Name | Gene Symbol |
| prolyl 4-hydroxylase, alpha polypeptide I | P4HA1 |
| prolyl 4-hydroxylase, beta polypeptide | P4HB |
| proliferation-associated 2G4, 38kDa | PA2G4 |
| poly(A) binding protein, cytoplasmic 1 | PABPC1 |
| poly(A) binding protein, cytoplasmic 1-like | PABPC1L |
| poly(A) binding protein, cytoplasmic 3 | PABPC3 |
| poly(A) binding protein, cytoplasmic 4 (inducible form) | PABPC4 |
| poly(A) binding protein, cytoplasmic 5 | PABPC5 |
| protein kinase C and casein kinase substrate in neurons 2 | PACSIN2 |
| protein kinase C and casein kinase substrate in neurons 3 | PACSIN3 |
| peptidyl arginine deiminase, type II | PADI2 |
| Paf1, RNA polymerase II associated factor, homolog (*S. cerevisiae*) | PAF1 |
| platelet-activating factor acetylhydrolase 1b, regulatory subunit 1 (45 kDa) | PAFAH1B1 |
| platelet-activating factor acetylhydrolase 1b, catalytic subunit 2 (30 kDa) | PAFAH1B2 |
| platelet-activating factor acetylhydrolase 1b, catalytic subunit 3 (29 kDa) | PAFAH1B3 |
| P antigen family, member 2 (prostate associated) | PAGE2 |
| phenylalanine hydroxylase | PAH |
| phosphoribosylaminoimidazole carboxylase, phosphoribosylaminoimidazole succinocarboxamide synthetase | PAICS |
| p21 protein (Cdc42/Rac)-activated kinase 2 | PAK2 |
| p21 protein (Cdc42/Rac)-activated kinase 4 | PAK4 |
| p21 protein (Cdc42/Rac)-activated kinase 6 | PAK6 |
| phosphatase domain containing, paladin 1 | PALD1 |
| paralemmin | PALM |
| peptidylglycine alpha-amidating monooxygenase | PAM |
| peptidase domain containing associated with muscle regeneration 1 | PAMR1 |
| PAN3 poly(A) specific ribonuclease subunit | PAN3 |
| pantothenate kinase 2 | PANK2 |
| pantothenate kinase 4 | PANK4 |
| pannexin 1 | PANX1 |
| pregnancy-associated plasma protein A, pappalysin 1 | PAPPA |
| PAPPA antisense RNA 1 | PAPPA-AS1 |
| 3'-phosphoadenosine 5'-phosphosulfate synthase 1 | PAPSS1 |
| 3'-phosphoadenosine 5'-phosphosulfate synthase 2 | PAPSS2 |
| par-3 family cell polarity regulator | PARD3 |
| par-6 family cell polarity regulator beta | PARD6B |
| parkinson protein 7 | PARK7 |
| poly (ADP-ribose) polymerase 1 | PARP1 |

TABLE 4-continued

Suitable extracellular vesicle associated proteins

| Gene Name | Gene Symbol |
| --- | --- |
| poly (ADP-ribose) polymerase family, member 10 | PARP10 |
| poly (ADP-ribose) polymerase family, member 12 | PARP12 |
| poly (ADP-ribose) polymerase family, member 14 | PARP14 |
| poly (ADP-ribose) polymerase family, member 16 | PARP16 |
| poly (ADP-ribose) polymerase family, member 4 | PARP4 |
| poly (ADP-ribose) polymerase family, member 9 | PARP9 |
| parvin, alpha | PARVA |
| parvin, beta | PARVB |
| parvin, gamma | PARVG |
| protein associated with topoisomerase II homolog 1 (yeast) | PATL1 |
| phenazine biosynthesis-like protein domain containing | PBLD |
| polybromo 1 | PBRM1 |
| pyruvate carboxylase | PC |
| pterin-4 alpha-carbinolamine dehydratase/dimerization cofactor of hepatocyte nuclear factor 1 alpha | PCBD1 |
| poly(rC) binding protein 1 | PCBP1 |
| poly(rC) binding protein 2 | PCBP2 |
| poly(rC) binding protein 3 | PCBP3 |
| protocadherin 1 | PCDH1 |
| protocadherin gamma subfamily B, 5 | PCDHGB5 |
| PCF11 cleavage and polyadenylation factor subunit | PCF11 |
| PCI domain containing 2 | PCID2 |
| PDX1 C-terminal inhibiting factor 1 | PCIF1 |
| phosphoenolpyruvate carboxykinase 1 (soluble) | PCK1 |
| piccolo presynaptic cytomatrix protein | PCLO |
| protein-L-isoaspartate (D-aspartate) O-methyltransferase | PCMT1 |
| proliferating cell nuclear antigen | PCNA |
| procollagen C-endopeptidase enhancer | PCOLCE |
| proprotein convertase subtilisin/kexin type 6 | PCSK6 |
| proprotein convertase subtilisin/kexin type 9 | PCSK9 |
| prenylcysteine oxidase 1 | PCYOX1 |
| phosphate cytidylyltransferase 1, choline, beta | PCYT1B |
| phosphate cytidylyltransferase 2, ethanolamine | PCYT2 |
| programmed cell death 10 | PDCD10 |
| programmed cell death 2 | PDCD2 |
| programmed cell death 2-like | PDCD2L |
| programmed cell death 4 (neoplastic transformation inhibitor) | PDCD4 |
| programmed cell death 5 | PDCD5 |
| programmed cell death 6 | PDCD6 |
| programmed cell death 6 interacting protein (Apoptosis-Linked Gene 2-Interacting Protein X | PDCD6IP,ALIX |
| Parkinson disease 7 domain containing 1 | PDDC1 |
| phosphodiesterase 12 | PDE12 |
| phosphodiesterase 1C, calmodulin-dependent 70 kDa | PDE1C |
| phosphodiesterase 4D interacting protein | PDE4DIP |

TABLE 4-continued

| Suitable extracellular vesicle associated proteins | |
| --- | --- |
| Gene Name | Gene Symbol |
| phosphodiesterase 5A, cGMP-specific | PDE5A |
| phosphodiesterase 8A | PDE8A |
| platelet-derived growth factor alpha polypeptide | PDGFA |
| platelet derived growth factor C | PDGFC |
| platelet-derived growth factor receptor, beta polypeptide | PDGFRB |
| pyruvate dehydrogenase (lipoamide) alpha 1 | PDHA1 |
| protein disulfide isomerase family A, member 2 | PDIA2 |
| protein disulfide isomerase family A, member 3 | PDIA3 |
| protein disulfide isomerase family A, member 4 | PDIA4 |
| protein disulfide isomerase family A, member 5 | PDIA5 |
| protein disulfide isomerase family A, member 6 | PDIA6 |
| PDZ and LIM domain 1 | PDLIM1 |
| PDZ and LIM domain 5 | PDLIM5 |
| PDZ and LIM domain 7 (enigma) | PDLIM7 |
| PDS5 cohesin associated factor A | PDS5A |
| PDS5 cohesin associated factor B | PDS5B |
| pyridoxal-dependent decarboxylase domain containing 1 | PDXDC1 |
| pyridoxal (pyridoxine, vitamin B6) kinase | PDXK |
| PDZ domain containing 1 | PDZK1 |
| PDZK1 interacting protein 1 | PDZK1IP1 |
| pseudopodium-enriched atypical kinase 1 | PEAK1 |
| platelet endothelial aggregation receptor 1 | PEAR1 |
| phosphatidylethanolamine binding protein 1 | PEBP1 |
| platelet/endothelial cell adhesion molecule 1 | PECAM1 |
| penta-EF-hand domain containing 1 | PEF1 |
| pellino E3 ubiquitin protein ligase 1 | PELI1 |
| pellino E3 ubiquitin protein ligase family member 2 | PELI2 |
| pelota homolog (Drosophila) | PELO |
| proline, glutamate and leucine rich protein 1 | PELP1 |
| peptidase D | PEPD |
| pescadillo ribosomal biogenesis factor 1 | PES1 |
| peroxisomal biogenesis factor 1 | PEX1 |
| peroxisomal biogenesis factor 3 | PEX3 |
| phosphoribosylformylglycinamidine synthase | PFAS |
| prefoldin subunit 2 | PFDN2 |
| prefoldin subunit 4 | PFDN4 |
| prefoldin subunit 5 | PFDN5 |
| 6-phosphofructo-2-kinase/fructose-2,6-biphosphatase 2 | PFKFB2 |
| 6-phosphofructo-2-kinase/fructose-2,6-biphosphatase 3 | PFKFB3 |
| phosphofructokinase, liver | PFKL |
| phosphofructokinase, muscle | PFKM |
| phosphofructokinase, platelet | PFKP |
| profilin 1 | PFN1 |
| profilin 2 | PFN2 |
| phosphoglycerate mutase 1 (brain) | PGAM1 |

TABLE 4-continued

Suitable extracellular vesicle associated proteins

| Gene Name | Gene Symbol |
|---|---|
| phosphoglycerate mutase 2 (muscle) | PGAM2 |
| phosphoglycerate mutase family member 4 | PGAM4 |
| phosphoglycerate mutase family member 5 | PGAM5 |
| phosphogluconate dehydrogenase | PGD |
| phosphoglycerate kinase 1 | PGK1 |
| phosphoglycerate kinase 2 | PGK2 |
| 6-phosphogluconolactonase | PGLS |
| peptidoglycan recognition protein 1 | PGLYRP1 |
| peptidoglycan recognition protein 2 | PGLYRP2 |
| phosphoglucomutase 1 | PGM1 |
| phosphoglucomutase 2 | PGM2 |
| phosphoglucomutase 2-like 1 | PGM2L1 |
| phosphoglucomutase 3 | PGM3 |
| phosphoglucomutase 5 | PGM5 |
| progesterone receptor membrane component 1 | PGRMC1 |
| progesterone receptor membrane component 2 | PGRMC2 |
| phosphatase and actin regulator 4 | PHACTR4 |
| prohibitin | PHB |
| prohibitin 2 | PHB2 |
| PHD finger protein 23 | PHF23 |
| PHD finger protein 5A | PHF5A |
| phosphoglycerate dehydrogenase | PHGDH |
| phosphorylase kinase, alpha 1 (muscle) | PHKA1 |
| phosphorylase kinase, alpha 2 (liver) | PHKA2 |
| phosphorylase kinase, beta | PHKB |
| pleckstrin homology-like domain, family A, member 1 | PHLDA1 |
| pleckstrin homology-like domain, family A, member 2 | PHLDA2 |
| pleckstrin homology-like domain, family B, member 1 | PHLDB1 |
| pleckstrin homology-like domain, family B, member 2 | PHLDB2 |
| phosphohistidine phosphatase 1 | PHPT1 |
| phosphatidylinositol 4-kinase type 2 alpha | PI4K2A |
| phosphatidylinositol 4-kinase, catalytic, alpha | PI4KA |
| phosphatidylinositol 4-kinase, catalytic, beta | PI4KB |
| phosphatidylinositol binding clathrin assembly protein | PICALM |
| polymeric immunoglobulin receptor | PIGR |
| phosphatidylinositol-4-phosphate 3-kinase, catalytic subunit type 2 alpha | PIK3C2A |
| phosphatidylinositol-4-phosphate 3-kinase, catalytic subunit type 2 beta | PIK3C2B |
| phosphatidylinositol 3-kinase, catalytic subunit type 3 | PIK3C3 |
| phosphatidylinositol-4,5-bisphosphate 3-kinase, catalytic subunit alpha | PIK3CA |
| phosphatidylinositol-4,5-bisphosphate 3-kinase, catalytic subunit beta | PIK3CB |
| phosphoinositide-3-kinase, regulatory subunit 1 (alpha) | PIK3R1 |
| phosphoinositide-3-kinase, regulatory subunit 4 | PIK3R4 |

TABLE 4-continued

| Suitable extracellular vesicle associated proteins | |
| --- | --- |
| Gene Name | Gene Symbol |
| paired immunoglobin-like type 2 receptor alpha | PILRA |
| peptidylprolyl cis/trans isomerase, NIMA-interacting 1 | PIN1 |
| peptidylprolyl cis/trans isomerase, NIMA-interacting 4 | PIN4 |
| prolactin-induced protein | PIP |
| phosphatidylinositol-5-phosphate 4-kinase, type II, alpha | PIP4K2A |
| phosphatidylinositol-5-phosphate 4-kinase, type II, beta | PIP4K2B |
| phosphatidylinositol-5-phosphate 4-kinase, type II, gamma | PIP4K2C |
| phosphatidylinositol-4-phosphate 5-kinase, type I, alpha | PIP5K1A |
| pirin (iron-binding nuclear protein) | PIR |
| PITH (C-terminal proteasome-interacting domain of thioredoxin-like) domain containing 1 | PITHD1 |
| phosphatidylinositol transfer protein, alpha | PITPNA |
| phosphatidylinositol transfer protein, beta | PITPNB |
| phosphatidylinositol transfer protein, membrane-associated 1 | PITPNM1 |
| polycystic kidney disease 1 (autosomal dominant) | PKD1 |
| polycystic kidney disease 1-like 3 | PKD1L3 |
| polycystic kidney disease 2 (autosomal dominant) | PKD2 |
| polycystic kidney disease 2-like 2 | PKD2L2 |
| polycystic kidney and hepatic disease 1 (autosomal recessive) | PKHD1 |
| polycystic kidney and hepatic disease 1 (autosomal recessive)-like 1 | PKHD1L1 |
| pyruvate kinase, liver and RBC | PKLR |
| pyruvate kinase, muscle | PKM |
| protein kinase N2 | PKN2 |
| protein kinase N3 | PKN3 |
| plakophilin 2 | PKP2 |
| plakophilin 3 | PKP3 |
| plakophilin 4 | PKP4 |
| phospholipase A2, group IIA (platelets, synovial fluid) | PLA2G2A |
| phospholipase A2-activating protein | PLAA |
| plasminogen activator, tissue | PLAT |
| plasminogen activator, urokinase | PLAU |
| plasminogen activator, urokinase receptor | PLAUR |
| phospholipase B domain containing 2 | PLBD2 |
| phospholipase C, beta 1 (phosphoinositide-specific) | PLCB1 |
| phospholipase C, beta 3 (phosphatidylinositol-specific) | PLCB3 |
| phospholipase C, beta 4 | PLCB4 |
| phospholipase C, delta 1 | PLCD1 |
| phospholipase C, delta 3 | PLCD3 |
| phospholipase C, epsilon 1 | PLCE1 |
| phospholipase C, gamma 1 | PLCG1 |
| phospholipase C, gamma 2 (phosphatidylinositol-specific) | PLCG2 |

TABLE 4-continued

| Suitable extracellular vesicle associated proteins | |
| --- | --- |
| Gene Name | Gene Symbol |
| phospholipase C-like 1 | PLCL1 |
| phospholipase C-like 2 | PLCL2 |
| phospholipase D1, phosphatidylcholine-specific | PLD1 |
| phospholipase D family, member 3 | PLD3 |
| plectin | PLEC |
| pleckstrin | PLEK |
| pleckstrin 2 | PLEK2 |
| pleckstrin homology domain containing, family A (phosphoinositide binding specific) member 1 | PLEKHA1 |
| pleckstrin homology domain containing, family A (phosphoinositide binding specific) member 4 | PLEKHA4 |
| pleckstrin homology domain containing, family A member 7 | PLEKHA7 |
| pleckstrin homology domain containing, family B (evectins) member 2 | PLEKHB2 |
| pleckstrin homology domain containing, family F (with FYVE domain) member 1 | PLEKHF1 |
| pleckstrin homology domain containing, family F (with FYVE domain) member 2 | PLEKHF2 |
| pleckstrin homology domain containing, family G (with RhoGef domain) member 3 | PLEKHG3 |
| pleckstrin homology domain containing, family G (with RhoGef domain) member 4B | PLEKHG4B |
| pleckstrin homology domain containing, family O member 2 | PLEKHO2 |
| plasminogen | PLG |
| perilipin 2 | PLIN2 |
| perilipin 3 | PLIN3 |
| procollagen-lysine, 2-oxoglutarate 5-dioxygenase 1 | PLOD1 |
| procollagen-lysine, 2-oxoglutarate 5-dioxygenase 2 | PLOD2 |
| procollagen-lysine, 2-oxoglutarate 5-dioxygenase 3 | PLOD3 |
| proteolipid protein 1 | PLP1 |
| proteolipid protein 2 (colonic epithelium-enriched) | PLP2 |
| pleiotropic regulator 1 | PLRG1 |
| plastin 1 | PLS1 |
| plastin 3 | PLS3 |
| phospholipid scramblase 1 | PLSCR1 |
| phospholipid scramblase 3 | PLSCR3 |
| phospholipid transfer protein | PLTP |
| plasmalemma vesicle associated protein | PLVAP |
| plexin domain containing 2 | PLXDC2 |
| plexin A1 | PLXNA1 |
| plexin A2 | PLXNA2 |
| plexin A3 | PLXNA3 |
| plexin A4 | PLXNA4 |
| plexin B1 | PLXNB1 |
| plexin B2 | PLXNB2 |
| plexin B3 | PLXNB3 |
| plexin C1 | PLXNC1 |
| plexin D1 | PLXND1 |
| peptidase M20 domain containing 1 | PM20D1 |
| peptidase M20 domain containing 2 | PM20D2 |
| premelanosome protein | PMEL |
| polyamine modulated factor 1 binding protein 1 | PMFBP1 |
| phosphomannomutase 2 | PMM2 |

TABLE 4-continued

| Suitable extracellular vesicle associated proteins | |
|---|---|
| Gene Name | Gene Symbol |
| phosphomevalonate kinase | PMVK |
| polynucleotide kinase 3'-phosphatase | PNKP |
| pinin, desmosome associated protein | PNN |
| partner of NOB1 homolog (*S. cerevisiae*) | PNO1 |
| purine nucleoside phosphorylase | PNP |
| patatin-like phospholipase domain containing 1 | PNPLA1 |
| patatin-like phospholipase domain containing 6 | PNPLA6 |
| podocan | PODN |
| podocalyxin-like | PODXL |
| protein O-fucosyltransferase 2 | POFUT2 |
| polymerase (DNA directed), beta | POLB |
| polymerase (DNA directed), delta 1, catalytic subunit | POLD1 |
| polymerase (DNA directed), delta 2, accessory subunit | POLD2 |
| polymerase (DNA directed) nu | POLN |
| polymerase (RNA) I polypeptide C, 30 kDa | POLR1C |
| polymerase (RNA) I polypeptide D, 16 kDa | POLR1D |
| polymerase (RNA) II (DNA directed) polypeptide A, 220 kDa | POLR2A |
| polymerase (RNA) II (DNA directed) polypeptide B, 140 kDa | POLR2B |
| polymerase (RNA) II (DNA directed) polypeptide C, 33 kDa | POLR2C |
| polymerase (RNA) II (DNA directed) polypeptide E, 25 kDa | POLR2E |
| polymerase (RNA) II (DNA directed) polypeptide H | POLR2H |
| polymerase (RNA) II (DNA directed) polypeptide L, 7.6 kDa | POLR2L |
| polymerase (RNA) III (DNA directed) polypeptide A, 155 kDa | POLR3A |
| polymerase (RNA) III (DNA directed) polypeptide B | POLR3B |
| polymerase (RNA) III (DNA directed) polypeptide C (62 kD) | POLR3C |
| polymerase (RNA) III (DNA directed) polypeptide E (80 kD) | POLR3E |
| polymerase (RNA) mitochondrial (DNA directed) | POLRMT |
| paraoxonase 1 | PON1 |
| paraoxonase 3 | PON3 |
| processing of precursor 1, ribonuclease P/MRP subunit (*S. cerevisiae*) | POP1 |
| P450 (cytochrome) oxidoreductase | POR |
| periostin, osteoblast specific factor | POSTN |
| POTE ankyrin domain family, member B2 | POTEB2 |
| POTE ankyrin domain family, member B3 | POTEB3 |
| POTE ankyrin domain family, member E | POTEE |
| POTE ankyrin domain family, member F | POTEF |
| POTE ankyrin domain family, member I | POTEI |

TABLE 4-continued

Suitable extracellular vesicle associated proteins

| Gene Name | Gene Symbol |
|---|---|
| POTE ankyrin domain family, member J | POTEJ |
| POTE ankyrin domain family, member K, pseudogene | POTEKP |
| POTE ankyrin domain family, member M | POTEM |
| POU class 2 homeobox 2 | POU2F2 |
| pyrophosphatase (inorganic) 1 | PPA1 |
| pyrophosphatase (inorganic) 2 | PPA2 |
| phosphatidic acid phosphatase type 2A | PPAP2A |
| phosphatidic acid phosphatase type 2B | PPAP2B |
| phosphatidic acid phosphatase type 2C | PPAP2C |
| peroxisome proliferator-activated receptor gamma | PPARG |
| phosphoribosyl pyrophosphate amidotransferase | PPAT |
| pro-platelet basic protein (chemokine (C-X-C motif) ligand 7) | PPBP |
| protein tyrosine phosphatase, receptor type, f polypeptide (PTPRF), interacting protein (liprin), alpha 1 | PPFIA1 |
| protein tyrosine phosphatase, receptor type, f polypeptide (PTPRF), interacting protein (liprin), alpha 2 | PPFIA2 |
| protein tyrosine phosphatase, receptor type, f polypeptide (PTPRF), interacting protein (liprin), alpha 3 | PPFIA3 |
| PTPRF interacting protein, binding protein 1 (liprin beta 1) | PPFIBP1 |
| PTPRF interacting protein, binding protein 2 (liprin beta 2) | PPFIBP2 |
| peptidylprolyl isomerase A (cyclophilin A) | PPIA |
| peptidylprolyl isomerase A (cyclophilin A) pseudogene 22 | PPIAP22 |
| peptidylprolyl isomerase A (cyclophilin A) pseudogene 31 | PPIAP31 |
| peptidylprolyl isomerase B (cyclophilin B) | PPIB |
| peptidylprolyl isomerase C (cyclophilin C) | PPIC |
| peptidylprolyl isomerase D | PPID |
| peptidylprolyl isomerase E (cyclophilin E) | PPIE |
| peptidylprolyl isomerase H (cyclophilin H) | PPIH |
| peptidylprolyl isomerase (cyclophilin)-like 1 | PPIL1 |
| diphosphoinositol pentakisphosphate kinase 2 | PPIP5K2 |
| periplakin | PPL |
| protein phosphatase, Mg2+/Mn2+ dependent, 1A | PPM1A |
| protein phosphatase, Mg2+/Mn2+ dependent, 1B | PPM1B |
| protein phosphatase, Mg2+/Mn2+ dependent, 1G | PPM1G |
| protein phosphatase, Mg2+/Mn2+ dependent, 1L | PPM1L |
| protein phosphatase methylesterase 1 | PPME1 |
| protein phosphatase 1, catalytic subunit, alpha isozyme | PPP1CA |
| protein phosphatase 1, catalytic subunit, beta isozyme | PPP1CB |

TABLE 4-continued

| Suitable extracellular vesicle associated proteins | |
| --- | --- |
| Gene Name | Gene Symbol |
| protein phosphatase 1, catalytic subunit, gamma isozyme | PPP1CC |
| protein phosphatase 1, regulatory subunit 12B | PPP1R12B |
| protein phosphatase 1, regulatory subunit 21 | PPP1R21 |
| protein phosphatase 1, regulatory subunit 7 | PPP1R7 |
| protein phosphatase 2, catalytic subunit, alpha isozyme | PPP2CA |
| protein phosphatase 2, catalytic subunit, beta isozyme | PPP2CB |
| protein phosphatase 2, regulatory subunit A, alpha | PPP2R1A |
| protein phosphatase 2, regulatory subunit A, beta | PPP2R1B |
| protein phosphatase 2, regulatory subunit B, alpha | PPP2R2A |
| protein phosphatase 2, regulatory subunit B, beta | PPP2R2B |
| protein phosphatase 2, regulatory subunit B, gamma | PPP2R2C |
| protein phosphatase 2, regulatory subunit B, delta | PPP2R2D |
| protein phosphatase 2A activator, regulatory subunit 4 | PPP2R4 |
| protein phosphatase 2, regulatory subunit B', gamma | PPP2R5C |
| protein phosphatase 2, regulatory subunit B', epsilon isoform | PPP2R5E |
| protein phosphatase 3, catalytic subunit, alpha isozyme | PPP3CA |
| protein phosphatase 4, catalytic subunit | PPP4C |
| protein phosphatase 4, regulatory subunit 1 | PPP4R1 |
| protein phosphatase 5, catalytic subunit | PPP5C |
| protein phosphatase 6, catalytic subunit | PPP6C |
| protein phosphatase 6, regulatory subunit 1 | PPP6R1 |
| palmitoyl-protein thioesterase 1 | PPT1 |
| prolylcarboxypeptidase (angiotensinase C) | PRCP |
| PR domain containing 16 | PRDM16 |
| peroxiredoxin 1 | PRDX1 |
| peroxiredoxin 2 | PRDX2 |
| peroxiredoxin 3 | PRDX3 |
| peroxiredoxin 4 | PRDX4 |
| peroxiredoxin 5 | PRDX5 |
| peroxiredoxin 6 | PRDX6 |
| proline/arginine-rich end leucine-rich repeat protein | PRELP |
| prolyl endopeptidase | PREP |
| proteoglycan 4 | PRG4 |
| protein kinase, AMP-activated, alpha 1 catalytic subunit | PRKAA1 |
| protein kinase, AMP-activated, alpha 2 catalytic subunit | PRKAA2 |
| protein kinase, AMP-activated, beta 2 non-catalytic subunit | PRKAB2 |
| protein kinase, cAMP-dependent, catalytic, alpha | PRKACA |
| protein kinase, cAMP-dependent, catalytic, beta | PRKACB |

TABLE 4-continued

| Gene Name | Gene Symbol |
| --- | --- |
| protein kinase, AMP-activated, gamma 1 non-catalytic subunit | PRKAG1 |
| protein kinase, AMP-activated, gamma 2 non-catalytic subunit | PRKAG2 |
| protein kinase, cAMP-dependent, regulatory, type I, alpha | PRKAR1A |
| protein kinase, cAMP-dependent, regulatory, type II, alpha | PRKAR2A |
| protein kinase, cAMP-dependent, regulatory, type II, beta | PRKAR2B |
| protein kinase C, alpha | PRKCA |
| protein kinase C, beta | PRKCB |
| protein kinase C, delta | PRKCD |
| protein kinase C, gamma | PRKCG |
| protein kinase C, eta | PRKCH |
| protein kinase C, iota | PRKCI |
| protein kinase C, theta | PRKCQ |
| protein kinase C substrate 80K-H | PRKCSH |
| protein kinase C, zeta | PRKCZ |
| protein kinase D1 | PRKD1 |
| protein kinase D2 | PRKD2 |
| protein kinase D3 | PRKD3 |
| protein kinase, DNA-activated, catalytic polypeptide | PRKDC |
| protein kinase, interferon-inducible double stranded RNA dependent activator | PRKRA |
| PRKR interacting protein 1 (IL11 inducible) | PRKRIP1 |
| protein kinase, X-linked | PRKX |
| protein arginine methyltransferase 1 | PRMT1 |
| protein arginine methyltransferase 5 | PRMT5 |
| prion protein | PRNP |
| protein C receptor, endothelial | PROCR |
| prominin 1 | PROM1 |
| prominin 2 | PROM2 |
| protein S (alpha) | PROS1 |
| protein Z, vitamin K-dependent plasma glycoprotein | PROZ |
| pre-mRNA processing factor 19 | PRPF19 |
| pre-mRNA processing factor 31 | PRPF31 |
| pre-mRNA processing factor 38B | PRPF38B |
| pre-mRNA processing factor 4 | PRPF4 |
| PRP40 pre-mRNA processing factor 40 homolog A (S. cerevisiae) | PRPF40A |
| pre-mRNA processing factor 4B | PRPF4B |
| pre-mRNA processing factor 6 | PRPF6 |
| pre-mRNA processing factor 8 | PRPF8 |
| peripherin | PRPH |
| peripherin 2 (retinal degeneration, slow) | PRPH2 |
| phosphoribosyl pyrophosphate synthetase 1 | PRPS1 |
| phosphoribosyl pyrophosphate synthetase 1-like 1 | PRPS1L1 |
| phosphoribosyl pyrophosphate synthetase 2 | PRPS2 |
| phosphoribosyl pyrophosphate synthetase-associated protein 1 | PRPSAP1 |
| phosphoribosyl pyrophosphate synthetase-associated protein 2 | PRPSAP2 |
| proline rich 14-like | PRR14L |

TABLE 4-continued

| Suitable extracellular vesicle associated proteins | |
|---|---|
| Gene Name | Gene Symbol |
| proline rich 27 | PRR27 |
| proline rich 36 | PRR36 |
| proline rich 4 (lacrimal) | PRR4 |
| proline-rich coiled-coil 2A | PRRC2A |
| proline rich Gla (G-carboxyglutamic acid) 1 | PRRG1 |
| proline-rich transmembrane protein 3 | PRRT3 |
| protease, serine, 16 (thymus) | PRSS16 |
| protease, serine, 22 | PRSS22 |
| protease, serine, 23 | PRSS23 |
| protease, serine, 3 | PRSS3 |
| protease, serine, 48 | PRSS48 |
| protease, serine, 8 | PRSS8 |
| proteinase 3 | PRTN3 |
| prosaposin | PSAP |
| phosphoserine aminotransferase 1 | PSAT1 |
| prostate stem cell antigen | PSCA |
| PC4 and SFRS1 interacting protein 1 | PSIP1 |
| proteasome (prosome, macropain) subunit, alpha type, 1 | PSMA1 |
| proteasome (prosome, macropain) subunit, alpha type, 2 | PSMA2 |
| proteasome (prosome, macropain) subunit, alpha type, 3 | PSMA3 |
| proteasome (prosome, macropain) subunit, alpha type, 4 | PSMA4 |
| proteasome (prosome, macropain) subunit, alpha type, 5 | PSMA5 |
| proteasome (prosome, macropain) subunit, alpha type, 6 | PSMA6 |
| proteasome (prosome, macropain) subunit, alpha type, 7 | PSMA7 |
| proteasome (prosome, macropain) subunit, alpha type, 8 | PSMA8 |
| proteasome (prosome, macropain) subunit, beta type, 1 | PSMB1 |
| proteasome (prosome, macropain) subunit, beta type, 10 | PSMB10 |
| proteasome (prosome, macropain) subunit, beta type, 11 | PSMB11 |
| proteasome (prosome, macropain) subunit, beta type, 2 | PSMB2 |
| proteasome (prosome, macropain) subunit, beta type, 3 | PSMB3 |
| proteasome (prosome, macropain) subunit, beta type, 4 | PSMB4 |
| proteasome (prosome, macropain) subunit, beta type, 5 | PSMB5 |
| proteasome (prosome, macropain) subunit, beta type, 6 | PSMB6 |
| proteasome (prosome, macropain) subunit, beta type, 7 | PSMB7 |
| proteasome (prosome, macropain) subunit, beta type, 8 | PSMB8 |

TABLE 4-continued

| Suitable extracellular vesicle associated proteins | |
| --- | --- |
| Gene Name | Gene Symbol |
| proteasome (prosome, macropain) subunit, beta type, 9 | PSMB9 |
| proteasome (prosome, macropain) 26S subunit, ATPase, 1 | PSMC1 |
| proteasome (prosome, macropain) 26S subunit, ATPase, 2 | PSMC2 |
| proteasome (prosome, macropain) 26S subunit, ATPase, 3 | PSMC3 |
| proteasome (prosome, macropain) 26S subunit, ATPase, 4 | PSMC4 |
| proteasome (prosome, macropain) 26S subunit, ATPase, 5 | PSMC5 |
| proteasome (prosome, macropain) 26S subunit, ATPase, 6 | PSMC6 |
| proteasome (prosome, macropain) 26S subunit, non-ATPase, 1 | PSMD1 |
| proteasome (prosome, macropain) 26S subunit, non-ATPase, 10 | PSMD10 |
| proteasome (prosome, macropain) 26S subunit, non-ATPase, 11 | PSMD11 |
| proteasome (prosome, macropain) 26S subunit, non-ATPase, 12 | PSMD12 |
| proteasome (prosome, macropain) 26S subunit, non-ATPase, 13 | PSMD13 |
| proteasome (prosome, macropain) 26S subunit, non-ATPase, 14 | PSMD14 |
| proteasome (prosome, macropain) 26S subunit, non-ATPase, 2 | PSMD2 |
| proteasome (prosome, macropain) 26S subunit, non-ATPase, 3 | PSMD3 |
| proteasome (prosome, macropain) 26S subunit, non-ATPase, 4 | PSMD4 |
| proteasome (prosome, macropain) 26S subunit, non-ATPase, 5 | PSMD5 |
| proteasome (prosome, macropain) 26S subunit, non-ATPase, 6 | PSMD6 |
| proteasome (prosome, macropain) 26S subunit, non-ATPase, 7 | PSMD7 |
| proteasome (prosome, macropain) 26S subunit, non-ATPase, 8 | PSMD8 |
| proteasome (prosome, macropain) 26S subunit, non-ATPase, 9 | PSMD9 |
| proteasome (prosome, macropain) activator subunit 1 (PA28 alpha) | PSME1 |
| proteasome (prosome, macropain) activator subunit 2 (PA28 beta) | PSME2 |
| proteasome (prosome, macropain) activator subunit 3 (PA28 gamma; Ki) | PSME3 |
| proteasome (prosome, macropain) activator subunit 4 | PSME4 |

TABLE 4-continued

| Suitable extracellular vesicle associated proteins | |
| --- | --- |
| Gene Name | Gene Symbol |
| proteasome (prosome, macropain) assembly chaperone 1 | PSMG1 |
| proteasome (prosome, macropain) assembly chaperone 2 | PSMG2 |
| paraspeckle component 1 | PSPC1 |
| phosphoserine phosphatase | PSPH |
| proline-serine-threonine phosphatase interacting protein 1 | PSTPIP1 |
| proline-serine-threonine phosphatase interacting protein 2 | PSTPIP2 |
| polypyrimidine tract binding protein 1 | PTBP1 |
| polypyrimidine tract binding protein 3 | PTBP3 |
| phosphotriesterase related | PTER |
| prostaglandin E synthase 2 | PTGES2 |
| prostaglandin E synthase 3 (cytosolic) | PTGES3 |
| PTGES3L-AARSD1 readthrough | PTGES3L-AARSD1 |
| prostaglandin F2 receptor inhibitor | PTGFRN |
| prostaglandin reductase 1 | PTGR1 |
| prostaglandin reductase 2 | PTGR2 |
| prostaglandin-endoperoxide synthase 1 (prostaglandin G/H synthase and cyclooxygenase) | PTGS1 |
| protein tyrosine kinase 2 | PTK2 |
| protein tyrosine kinase 2 beta | PTK2B |
| protein tyrosine kinase 7 (inactive) | PTK7 |
| prothymosin, alpha | PTMA |
| parathymosin | PTMS |
| protein tyrosine phosphatase type IVA, member 1 | PTP4A1 |
| protein tyrosine phosphatase type IVA, member 2 | PTP4A2 |
| protein tyrosine phosphatase, non-receptor type 1 | PTPN1 |
| protein tyrosine phosphatase, non-receptor type 11 | PTPN11 |
| protein tyrosine phosphatase, non-receptor type 13 (APO-1/CD95 (Fas)-associated phosphatase) | PTPN13 |
| protein tyrosine phosphatase, non-receptor type 18 (brain-derived) | PTPN18 |
| protein tyrosine phosphatase, non-receptor type 2 | PTPN2 |
| protein tyrosine phosphatase, non-receptor type 23 | PTPN23 |
| protein tyrosine phosphatase, non-receptor type 6 | PTPN6 |
| protein tyrosine phosphatase, non-receptor type 7 | PTPN7 |
| protein tyrosine phosphatase, non-receptor type 9 | PTPN9 |
| protein tyrosine phosphatase, receptor type, A | PTPRA |
| protein tyrosine phosphatase, receptor type, B | PTPRB |
| protein tyrosine phosphatase, receptor type, C | PTPRC |
| protein tyrosine phosphatase, receptor type, C-associated protein | PTPRCAP |
| protein tyrosine phosphatase, receptor type, F | PTPRF |
| protein tyrosine phosphatase, receptor type, G | PTPRG |

TABLE 4-continued

| Suitable extracellular vesicle associated proteins | |
| --- | --- |
| Gene Name | Gene Symbol |
| protein tyrosine phosphatase, receptor type, J | PTPRJ |
| protein tyrosine phosphatase, receptor type, K | PTPRK |
| protein tyrosine phosphatase, receptor type, O | PTPRO |
| protein tyrosine phosphatase, receptor type, S | PTPRS |
| polymerase I and transcript release factor | PTRF |
| peptidyl-tRNA hydrolase 2 | PTRH2 |
| pituitary tumor-transforming 1 interacting protein | PTTG1IP |
| pentraxin 3, long | PTX3 |
| poly-U binding splicing factor 60 KDa | PUF60 |
| purine-rich element binding protein A | PURA |
| purine-rich element binding protein B | PURB |
| pseudouridylate synthase 1 | PUS1 |
| poliovirus receptor | PVR |
| poliovirus receptor-related 2 (herpesvirus entry mediator B) | PVRL2 |
| peroxidasin | PXDN |
| paxillin | PXN |
| pyrroline-5-carboxylate reductase-like | PYCRL |
| phosphorylase, glycogen; brain | PYGB |
| phosphorylase, glycogen, liver | PYGL |
| phosphorylase, glycogen, muscle | PYGM |
| pregnancy-zone protein | PZP |
| glutaminyl-tRNA synthetase | QARS |
| quinoid dihydropteridine reductase | QDPR |
| glutaminyl-peptide cyclotransferase | QPCT |
| glutaminyl-peptide cyclotransferase-like | QPCTL |
| quinolinate phosphoribosyltransferase | QPRT |
| quiescin Q6 sulfhydryl oxidase 1 | QSOX1 |
| quiescin Q6 sulfhydryl oxidase 2 | QSOX2 |
| queuine tRNA-ribosyltransferase 1 | QTRT1 |
| RAB10, member RAS oncogene family | RAB10 |
| RAB11A, member RAS oncogene family | RAB11A |
| RAB11B, member RAS oncogene family | RAB11B |
| RAB11 family interacting protein 1 (class I) | RAB11FIP1 |
| RAB12, member RAS oncogene family | RAB12 |
| RAB13, member RAS oncogene family | RAB13 |
| RAB14, member RAS oncogene family | RAB14 |
| RAB15, member RAS oncogene family | RAB15 |
| RAB17, member RAS oncogene family | RAB17 |
| RAB18, member RAS oncogene family | RAB18 |
| RAB19, member RAS oncogene family | RAB19 |
| RAB1A, member RAS oncogene family | RAB1A |
| RAB1B, member RAS oncogene family | RAB1B |

TABLE 4-continued

| Suitable extracellular vesicle associated proteins | |
| --- | --- |
| Gene Name | Gene Symbol |
| RAB1C, member RAS oncogene family pseudogene | RAB1C |
| RAB20, member RAS oncogene family | RAB20 |
| RAB21, member RAS oncogene family | RAB21 |
| RAB22A, member RAS oncogene family | RAB22A |
| RAB23, member RAS oncogene family | RAB23 |
| RAB25, member RAS oncogene family | RAB25 |
| RAB27A, member RAS oncogene family | RAB27A |
| RAB27B, member RAS oncogene family | RAB27B |
| RAB29, member RAS oncogene family | RAB29 |
| RAB2A, member RAS oncogene family | RAB2A |
| RAB2B, member RAS oncogene family | RAB2B |
| RAB30, member RAS oncogene family | RAB30 |
| RAB32, member RAS oncogene family | RAB32 |
| RAB33A, member RAS oncogene family | RAB33A |
| RAB33B, member RAS oncogene family | RAB33B |
| RAB34, member RAS oncogene family | RAB34 |
| RAB35, member RAS oncogene family | RAB35 |
| RAB37, member RAS oncogene family | RAB37 |
| RAB38, member RAS oncogene family | RAB38 |
| RAB39A, member RAS oncogene family | RAB39A |
| RAB39B, member RAS oncogene family | RAB39B |
| RAB3A, member RAS oncogene family | RAB3A |
| RAB3B, member RAS oncogene family | RAB3B |
| RAB3C, member RAS oncogene family | RAB3C |
| RAB3D, member RAS oncogene family | RAB3D |
| RAB3 GTPase activating protein subunit 1 (catalytic) | RAB3GAP1 |
| RAB3 GTPase activating protein subunit 2 (non-catalytic) | RAB3GAP2 |
| RAB43, member RAS oncogene family | RAB43 |
| RAB4A, member RAS oncogene family | RAB4A |
| RAB4B, member RAS oncogene family | RAB4B |
| RAB5A, member RAS oncogene family | RAB5A |
| RAB5B, member RAS oncogene family | RAB5B |
| RAB5C, member RAS oncogene family | RAB5C |
| RAB6A, member RAS oncogene family | RAB6A |
| RAB6B, member RAS oncogene family | RAB6B |
| RAB6C, member RAS oncogene family | RAB6C |
| RAB7A, member RAS oncogene family | RAB7A |

TABLE 4-continued

| Gene Name | Gene Symbol |
| --- | --- |
| Suitable extracellular vesicle associated proteins | |
| RAB8A, member RAS oncogene family | RAB8A |
| RAB8B, member RAS oncogene family | RAB8B |
| RAB9A, member RAS oncogene family | RAB9A |
| RAB9B, member RAS oncogene family | RAB9B |
| RAB GTPase activating protein 1 | RABGAP1 |
| ras-related C3 botulinum toxin substrate 1 (rho family, small GTP binding protein Rac1) | RAC1 |
| ras-related C3 botulinum toxin substrate 2 (rho family, small GTP binding protein Rac2) | RAC2 |
| ras-related C3 botulinum toxin substrate 3 (rho family, small GTP binding protein Rac3) | RAC3 |
| Rac GTPase activating protein 1 | RACGAP1 |
| RAD21 homolog (*S. pombe*) | RAD21 |
| RAD23 homolog B (*S. cerevisiae*) | RAD23B |
| RAD50 homolog (*S. cerevisiae*) | RAD50 |
| ribonucleic acid export 1 | RAE1 |
| Raf-1 proto-oncogene, serine/threonine kinase | RAF1 |
| retinoic acid induced 14 | RAI14 |
| v-ral simian leukemia viral oncogene homolog A (ras related) | RALA |
| v-ral simian leukemia viral oncogene homolog B | RALB |
| Ral GTPase activating protein, beta subunit (non-catalytic) | RALGAPB |
| RALY heterogeneous nuclear ribonucleoprotein | RALY |
| RALY RNA binding protein-like | RALYL |
| RAN, member RAS oncogene family | RAN |
| RAN binding protein 1 | RANBP1 |
| RAN binding protein 10 | RANBP10 |
| RAN binding protein 2 | RANBP2 |
| RAN binding protein 3 | RANBP3 |
| RAN binding protein 9 | RANBP9 |
| Ran GTPase activating protein 1 | RANGAP1 |
| RAN, member RAS oncogene family pseudogene 1 | RANP1 |
| RAP1 A, member of RAS oncogene family | RAP1A |
| RAP1B, member of RAS oncogene family | RAP1B |
| RAP1B, member of RAS oncogene family pseudogene | RAP1BL |
| RAP1 GTPase activating protein 2 | RAP1GAP2 |
| RAP1, GTP-GDP dissociation stimulator 1 | RAP1GDS1 |
| RAP2A, member of RAS oncogene family | RAP2A |
| RAP2B, member of RAS oncogene family | RAP2B |
| RAP2C, member of RAS oncogene family | RAP2C |
| Rap guanine nucleotide exchange factor (GEF) 1 | RAPGEF1 |
| Rap guanine nucleotide exchange factor (GEF) 3 | RAPGEF3 |
| Rap guanine nucleotide exchange factor (GEF) 6 | RAPGEF6 |
| retinoic acid receptor, alpha | RARA |

TABLE 4-continued

| Suitable extracellular vesicle associated proteins | |
| --- | --- |
| Gene Name | Gene Symbol |
| retinoic acid receptor responder (tazarotene induced) 1 | RARRES1 |
| arginyl-tRNA synthetase | RARS |
| RAS p21 protein activator (GTPase activating protein) 1 | RASA1 |
| RAS p21 protein activator 2 | RASA2 |
| RAS p21 protein activator 3 | RASA3 |
| RAS p21 protein activator 4 | RASA4 |
| RAS p21 protein activator 4C, pseudogene | RASA4CP |
| RAS protein activator like 1 (GAP1 like) | RASAL1 |
| RAS protein activator like 3 | RASAL3 |
| RAS guanyl releasing protein 2 (calcium and DAG-regulated) | RASGRP2 |
| Ras association (RalGDS/AF-6) domain family member 2 | RASSF2 |
| RB1-inducible coiled-coil 1 | RB1CC1 |
| retinoblastoma binding protein 4 | RBBP4 |
| retinoblastoma binding protein 6 | RBBP6 |
| retinoblastoma binding protein 7 | RBBP7 |
| retinoblastoma-like 2 | RBL2 |
| RNA binding motif protein 12 | RBM12 |
| RNA binding motif protein 14 | RBM14 |
| RBM14-RBM4 readthrough | RBM14-RBM4 |
| RNA binding motif protein 19 | RBM19 |
| RNA binding motif protein 22 | RBM22 |
| RNA binding motif protein 25 | RBM25 |
| RNA binding motif protein 28 | RBM28 |
| RNA binding motif (RNP1, RRM) protein 3 | RBM3 |
| RNA binding motif protein 39 | RBM39 |
| RNA binding motif protein 4 | RBM4 |
| RNA binding motif protein 6 | RBM6 |
| RNA binding motif protein 8A | RBM8A |
| RNA binding motif protein, X-linked | RBMX |
| retinol binding protein 1, cellular | RBP1 |
| retinol binding protein 4, plasma | RBP4 |
| retinol binding protein 5, cellular | RBP5 |
| ring-box 1, E3 ubiquitin protein ligase | RBX1 |
| ring finger and CCCH-type domains 1 | RC3H1 |
| regulator of chromosome condensation 1 | RCC1 |
| regulator of chromosome condensation 2 | RCC2 |
| RNA terminal phosphate cyclase-like 1 | RCL1 |
| reticulocalbin 1, EF-hand calcium binding domain | RCN1 |
| reticulocalbin 2, EF-hand calcium binding domain | RCN2 |
| REST corepressor 2 | RCOR2 |
| retinol dehydrogenase 11 (all-trans/9-cis/11-cis) | RDH11 |
| retinol dehydrogenase 14 (all-trans/9-cis/11-cis) | RDH14 |
| retinol dehydrogenase 5 (11-cis/9-cis) | RDH5 |
| radixin | RDX |
| RecQ helicase-like | RECQL |
| receptor accessory protein 5 | REEP5 |
| regenerating islet-derived family, member 4 | REG4 |
| v-rel avian reticuloendotheliosis viral oncogene homolog | REL |
| RELT-like 1 | RELL1 |
| reelin | RELN |
| renin binding protein | RENBP |

TABLE 4-continued

| Suitable extracellular vesicle associated proteins | |
| --- | --- |
| Gene Name | Gene Symbol |
| retention in endoplasmic reticulum sorting receptor 1 | RER1 |
| ret proto-oncogene | RET |
| resistin | RETN |
| replication factor C (activator 1) 1, 145 kDa | RFC1 |
| replication factor C (activator 1) 2, 40 kDa | RFC2 |
| replication factor C (activator 1) 3, 38 kDa | RFC3 |
| replication factor C (activator 1) 4, 37 kDa | RFC4 |
| replication factor C (activator 1) 5, 36.5 kDa | RFC5 |
| ring finger and FYVE-like domain containing E3 ubiquitin protein ligase | RFFL |
| raftlin, lipid raft linker 1 | RFTN1 |
| regucalcin | RGN |
| regulator of G-protein signaling 10 | RGS10 |
| regulator of G-protein signaling 16 | RGS16 |
| regulator of G-protein signaling 18 | RGS18 |
| regulator of G-protein signaling 20 | RGS20 |
| regulator of G-protein signaling 3 | RGS3 |
| regulator of G-protein signaling 6 | RGS6 |
| rhomboid 5 homolog 1 (Drosophila) | RHBDF1 |
| rhomboid 5 homolog 2 (Drosophila) | RHBDF2 |
| Rh family, C glycoprotein | RHCG |
| Ras homolog enriched in brain | RHEB |
| ras homolog family member A | RHOA |
| ras homolog family member B | RHOB |
| Rho-related BTB domain containing 3 | RHOBTB3 |
| ras homolog family member C | RHOC |
| ras homolog family member F (in filopodia) | RHOF |
| ras homolog family member G | RHOG |
| ras homolog family member Q | RHOQ |
| rhophilin, Rho GTPase binding protein 2 | RHPN2 |
| RIC8 guanine nucleotide exchange factor A | RIC8A |
| RIC8 guanine nucleotide exchange factor B | RIC8B |
| RPTOR independent companion of MTOR, complex 2 | RICTOR |
| RIO kinase 3 | RIOK3 |
| RGD motif, leucine rich repeats, tropomodulin domain and proline-rich containing | RLTPR |
| regulator of microtubule dynamics 2 | RMDN2 |
| required for meiotic nuclear division 5 homolog A (S. cerevisiae) | RMND5A |
| ribonuclease, RNase A family, 2 (liver, eosinophil-derived neurotoxin) | RNASE2 |
| ribonuclease, RNase A family, 4 | RNASE4 |
| ribonuclease, RNase A family, 7 | RNASE7 |
| ribonuclease H2, subunit A | RNASEH2A |
| RNF103-CHMP3 readthrough | RNF103-CHMP3 |
| ring finger protein 11 | RNF11 |
| ring finger protein 123 | RNF123 |

TABLE 4-continued

| Suitable extracellular vesicle associated proteins | |
|---|---|
| Gene Name | Gene Symbol |
| ring finger protein 149 | RNF149 |
| ring finger protein 20, E3 ubiquitin protein ligase | RNF20 |
| ring finger protein 213 | RNF213 |
| ring finger protein 40, E3 ubiquitin protein ligase | RNF40 |
| RNA guanylyltransferase and 5'-phosphatase | RNGTT |
| ribonuclease/angiogenin inhibitor 1 | RNH1 |
| arginyl aminopeptidase (aminopeptidase B) | RNPEP |
| RNA binding protein S1, serine-rich domain | RNPS1 |
| roundabout, axon guidance receptor, homolog 2 (Drosophila) | ROBO2 |
| Rho-associated, coiled-coil containing protein kinase 1 | ROCK1 |
| Rho-associated, coiled-coil containing protein kinase 2 | ROCK2 |
| rogdi homolog (Drosophila) | ROGDI |
| receptor tyrosine kinase-like orphan receptor 1 | ROR1 |
| retinitis pigmentosa 2 (X-linked recessive) | RP2 |
| replication protein A1, 70 kDa | RPA1 |
| replication protein A2, 32 kDa | RPA2 |
| RPGRIP1-like | RPGRIP1L |
| ribose 5-phosphate isomerase A | RPIA |
| ribosomal protein L10 | RPL10 |
| ribosomal protein L10a | RPL10A |
| ribosomal protein L10a pseudogene 6 | RPL10AP6 |
| ribosomal protein L10a pseudogene 9 | RPL10AP9 |
| ribosomal protein L10-like | RPL10L |
| ribosomal protein L11 | RPL11 |
| ribosomal protein L12 | RPL12 |
| ribosomal protein L12 pseudogene 14 | RPL12P14 |
| ribosomal protein L12 pseudogene 19 | RPL12P19 |
| ribosomal protein L12 pseudogene 2 | RPL12P2 |
| ribosomal protein L12 pseudogene 32 | RPL12P32 |
| ribosomal protein L12 pseudogene 35 | RPL12P35 |
| ribosomal protein L12 pseudogene 6 | RPL12P6 |
| ribosomal protein L13 | RPL13 |
| ribosomal protein L13a | RPL13A |
| ribosomal protein L14 | RPL14 |
| ribosomal protein L15 | RPL15 |
| ribosomal protein L15 pseudogene 17 | RPL15P17 |
| ribosomal protein L15 pseudogene 18 | RPL15P18 |
| ribosomal protein L15 pseudogene 22 | RPL15P22 |
| ribosomal protein L15 pseudogene 3 | RPL15P3 |
| ribosomal protein L15 pseudogene 7 | RPL15P7 |
| ribosomal protein L17 | RPL17 |
| RPL17-C18orf32 readthrough | RPL17-C18orf32 |
| ribosomal protein L18 | RPL18 |
| ribosomal protein L18a | RPL18A |
| ribosomal protein L19 | RPL19 |
| ribosomal protein L21 | RPL21 |
| ribosomal protein L22 | RPL22 |
| ribosomal protein L22-like 1 | RPL22L1 |
| ribosomal protein L23 | RPL23 |

TABLE 4-continued

| Suitable extracellular vesicle associated proteins | |
| --- | --- |
| Gene Name | Gene Symbol |
| ribosomal protein L23a | RPL23A |
| ribosomal protein L23a pseudogene 32 | RPL23AP32 |
| ribosomal protein L23a pseudogene 42 | RPL23AP42 |
| ribosomal protein L23 pseudogene 6 | RPL23P6 |
| ribosomal protein L24 | RPL24 |
| ribosomal protein L26 | RPL26 |
| ribosomal protein L26-like 1 | RPL26L1 |
| ribosomal protein L27 | RPL27 |
| ribosomal protein L27a | RPL27A |
| ribosomal protein L28 | RPL28 |
| ribosomal protein L29 | RPL29 |
| ribosomal protein L29 pseudogene 11 | RPL29P11 |
| ribosomal protein L29 pseudogene 12 | RPL29P12 |
| ribosomal protein L29 pseudogene 26 | RPL29P26 |
| ribosomal protein L29 pseudogene 9 | RPL29P9 |
| ribosomal protein L3 | RPL3 |
| ribosomal protein L30 | RPL30 |
| ribosomal protein L31 | RPL31 |
| ribosomal protein L32 | RPL32 |
| ribosomal protein L34 | RPL34 |
| ribosomal protein L35 | RPL35 |
| ribosomal protein L35a | RPL35A |
| ribosomal protein L36 | RPL36 |
| ribosomal protein L37a | RPL37A |
| ribosomal protein L38 | RPL38 |
| ribosomal protein L4 | RPL4 |
| ribosomal protein L5 | RPL5 |
| ribosomal protein L6 | RPL6 |
| ribosomal protein L7 | RPL7 |
| ribosomal protein L7a | RPL7A |
| ribosomal protein L8 | RPL8 |
| ribosomal protein L9 | RPL9 |
| ribosomal protein, large, PO | RPLP0 |
| ribosomal protein, large, P0 pseudogene 2 | RPLP0P2 |
| ribosomal protein, large, PO pseudogene 3 | RPLP0P3 |
| ribosomal protein, large, PO pseudogene 6 | RPLP0P6 |
| ribosomal protein, large, P1 | RPLP1 |
| ribosomal protein, large, P2 | RPLP2 |
| ribophorin I | RPN1 |
| ribophorin II | RPN2 |
| ribonuclease P/MRP 30 kDa subunit | RPP30 |
| regulation of nuclear pre-mRNA domain containing 1B | RPRD1B |
| ribosomal protein S10 | RPS10 |
| ribosomal protein S10 pseudogene 11 | RPS10P11 |
| ribosomal protein S10 pseudogene 13 | RPS10P13 |
| ribosomal protein S10 pseudogene 22 | RPS10P22 |
| ribosomal protein S10 pseudogene 4 | RPS10P4 |
| ribosomal protein S10 pseudogene 7 | RPS10P7 |
| ribosomal protein S11 | RPS11 |
| ribosomal protein S12 | RPS12 |
| ribosomal protein S13 | RPS13 |
| ribosomal protein S14 | RPS14 |
| ribosomal protein S15 | RPS15 |
| ribosomal protein S15a | RPS15A |
| ribosomal protein S16 | RPS16 |
| ribosomal protein S16 pseudogene 1 | RPS16P1 |
| ribosomal protein S16 pseudogene 10 | RPS16P10 |

TABLE 4-continued

| Suitable extracellular vesicle associated proteins | |
| --- | --- |
| Gene Name | Gene Symbol |
| ribosomal protein S17 | RPS17 |
| ribosomal protein S18 | RPS18 |
| ribosomal protein S18 pseudogene 12 | RPS18P12 |
| ribosomal protein S18 pseudogene 5 | RPS18P5 |
| ribosomal protein S19 | RPS19 |
| ribosomal protein S2 | RPS2 |
| ribosomal protein S20 | RPS20 |
| ribosomal protein S21 | RPS21 |
| ribosomal protein S23 | RPS23 |
| ribosomal protein S24 | RPS24 |
| ribosomal protein S25 | RPS25 |
| ribosomal protein S26 | RPS26 |
| ribosomal protein S27 | RPS27 |
| ribosomal protein S27a | RPS27A |
| ribosomal protein S27a pseudogene 11 | RPS27AP11 |
| ribosomal protein S27a pseudogene 12 | RPS27AP12 |
| ribosomal protein S27a pseudogene 16 | RPS27AP16 |
| ribosomal protein S27-like | RPS27L |
| ribosomal protein S28 | RPS28 |
| ribosomal protein S29 | RPS29 |
| ribosomal protein S2 pseudogene 11 | RPS2P11 |
| ribosomal protein S2 pseudogene 12 | RPS2P12 |
| ribosomal protein S2 pseudogene 17 | RPS2P17 |
| ribosomal protein S2 pseudogene 20 | RPS2P20 |
| ribosomal protein S2 pseudogene 5 | RPS2P5 |
| ribosomal protein S2 pseudogene 51 | RPS2P51 |
| ribosomal protein S2 pseudogene 55 | RPS2P55 |
| ribosomal protein S2 pseudogene 8 | RPS2P8 |
| ribosomal protein S3 | RPS3 |
| ribosomal protein S3A | RPS3A |
| ribosomal protein S3 pseudogene 3 | RPS3P3 |
| ribosomal protein S4, X-linked | RPS4X |
| ribosomal protein S4X pseudogene 13 | RPS4XP13 |
| ribosomal protein S4X pseudogene 6 | RPS4XP6 |
| ribosomal protein S4, Y-linked 1 | RPS4Y1 |
| ribosomal protein S4, Y-linked 2 | RPS4Y2 |
| ribosomal protein S5 | RPS5 |
| ribosomal protein S6 | RPS6 |
| ribosomal protein S6 kinase, 90 kDa, polypeptide 1 | RPS6KA1 |
| ribosomal protein S6 kinase, 90 kDa, polypeptide 3 | RPS6KA3 |
| ribosomal protein S6 kinase, 90 kDa, polypeptide 4 | RPS6KA4 |
| ribosomal protein S6 kinase, 90 kDa, polypeptide 5 | RPS6KA5 |
| ribosomal protein S6 kinase, 90 kDa, polypeptide 6 | RPS6KA6 |
| ribosomal protein S7 | RPS7 |
| ribosomal protein S8 | RPS8 |
| ribosomal protein S9 | RPS9 |
| ribosomal protein SA | RPSA |
| ribosomal protein SA pseudogene 12 | RPSAP12 |
| ribosomal protein SA pseudogene 15 | RPSAP15 |
| ribosomal protein SA pseudogene 18 | RPSAP18 |
| ribosomal protein SA pseudogene 19 | RPSAP19 |

TABLE 4-continued

| Suitable extracellular vesicle associated proteins | |
| --- | --- |
| Gene Name | Gene Symbol |
| ribosomal protein SA pseudogene 29 | RPSAP29 |
| ribosomal protein SA pseudogene 58 | RPSAP58 |
| ribosomal protein SA pseudogene 61 | RPSAP61 |
| ribosomal protein SA pseudogene 8 | RPSAP8 |
| ribosomal protein SA pseudogene 9 | RPSAP9 |
| repetin | RPTN |
| regulatory associated protein of MTOR, complex 1 | RPTOR |
| RCD1 required for cell differentiation1 homolog (*S. pombe*) | RQCD1 |
| Ras-related GTP binding A | RRAGA |
| Ras-related GTP binding B | RRAGB |
| Ras-related GTP binding C | RRAGC |
| Ras-related GTP binding D | RRAGD |
| related RAS viral (r-ras) oncogene homolog | RRAS |
| related RAS viral (r-ras) oncogene homolog 2 | RRAS2 |
| ras responsive element binding protein 1 | RREB1 |
| ribonucleotide reductase M1 | RRM1 |
| ribonucleotide reductase M2 | RRM2 |
| ribosomal RNA processing 12 homolog (*S. cerevisiae*) | RRP12 |
| ribosomal RNA processing 1B | RRP1B |
| ribosomal RNA processing 9, small subunit (SSU) processome component, homolog (yeast) | RRP9 |
| RRS1 ribosome biogenesis regulator homolog (*S. cerevisiae*) | RRS1 |
| ribosomal L1 domain containing 1 | RSL1D1 |
| ring finger and SPRY domain containing 1 | RSPRY1 |
| Ras suppressor protein 1 | RSU1 |
| RNA 3'-terminal phosphate cyclase | RTCA |
| RNA 2',3'-cyclic phosphate and 5'-OH ligase | RTCB |
| regulator of telomere elongation helicase 1 | RTEL1 |
| rhotekin | RTKN |
| retrotransposon-like 1 | RTL1 |
| reticulon 2 | RTN2 |
| reticulon 3 | RTN3 |
| reticulon 4 | RTN4 |
| reticulon 4 receptor | RTN4R |
| RUN and FYVE domain containing 1 | RUFY1 |
| RUN and SH3 domain containing 2 | RUSC2 |
| RuvB-like AAA ATPase 1 | RUVBL1 |
| RuvB-like AAA ATPase 2 | RUVBL2 |
| ryanodine receptor 1 (skeletal) | RYR1 |
| ryanodine receptor 2 (cardiac) | RYR2 |
| S100 calcium binding protein A10 | S100A10 |
| S100 calcium binding protein A11 | S100A11 |
| S100 calcium binding protein A11 pseudogene 1 | S100A11P1 |
| S100 calcium binding protein A13 | S100A13 |
| S100 calcium binding protein A14 | S100A14 |
| S100 calcium binding protein A16 | S100A16 |
| S100 calcium binding protein A4 | S100A4 |
| S100 calcium binding protein A6 | S100A6 |
| S100 calcium binding protein A7 | S100A7 |
| S100 calcium binding protein A7A | S100A7A |
| S100 calcium binding protein A8 | S100A8 |

TABLE 4-continued

| Suitable extracellular vesicle associated proteins | |
| --- | --- |
| Gene Name | Gene Symbol |
| S100 calcium binding protein A9 | S100A9 |
| S100 calcium binding protein P | S100P |
| S100P binding protein | S100PBP |
| serum amyloid A1 | SAA1 |
| serum amyloid A2 | SAA2 |
| serum amyloid A4, constitutive | SAA4 |
| SAC1 suppressor of actin mutations 1-like (yeast) | SACM1L |
| sacsin molecular chaperone | SACS |
| SUMO1 activating enzyme subunit 1 | SAE1 |
| S-antigen; retina and pineal gland (arrestin) | SAG |
| spalt-like transcription factor 1 | SALL1 |
| sterile alpha motif domain containing 4A | SAMD4A |
| sterile alpha motif domain containing 9 | SAMD9 |
| sterile alpha motif domain containing 9-like | SAMD9L |
| SAM domain and HD domain 1 | SAMHD1 |
| SAMM50 sorting and assembly machinery component | SAMM50 |
| Sin3A-associated protein, 18 kDa | SAP18 |
| Sin3A-associated protein, 30 kDa | SAP30 |
| secretion associated, Ras related GTPase 1A | SAR1A |
| secretion associated, Ras related GTPase 1B | SAR1B |
| seryl-tRNA synthetase | SARS |
| squamous cell carcinoma antigen recognized by T cells 3 | SART3 |
| spindle assembly 6 homolog (*C. elegans*) | SASS6 |
| spermidine/spermine N1-acetyltransferase family member 2 | SAT2 |
| SATB homeobox 1 | SATB1 |
| Shwachman-Bodian-Diamond syndrome | SBDS |
| SET binding factor 1 | SBF1 |
| suprabasin | SBSN |
| secretory carrier membrane protein 1 | SCAMP1 |
| secretory carrier membrane protein 2 | SCAMP2 |
| secretory carrier membrane protein 3 | SCAMP3 |
| secretory carrier membrane protein 4 | SCAMP4 |
| scavenger receptor class B, member 1 | SCARB1 |
| scavenger receptor class B, member 2 | SCARB2 |
| saccharopine dehydrogenase (putative) | SCCPDH |
| sciellin | SCEL |
| sec1 family domain containing 1 | SCFD1 |
| single-chain Fv fragment | SCFV |
| secretoglobin, family 2A, member 1 | SCGB2A1 |
| secretoglobin, family 3A, member 1 | SCGB3A1 |
| scinderin | SCIN |
| sodium channel, voltage gated, type X alpha subunit | SCN10A |
| sodium channel, voltage gated, type XI alpha subunit | SCN11A |
| sodium channel, voltage gated, type V alpha subunit | SCN5A |
| short coiled-coil protein | SCOC |

TABLE 4-continued

| Suitable extracellular vesicle associated proteins | |
| --- | --- |
| Gene Name | Gene Symbol |
| serine carboxypeptidase 1 | SCPEP1 |
| scribbled planar cell polarity protein | SCRIB |
| secernin 1 | SCRN1 |
| secernin 2 | SCRN2 |
| scratch family zinc finger 1 | SCRT1 |
| SCY1-like 1 (*S. cerevisiae*) | SCYL1 |
| SCY1-like 2 (*S. cerevisiae*) | SCYL2 |
| syndecan 1 | SDC1 |
| syndecan 2 | SDC2 |
| syndecan 4 | SDC4 |
| syndecan binding protein (syntenin) | SDCBP |
| syndecan binding protein (syntenin) 2 | SDCBP2 |
| stromal cell-derived factor 2-like 1 | SDF2L1 |
| stromal cell derived factor 4 | SDF4 |
| succinate dehydrogenase complex, subunit A, flavoprotein (Fp) | SDHA |
| sidekick cell adhesion molecule 2 | SDK2 |
| serum deprivation response | SDPR |
| SEC11 homolog A (*S. cerevisiae*) | SEC11A |
| SEC13 homolog (*S. cerevisiae*) | SEC13 |
| SEC14-like 4 (*S. cerevisiae*) | SEC14L4 |
| SEC16 homolog A (*S. cerevisiae*) | SEC16A |
| SEC22 vesicle trafficking protein homolog B (*S. cerevisiae*) (gene/pseudogene) | SEC22B |
| Sec23 homolog A (*S. cerevisiae*) | SEC23A |
| Sec23 homolog B (*S. cerevisiae*) | SEC23B |
| SEC23 interacting protein | SEC23IP |
| SEC24 family member A | SEC24A |
| SEC24 family member B | SEC24B |
| SEC24 family member C | SEC24C |
| SEC24 family member D | SEC24D |
| SEC31 homolog A (*S. cerevisiae*) | SEC31A |
| Sec61 beta subunit | SEC61B |
| secreted and transmembrane 1 | SECTM1 |
| SEH1-like (*S. cerevisiae*) | SEH1L |
| selenium binding protein 1 | SELENBP1 |
| selectin L | SELL |
| selectin P (granule membrane protein 140 kDa, antigen CD62) | SELP |
| selectin P ligand | SELPLG |
| sema domain, immunoglobulin domain (Ig), short basic domain, secreted, (semaphorin) 3C | SEMA3C |
| sema domain, immunoglobulin domain (Ig), short basic domain, secreted, (semaphorin) 3F | SEMA3F |
| sema domain, immunoglobulin domain (Ig), short basic domain, secreted, (semaphorin) 3G | SEMA3G |
| sema domain, immunoglobulin domain (Ig), transmembrane domain (TM) and short cytoplasmic domain, (semaphorin) 4C | SEMA4C |
| sema domain, seven thrombospondin repeats (type 1 and type 1-like), transmembrane domain (TM) | SEMA5A |

TABLE 4-continued

| Suitable extracellular vesicle associated proteins | |
| --- | --- |
| Gene Name | Gene Symbol |
| and short cytoplasmic domain, (semaphorin) 5A | |
| semenogelin I | SEMG1 |
| semenogelin II | SEMG2 |
| selenoprotein P, plasma, 1 | SEPP1 |
| septin 1 | SEPT1 |
| septin 10 | SEPT10 |
| septin 11 | SEPT11 |
| septin 2 | SEPT2 |
| septin 5 | SEPT5 |
| septin 6 | SEPT6 |
| septin 7 | SEPT7 |
| septin 8 | SEPT8 |
| septin 9 | SEPT9 |
| SERPINE1 mRNA binding protein 1 | SERBP1 |
| serine incorporator 1 | SERINC1 |
| serine incorporator 2 | SERINC2 |
| serine incorporator 3 | SERINC3 |
| serine incorporator 5 | SERINC5 |
| serpin peptidase inhibitor, clade A (alpha-1 antiproteinase, antitrypsin), member 1 | SERPINA1 |
| serpin peptidase inhibitor, clade A (alpha-1 antiproteinase, antitrypsin), member 3 | SERPINA3 |
| serpin peptidase inhibitor, clade A (alpha-1 antiproteinase, antitrypsin), member 4 | SERPINA4 |
| serpin peptidase inhibitor, clade A (alpha-1 antiproteinase, antitrypsin), member 5 | SERPINA5 |
| serpin peptidase inhibitor, clade A (alpha-1 antiproteinase, antitrypsin), member 7 | SERPINA7 |
| serpin peptidase inhibitor, clade B (ovalbumin), member 1 | SERPINB1 |
| serpin peptidase inhibitor, clade B (ovalbumin), member 12 | SERPINB12 |
| serpin peptidase inhibitor, clade B (ovalbumin), member 13 | SERPINB13 |
| serpin peptidase inhibitor, clade B (ovalbumin), member 3 | SERPINB3 |
| serpin peptidase inhibitor, clade B (ovalbumin), member 4 | SERPINB4 |
| serpin peptidase inhibitor, clade B (ovalbumin), member 5 | SERPINB5 |
| serpin peptidase inhibitor, clade B (ovalbumin), member 6 | SERPINB6 |
| serpin peptidase inhibitor, clade B (ovalbumin), member 9 | SERPINB9 |
| serpin peptidase inhibitor, clade C (antithrombin), member 1 | SERPINC1 |
| serpin peptidase inhibitor, clade D (heparin cofactor), member 1 | SERPIND1 |
| serpin peptidase inhibitor, clade E (nexin, plasminogen activator inhibitor type 1), member 1 | SERPINE1 |
| serpin peptidase inhibitor, clade E (nexin, plasminogen activator inhibitor type 1), member 2 | SERPINE2 |
| serpin peptidase inhibitor, clade F (alpha-2 antiplasmin, pigment epithelium derived factor), member 1 | SERPINF1 |
| serpin peptidase inhibitor, clade F (alpha-2 antiplasmin, | SERPINF2 |

TABLE 4-continued

| Suitable extracellular vesicle associated proteins | |
| --- | --- |
| Gene Name | Gene Symbol |
| pigment epithelium derived factor), member 2 | |
| serpin peptidase inhibitor, clade G (C1 inhibitor), member 1 | SERPING1 |
| serpin peptidase inhibitor, clade H (heat shock protein 47), member 1, (collagen binding protein 1) | SERPINH1 |
| SEC14 and spectrin domains 1 | SESTD1 |
| SET nuclear proto-oncogene | SET |
| SET domain containing 4 | SETD4 |
| splicing factor 3a, subunit 1, 120 kDa | SF3A1 |
| splicing factor 3a, subunit 2, 66 kDa | SF3A2 |
| splicing factor 3a, subunit 3, 60 kDa | SF3A3 |
| splicing factor 3b, subunit 1, 155 kDa | SF3B1 |
| splicing factor 3b, subunit 2, 145 kDa | SF3B2 |
| splicing factor 3b, subunit 3, 130 kDa | SF3B3 |
| splicing factor 3b, subunit 4, 49 kDa | SF3B4 |
| splicing factor 3b, subunit 6, 14 kDa | SF3B6 |
| Sfi1 homolog, spindle assembly associated (yeast) | SFI1 |
| Scm-like with four mbt domains 1 | SFMBT1 |
| stratifin | SFN |
| splicing factor proline/glutamine-rich | SFPQ |
| secreted frizzled-related protein 1 | SFRP1 |
| secreted frizzled-related protein 4 | SFRP4 |
| SFT2 domain containing 2 | SFT2D2 |
| sideroflexin 1 | SFXN1 |
| sphingosine-1-phosphate lyase 1 | SGPL1 |
| small glutamine-rich tetratricopeptide repeat (TPR)-containing, alpha | SGTA |
| SH2B adaptor protein 1 | SH2B1 |
| SH2 domain containing 1A | SH2D1A |
| SH3 domain binding glutamate-rich protein like | SH3BGRL |
| SH3 domain binding glutamate-rich protein like 3 | SH3BGRL3 |
| SH3-domain binding protein 4 | SH3BP4 |
| SH3-domain GRB2-like 1 | SH3GL1 |
| SH3-domain GRB2-like endophilin B1 | SH3GLB1 |
| SH3-domain kinase binding protein 1 | SH3KBP1 |
| SH3 and multiple ankyrin repeat domains 3 | SHANK3 |
| sex hormone-binding globulin | SHBG |
| SHC (Src homology 2 domain containing) transforming protein 1 | SHC1 |
| SHC (Src homology 2 domain containing) transforming protein 2 | SHC2 |
| shisa family member 2 | SHISA2 |
| serine hydroxymethyltransferase 1 (soluble) | SHMT1 |
| serine hydroxymethyltransferase 2 (mitochondrial) | SHMT2 |
| soc-2 suppressor of clear homolog (C. elegans) | SHOC2 |

TABLE 4-continued

Suitable extracellular vesicle associated proteins

| Gene Name | Gene Symbol |
|---|---|
| sedoheptulokinase | SHPK |
| shroom family member 1 | SHROOM1 |
| shroom family member 2 | SHROOM2 |
| shroom family member 3 | SHROOM3 |
| sucrase-isomaltase (alpha-glucosidase) | SI |
| sialic acid acetylesterase | SIAE |
| single immunoglobulin and toll-interleukin 1 receptor (TIR) domain | SIGIRR |
| sialic acid binding Ig-like lectin 1, sialoadhesin | SIGLEC1 |
| signal-induced proliferation-associated 1 like 1 | SIPA1L1 |
| signal-regulatory protein alpha | SIRPA |
| signal-regulatory protein beta 1 | SIRPB1 |
| signaling threshold regulating transmembrane adaptor 1 | SIT1 |
| src kinase associated phosphoprotein 1 | SKAP1 |
| src kinase associated phosphoprotein 2 | SKAP2 |
| superkiller viralicidic activity 2-like (*S. cerevisiae*) | SKIV2L |
| superkiller viralicidic activity 2-like 2 (*S. cerevisiae*) | SKIV2L2 |
| SKI family transcriptional corepressor 2 | SKOR2 |
| S-phase kinase-associated protein 1 | SKP1 |
| Src-like-adaptor 2 | SLA2 |
| SLAIN motif family, member 1 | SLAIN1 |
| signaling lymphocytic activation molecule family member 1 | SLAMF1 |
| SLAM family member 6 | SLAMF6 |
| solute carrier family 10, member 3 | SLC10A3 |
| solute carrier family 12 (sodium/potassium/chloride transporter), member 1 | SLC12A1 |
| solute carrier family 12 (sodium/potassium/chloride transporter), member 2 | SLC12A2 |
| solute carrier family 12 (sodium/chloride transporter), member 3 | SLC12A3 |
| solute carrier family 12 (potassium/chloride transporter), member 4 | SLC12A4 |
| solute carrier family 12 (potassium/chloride transporter), member 5 | SLC12A5 |
| solute carrier family 12 (potassium/chloride transporter), member 6 | SLC12A6 |
| solute carrier family 12 (potassium/chloride transporter), member 7 | SLC12A7 |
| solute carrier family 12, member 9 | SLC12A9 |
| solute carrier family 13 (sodium-dependent dicarboxylate transporter), member 2 | SLC13A2 |
| solute carrier family 13 (sodium-dependent dicarboxylate transporter), member 3 | SLC13A3 |
| solute carrier family 15 (oligopeptide transporter), member 2 | SLC15A2 |
| solute carrier family 16 (monocarboxylate transporter), member 1 | SLC16A1 |

TABLE 4-continued

| Suitable extracellular vesicle associated proteins | |
| --- | --- |
| Gene Name | Gene Symbol |
| solute carrier family 16 (aromatic amino acid transporter), member 10 | SLC16A10 |
| solute carrier family 16 (monocarboxylate transporter), member 3 | SLC16A3 |
| solute carrier family 16, member 6 | SLC16A6 |
| solute carrier family 19 (folate transporter), member 1 | SLC19A1 |
| solute carrier family 19 (thiamine transporter), member 2 | SLC19A2 |
| solute carrier family 1 (neuronal/epithelial high affinity glutamate transporter, system Xag), member 1 | SLC1A1 |
| solute carrier family 1 (glial high affinity glutamate transporter), member 3 | SLC1A3 |
| solute carrier family 1 (glutamate/neutral amino acid transporter), member 4 | SLC1A4 |
| solute carrier family 1 (neutral amino acid transporter), member 5 | SLC1A5 |
| solute carrier family 20 (phosphate transporter), member 1 | SLC20A1 |
| solute carrier family 20 (phosphate transporter), member 2 | SLC20A2 |
| solute carrier family 22 (organic anion/urate transporter), member 11 | SLC22A11 |
| solute carrier family 22 (organic anion/urate transporter), member 12 | SLC22A12 |
| solute carrier family 22 (organic anion/urate transporter), member 13 | SLC22A13 |
| solute carrier family 22 (organic cation/carnitine transporter), member 16 | SLC22A16 |
| solute carrier family 22 (organic cation transporter), member 2 | SLC22A2 |
| solute carrier family 22 (organic cation/carnitine transporter), member 5 | SLC22A5 |
| solute carrier family 22 (organic anion transporter), member 6 | SLC22A6 |
| solute carrier family 22 (organic anion transporter), member 8 | SLC22A8 |
| solute carrier family 23 (ascorbic acid transporter), member 1 | SLC23A1 |
| solute carrier family 23 (ascorbic acid transporter), member 2 | SLC23A2 |
| solute carrier family 25 (mitochondrial carrier; citrate transporter), member 1 | SLC25A1 |
| solute carrier family 25 (mitochondrial carrier; dicarboxylate transporter), member 10 | SLC25A10 |
| solute carrier family 25 (mitochondrial carrier; oxoglutarate carrier), member 11 | SLC25A11 |
| solute carrier family 25 (aspartate/glutamate carrier), member 13 | SLC25A13 |

TABLE 4-continued

| Suitable extracellular vesicle associated proteins | |
| --- | --- |
| Gene Name | Gene Symbol |
| solute carrier family 25 (mitochondrial carrier; phosphate carrier), member 3 | SLC25A3 |
| solute carrier family 25 (mitochondrial carrier; adenine nucleotide translocator), member 31 | SLC25A31 |
| solute carrier family 25 (mitochondrial carrier; adenine nucleotide translocator), member 4 | SLC25A4 |
| solute carrier family 25 (mitochondrial carrier; adenine nucleotide translocator), member 5 | SLC25A5 |
| solute carrier family 25 (mitochondrial carrier; adenine nucleotide translocator), member 6 | SLC25A6 |
| solute carrier family 26 (anion exchanger), member 11 | SLC26A11 |
| solute carrier family 26 (anion exchanger), member 2 | SLC26A2 |
| solute carrier family 26 (anion exchanger), member 4 | SLC26A4 |
| solute carrier family 26 (anion exchanger), member 6 | SLC26A6 |
| solute carrier family 26 (anion exchanger), member 9 | SLC26A9 |
| solute carrier family 27 (fatty acid transporter), member 2 | SLC27A2 |
| solute carrier family 29 (equilibrative nucleoside transporter), member 1 | SLC29A1 |
| solute carrier family 29 (equilibrative nucleoside transporter), member 2 | SLC29A2 |
| solute carrier family 2 (facilitated glucose transporter), member 1 | SLC2A1 |
| solute carrier family 2 (facilitated glucose transporter), member 12 | SLC2A12 |
| solute carrier family 2 (facilitated glucose transporter), member 14 | SLC2A14 |
| solute carrier family 2 (facilitated glucose transporter), member 3 | SLC2A3 |
| solute carrier family 2 (facilitated glucose/fructose transporter), member 5 | SLC2A5 |
| solute carrier family 30 (zinc transporter), member 1 | SLC30A1 |
| solute carrier family 34 (type II sodium/phosphate cotransporter), member 1 | SLC34A1 |
| solute carrier family 34 (type II sodium/phosphate cotransporter), member 2 | SLC34A2 |
| solute carrier family 35 (adenosine 3'-phospho 5'-phosphosulfate transporter), member B2 | SLC35B2 |
| solute carrier family 35 (UDP-GlcNAc/UDP-glucose transporter), member D2 | SLC35D2 |
| solute carrier family 35, member D3 | SLC35D3 |
| solute carrier family 35, member F6 | SLC35F6 |
| solute carrier family 36 (proton/amino acid symporter), member 2 | SLC36A2 |

TABLE 4-continued

Suitable extracellular vesicle associated proteins

| Gene Name | Gene Symbol |
| --- | --- |
| solute carrier family 37 (glucose-6-phosphate transporter), member 2 | SLC37A2 |
| solute carrier family 38, member 1 | SLC38A1 |
| solute carrier family 38, member 2 | SLC38A2 |
| solute carrier family 38, member 3 | SLC38A3 |
| solute carrier family 38, member 5 | SLC38A5 |
| solute carrier family 39 (zinc transporter), member 1 | SLC39A1 |
| solute carrier family 39 (zinc transporter), member 10 | SLC39A10 |
| solute carrier family 39 (zinc transporter), member 14 | SLC39A14 |
| solute carrier family 39 (zinc transporter), member 4 | SLC39A4 |
| solute carrier family 39 (zinc transporter), member 5 | SLC39A5 |
| solute carrier family 39 (zinc transporter), member 6 | SLC39A6 |
| solute carrier family 39, member 9 | SLC39A9 |
| solute carrier family 3 (amino acid transporter heavy chain), member 1 | SLC3A1 |
| solute carrier family 3 (amino acid transporter heavy chain), member 2 | SLC3A2 |
| solute carrier family 43, member 3 | SLC43A3 |
| solute carrier family 44 (choline transporter), member 1 | SLC44A1 |
| solute carrier family 44 (choline transporter), member 2 | SLC44A2 |
| solute carrier family 44, member 4 | SLC44A4 |
| solute carrier family 45, member 2 | SLC45A2 |
| solute carrier family 46 (folate transporter), member 1 | SLC46A1 |
| solute carrier family 46, member 3 | SLC46A3 |
| solute carrier family 4 (anion exchanger), member 1 (Diego blood group) | SLC4A1 |
| solute carrier family 4, sodium borate transporter, member 11 | SLC4A11 |
| solute carrier family 4 (anion exchanger), member 2 | SLC4A2 |
| solute carrier family 4 (sodium bicarbonate cotransporter), member 4 | SLC4A4 |
| solute carrier family 4, sodium bicarbonate cotransporter, member 7 | SLC4A7 |
| solute carrier family 4, sodium bicarbonate cotransporter, member 8 | SLC4A8 |
| solute carrier family 5 (sodium/glucose cotransporter), member 1 | SLC5A1 |
| solute carrier family 5 (sodium/sugar cotransporter), member 10 | SLC5A10 |
| solute carrier family 5 (sodium/monocarboxylate cotransporter), member 12 | SLC5A12 |
| solute carrier family 5 (sodium/glucose cotransporter), member 2 | SLC5A2 |
| solute carrier family 5 (sodium/myo-inositol cotransporter), member 3 | SLC5A3 |

TABLE 4-continued

| Suitable extracellular vesicle associated proteins | |
| --- | --- |
| Gene Name | Gene Symbol |
| solute carrier family 5 (sodium/iodide cotransporter), member 5 | SLC5A5 |
| solute carrier family 5 (sodium/multivitamin and iodide cotransporter), member 6 | SLC5A6 |
| solute carrier family 5 (sodium/monocarboxylate cotransporter), member 8 | SLC5A8 |
| solute carrier family 5 (sodium/sugar cotransporter), member 9 | SLC5A9 |
| solute carrier family 6 (neurotransmitter transporter), member 13 | SLC6A13 |
| solute carrier family 6 (amino acid transporter), member 14 | SLC6A14 |
| solute carrier family 6 (neutral amino acid transporter), member 15 | SLC6A15 |
| solute carrier family 6 (neutral amino acid transporter), member 17 | SLC6A17 |
| solute carrier family 6 (neutral amino acid transporter), member 19 | SLC6A19 |
| solute carrier family 6 (neurotransmitter transporter), member 4 | SLC6A4 |
| solute carrier family 6 (neurotransmitter transporter), member 6 | SLC6A6 |
| solute carrier family 6 (neurotransmitter transporter), member 8 | SLC6A8 |
| solute carrier family 6 (neurotransmitter transporter, glycine), member 9 | SLC6A9 |
| solute carrier family 7 (cationic amino acid transporter, y+ system), member 1 | SLC7A1 |
| solute carrier family 7 (neutral amino acid transporter light chain, asc system), member 10 | SLC7A10 |
| solute carrier family 7 (anionic amino acid transporter light chain, xc− system), member 11 | SLC7A11 |
| solute carrier family 7 (cationic amino acid transporter, y+ system), member 2 | SLC7A2 |
| solute carrier family 7 (amino acid transporter light chain, L system), member 5 | SLC7A5 |
| solute carrier family 7 (amino acid transporter light chain, L system), member 8 | SLC7A8 |
| solute carrier family 8 (sodium/calcium exchanger), member 1 | SLC8A1 |
| solute carrier family 9, subfamily A (NHE1, cation proton antiporter 1), member 1 | SLC9A1 |
| solute carrier family 9, subfamily A (NHE3, cation proton antiporter 3), member 3 | SLC9A3 |
| solute carrier family 9, subfamily A (NHE3, cation proton antiporter 3), member 3 regulator 1 | SLC9A3R1 |

TABLE 4-continued

| Suitable extracellular vesicle associated proteins | |
|---|---|
| Gene Name | Gene Symbol |
| solute carrier family 9, subfamily A (NHE3, cation proton antiporter 3), member 3 regulator 2 | SLC9A3R2 |
| solute carrier family 9, subfamily A (NHE9, cation proton antiporter 9), member 9 | SLC9A9 |
| solute carrier family 9, subfamily C (Na+-transporting carboxylic acid decarboxylase), member 1 | SLC9C1 |
| solute carrier organic anion transporter family, member 3A1 | SLCO3A1 |
| solute carrier organic anion transporter family, member 4A1 | SLCO4A1 |
| solute carrier organic anion transporter family, member 4C1 | SLCO4C1 |
| schlafen family member 11 | SLFN11 |
| schlafen family member 5 | SLFN5 |
| slit homolog 2 (*Drosophila*) | SLIT2 |
| STE20-like kinase | SLK |
| secretory leukocyte peptidase inhibitor | SLPI |
| SAFB-like, transcription modulator | SLTM |
| SMAD family member 2 | SMAD2 |
| SMAD family member 5 | SMAD5 |
| SWI/SNF related, matrix associated, actin dependent regulator of chromatin, subfamily a, member 4 | SMARCA4 |
| SWI/SNF related, matrix associated, actin dependent regulator of chromatin, subfamily a, member 5 | SMARCA5 |
| SWI/SNF related, matrix associated, actin dependent regulator of chromatin, subfamily b, member 1 | SMARCB1 |
| SWI/SNF related, matrix associated, actin dependent regulator of chromatin, subfamily c, member 1 | SMARCC1 |
| SWI/SNF related, matrix associated, actin dependent regulator of chromatin, subfamily c, member 2 | SMARCC2 |
| SWI/SNF related, matrix associated, actin dependent regulator of chromatin, subfamily d, member 1 | SMARCD1 |
| SWI/SNF related, matrix associated, actin dependent regulator of chromatin, subfamily d, member 2 | SMARCD2 |
| SWI/SNF related, matrix associated, actin dependent regulator of chromatin, subfamily e, member 1 | SMARCE1 |
| structural maintenance of chromosomes 1A | SMC1A |
| structural maintenance of chromosomes 2 | SMC2 |
| structural maintenance of chromosomes 3 | SMC3 |
| structural maintenance of chromosomes 4 | SMC4 |
| structural maintenance of chromosomes 5 | SMC5 |
| structural maintenance of chromosomes flexible hinge domain containing 1 | SMCHD1 |

TABLE 4-continued

| Suitable extracellular vesicle associated proteins | |
| --- | --- |
| Gene Name | Gene Symbol |
| small integral membrane protein 22 | SMIM22 |
| small integral membrane protein 24 | SMIM24 |
| survival of motor neuron 1, telomeric | SMN1 |
| survival of motor neuron 2, centromeric | SMN2 |
| smoothened, frizzled class receptor | SMO |
| sphingomyelin phosphodiesterase, acid-like 3B | SMPDL3B |
| spermine synthase | SMS |
| smoothelin | SMTN |
| smu-1 suppressor of mec-8 and unc-52 homolog (*C. elegans*) | SMU1 |
| SMAD specific E3 ubiquitin protein ligase 1 | SMURF1 |
| synaptosomal-associated protein, 23 kDa | SNAP23 |
| synaptosomal-associated protein, 25 kDa | SNAP25 |
| synaptosomal-associated protein, 29 kDa | SNAP29 |
| synuclein, alpha (non A4 component of amyloid precursor) | SNCA |
| synuclein, beta | SNOB |
| synuclein, gamma (breast cancer-specific protein 1) | SNCG |
| staphylococcal nuclease and tudor domain containing 1 | SND1 |
| SNF8, ESCRT-II complex subunit | SNF8 |
| small nucleolar RNA, H/ACA box 27 | SNORA27 |
| small nuclear ribonucleoprotein 200 kDa (U5) | SNRNP200 |
| small nuclear ribonucleoprotein 40 kDa (U5) | SNRNP40 |
| small nuclear ribonucleoprotein 70 kDa (U1) | SNRNP70 |
| small nuclear ribonucleoprotein polypeptide A | SNRPA |
| small nuclear ribonucleoprotein polypeptide A' | SNRPA1 |
| small nuclear ribonucleoprotein polypeptides B and B1 | SNRPB |
| small nuclear ribonucleoprotein polypeptide B | SNRPB2 |
| small nuclear ribonucleoprotein D1 polypeptide 16 kDa | SNRPD1 |
| small nuclear ribonucleoprotein D2 polypeptide 16.5 kDa | SNRPD2 |
| small nuclear ribonucleoprotein D3 polypeptide 18 kDa | SNRPD3 |
| small nuclear ribonucleoprotein polypeptide E | SNRPE |
| small nuclear ribonucleoprotein polypeptide F | SNRPF |
| small nuclear ribonucleoprotein polypeptide G | SNRPG |

TABLE 4-continued

| Suitable extracellular vesicle associated proteins | |
| --- | --- |
| Gene Name | Gene Symbol |
| small nuclear ribonucleoprotein polypeptide N | SNRPN |
| syntrophin, alpha 1 | SNTA1 |
| syntrophin, beta 1 (dystrophin-associated protein A1, 59 kDa, basic component 1) | SNTB1 |
| syntrophin, beta 2 (dystrophin-associated protein A1, 59 kDa, basic component 2) | SNTB2 |
| sorting nexin 1 | SNX1 |
| sorting nexin 12 | SNX12 |
| sorting nexin 17 | SNX17 |
| sorting nexin 18 | SNX18 |
| sorting nexin 2 | SNX2 |
| sorting nexin 25 | SNX25 |
| sorting nexin family member 27 | SNX27 |
| sorting nexin 3 | SNX3 |
| sorting nexin 33 | SNX33 |
| sorting nexin 4 | SNX4 |
| sorting nexin 5 | SNX5 |
| sorting nexin 6 | SNX6 |
| sorting nexin 9 | SNX9 |
| superoxide dismutase 1, soluble | SOD1 |
| superoxide dismutase 3, extracellular | SOD3 |
| suppressor of glucose, autophagy associated 1 | SOGA1 |
| SON DNA binding protein | SON |
| sorbin and SH3 domain containing 1 | SORBS1 |
| sorbin and SH3 domain containing 3 | SORBS3 |
| sortilin-related VPS10 domain containing receptor 2 | SORCS2 |
| sorbitol dehydrogenase | SORD |
| sortilin-related receptor, L(DLR class) A repeats containing | SORL1 |
| sortilin 1 | SORT1 |
| SRY (sex determining region Y)-box 1 | SOX1 |
| SRY (sex determining region Y)-box 18 | SOX18 |
| sperm acrosome associated 1 | SPACA1 |
| sperm associated antigen 1 | SPAG1 |
| sperm associated antigen 5 | SPAG5 |
| sperm associated antigen 9 | SPAG9 |
| secreted protein, acidic, cysteine-rich (osteonectin) | SPARC |
| spastin | SPAST |
| spermatogenesis associated 21 | SPATA21 |
| spermatogenesis associated 5 | SPATA5 |
| spermatogenesis associated 5-like 1 | SPATA5L1 |
| spermatogenesis associated 7 | SPATA7 |
| signal peptidase complex subunit 2 homolog (S. cerevisiae) | SPCS2 |
| signal peptidase complex subunit 3 homolog (S. cerevisiae) | SPCS3 |
| sperm antigen with calponin homology and coiled-coil domains 1 | SPECC1 |
| sperm antigen with calponin homology and coiled-coil domains 1-like | SPECC1L |
| sperm flagellar 2 | SPEF2 |

TABLE 4-continued

| Suitable extracellular vesicle associated proteins | |
|---|---|
| Gene Name | Gene Symbol |
| spen family transcriptional repressor | SPEN |
| spastic paraplegia 11 (autosomal recessive) | SPG11 |
| spastic paraplegia 20 (Troyer syndrome) | SPG20 |
| spastic paraplegia 21 (autosomal recessive, Mast syndrome) | SPG21 |
| scaffolding protein involved in DNA repair | SPIDR |
| serine peptidase inhibitor, Kazal type 1 | SPINK1 |
| serine peptidase inhibitor, Kazal type 5 | SPINK5 |
| serine peptidase inhibitor, Kunitz type 1 | SPINT1 |
| serine peptidase inhibitor, Kunitz type, 2 | SPINT2 |
| spire-type actin nucleation factor 1 | SPIRE1 |
| sialophorin | SPN |
| spinster homolog 1 (*Drosophila*) | SPNS1 |
| sparc/osteonectin, cwcv and kazal-like domains proteoglycan (testican) 1 | SPOCK1 |
| spondin 1, extracellular matrix protein | SPON1 |
| spondin 2, extracellular matrix protein | SPON2 |
| secreted phosphoprotein 1 | SPP1 |
| secreted phosphoprotein 2, 24 kDa | SPP2 |
| signal peptide peptidase like 2A | SPPL2A |
| sepiapterin reductase (7,8-dihydrobiopterin:NADP+ oxidoreductase) | SPR |
| small proline-rich protein 3 | SPRR3 |
| sprouty homolog 1, antagonist of FGF signaling (*Drosophila*) | SPRY1 |
| sprouty homolog 4 (*Drosophila*) | SPRY4 |
| SPRY domain containing 7 | SPRYD7 |
| spectrin, alpha, non-erythrocytic 1 | SPTAN1 |
| spectrin, beta, erythrocytic | SPTB |
| spectrin, beta, non-erythrocytic 1 | SPTBN1 |
| spectrin, beta, non-erythrocytic 2 | SPTBN2 |
| spectrin, beta, non-erythrocytic 4 | SPTBN4 |
| spectrin, beta, non-erythrocytic 5 | SPTBN5 |
| serine palmitoyltransferase, long chain base subunit 1 | SPTLC1 |
| sequestosome 1 | SQSTM1 |
| steroid receptor RNA activator 1 | SRA1 |
| SRC proto-oncogene, non-receptor tyrosine kinase | SRC |
| splicing regulatory glutamine/lysine-rich protein 1 | SREK1 |
| SLIT-ROBO Rho GTPase activating protein 1 | SRGAP1 |
| SLIT-ROBO Rho GTPase activating protein 2 | SRGAP2 |
| serglycin | SRGN |
| sorcin | SRI |
| spermidine synthase | SRM |
| signal recognition particle 14 kDa (homologous Alu RNA binding protein) | SRP14 |

TABLE 4-continued

| Suitable extracellular vesicle associated proteins | |
| --- | --- |
| Gene Name | Gene Symbol |
| signal recognition particle 54 kDa | SRP54 |
| signal recognition particle 68 kDa | SRP68 |
| signal recognition particle 72 kDa | SRP72 |
| signal recognition particle 9 kDa | SRP9 |
| SRSF protein kinase 1 | SRPK1 |
| SRSF protein kinase 2 | SRPK2 |
| signal recognition particle receptor (docking protein) | SRPR |
| signal recognition particle receptor, B subunit | SRPRB |
| sushi-repeat containing protein, X-linked | SRPX |
| sushi-repeat containing protein, X-linked 2 | SRPX2 |
| serine/arginine repetitive matrix 2 | SRRM2 |
| serrate, RNA effector molecule | SRRT |
| serine/arginine-rich splicing factor 1 | SRSF1 |
| serine/arginine-rich splicing factor 10 | SRSF10 |
| serine/arginine-rich splicing factor 2 | SRSF2 |
| serine/arginine-rich splicing factor 3 | SRSF3 |
| serine/arginine-rich splicing factor 4 | SRSF4 |
| serine/arginine-rich splicing factor 5 | SRSF5 |
| serine/arginine-rich splicing factor 6 | SRSF6 |
| serine/arginine-rich splicing factor 7 | SRSF7 |
| serine/arginine-rich splicing factor 9 | SRSF9 |
| Sjogren syndrome antigen B (autoantigen La) | SSB |
| single-stranded DNA binding protein 1, mitochondrial | SSBP1 |
| SCO-spondin | SSPO |
| signal sequence receptor, alpha | SSR1 |
| signal sequence receptor, gamma (translocon-associated protein gamma) | SSR3 |
| signal sequence receptor, delta | SSR4 |
| structure specific recognition protein 1 | SSRP1 |
| suppression of tumorigenicity 13 (colon carcinoma) (Hsp70 interacting protein) | ST13 |
| suppression of tumorigenicity 13 (colon carcinoma) (Hsp70 interacting protein) pseudogene 4 | ST13P4 |
| suppression of tumorigenicity 13 (colon carcinoma) (Hsp70 interacting protein) pseudogene 5 | ST13P5 |
| suppression of tumorigenicity 14 (colon carcinoma) | ST14 |
| ST3 beta-galactoside alpha-2,3-sialyltransferase 1 | ST3GAL1 |
| ST3 beta-galactoside alpha-2,3-sialyltransferase 6 | ST3GAL6 |
| ST6 (alpha-N-acetyl-neuraminyl-2,3-beta-galactosyl-1,3)-N-acetylgalactosaminide alpha-2,6-sialyltransferase 6 | ST6GALNAC6 |

TABLE 4-continued

Suitable extracellular vesicle associated proteins

| Gene Name | Gene Symbol |
| --- | --- |
| stromal antigen 2 | STAG2 |
| stromal antigen 3 | STAG3 |
| signal transducing adaptor molecule (SH3 domain and ITAM motif) 1 | STAM |
| signal transducing adaptor molecule (SH3 domain and ITAM motif) 2 | STAM2 |
| STAM binding protein | STAMBP |
| StAR-related lipid transfer (START) domain containing 9 | STARD9 |
| signal transducer and activator of transcription 1, 91 kDa | STAT1 |
| signal transducer and activator of transcription 2, 113 kDa | STAT2 |
| signal transducer and activator of transcription 3 (acute-phase response factor) | STAT3 |
| signal transducer and activator of transcription 5A | STAT5A |
| signal transducer and activator of transcription 6, interleukin-4 induced | STAT6 |
| staufen double-stranded RNA binding protein 1 | STAU1 |
| staufen double-stranded RNA binding protein 2 | STAU2 |
| stanniocalcin 1 | STC1 |
| stanniocalcin 2 | STC2 |
| STEAP family member 3, metalloreductase | STEAP3 |
| STEAP family member 4 | STEAP4 |
| stromal interaction molecule 1 | STIM1 |
| stress-induced phosphoprotein 1 | STIP1 |
| serine/threonine kinase 10 | STK10 |
| serine/threonine kinase 11 | STK11 |
| serine/threonine kinase 17b | STK17B |
| serine/threonine kinase 24 | STK24 |
| serine/threonine kinase 25 | STK25 |
| serine/threonine protein kinase 26 | STK26 |
| serine/threonine kinase 38 | STK38 |
| serine/threonine kinase 38 like | STK38L |
| serine threonine kinase 39 | STK39 |
| serine/threonine kinase 4 | STK4 |
| stathmin 1 | STMN1 |
| stomatin | STOM |
| stomatin (EPB72)-like 2 | STOML2 |
| stomatin (EPB72)-like 3 | STOML3 |
| stonin 2 | STON2 |
| stimulated by retinoic acid 6 | STRA6 |
| serine/threonine kinase receptor associated protein | STRAP |
| spermatid perinuclear RNA binding protein | STRBP |
| striatin interacting protein 1 | STRIP1 |
| striatin, calmodulin binding protein 3 | STRN3 |
| STT3A, subunit of the oligosaccharyltransferase complex (catalytic) | STT3A |
| STT3B, subunit of the oligosaccharyltransferase complex (catalytic) | STT3B |
| STIP1 homology and U-box containing protein 1, E3 ubiquitin protein ligase | STUB1 |
| syntaxin 10 | STX10 |
| syntaxin 11 | STX11 |
| syntaxin 12 | STX12 |
| syntaxin 16 | STX16 |
| syntaxin 1A (brain) | STX1A |

TABLE 4-continued

| Suitable extracellular vesicle associated proteins | |
| --- | --- |
| Gene Name | Gene Symbol |
| syntaxin 1B | STX1B |
| syntaxin 2 | STX2 |
| syntaxin 3 | STX3 |
| syntaxin 4 | STX4 |
| syntaxin 6 | STX6 |
| syntaxin 7 | STX7 |
| syntaxin 8 | STX8 |
| syntaxin binding protein 1 | STXBP1 |
| syntaxin binding protein 2 | STXBP2 |
| syntaxin binding protein 3 | STXBP3 |
| syntaxin binding protein 4 | STXBP4 |
| syntaxin binding protein 5 (tomosyn) | STXBP5 |
| syntaxin binding protein 6 (amisyn) | STXBP6 |
| SUB1 homolog (*S. cerevisiae*) | SUB1 |
| succinate-CoA ligase, ADP-forming, beta subunit | SUCLA2 |
| succinate-CoA ligase, GDP-forming, beta subunit | SUCLG2 |
| succinate receptor 1 | SUCNR1 |
| SGT1, suppressor of G2 allele of SKP1 (*S. cerevisiae*) | SUGT1 |
| sulfatase 2 | SULF2 |
| sulfotransferase family, cytosolic, 1A, phenol-preferring, member 1 | SULT1A1 |
| small ubiquitin-like modifier 2 | SUMO2 |
| small ubiquitin-like modifier 3 | SUMO3 |
| small ubiquitin-like modifier 4 | SUMO4 |
| suppressor of Ty 16 homolog (*S. cerevisiae*) | SUPT16H |
| suppressor of Ty 20 homolog (*S. cerevisiae*) | SUPT20H |
| suppressor of Ty 5 homolog (*S. cerevisiae*) | SUPT5H |
| surfeit 4 | SURF4 |
| sushi domain containing 1 | SUSD1 |
| sushi domain containing 2 | SUSD2 |
| sushi domain containing 3 | SUSD3 |
| sushi, von Willebrand factor type A, EGF and pentraxin domain containing 1 | SVEP1 |
| small VCP/p97-interacting protein | SVIP |
| SWAP switching B-cell complex 70 kDa subunit | SWAP70 |
| synaptonemal complex protein 2 | SYCP2 |
| spleen tyrosine kinase | SYK |
| symplekin | SYMPK |
| synapsin II | SYN2 |
| synaptotagmin binding, cytoplasmic RNA interacting protein | SYNCRIP |
| spectrin repeat containing, nuclear envelope 1 | SYNE1 |
| spectrin repeat containing, nuclear envelope 2 | SYNE2 |
| synaptogyrin 1 | SYNGR1 |
| synaptogyrin 2 | SYNGR2 |
| synaptojanin 2 | SYNJ2 |
| synergin, gamma | SYNRG |
| synaptophysin-like 1 | SYPL1 |
| synaptotagmin I | SYT1 |
| synaptotagmin V | SYT5 |
| synaptotagmin IX | SYT9 |
| synaptotagmin-like 1 | SYTL1 |
| synaptotagmin-like 2 | SYTL2 |
| synaptotagmin-like 4 | SYTL4 |
| synaptotagmin-like 5 | SYTL5 |
| seizure threshold 2 homolog (mouse) | SZT2 |
| trace amine associated receptor 2 | TAAR2 |

TABLE 4-continued

| Suitable extracellular vesicle associated proteins | |
| --- | --- |
| Gene Name | Gene Symbol |
| transforming, acidic coiled-coil containing protein 2 | TACC2 |
| tumor-associated calcium signal transducer 2 | TACSTD2 |
| TAF10 RNA polymerase II, TATA box binding protein (TBP)-associated factor, 30 kDa | TAF10 |
| transgelin | TAGLN |
| transgelin 2 | TAGLN2 |
| transaldolase 1 | TALDO1 |
| tetratricopeptide repeat, ankyrin repeat and coiled-coil containing 1 | TANC1 |
| TAO kinase 1 | TAOK1 |
| TAO kinase 2 | TAOK2 |
| TAO kinase 3 | TAOK3 |
| transporter 1, ATP-binding cassette, sub-family B (MDR/TAP) | TAP1 |
| TAP binding protein (tapasin) | TAPBP |
| TAR (HIV-1) RNA binding protein 1 | TARBP1 |
| TAR DNA binding protein | TARDBP |
| threonyl-tRNA synthetase | TARS |
| threonyl-tRNA synthetase-like 2 | TARSL2 |
| taste receptor, type 2, member 60 | TAS2R60 |
| Taxi (human T-cell leukemia virus type 1) binding protein 1 | TAX1BP1 |
| Taxi (human T-cell leukemia virus type I) binding protein 3 | TAX1BP3 |
| TBC1 (tre-2/USP6, BUB2, cdc16) domain family, member 1 | TBC1D1 |
| TBC1 domain family, member 10A | TBC1D10A |
| TBC1 domain family, member 10B | TBC1D10B |
| TBC1 domain family, member 15 | TBC1D15 |
| TBC1 domain family, member 2 | TBC1D2 |
| TBC1 domain family, member 21 | TBC1D21 |
| TBC1 domain family, member 24 | TBC1D24 |
| TBC1 domain family, member 32 | TBC1D32 |
| tubulin folding cofactor A | TBCA |
| tubulin folding cofactor B | TBCB |
| tubulin folding cofactor D | TBCD |
| tubulin folding cofactor E | TBCE |
| TANK-binding kinase 1 | TBK1 |
| transducin (beta)-like 1 X-linked receptor 1 | TBL1XR1 |
| thromboxane A2 receptor | TBXA2R |
| thromboxane A synthase 1 (platelet) | TBXAS1 |
| tandem C2 domains, nuclear | TC2N |
| TRPM8 channel-associated factor 1 | TCAF1 |
| transcription elongation factor A (SII), 1 | TCEA1 |
| transcription elongation factor B (SIII), polypeptide 1 (15 kDa, elongin C) | TCEB1 |
| transcription elongation factor B (SIII), polypeptide 2 (18 kDa, elongin B) | TCEB2 |
| T-cell, immune regulator 1, ATPase, H + transporting, lysosomal VO subunit A3 | TCIRG1 |
| transcobalamin I (vitamin B12 binding protein, R binder family) | TCN1 |

TABLE 4-continued

| Gene Name | Gene Symbol |
| --- | --- |
| Suitable extracellular vesicle associated proteins | |
| Treacher Collins-Franceschetti syndrome 1 | TCOF1 |
| t-complex 1 | TCP1 |
| tyrosyl-DNA phosphodiesterase 2 | TDP2 |
| tudor domain containing 9 | TDRD9 |
| tec protein tyrosine kinase | TEC |
| tectorin alpha | TECTA |
| tektin 3 | TEKT3 |
| telomere maintenance 2 | TELO2 |
| teneurin transmembrane protein 3 | TENM3 |
| teneurin transmembrane protein 4 | TENM4 |
| telomerase-associated protein 1 | TEP1 |
| telomeric repeat binding factor (NIMA-interacting) 1 | TERF1 |
| telomeric repeat binding factor (NIMA-interacting) 1 pseudogene 2 | TERF1P2 |
| telomeric repeat binding factor (NIMA-interacting) 1 pseudogene 3 | TERF1P3 |
| telomeric repeat binding factor (NIMA-interacting) 1 pseudogene 5 | TERF1P5 |
| telomeric repeat binding factor 2, interacting protein | TERF2IP |
| testin LIM domain protein | TES |
| tescalcin | TESC |
| testis-specific kinase 1 | TESK1 |
| testis expressed 10 | TEX10 |
| transferrin | TF |
| TRK-fused gene | TFG |
| tissue factor pathway inhibitor (lipoprotein-associated coagulation inhibitor) | TFPI |
| transferrin receptor | TFRC |
| transforming growth factor, beta 1 | TGFB1 |
| transforming growth factor, beta 2 | TGFB2 |
| transforming growth factor, beta-induced, 68kDa | TGFBI |
| transforming growth factor, beta receptor II (70/80 kDa) | TGFBR2 |
| transforming growth factor, beta receptor III | TGFBR3 |
| transforming growth factor, beta receptor associated protein 1 | TGFBRAP1 |
| transglutaminase 1 | TGM1 |
| transglutaminase 2 | TGM2 |
| transglutaminase 3 | TGM3 |
| transglutaminase 4 | TGM4 |
| trans-golgi network protein 2 | TGOLN2 |
| thyroid adenoma associated | THADA |
| THAP domain containing 11 | THAP11 |
| thrombospondin 1 | THBS1 |
| thrombospondin 2 | THBS2 |
| thrombospondin 4 | THBS4 |
| thymocyte selection associated | THEMIS |
| thymocyte selection associated family member 2 | THEMIS2 |
| threonine synthase-like 1 (S. cerevisiae) | THNSL1 |
| threonine synthase-like 2 (S. cerevisiae) | THNSL2 |
| THO complex 1 | THOC1 |
| THO complex 2 | THOC2 |
| THO complex 5 | THOC5 |
| THO complex 6 | THOC6 |
| THO complex 7 | THOC7 |
| thimet oligopeptidase 1 | THOP1 |

TABLE 4-continued

| Suitable extracellular vesicle associated proteins | |
| --- | --- |
| Gene Name | Gene Symbol |
| thyroid hormone receptor associated protein 3 | THRAP3 |
| thrombospondin, type I, domain containing 1 | THSD1 |
| thrombospondin, type I, domain containing 4 | THSD4 |
| thrombospondin, type I, domain containing 7A | THSD7A |
| Thy-1 cell surface antigen | THY1 |
| thymocyte nuclear protein 1 | THYN1 |
| TIA1 cytotoxic granule-associated RNA binding protein-like 1 | TIAL1 |
| T-cell lymphoma invasion and metastasis 2 | TIAM2 |
| tigger transposable element derived 4 | TIGD4 |
| translocase of inner mitochondrial membrane 50 homolog (*S. cerevisiae*) | TIMM50 |
| TIMP metallopeptidase inhibitor 1 | TIMP1 |
| TIMP metallopeptidase inhibitor 2 | TIMP2 |
| TIMP metallopeptidase inhibitor 3 | TIMP3 |
| tubulointerstitial nephritis antigen-like 1 | TINAGL1 |
| TOR signaling pathway regulator | TIPRL |
| tight junction protein 1 | TJP1 |
| tight junction protein 2 | TJP2 |
| triokinase/FMN cyclase | TKFC |
| transketolase | TKT |
| talin 1 | TLN1 |
| talin 2 | TLN2 |
| toll-like receptor 2 | TLR2 |
| transmembrane 7 superfamily member 3 | TM7SF3 |
| transmembrane 9 superfamily member 2 | TM9SF2 |
| transmembrane 9 superfamily member 3 | TM9SF3 |
| transmembrane 9 superfamily protein member 4 | TM9SF4 |
| transmembrane BAX inhibitor motif containing 1 | TMBIM1 |
| transmembrane BAX inhibitor motif containing 6 | TMBIM6 |
| transmembrane channel-like 6 | TMC6 |
| transmembrane channel-like 7 | TMC7 |
| transmembrane channel-like 8 | TMC8 |
| transmembrane and coiled-coil domains 1 | TMCO1 |
| transmembrane emp24 protein transport domain containing 1 | TMED1 |
| transmembrane emp24-like trafficking protein 10 (yeast) | TMED10 |
| transmembrane emp24 domain trafficking protein 2 | TMED2 |
| transmembrane emp24 protein transport domain containing 4 | TMED4 |
| transmembrane emp24 protein transport domain containing 5 | TMED5 |
| transmembrane emp24 protein transport domain containing 7 | TMED7 |
| TMED7-TICAM2 readthrough | TMED7-TICAM2 |
| transmembrane emp24 protein transport domain containing 8 | TMED8 |

TABLE 4-continued

| Suitable extracellular vesicle associated proteins | |
| --- | --- |
| Gene Name | Gene Symbol |
| transmembrane emp24 protein transport domain containing 9 | TMED9 |
| transmembrane protein 100 | TMEM100 |
| transmembrane protein 104 | TMEM104 |
| transmembrane protein 109 | TMEM109 |
| transmembrane protein 117 | TMEM117 |
| transmembrane protein 165 | TMEM165 |
| TMEM189-UBE2V1 readthrough | TMEM189-UBE2V1 |
| transmembrane protein 192 | TMEM192 |
| transmembrane protein 2 | TMEM2 |
| transmembrane protein 200A | TMEM200A |
| transmembrane protein 237 | TMEM237 |
| transmembrane protein 256 | TMEM256 |
| transmembrane protein 27 | TMEM27 |
| transmembrane protein 30A | TMEM30A |
| transmembrane protein 30B | TMEM30B |
| transmembrane protein 33 | TMEM33 |
| transmembrane protein 38A | TMEM38A |
| transmembrane protein 40 | TMEM40 |
| transmembrane protein 43 | TMEM43 |
| transmembrane protein 45B | TMEM45B |
| transmembrane protein 47 | TMEM47 |
| transmembrane protein 50A | TMEM50A |
| transmembrane protein 51 | TMEM51 |
| transmembrane protein 52B | TMEM52B |
| transmembrane protein 55A | TMEM55A |
| transmembrane protein 55B | TMEM55B |
| transmembrane protein 59 | TMEM59 |
| transmembrane protein 63A | TMEM63A |
| transmembrane protein 63B | TMEM63B |
| transmembrane protein 87A | TMEM87A |
| transmembrane protein 87B | TMEM87B |
| transmembrane protein 9 | TMEM9 |
| TATA element modulatory factor 1 | TMF1 |
| tropomodulin 2 (neuronal) | TMOD2 |
| tropomodulin 3 (ubiquitous) | TMOD3 |
| thymopoietin | TMPO |
| transmembrane protease, serine 11B | TMPRSS11B |
| transmembrane protease, serine 11D | TMPRSS11D |
| transmembrane protease, serine 2 | TMPRSS2 |
| transmembrane protease, serine 4 | TMPRSS4 |
| thioredoxin-related transmembrane protein 1 | TMX1 |
| thioredoxin-related transmembrane protein 2 | TMX2 |
| tenascin C | TNC |
| tumor necrosis factor, alpha-induced protein 2 | TNFAIP2 |
| tumor necrosis factor, alpha-induced protein 3 | TNFAIP3 |
| tumor necrosis factor, alpha-induced protein 8 | TNFAIP8 |
| tumor necrosis factor receptor superfamily, member 10a | TNFRSF10A |
| tumor necrosis factor receptor superfamily, member 10b | TNFRSF10B |
| tumor necrosis factor receptor superfamily, member 10d, decoy with truncated death domain | TNFRSF10D |
| tumor necrosis factor receptor superfamily, member 11a, RANK | TNFRSF11A, RANK |
| tumor necrosis factor receptor superfamily, member 11b | TNFRSF11B |
| tumor necrosis factor receptor superfamily, member 12A | TNFRSF12A |
| tumor necrosis factor receptor superfamily, member 1A | TNFRSF1A |

TABLE 4-continued

| Suitable extracellular vesicle associated proteins | |
| --- | --- |
| Gene Name | Gene Symbol |
| tumor necrosis factor receptor superfamily, member 21 | TNFRSF21 |
| tumor necrosis factor receptor superfamily, member 8 | TNFRSF8 |
| tumor necrosis factor (ligand) superfamily, member 10, tumor necrosis factor-related apoptosis-inducing ligand (TRAIL) | TNFSF10,TRAIL |
| tumor necrosis factor (ligand) superfamily, member 12 | TNFSF12 |
| tumor necrosis factor (ligand) superfamily, member 13 | TNFSF13 |
| tumor necrosis factor (ligand) superfamily, member 18 | TNFSF18 |
| TRAF2 and NCK interacting kinase | TNIK |
| TNFAIP3 interacting protein 1 | TNIP1 |
| tankyrase 1 binding protein 1, 182 kDa | TNKS1BP1 |
| troponin I type 2 (skeletal, fast) | TNNI2 |
| transportin 1 | TNPO1 |
| transportin 2 | TNPO2 |
| transportin 3 | TNPO3 |
| tensin 3 | TNS3 |
| tensin 4 | TNS4 |
| target of EGR1, member 1 (nuclear) | TOE1 |
| toll interacting protein | TOLLIP |
| target of myb1 (chicken) | TOM1 |
| target of myb1 (chicken)-like 1 | TOM1L1 |
| target of myb1-like 2 (chicken) | TOM1L2 |
| Mitochondrial import receptor subunit TOM20 | TOM20 |
| translocase of outer mitochondrial membrane 22 homolog (yeast) | TOMM22 |
| translocase of outer mitochondrial membrane 34 | TOMM34 |
| translocase of outer mitochondrial membrane 40 homolog (yeast) | TOMM40 |
| translocase of outer mitochondrial membrane 70 homolog A (*S. cerevisiae*) | TOMM70A |
| topoisomerase (DNA) I | TOP1 |
| topoisomerase (DNA) II alpha 170 kDa | TOP2A |
| topoisomerase (DNA) II beta 180 kDa | TOP2B |
| torsin family 1, member A (torsin A) | TOR1A |
| torsin family 1, member B (torsin B) | TOR1B |
| torsin family 3, member A | TOR3A |
| torsin family 4, member A | TOR4A |
| TP53 regulating kinase | TP53RK |
| trophoblast glycoprotein | TPBG |
| trophoblast glycoprotein-like | TPBGL |
| two pore segment channel 1 | TPCN1 |
| tumor protein D52 | TPD52 |
| tumor protein D52-like 2 | TPD52L2 |
| triosephosphate isomerase 1 | TPI1 |
| triosephosphate isomerase 1 pseudogene 1 | TPI1P1 |
| tropomyosin 1 (alpha) | TPM1 |
| tropomyosin 2 (beta) | TPM2 |
| tropomyosin 3 | TPM3 |
| tropomyosin 4 | TPM4 |
| thiopurine S-methyltransferase | TPMT |
| tripeptidyl peptidase I | TPP1 |
| tripeptidyl peptidase II | TPP2 |
| tubulin polymerization promoting protein | TPPP |

TABLE 4-continued

| Suitable extracellular vesicle associated proteins | |
| --- | --- |
| Gene Name | Gene Symbol |
| tumor protein p63 regulated 1-like | TPRG1L |
| taperin | TPRN |
| tyrosylprotein sulfotransferase 2 | TPST2 |
| tumor protein, translationally-controlled 1 | TPT1 |
| transformer 2 alpha homolog (*Drosophila*) | TRA2A |
| transformer 2 beta homolog (*Drosophila*) | TRA2B |
| TNFRSF1A-associated via death domain | TRADD |
| TNF receptor-associated factor 1 | TRAF1 |
| TNF receptor-associated factor 4 | TRAF4 |
| trafficking protein, kinesin binding 1 | TRAK1 |
| tetratricopeptide repeat and ankyrin repeat containing 1 | TRANK1 |
| TNF receptor-associated protein 1 | TRAP1 |
| trafficking protein particle complex 10 | TRAPPC10 |
| trafficking protein particle complex 11 | TRAPPC11 |
| trafficking protein particle complex 12 | TRAPPC12 |
| trafficking protein particle complex 13 | TRAPPC13 |
| trafficking protein particle complex 3 | TRAPPC3 |
| trafficking protein particle complex 4 | TRAPPC4 |
| trafficking protein particle complex 5 | TRAPPC5 |
| trafficking protein particle complex 8 | TRAPPC8 |
| trafficking protein particle complex 9 | TRAPPC9 |
| T cell receptor associated transmembrane adaptor 1 | TRAT1 |
| trehalase (brush-border membrane glycoprotein) | TREH |
| triggering receptor expressed on myeloid cells 1 | TREM1 |
| triggering receptor expressed on myeloid cells-like 1 | TREML1 |
| triggering receptor expressed on myeloid cells-like 2 | TREML2 |
| triggering receptor expressed on myeloid cells-like 5, pseudogene | TREML5P |
| thyrotropin-releasing hormone degrading enzyme | TRHDE |
| tripartite motif containing 16 | TRIM16 |
| tripartite motif containing 21 | TRIM21 |
| tripartite motif containing 23 | TRIM23 |
| tripartite motif containing 25 | TRIM25 |
| tripartite motif containing 26 | TRIM26 |
| tripartite motif containing 28 | TRIM28 |
| tripartite motif containing 32 | TRIM32 |
| tripartite motif containing 38 | TRIM38 |
| tripartite motif containing 40 | TRIM40 |
| tripartite motif containing 41 | TRIM41 |
| tripartite motif containing 56 | TRIM56 |
| tripartite motif containing 58 | TRIM58 |
| tripartite motif containing 65 | TRIM65 |
| tripartite motif containing 69 | TRIM69 |
| trio Rho guanine nucleotide exchange factor | TRIO |
| TRIO and F-actin binding protein | TRIOBP |
| thyroid hormone receptor interactor 10 | TRIP10 |

TABLE 4-continued

| Suitable extracellular vesicle associated proteins | |
| --- | --- |
| Gene Name | Gene Symbol |
| thyroid hormone receptor interactor 11 | TRIP11 |
| thyroid hormone receptor interactor 12 | TRIP12 |
| thyroid hormone receptor interactor 13 | TRIP13 |
| thyroid hormone receptor interactor 6 | TRIP6 |
| tRNA methyltransferase 10 homolog A (*S. cerevisiae*) | TRMT10A |
| tRNA methyltransferase 11-2 homolog (*S. cerevisiae*) | TRMT112 |
| tRNA methyltransferase 1 homolog (*S. cerevisiae*)-like | TRMT1L |
| tRNA methyltransferase 2 homolog A (*S. cerevisiae*) | TRMT2A |
| tRNA methyltransferase 61A | TRMT61A |
| TROVE domain family, member 2 | TROVE2 |
| transient receptor potential cation channel, subfamily C, member 6 | TRPC6 |
| transient receptor potential cation channel, subfamily M, member 4 | TRPM4 |
| transient receptor potential cation channel, subfamily V, member 4 | TRPV4 |
| transformation/transcription domain-associated protein | TRRAP |
| TruB pseudouridine (psi) synthase family member 1 | TRUB1 |
| tuberous sclerosis 2 | TSC2 |
| tumor susceptibility 101 | TSG101 |
| thyroid stimulating hormone receptor | TSHR |
| teashirt zinc finger homeobox 1 | TSHZ1 |
| translin | TSN |
| translin-associated factor X | TSNAX |
| translin-associated factor X interacting protein 1 | TSNAXIP1 |
| tetraspanin 1 | TSPAN1 |
| tetraspanin 10 | TSPAN10 |
| tetraspanin 14 | TSPAN14 |
| tetraspanin 15 | TSPAN15 |
| tetraspanin 3 | TSPAN3 |
| tetraspanin 33 | TSPAN33 |
| tetraspanin 4 | TSPAN4 |
| tetraspanin 6 | TSPAN6 |
| tetraspanin 8 | TSPAN8 |
| tetraspanin 9 | TSPAN9 |
| translocator protein (18 kDa) | TSPO |
| TSPY-like 4 | TSPYL4 |
| TSR1, 20S rRNA accumulation, homolog (*S. cerevisiae*) | TSR1 |
| tumor suppressing subtransferable candidate 1 | TSSC1 |
| thiosulfate sulfurtransferase (rhodanese) | TST |
| tissue specific transplantation antigen P35B | TSTA3 |
| tau tubulin kinase 2 | TTBK2 |
| tetratricopeptide repeat domain 17 | TTC17 |
| tetratricopeptide repeat domain 21B | TTC21B |
| tetratricopeptide repeat domain 27 | TTC27 |
| tetratricopeptide repeat domain 37 | TTC37 |
| tetratricopeptide repeat domain 38 | TTC38 |
| tetratricopeptide repeat domain 39A | TTC39A |

TABLE 4-continued

| Gene Name | Gene Symbol |
| --- | --- |
| | Suitable extracellular vesicle associated proteins |
| tetratricopeptide repeat domain 7A | TTC7A |
| tetratricopeptide repeat domain 7B | TTC7B |
| TELO2 interacting protein 1 | TTI1 |
| TELO2 interacting protein 2 | TTI2 |
| tubulin tyrosine ligase-like family member 12 | TTLL12 |
| tubulin tyrosine ligase-like family member 3 | TTLL3 |
| titin | TTN |
| transthyretin | TTR |
| tweety family member 2 | TTYH2 |
| tweety family member 3 | TTYH3 |
| tubulin, alpha 1a | TUBA1A |
| tubulin, alpha 1b | TUBA1B |
| tubulin, alpha 1c | TUBA1C |
| tubulin, alpha 3c | TUBA3C |
| tubulin, alpha 3d | TUBA3D |
| tubulin, alpha 3e | TUBA3E |
| tubulin, alpha 4a | TUBA4A |
| tubulin, alpha 4b | TUBA4B |
| tubulin, alpha 8 | TUBA8 |
| tubulin, alpha-like 3 | TUBAL3 |
| tubulin, alpha pseudogene 2 | TUBAP2 |
| tubulin, beta class I | TUBB |
| tubulin, beta 1 class VI | TUBB1 |
| tubulin, beta 2A class IIa | TUBB2A |
| tubulin, beta 2B class IIb | TUBB2B |
| tubulin, beta 3 class III | TUBB3 |
| tubulin, beta 4A class IVa | TUBB4A |
| tubulin, beta 4B class IVb | TUBB4B |
| tubulin, beta 6 class V | TUBB6 |
| tubulin, beta 7, pseudogene | TUBB7P |
| tubulin, beta 8 class VIII | TUBB8 |
| tubulin, beta pseudogene 1 | TUBBP1 |
| tubulin, beta pseudogene 2 | TUBBP2 |
| tubulin, beta class I pseudogene 6 | TUBBP6 |
| tubulin, gamma 1 | TUBG1 |
| tubulin, gamma complex associated protein 2 | TUBGCP2 |
| tubulin, gamma complex associated protein 3 | TUBGCP3 |
| tubulin, gamma complex associated protein 4 | TUBGCP4 |
| Tu translation elongation factor, mitochondrial | TUFM |
| twinfilin actin binding protein 1 | TWF1 |
| twinfilin actin binding protein 2 | TWF2 |
| taxilin alpha | TXLNA |
| thioredoxin | TXN |
| thioredoxin domain containing 16 | TXNDC16 |
| thioredoxin domain containing 17 | TXNDC17 |
| thioredoxin domain containing 5 (endoplasmic reticulum) | TXNDC5 |
| thioredoxin domain containing 8 (spermatozoa) | TXNDC8 |
| thioredoxin-like 1 | TXNL1 |
| thioredoxin reductase 1 | TXNRD1 |
| tyrosine kinase 2 | TYK2 |
| thymidine phosphorylase | TYMP |
| tyrosinase-related protein 1 | TYRP1 |
| tRNA-yW synthesizing protein 5 | TYW5 |
| U2 small nuclear RNA auxiliary factor 1 | U2AF1 |
| U2 small nuclear RNA auxiliary factor 1-like 4 | U2AF1L4 |
| U2 small nuclear RNA auxiliary factor 2 | U2AF2 |
| U2 snRNP-associated SURP domain containing | U2SURP |
| uveal autoantigen with coiled-coil domains and ankyrin repeats | UACA |

TABLE 4-continued

Suitable extracellular vesicle associated proteins

| Gene Name | Gene Symbol |
| --- | --- |
| UDP-N-acetylglucosamine pyrophosphorylase 1 | UAP1 |
| UDP-N-acetylglucosamine pyrophosphorylase 1 like 1 | UAP1L1 |
| ubiquitin-like modifier activating enzyme 1 | UBA1 |
| ubiquitin-like modifier activating enzyme 2 | UBA2 |
| ubiquitin-like modifier activating enzyme 5 | UBA5 |
| ubiquitin A-52 residue ribosomal protein fusion product 1 | UBA52 |
| ubiquitin-like modifier activating enzyme 6 | UBA6 |
| ubiquitin-like modifier activating enzyme 7 | UBA7 |
| UBA domain containing 1 | UBAC1 |
| UBA domain containing 2 | UBAC2 |
| ubiquitin associated protein 1 | UBAP1 |
| ubiquitin associated protein 2-like | UBAP2L |
| ubiquitin associated and SH3 domain containing B | UBASH3B |
| ubiquitin B | UBB |
| ubiquitin C | UBC |
| ubiquitin-conjugating enzyme E2D 2 | UBE2D2 |
| ubiquitin-conjugating enzyme E2D 3 | UBE2D3 |
| ubiquitin-conjugating enzyme E2G 1 | UBE2G1 |
| ubiquitin-conjugating enzyme E2K | UBE2K |
| ubiquitin-conjugating enzyme E2L 3 | UBE2L3 |
| ubiquitin-conjugating enzyme E2M | UBE2M |
| ubiquitin-conjugating enzyme E2N | UBE2N |
| ubiquitin-conjugating enzyme E2N-like (gene/pseudogene) | UBE2NL |
| ubiquitin-conjugating enzyme E2O | UBE2O |
| ubiquitin-conjugating enzyme E2 variant 1 | UBE2V1 |
| ubiquitin-conjugating enzyme E2 variant 2 | UBE2V2 |
| ubiquitin-conjugating enzyme E2Z | UBE2Z |
| ubiquitin protein ligase E3A | UBE3A |
| ubiquitin protein ligase E3B | UBE3B |
| ubiquitin protein ligase E3C | UBE3C |
| ubiquitination factor E4A | UBE4A |
| ubiquitination factor E4B | UBE4B |
| ubiquitin-like 3 | UBL3 |
| ubiquilin 1 | UBQLN1 |
| ubiquilin 2 | UBQLN2 |
| ubiquilin 4 | UBQLN4 |
| ubiquitin protein ligase E3 component n-recognin 2 | UBR2 |
| ubiquitin protein ligase E3 component n-recognin 4 | UBR4 |
| ubiquitin domain containing 1 | UBTD1 |
| ubiquitin domain containing 2 | UBTD2 |
| UBX domain protein 1 | UBXN1 |
| UBX domain protein 6 | UBXN6 |
| ubiquitin carboxyl-terminal esterase L1 (ubiquitin thiolesterase) | UCHL1 |
| ubiquitin carboxyl-terminal esterase L3 (ubiquitin thiolesterase) | UCHL3 |
| ubiquitin carboxyl-terminal hydrolase L5 | UCHL5 |
| uridine-cytidine kinase 2 | UCK2 |

TABLE 4-continued

| Suitable extracellular vesicle associated proteins | |
| --- | --- |
| Gene Name | Gene Symbol |
| UEV and lactate/malate dehyrogenase domains | UEVLD |
| ubiquitin-fold modifier conjugating enzyme 1 | UFC1 |
| ubiquitin fusion degradation 1 like (yeast) | UFD1L |
| UFM1-specific ligase 1 | UFL1 |
| UDP-glucose ceramide glucosyltransferase | UGCG |
| UDP-glucose 6-dehydrogenase | UGDH |
| UDP-glucose glycoprotein glucosyltransferase 1 | UGGT1 |
| UDP-glucose pyrophosphorylase 2 | UGP2 |
| ubiquitin-like with PHD and ring finger domains 1 | UHRF1 |
| unc-51 like kinase 3 | ULK3 |
| uromodulin | UMOD |
| uridine monophosphate synthetase | UMPS |
| unc-119 homolog B (*C. elegans*) | UNC119B |
| unc-13 homolog B (*C. elegans*) | UNC13B |
| unc-13 homolog C (*C. elegans*) | UNC13C |
| unc-13 homolog D (*C. elegans*) | UNC13D |
| unc-45 homolog A (*C. elegans*) | UNC45A |
| unc-5 homolog D (*C. elegans*) | UNC5D |
| unc-80 homolog (*C. elegans*) | UNC80 |
| ureidopropionase, beta | UPB1 |
| UPF1 regulator of nonsense transcripts homolog (yeast) | UPF1 |
| uroplakin 1A | UPK1A |
| uroplakin 1B | UPK1B |
| uroplakin 2 | UPK2 |
| uroplakin 3A | UPK3A |
| uroplakin 3B-like | UPK3BL |
| uridine phosphorylase 1 | UPP1 |
| ubiquinol-cytochrome c reductase core protein I | UQCRC1 |
| ubiquinol-cytochrome c reductase core protein II | UQCRC2 |
| URB1 ribosome biogenesis 1 homolog (*S. cerevisiae*) | URB1 |
| uroporphyrinogen decarboxylase | UROD |
| USO1 vesicle transport factor | USO1 |
| ubiquitin specific peptidase 1 | USP1 |
| ubiquitin specific peptidase 11 | USP11 |
| ubiquitin specific peptidase 14 (tRNA-guanine transglycosylase) | USP14 |
| ubiquitin specific peptidase 15 | USP15 |
| ubiquitin specific peptidase 24 | USP24 |
| ubiquitin specific peptidase 39 | USP39 |
| ubiquitin specific peptidase 4 (proto-oncogene) | USP4 |
| ubiquitin specific peptidase 46 | USP46 |
| ubiquitin specific peptidase 49 | USP49 |
| ubiquitin specific peptidase 5 (isopeptidase T) | USP5 |
| USP6 N-terminal like | USP6NL |
| ubiquitin specific peptidase 7 (herpes virus-associated) | USP7 |
| ubiquitin specific peptidase 9, X-linked | USP9X |
| ubiquitin specific peptidase 9, Y-linked | USP9Y |

TABLE 4-continued

Suitable extracellular vesicle associated proteins

| Gene Name | Gene Symbol |
| --- | --- |
| UTP14, U3 small nucleolar ribonucleoprotein, homolog A (yeast) | UTP14A |
| UTP20, small subunit (SSU) processome component, homolog (yeast) | UTP20 |
| utrophin | UTRN |
| urotensin 2 | UTS2 |
| UDP-glucuronate decarboxylase 1 | UXS1 |
| Vac14 homolog (*S. cerevisiae*) | VAC14 |
| vesicle-associated membrane protein 1 (synaptobrevin 1) | VAMP1 |
| vesicle-associated membrane protein 2 (synaptobrevin 2) | VAMP2 |
| vesicle-associated membrane protein 3 | VAMP3 |
| vesicle-associated membrane protein 5 | VAMP5 |
| vesicle-associated membrane protein 7 | VAMP7 |
| vesicle-associated membrane protein 8 | VAMP8 |
| VANGL planar cell polarity protein 1 | VANGL1 |
| VAMP (vesicle-associated membrane protein)-associated protein A, 33 kDa | VAPA |
| VAMP (vesicle-associated membrane protein)-associated protein B and C | VAPB |
| valyl-tRNA synthetase | VARS |
| vasorin | VASN |
| vasodilator-stimulated phosphoprotein | VASP |
| vesicle amine transport 1 | VAT1 |
| vesicle amine transport 1-like | VAT1L |
| vav 1 guanine nucleotide exchange factor | VAV1 |
| von Hippel-Lindau binding protein 1 | VBP1 |
| versican | VCAN |
| vinculin | VCL |
| valosin containing protein | VCP |
| valosin containing protein (p97)/p47 complex interacting protein 1 | VCPIP1 |
| voltage-dependent anion channel 1 | VDAC1 |
| voltage-dependent anion channel 2 | VDAC2 |
| voltage-dependent anion channel 3 | VDAC3 |
| vascular endothelial growth factor C | VEGFC |
| villin 1 | VIL1 |
| vimentin | VIM |
| vitelline membrane outer layer 1 homolog (chicken) | VMO1 |
| vanin 1 | VNN1 |
| vacuolar protein sorting 11 homolog (*S. cerevisiae*) | VPS11 |
| vacuolar protein sorting 13 homolog C (*S. cerevisiae*) | VPS13C |
| vacuolar protein sorting 13 homolog D (*S. cerevisiae*) | VPS13D |
| vacuolar protein sorting 16 homolog (*S. cerevisiae*) | VPS16 |
| vacuolar protein sorting 18 homolog (*S. cerevisiae*) | VPS18 |
| vacuolar protein sorting 25 homolog (*S. cerevisiae*) | VPS25 |
| vacuolar protein sorting 26 homolog A (*S. pombe*) | VPS26A |

TABLE 4-continued

| Suitable extracellular vesicle associated proteins | |
|---|---|
| Gene Name | Gene Symbol |
| vacuolar protein sorting 26 homolog B (*S. pombe*) | VPS26B |
| vacuolar protein sorting 28 homolog (*S. cerevisiae*) | VPS28 |
| vacuolar protein sorting 29 homolog (*S. cerevisiae*) | VPS29 |
| vacuolar protein sorting 33 homolog A (*S. cerevisiae*) | VPS33A |
| vacuolar protein sorting 33 homolog B (yeast) | VPS33B |
| vacuolar protein sorting 35 homolog (*S. cerevisiae*) | VPS35 |
| vacuolar protein sorting 36 homolog (*S. cerevisiae*) | VPS36 |
| vacuolar protein sorting 37 homolog B (*S. cerevisiae*) | VPS37B |
| vacuolar protein sorting 37 homolog C (*S. cerevisiae*) | VPS37C |
| vacuolar protein sorting 37 homolog D (*S. cerevisiae*) | VPS37D |
| vacuolar protein sorting 39 homolog (*S. cerevisiae*) | VPS39 |
| vacuolar protein sorting 41 homolog (*S. cerevisiae*) | VPS41 |
| vacuolar protein sorting 45 homolog (*S. cerevisiae*) | VPS45 |
| vacuolar protein sorting 4 homolog A (*S. cerevisiae*) | VPS4A |
| vacuolar protein sorting 4 homolog B (*S. cerevisiae*) | VPS4B |
| vacuolar protein sorting 51 homolog (*S. cerevisiae*) | VPS51 |
| vacuolar protein sorting 52 homolog (*S. cerevisiae*) | VPS52 |
| vacuolar protein sorting 53 homolog (*S. cerevisiae*) | VPS53 |
| vacuolar protein sorting 8 homolog (*S. cerevisiae*) | VPS8 |
| vaccinia related kinase 1 | VRK1 |
| vaccinia related kinase 3 | VRK3 |
| visual system homeobox 2 | VSX2 |
| vesicle (multivesicular body) trafficking 1 | VTA1 |
| vesicle transport through interaction with t-SNAREs 1A | VTI1A |
| vesicle transport through interaction with t-SNAREs 1B | VTI1B |
| vitronectin | VTN |
| von Willebrand factor A domain containing 1 | VWA1 |
| von Willebrand factor A domain containing 2 | VWA2 |
| von Willebrand factor A domain containing 3B | VWA3B |
| von Willebrand factor | VWF |
| tryptophanyl-tRNA synthetase | WARS |
| Wiskott-Aldrich syndrome | WAS |
| WAS protein family, member 1 | WASF1 |
| WAS protein family, member 2 | WASF2 |
| WAS protein family, member 3 | WASF3 |
| Wiskott-Aldrich syndrome-like | WASL |
| WW domain binding protein 2 | WBP2 |
| WD repeat and FYVE domain containing 1 | WDFY1 |
| WDFY family member 4 | WDFY4 |
| WD repeat domain 1 | WDR1 |
| WD repeat domain 11 | WDR11 |
| WD repeat domain 18 | WDR18 |
| WD repeat domain 26 | WDR26 |
| WD repeat domain 33 | WDR33 |
| WD repeat domain 37 | WDR37 |
| WD repeat domain 4 | WDR4 |
| WD repeat domain 44 | WDR44 |
| WD repeat domain 48 | WDR48 |
| WD repeat domain 49 | WDR49 |
| WD repeat domain 5 | WDR5 |

TABLE 4-continued

| Suitable extracellular vesicle associated proteins | |
| --- | --- |
| Gene Name | Gene Symbol |
| WD repeat domain 61 | WDR61 |
| WD repeat domain 63 | WDR63 |
| WD repeat domain 7 | WDR7 |
| WD repeat domain 70 | WDR70 |
| WD repeat domain 77 | WDR77 |
| WD repeat domain 82 | WDR82 |
| WD repeat domain 92 | WDR92 |
| WD and tetratricopeptide repeats 1 | WDTC1 |
| WEE1 G2 checkpoint kinase | WEE1 |
| Wolf-Hirschhorn syndrome candidate 1 | WHSC1 |
| WAS/WASL interacting protein family, member 1 | WIPF1 |
| widely interspaced zinc finger motifs | WIZ |
| wingless-type MMTV integration site family, member 10B | WNT10B |
| wingless-type MMTV integration site family, member 5A | WNT5A |
| wingless-type MMTV integration site family, member 5B | WNT5B |
| Werner helicase interacting protein 1 | WRNIP1 |
| RAB6C-like | WTH3DI |
| WW domain containing E3 ubiquitin protein ligase 1 | WWP1 |
| WW domain containing E3 ubiquitin protein ligase 2 | WWP2 |
| XPA binding protein 2 | XAB2 |
| xanthine dehydrogenase | XDH |
| X-prolyl aminopeptidase (aminopeptidase P) 1, soluble | XPNPEP1 |
| X-prolyl aminopeptidase (aminopeptidase P) 2, membrane-bound | XPNPEP2 |
| X-prolyl aminopeptidase 3, mitochondrial | XPNPEP3 |
| exportin 1 | XPO1 |
| exportin 4 | XPO4 |
| exportin 5 | XPO5 |
| exportin 6 | XPO6 |
| exportin 7 | XPO7 |
| exportin, tRNA | XPOT |
| xenotropic and polytropic retrovirus receptor 1 | XPR1 |
| X-ray repair complementing defective repair in Chinese hamster cells 5 (double-strand-break rejoining) | XRCC5 |
| X-ray repair complementing defective repair in Chinese hamster cells 6 | XRCC6 |
| 5'-3' exoribonuclease 2 | XRN2 |
| xylulokinase homolog (H. influenzae) | XYLB |
| tyrosyl-tRNA synthetase | YARS |
| Y box binding protein 1 | YBX1 |
| Y box binding protein 2 | YBX2 |
| Y box binding protein 3 | YBX3 |
| YES proto-oncogene 1, Src family tyrosine kinase | YES1 |
| Yip1 interacting factor homolog B (S. cerevisiae) | YIF1B |
| Yip1 domain family, member 2 | YIPF2 |
| Yip1 domain family, member 6 | YIPF6 |
| YKT6 v-SNARE homolog (S. cerevisiae) | YKT6 |
| YTH domain containing 2 | YTHDC2 |
| tyrosine 3-monooxygenase/tryptophan 5-monooxygenase activation protein, beta | YWHAB |

TABLE 4-continued

| Suitable extracellular vesicle associated proteins | |
| --- | --- |
| Gene Name | Gene Symbol |
| tyrosine 3-monooxygenase/tryptophan 5-monooxygenase activation protein, epsilon | YWHAE |
| tyrosine 3-monooxygenase/tryptophan 5-monooxygenase activation protein, epsilon pseudogene 5 | YWHAEP5 |
| tyrosine 3-monooxygenase/tryptophan 5-monooxygenase activation protein, gamma | YWHAG |
| tyrosine 3-monooxygenase/tryptophan 5-monooxygenase activation protein, eta | YWHAH |
| tyrosine 3-monooxygenase/tryptophan 5-monooxygenase activation protein, theta | YWHAQ |
| tyrosine 3-monooxygenase/tryptophan 5-monooxygenase activation protein, zeta | YWHAZ |
| zeta-chain (TOR) associated protein kinase 70 kDa | ZAP70 |
| zinc finger and BTB domain containing 10 | ZBTB10 |
| zinc finger and BTB domain containing 4 | ZBTB4 |
| zinc finger and BTB domain containing 49 | ZBTB49 |
| zinc finger CCCH-type, antiviral 1 | ZC3HAV1 |
| zinc finger CCCH-type, antiviral 1-like | ZC3HAV1L |
| zinc finger, C4H2 domain containing | ZC4H2 |
| zinc finger, CCHC domain containing 11 | ZCCHC11 |
| zinc finger, DHHC-type containing 1 | ZDHHC1 |
| zinc finger, DHHC-type containing 13 | ZDHHC13 |
| zinc finger, DHHC-type containing 18 | ZDHHC18 |
| zinc finger, DHHC-type containing 20 | ZDHHC20 |
| zinc finger, DHHC-type containing 5 | ZDHHC5 |
| zinc finger, AN1-type domain 5 | ZFAND5 |
| zinc finger, C3H1-type containing | ZFC3H1 |
| zinc finger protein, FOG family member 1 | ZFPM1 |
| zinc finger, FYVE domain containing 26 | ZFYVE26 |
| zymogen granule protein 16B | ZG16B |
| zinc finger, GRF-type containing 1 | ZGRF1 |
| zinc finger with KRAB and SCAN domains 5 | ZKSCAN5 |
| zinc metallopeptidase STE24 | ZMPSTE24 |
| zinc finger, MYM-type 1 | ZMYM1 |
| zinc finger protein 114 | ZNF114 |
| zinc finger protein 134 | ZNF134 |
| zinc finger protein 169 | ZNF169 |
| zinc finger protein 185 (LIM domain) | ZNF185 |
| zinc finger protein 205 | ZNF205 |
| zinc finger protein 217 | ZNF217 |
| zinc finger protein 254 | ZNF254 |
| zinc finger protein 28 | ZNF28 |
| zinc finger protein 326 | ZNF326 |
| zinc finger protein 33A | ZNF33A |

TABLE 4-continued

| Suitable extracellular vesicle associated proteins | |
| --- | --- |
| Gene Name | Gene Symbol |
| zinc finger protein 486 | ZNF486 |
| zinc finger protein 503 | ZNF503 |
| zinc finger protein 518A | ZNF518A |
| zinc finger protein 541 | ZNF541 |
| zinc finger protein 571 | ZNF571 |
| zinc finger protein 614 | ZNF614 |
| zinc finger protein 624 | ZNF624 |
| zinc finger protein 638 | ZNF638 |
| zinc finger protein 764 | ZNF764 |
| zinc finger protein 792 | ZNF792 |
| zinc finger protein 862 | ZNF862 |
| zinc finger, HIT-type containing 6 | ZNHIT6 |
| zona pellucida glycoprotein 3 (sperm receptor) | ZP3 |
| zw10 kinetochore protein | ZW10 |
| zyxin | ZYX |
| zinc finger, ZZ-type with EF-hand domain 1 | ZZEF1 |

The invention claimed is:

1. A method for producing synthetic extracellular vesicles comprising:
   a) providing a water phase comprising at least two lipids, and one or more extracellular vesicle associated proteins or fragments thereof, wherein the at least two lipids are a negative charged lipid, and a lipid coupled to a functional ligand for conjugation to the one or more extracellular vesicle associated protein or fragments thereof;
   b) providing an amphiphilic copolymer dissolved in an oil phase, wherein the amphiphilic copolymer is a diblock copolymer consisting of a hydrophobic polymer block and a hydrophilic polymer block, or a triblock copolymer consisting of two hydrophobic polymer blocks and a hydrophilic polymer block, and wherein the oil phase comprises a fluorosurfactant triblock;
   c) combining said water phase and said oil phase;
   d) producing polymer shell-stabilized synthetic extracellular vesicles by emulsifying the combined phases of c) using a mechanic or electronic emulsifier;
   wherein the amphiphilic copolymer forms a polymer shell stabilizing the synthetic extracellular vesicle,
   wherein the one or two hydrophobic polymer blocks are arranged at the outer side and the hydrophilic polymer block is arranged at the inner side of the polymer shell,
   wherein the vesicles are homogenous in size showing a coefficient of variation in size lower than 13%, and
   wherein the synthetic extracellular vesicles have a hydrodynamic radius between 70 nm and 5000 nm.

2. The method according to claim 1, wherein the water phase further comprises one or more nucleic acid molecules.

3. The method according to claim 1, further comprising d') and e) after d):
   d') removing the polymer shell from the polymer shell-stabilized synthetic extracellular vesicles obtained in d) by adding a surfactant; and
   e) purifying the synthetic extracellular vesicles by centrifugation.

4. The method according to claim 1, wherein the water phase of a) comprises at least one lipid coupled to a functional ligand selected from biotin, N-hydroxysuccinimide ester, N-hydroxysulfosuccinimide, nitrilotriacetic acid-nickel, amine, carboxylic acid, maleimide, aromatic male-imid, dithiopyridinyl, pyridyl disulfide, pyridyldithiopropionate, N-benzylguanine, cyanuric chloride, carboxyacyl, cyanur, folate, square, galloyl, glycan, thiol, arginylglycylaspartic acid, a fluorescent dye molecule, a magnetic resonance imaging reagent, a chelator; and
   wherein the method optionally comprises after e) the following step:
   f) coupling the synthetic extracellular vesicles with at least one macromolecule comprising at least one moiety reacting with one of said functional ligands, wherein the macromolecule is selected from the group comprising an extracellular vesicle associated protein or a fragment thereof, a carbohydrate, a nucleic acid, a polypeptide, a cell receptor, an imaging probe.

5. The method according to claim 1, wherein the extracellular vesicle associated protein, or a fragment thereof, is selected from the group comprising:
   a transmembrane protein selected from the group comprising tetraspanin proteins CD9, CD37, CD47, CD53, CD63, CD81, CD82, CD151, Tspan8, heterotrimeric G protein subunit alpha, integrin α-chains, integrin β-chains, transferrin receptor 1, transferrin receptor 2, lysosome associated membrane proteins, heparan sulfate proteoglycans, syndecans, extracellular matrix metalloproteinase inducer, A Disintegrin And Metalloproteinase Domain 10, CD3, CD11c, CD14, CD29, CD31, CD41, CD42a, CD44, CD45, CD50 or intercellular adhesion molecule 1, CD55, CD59, CD73, CD80, CD86, CD90, sonic hedgehog, major histocompatibility complex I, major histocompatibility complex II, epidermal growth factor receptor 2, epithelial cell adhesion molecule, glycophorin A, Acetylcholinesterase S and E, amyloid beta precursor protein, multidrug resistance-associated protein 1, stem cells antigen-1, or a fragment thereof;
   a cytosolic protein selected from the group comprising the protein complexes endosomal sorting complexes required for transport I, II and III, tumour susceptibility gene 101, charged multivesicular body protein, Apoptosis-Linked Gene 2-Interacting Protein X, vacuolar protein sorting 4 homolog A 4A and 4B, arrestin domain-containing protein, flotillin-1, flotillin-2; caveolins, EH-domain containing 1-4, ras homolog family member A, annexins, heat shock proteins, ADP-ribosylation factor 6, syntenin, microtubule-associated protein Tau, or a fragment thereof;

a functional protein selected from the group comprising cytokines, growth factors, interleukins, milk fat globule-EGF factor 8 protein, adhesion proteins, extracellular matrix proteins, nicotinamide phosphoribosyltransferase, signal transduction proteins, Wnta, Wntb, Fas, Fas Ligand, RANK, RANK Ligand, indolamin-2,3-dioxygenase, cytotoxic T-lymphocyte-associated protein 4-immunoglobulin fusion protein, tumor necrosis factor-related apoptosis-inducing ligand, or a fragment thereof; and a protein associated to intracellular compartments selected from the group comprising histone proteins, lamin A/C, inner membrane mitochondrial protein, cytochrome C-1, mitochondrial import receptor subunit TOM20, calnexin, heat shock protein 90 kDa beta, member 1, heat shock 70 kDa protein 5, Golgin A2, Autophagy Related 9A, actinin1, actinin4, cytokeratin 18, or a fragment thereof.

6. The method according to claim 2, wherein the water phase of a) comprises one or more nucleic acid molecules selected from the group comprising miRNA molecules miR-17, miR-18a, miR-19a, miR-19b-1, miR-20a, miR-92a; miR-21, miR-30d-5p, miR-33b, miR-124, miR-125, miR-126, miR-130, miR-132, miR-133b, miR-140-5p, miR-191, miR-222, miR-451, miR-494, miR-575, miR-630, miR-638, miR-1202, miR-1207-5p, miR-1225-5p, miR-1268, miR-6087, miR-92a-3p-e, miR-K12-3, let-7a.

7. The method according to claim 1, wherein the water phase of a) comprises at least two lipids selected from the group comprising:

a neutral lipid selected from the group comprising ceramide, sphingomyelin, cephalin, cholesterol, cerebrosides, diacylglycerols, phosphatidylcholines, lysophosphatidylcholines, phosphatidylethanolamines, lysophosphatidylethanolamine, lysoethanolamines, inverted headgroup lipids, sphingosins, sterol-modified phospholipids, ether ester lipids, diether lipids, vinyl ether, plasmalogen;

an anionic lipid selected from the group comprising phosphatidic acids, lysophosphatidic acid derivatives, phosphatidylglycerols, lysophosphatidylglycerols, phosphatidylserines, lysophosphatidylserines, phosphatidylinositols, phosphatidylinositolphosphates, cardiolipins, Bis(Monoacylglycero)Phosphate derivatives;

a cationic lipid selected from the group comprising diol-eyl-N,N-dimethylammonium chloride; N-(2,3-dioley-loxy)propyl)-N,N,N-trimethylammonium chloride; N,N-distearyl-N,N-dimethylammonium bromide; N-(2,3-dioleyloxy)propyl)-N,N,N-trimethylammonium chloride; 3β-(N-(N',N'-dimethylaminoethane)-carbamoyl) cholesterol; 1,2-dimyristyloxypropyl-3-dimethyl-hydroxy ethyl ammonium bromide; 2,3-dioleyloxy-N-[2 (sperminecarboxamido) ethyl]-N,N-dimethyl-1-propanaminium trifluoroacetate; dioctadecylamidoglycyl carboxyspermine; N-(2,3-dioleyloxy)propyl)-N,N-dimethylammonium chloride and 1,2-Dioleoyl-3-dimethylammonium-propane;

a pH-sensitive lipid selected from the group comprising lipid N-(4-carboxybenzyl)-N,N-dimethyl-2,3-bis (oleoyloxy)propan-1-aminium, 1,2-distearoyl-3-dimethylammonium-propane, 1,2-dipalmitoyl-sn-glycero-3-succinate, 1,2-dioleoyl-sn-glycero-3-succinate, N-palmitoyl homocysteine;

a photoswitchable lipid;

acylglycine derivatives, prenol derivatives, prostaglandine derivatives, glycosylated diacyl glycerols, eicosanoid derivatives, (palmitoyloxy) octadecanoic acid derivatives, diacetylene derivatives, diphytanoyl derivatives, fluorinated lipids, brominated lipids, lipopolysaccharides;

one of the aforementioned lipids coupled to a functional ligand selected from the group comprising biotin, N-hydroxysuccinimide ester, nitrilotriacetic acid-nickel, amine, carboxylic acid, maleimides, aromatic maleimid, dithiopyridinyl, pyridyl disulfide, pyridyldithiopropionate, N-benzylguanine, cyanuric chloride, carboxyacyl, cyanur, folate, square, galloyl, glycan, thiol, arginylglycylaspartic acid, a fluorescent dye molecule, a magnetic resonance imaging reagent, a chelator; and one of the aforementioned lipids coupled to polyethyleneglycol with a molecular weight comprised between 350 and 50,000 g/mole.

8. The method according to claim 1, wherein d) comprises producing polymer shell stabilized synthetic extracellular vesicles by emulsifying the combined phases at c) using a mechanic or electronic emulsifier for at least 5 seconds at speed higher than 1,000 rpm.

9. A synthetic extracellular vesicle having a hydrodynamic radius between 70 nm and 5000 nm, comprising:

a lipid bilayer comprising at least two lipids selected from the group comprising:

a neutral lipid selected from the group comprising ceramide, sphingomyelin, cephalin, cholesterol, cerebrosides, diacylglycerols, phosphatidylcholines, lysophosphatidylcholines, phosphatidylethanolamines, lysophosphatidylethanolamine, lysoethanolamines, inverted headgroup lipids, sphingosins, sterol-modified phospholipids, ether ester lipids, diether lipids, vinyl ether (plasmalogen);

an anionic lipid selected from the group comprising phosphatidic acids, lysophosphatidic acid derivatives, phosphatidylglycerols, lysophosphatidylglycerols, phosphatidylserines, lysophosphatidylserines, phosphatidylinositols, phosphatidylinositolphosphates, cardiolipins, Bis(Monoacylglycero)Phosphate derivatives;

a cationic lipid selected from the group comprising diol-eyl-N,N-dimethylammonium chloride; N-(2,3-dioley-loxy)propyl)-N,N,N-trimethylammonium chloride; N,N-distearyl-N,N-dimethylammonium bromide; N-(2,3-dioleyloxy)propyl)-N,N,N-trimethylammonium chloride; 3β-(N-(N',N'-dimethylaminoethane)-carbamoyl) cholesterol; 1,2-dimyristyloxypropyl-3-dimethyl-hydroxy ethyl ammonium bromide; 2,3-dioleyloxy-N-[2 (sperminecarboxamido) ethyl]-N,N-dimethyl-1-propanaminium trifluoroacetate; dioctadecylamidoglycyl carboxyspermine; N-(2,3-dioleyloxy)propyl)-N,N-dimethylammonium chloride and 1,2-Dioleoyl-3-dimethylammonium-propane;

a pH-sensitive lipid selected from the group comprising lipid N-(4-carboxybenzyl)-N,N-dimethyl-2,3-bis (oleoyloxy)propan-1-aminium, 1,2-distearoyl-3-dimethylammonium-propane, 1,2-dipalmitoyl-sn-glycero-3-succinate, 1,2-dioleoyl-sn-glycero-3-succinate, N-palmitoyl homocysteine;

a photoswitchable lipid;

acylglycine derivatives, prenol derivatives, prostaglandine derivatives, glycosylated diacyl glycerols, eicosanoid derivatives, (palmitoyloxy) octadecanoic acid derivatives, diacetylene derivatives, diphytanoyl derivatives, fluorinated lipids, brominated lipids, lipopolysaccharides;

one of the aforementioned lipids coupled to a functional ligand selected from the group comprising biotin, N-hydroxysuccinimide ester, nitrilotriacetic acid-nickel, amine, carboxylic acid, maleimides, aromatic maleimid, dithiopyridinyl, pyridyl disulfide, pyridyldi-thiopropionate, N-benzylguanine, cyanuric chloride, carboxyacyl, cyanur, folate, square, galloyl, glycan, thiol, arginylglycylaspartic acid, a fluorescent dye molecule, a magnetic resonance imaging reagent, a chelator;

one of the aforementioned lipids coupled to polyethyleneglycol with a molecular weight comprised between 350 and 50,000 g/mole; and one or more extracellular vesicle associated proteins selected from the group comprising CD9, CD37, CD47, CD53, CD63, CD81, CD82, CD151, Tspan8, heterotrimeric G protein subunit alpha, integrin α-chains, integrin β-chains, transferrin receptor 1, transferrin receptor 2, lysosome associated membrane proteins, heparan sulfate proteoglycans, syndecans, extracellular matrix metalloproteinase inducer, A Disintegrin And Metalloproteinase Domain 10, CD3, CD11c, CD14, CD29, CD31, CD41, CD42a, CD44, CD45, CD50 or intercellular adhesion molecule 1, CD55, CD59, CD73, CD80, CD86, CD90, sonic hedgehog, major histocompatibility complex I, major histocompatibility complex II, epidermal growth factor receptor 2, epithelial cell adhesion molecule, glycophorin A, acetylcholinesterase S and E, amyloid beta precursor protein, multidrug resistance-associated protein 1, stem cells antigen-1, protein complexes endosomal sorting complexes required for transport I, II and III, tumour susceptibility gene 101, charged multivesicular body protein, Apoptosis-Linked Gene 2-Interacting Protein X, vacuolar protein sorting 4 homolog A 4A and 4B, arrestin domain-containing protein, flotillin-1, flotillin-2; caveolins, EH-domain containing 1-4, ras homolog family member A, annexins, heat shock proteins, ADP-ribosylation factor 6, syntenin, microtubule-associated protein Tau, cytokines, growth factors, interleukins, milk fat globule-EGF factor 8 protein, adhesion proteins, extracellular matrix proteins, nicotinamide phosphoribosyltransferase, signal transduction proteins, Wnta, Wntb, Fas, Fas Ligand, RANK, RANK Ligand, indolamin-2,3-dioxygenase, cytotoxic T-lymphocyte-associated protein 4-immunoglobulin fusion protein, tumor necrosis factor-related apoptosis-inducing ligand, histone proteins, lamin A/C, inner membrane mitochondrial protein, cytochrome C-1, mitochondrial import receptor subunit TOM20, calnexin, heat shock protein 90 kDa beta, member 1, heat shock 70 kDa protein 5, Golgin A2, Autophagy Related 9A, actinin1, actinin4, cytokeratin 18, or a fragment thereof.

10. The synthetic extracellular vesicle according to claim 9, further comprising one or more nucleic acid molecules selected from the group comprising DNA, cDNA, mRNA, siRNA, antisense nucleotides, shRNA, piRNA, snRNA, lncRNA, PNA, left handed DNA, Clustered Regularly Interspaced Short Palindromic Repeats guide RNA, miRNA.

11. The synthetic extracellular vesicle according to claim 10, wherein the miRNA is selected from the group comprising miR-17, miR-18a, miR-19a, miR-19b-1, miR-20a, miR-92a; miR-21, miR-30d-5p, miR-33b, miR-124, miR- 125, miR-126, miR-130, miR-132, miR-133b, miR-140-5p, miR-191, miR-222, miR-451, miR-494, miR-575, miR-630, miR-638, miR-1202, miR-1207-5p, miR-1225-5p, miR-1268, miR-6087, miR-92a-3p-e, miR-K12-3, and let-7a.

12. The synthetic extracellular vesicle according to claim 9, comprising:

a lipid bilayer comprising cholesterol, N-stearoyl-D-erythro-sphingosylphosphorylcholine, 1,2-dioleoyl-sn-glycero-3-phosphocholine, 1,2-dioleoyl-sn-glycero-3-phospho-L-serine, 1,2-dioleoyl-sn-glycero-3-phosphoethanolamine, 1,2-dioleoyl-sn-glycero-3-phospho-rac-(1-glycerol), 1,2-dioleoyl-sn-glycero-3-phosphate (sodium salt), diacylglycerol, phosphatidylinositol, 1,2-dioleoyl-sn-glycero-3-phosphoethanolamine-N-(lissamine rhodamine B sulfonyl), 1,2-dioleoyl-sn-glycero-3-[(N-(5-amino-1-carboxypentyl)iminodiacetic acid) succinyl] (nickel salt);

one or more nucleic acid molecules selected from the group comprising miRNA miR-21, miR-124, miR-125, miR-126, miR-130 and miR-132; and one or more transmembrane proteins selected from the group comprising tetraspanin proteins CD9, CD63 and CD81, or a fragment thereof.

13. The synthetic extracellular vesicle according to claim 9, comprising:

one or more functional protein nicotinamide phosphoribosyltransferase, or a fragment thereof;

one or more transmembrane proteins selected from the group comprising tetraspanin proteins CD9, CD63 and CD81, or a fragment thereof; and one or more cytosolic proteins selected from the group comprising Apoptosis-Linked Gene 2-Interacting Protein X, tumour susceptibility gene 101 protein, or a fragment thereof;

wherein the synthetic extracellular vesicle does not comprise transferrin and albumin.

14. The synthetic extracellular vesicle according to claim 9, comprising:

one or more transmembrane proteins selected from the group comprising MHCII, CD80, and CD86;

optionally one or more transmembrane proteins selected from the group comprising CD11c, MHCI, integrin α, integrin β-chains, intercellular adhesion molecule-1, and CD71, or a fragment thereof;

one or more functional proteins selected from the group comprising cytokines, interleukins, interleukin 4, milk fat globule-EGF factor 8 protein, growth factors, Fas, Fas Ligand, indolamin-2,3-dioxygenase, cytotoxic T-lymphocyte-associated protein 4-immunoglobulin fusion protein, tumor necrosis factor-related apoptosis-inducing ligand, or a fragment thereof.

15. The synthetic extracellular vesicle according to claim 9, comprising:

a lipid bilayer comprising 1,2-dioleoyl-sn-glycero-3-phosphocholine, 1,2-dioleoyl-sn-glycero-3-phospho-rac-(1-glycerol), 1,2-dioleoyl-sn-glycero-3-phosphoethanolamine-N-(lissamine rhodamine B sulfonyl), 1,2-dioleoyl-sn-glycero-3-[(N-(5-amino-1-carboxypentyl)iminodiacetic acid) succinyl] (nickel salt);

functional protein Fas Ligand, or a fragment thereof; and optionally functional protein intercellular adhesion protein-1, or a fragment thereof.

16. The synthetic extracellular vesicle according to claim 9, comprising:

one or more transmembrane proteins selected from the group comprising CD29, CD44, CD90, CD73, Sca-1, or a fragment thereof;

one or more transmembrane proteins selected from the group comprising tetraspanin proteins CD9, CD63, and CD81, or a fragment thereof;

one or more functional proteins selected from the group comprising Wnta and Wntb, or a fragment thereof;

at least one nucleic acid molecule selected from the group comprising miR-140-5p, miR-92a-3p-e;

one or more nucleic acid molecules selected from the group comprising miR-17, miR-18a, miR-19a, miR-19b-1, miR-20a, miR-92a, let-7a, miR-21, miR124, miR126, miR-133b, miR-191, miR-222, miR-494, miR-6087, miR-30d-5p; and optionally one or more nucleic acid molecules selected from the group comprising miR-33b, miR-451, miR-575, miR-630, miR-638, miR-1202, miR-1207-5p, miR-1225-5p, miR-1268, miR-K12-3.

17. The synthetic extracellular vesicle according to claim 9, comprising:

a lipid bilayer comprising 1,2-dioleoyl-sn-glycero-3-phosphocholine, 1,2-dioleoyl-sn-glycero-3-phosphorac-(1-glycerol), 1,2-dioleoyl-sn-glycero-3-phosphoethanolamine-N-(lissamine rhodamine B sulfonyl), 1,2-dioleoyl-sn-glycero-3-[(N-(5-amino-1-carboxypentyl)iminodiacetic acid) succinyl] (nickel salt); and functional protein RANK, or a fragment thereof.

18. A method for treating or ameliorating a disorder comprising administering to a patient suffering from said disorder a therapeutically effective amount of a synthetic extracellular vesicle according to claim 9, wherein the disorder is selected from the group consisting of inflammation, cancer, rheumatic disorder, osteoarthritis, cardiovascular disorder, epithelial diseases, neurodegenerative disorders, autoimmune disorders, bone and cartilage disorders, osteoporosis, renal osteodystrophy, Paget's disease of bone, osteopetrosis, rickets, neurological disorders, intoxication, neuroendocrinology disorders, endocrinology disorders, genetic disorders, infectious diseases, dental disorders, cosmetic procedures, coagulation disorders, dermatoses, diabetes, age-associated disorders.

\* \* \* \* \*